US008735584B2

(12) United States Patent
Huck et al.

(10) Patent No.: US 8,735,584 B2
(45) Date of Patent: May 27, 2014

(54) PROTEIN KINASE INHIBITORS AND USE THEREOF

(75) Inventors: Bayard R. Huck, Sudbury, MA (US);
Xiaoling Chen, Chestnut Hill, MA (US);
Lizbeth Celeste Deselm, Melrose, MA (US); Christopher Charles Victor Jones, Arlington, MA (US); Srinivasa R. Karra, Pembroke, MA (US); Yufang Xiao, Lexington, MA (US); Andreas Goutopoulos, Boston, MA (US);
Amanda E. Sutton, Hingham, MA (US)

(73) Assignee: Merck Patent GmbH, Darmstadt (DE)

( * ) Notice: Subject to any disclaimer, the term of this patent is extended or adjusted under 35 U.S.C. 154(b) by 301 days.

(21) Appl. No.: 12/919,136

(22) PCT Filed: Feb. 25, 2009

(86) PCT No.: PCT/US2009/035089
§ 371 (c)(1),
(2), (4) Date: Nov. 18, 2010

(87) PCT Pub. No.: WO2009/108670
PCT Pub. Date: Sep. 3, 2009

(65) Prior Publication Data
US 2011/0053906 A1 Mar. 3, 2011

Related U.S. Application Data

(60) Provisional application No. 61/067,492, filed on Feb. 28, 2008.

(51) Int. Cl.
*C07D 471/04* (2006.01)
*C07D 471/06* (2006.01)
(52) U.S. Cl.
USPC ........................................... 546/81; 514/290
(58) Field of Classification Search
USPC ........................................... 546/81; 514/290
See application file for complete search history.

(56) References Cited

FOREIGN PATENT DOCUMENTS

| WO | 97/22596 | A1 | 6/1997 |
|---|---|---|---|
| WO | 97/30035 | A1 | 8/1997 |
| WO | 97/32856 | A1 | 9/1997 |
| WO | 98/13354 | A1 | 4/1998 |
| WO | 99/02166 | A1 | 1/1999 |
| WO | 00/40529 | A1 | 7/2000 |
| WO | 00/41669 | A2 | 7/2000 |
| WO | 01/92224 | A1 | 12/2001 |
| WO | 02/04434 | A1 | 1/2002 |
| WO | 02/08213 | A1 | 1/2002 |
| WO | 02/44183 | A2 | 6/2002 |

OTHER PUBLICATIONS

Deady L et al, Nucleophilic Substitution Reactions in Benzo [1,8] naphthyridines, 1986.*
Dorwald F. A., Side Reactions in Organic Synthesis, 2005, Wiley: VCH, Weinheim p. IX of Preface.*
Alessi, Dario, et al., Molecular basis for the substrate specificity of protein kinase B; comparison with MAPKAP kinase-1 and p70 S6 kinase, FEBS Letters, 1996, pp. 333-338, vol. 399(3).
Ausprunk, Dianna H., et al., Differentiation of Vascular Endothelium in the Chick Chorioallantois: A Structural and Autoradiographic Study, Developmental Biology, 1974, pp. 237-248, vol. 38(2).
Bishop, John D., and Schumacher, Jill M., Phosphorylation of the Carboxyl Terminus of Inner Centromere Protein (INCENP) by the Aurora B Kinase Stimulates Aurora B Kinase Activity, The Journal of Biological Chemistry, 2002, pp. 27577-27580, vol. 277(31).
Campos-González, Roberto, and Glenney, Jr., John R., Tyrosine Phosphorylation of Mitogen-activated Protein Kinase in Cells with Tyrosine Kinase-negative Epidermal Growth Factor Receptors, The Journal of Biological Chemistry,1992, pp. 14535-14538, vol. 267(21).
Davies, Stephen P., et al., Specificity and mechanism of action of some commonly used protein kinase inhibitors, Biochem J., 2000, pp. 95-105, vol. 351.
Dhanabal, Mohahnraj, et al., Endostatin: Yeast Production, Mutants, and Antitumor Effect in Renal Cell Carcinoma, Cancer Research, 1999, pp. 189-197, vol. 59.
Ditchfield, Claire, et al., Aurora B couples chromosome alignment with anaphase by targeting BubR1, Mad2, and Cenp-E to kinetochores, The Journal of Cell Biology, 2003, pp. 267-280, vol. 161(2).
Emanuel, Stuart, et al., The In vitro and In vivo Effects of JNJ-7706621: A Dual Inhibitor of Cyclin-Dependent Kinases and Aurora Kinases, Cancer Research, 2005, 9038-9046, vol. 65(19).
Gimbrone, Michael A. Jr., et al., Tumor Growth and Neovascularization: An Experimental Model Using the Rabbit Cornea, Journal of the National Cancer Institute, 1974, pp. 413-427, vol. 52(2).
Harrington, Elizabeth A., et al., VX-680, a potent and selective small-molecule inhibitor of the Aurora kinases, suppresses tumor growth in vivo, Nature Medicine, 2004, pp. 262-267, vol. 10(3).
Hauf, Silke, et al., The small molecule Hesperadin reveals a role for Aurora B in correcting kinetochore-microtubule attachment and in maintaining the spindle assembly checkpoint, The Journal of Cell Biology, 2003, pp. 281-294, vol. 161(2).
Khwaja, Asim, et al., Matrix adhesion and Ras transformation both activate a phosphoinositide 3-OH kinase and protein kinase B/Akt cellular survival pathway, The EMBO Journal, 1997, pp. 2783-2793, vol. 16(10).
Marumoto, Tomotoshi, et al., Aurora-A,—A Guardian of Poles, Nature, 2005, pp. 42-50, vol. 5.

(Continued)

*Primary Examiner* — Rita Desai
(74) *Attorney, Agent, or Firm* — EMD Serono Research and Development Institute; Thomas W. Brown

(57) ABSTRACT

Disclosed are benzonaphthyridinyl derivative compounds and analogs thereof, pharmaceutical compositions comprising such compounds and processes for preparing the same. The compounds are useful in the treatment of diseases amenable to kinase signal transduction inhibition, regulation or modulation.

2 Claims, No Drawings

(56) References Cited

OTHER PUBLICATIONS

Minoshima, Yukinori, et al., Phosphorylation by Aurora B Converts MgcRacGAP to a RhoGAP during Cytokinesis, Developmental Cell, 2003, pp. 549-560, vol. 4.

Nicosia, Roberto F., et al., Hisotypic Angiogenesis in Vitro: Light Microscopic, Ultrastructural, and Radioautographic Studies, 1982, pp. 538-549, vol. 18(6).

Núñez, Araceli, et al., Pyridinium N-2'-pyridylaminide: radical cyclization for the synthesis of benzonaphthyridine derivatives, Tetrahedon, 2007, pp. 6774-6783, vol. 63(29).

Ross, Heike, et al., A non-radioactive method for the assay of many serine/threonine-specific protein kinases, Biochemical Journal, 2002, pp. 977-981, vol. 366.

Sausville, Edward A., Aurora kinases dawn as cancer drug targets, Nature Medicine, 2004, pp. 234-235, vol. 10 (3).

Sheu, Joen R., et al, Effect of U-995, a Potent Shark Cartilage-Derived Angiogenesis Inhibitor, on Anti-Angiogenesis and Anti-Tumor Activities, Anticancer Research, 1998, pp. 4435-4442, vol. 18.

Sills, Matthew A. et al., Comparison of Assay Technologies for a Tyrosine Kinase Assay Generates Different Results in High Throughput Screening, Journal of Biomolecular Screening, 2002, pp. 191-214, vol. 7.

Sorg, Gabriele, et al., Automated High Throughput Screening for Serine Kinase Inhibitors Using a Leadseeker™ Scintillation Proximity Assay in the 1536-Well Format, 2002, Journal of Biomolecular Screening, pp. 11-19, vol. 7(1).

Tyle, Praveen, Iontophoretic Devices for Drug Delivery, Pharmaceutical Research, 1986, pp. 318-326, vol. 3(6).

Warner, Steven L. et al., Targeting Aurora-2 Kinase in Cancer, Molecular Cancer Therapeutics, 2003, pp. 589-595, vol. 2.

White, Donald E., et al., Mammary epithelial-specific expression of the integrin linked kinase (ILK) results in the induction of mammary gland hyperplasias and tumors in transgenic mice, Oncogene, 2001, pp. 7064-7072, vol. 20.

Xin, Xiaohua, et al., Peroxisome Proliferator-activated Receptor γ Ligands Are Potent Inhibitors of Angiogenesis in Vitro and in Vivo, The Journal of Biological Chemistry, 1999, pp. 9116-9121, vol. 274(13).

Yoshida, Masaru, Study of biodegradable copoly(L-lactic-acid/glycolic acid) formulations with controlled release of Z-100 for application in radiation therapy, International Journal of Pharmaceutics, 1995, pp. 61-67, vol. 115.

Office Action mailed Aug. 13, 2013 in the prosecution of JP patent application serial No. 2010-548836 entitled "Protein Kinase Inhibitors and Use Thereof."

Cherubim, P., and Deady, L., Nucleophilic Substitution Reactions in Benzo[c][1,8]naphthyridines. II, Australian Journal of Chemistry, 1990, pp. 1469-1473, vol. 43(8).

Deady, Leslie W., and Werden, Dianne, M., Nucleophilic Substitution Reactions in Benzo[c][1,8]naphthyridines, Australian Journal of Chemistry, 1986, pp. 667-675, vol. 39(4).

\* cited by examiner

PROTEIN KINASE INHIBITORS AND USE THEREOF

BACKGROUND OF INVENTION

The present invention relates to protein kinase inhibitors, compositions comprising such inhibitors, and methods of use thereof. More particularly, the invention relates to inhibitors of Aurora protein kinase. The invention also relates to pharmaceutical compositions, as well as to methods of treating diseases associated with protein kinases, especially diseases associated with Aurora A and Aurora B, such as cancer and further proliferative diseases.

Protein kinases represent a large family of proteins, which play a central role in the regulation of a wide variety of cellular processes, thus maintaining control over cellular function. A partial list of such kinases includes Akt, Axl, Aurora A, Aurora B, dyrk2, epha2, fgfr3, flt-3, vegfr3, igf1r, IKK2, JNK3, Vegfr2, MEK1, MET, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt3, Flt1, PDK1 and Erk. Inhibition of such kinases has become an important therapeutic target.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds of the invention are novel, selective, and highly potent adenosine triphosphate (ATP) competitive inhibitors of Aurora kinases (A, B and C). The Aurora family of conserved serine/threonine kinases perform essential functions during cell division. The three mammalian paralogues are very similar in sequence, but differ significantly in their localization, function, substrates and regulatory partners. Aurora A is mainly associated with the spindle poles during mitosis, where it is required for centrosome separation and maturation (Sausville EA. Aurora kinases dawn as cancer drug targets, *Nat. Med.*, (2004)10: 234-235 (2004). Spindle assembly requires that targeting protein for XKLP 2 (TPX2) targets Aurora A to spindle pole microtubules through a mechanism that requires Ran-GTP (Marumoto T, Zhang D, Saya H. Aurora A—A guardian of poles, *Nature*, (2005) δ 42-50 (2005). Aurora A also functions in meiosis promoting oocyte maturation, polar-body extrusion, spindle positioning and exit from metaphase I. Regulation of Aurora A occurs through phosphorylation/dephosphorylation and degradation. Protein phosphatase 1 negatively regulates Aurora and this interaction is modulated by TPX2. Aurora B is a chromosomal-passenger protein with multiple functions in mitosis. Inner centromere protein (INCENP) and survivin, two other components of the passenger complex, function as targeting and regulatory factors for the kinase (Bishop J D and Shumacher J M. Phosphorylation of the Carboxyl Terminus of Inner Centromere Protein (INCENP) by the aurora B Kinase Stimulates aurora B Kinase Activity, *J. Biol. Chem.* (2002) 277:27577-27580. Aurora B is required for phosphorylation of histone H3, targeting of condensin and normal chromosome compaction. It has also been recently shown to be essential for chromosome biorientation, kinetochore-microtubule interactions and the spindle-assembly checkpoint. Aurora B is essential for completion of cytokinesis. Myosin II regulatory chain, vimentin, desmin and glial fibrillary acidic protein are among its cleavage furrow substrates. Aurora B phosphorylates MgcRacGAP, transforming it into an activator of RhoA in the contractile ring (Minoshima Y, Kawashima T, Hirose K, Tonozuka Y, Kawajiri A, Bao Y, Deng X, Tatsuka M, Narumiya S, May W Phosphorylation by aurora B converts MgcRacGAP to a RhoGAP during cytokinesis. *Dev. Cell*, (2003) 4:549-560. Much less is known about Aurora C kinase, other than that it seems to be preferentially expressed in meiotic cells. During the cell cycle, Aurora kinases travel to their subcellular targets aided by their binding partner-substrates, INCENP, survivin and TPX2. This provides an additional level of regulation that might be essential for the choreography of mitotic events.

Aurora A and B kinases are frequently elevated in human cancers making them attractive targets for therapeutic intervention. Small molecule inhibitors of Aurora kinases have recently been reported, but their effect on cytokinesis has yet to be investigated in detail. For example a high selective and potent small-molecule inhibitor of Aurora kinases, VX-680, blocks cell-cycle progression and induces apoptosis in a diverse range of human tumor types. This compound causes profound inhibition of tumor growth in a variety of in vivo xenograft models, leading to regression of leukemia, colon and pancreatic tumors at well-tolerated doses (Harrington E A, Bebbington D, Moore J, Rasmussen R K, Ajose-Adeogun A O, Nakayama T. Graham J A, Demur C, Hercend T, Diu-Hercend A, Su M, Golec J M, Miller K M VX-680, a potent and selective small-molecule inhibitor of the aurora kinases, suppresses tumor growth in vivo, *Nat. Med.*, (2004) 10: 262-267. Another novel cell cycle inhibitor, JNJ-7706621, showed potent inhibition of several cyclin-dependent kinases (CDK) and Aurora kinases and selectively blocked proliferation of tumor cells of various origins, but was about 10-fold less effective at inhibiting normal human cell growth in vitro. In human cancer cells, treatment with JNJ-7706621 inhibited cell growth independent of p53, retinoblastoma, or P-glycoprotein status; activated apoptosis; and reduced colony formation. At low concentrations, JNJ-7706621 slowed the growth of cells and at higher concentrations induced cytotoxicity. Inhibition of CDK1 kinase activity, altered CDK1 phosphorylation status, and interference with downstream substrates such as retinoblastoma were also shown in human tumor cells following drug treatment. JNJ-7706621 delayed progression through G1 and arrested the cell cycle at the G2-M phase (Emanuel S, Rugg C A, Gruninger R H, Lin R, Fuentes-Pesquera A, Connolly P J, Wetter S K, Hollister B, Kruger W W, Napier C, Jolliffe L, Middleton S A, The in vitro and in vivo effects of JNJ-7706621: A dual inhibitor of cyclin-dependent kinases and aurora kinases, *Cancer Res.*, (2005) 65:9038-9046). Additional cellular effects due to inhibition of Aurora kinases included endoreduplication and inhibition of histone H3 phosphorylation. In a human tumor xenograft model, several intermittent dosing schedules were identified that produced significant antitumor activity.

As noted above, Aurora kinases are overexpressed in certain types of cancers, including colon, breast, and other solid-tumor cancers. The genes encoding the Aurora B and A kinases tend to be amplified in certain types of cancers, while the gene encoding the Aurora C kinase resides in a region of the chromosome that is subject to rearrangement and deletion. Aurora A has been associated with a variety of malignancies, including primary colon, colorectal, breast, stomach, ovarian, prostate, and cervical cancer, neuroblastoma, and other solid-tumor cancers (Warner et al. (2003) *Molecular Cancer Therapeutics* 2:589-95).

Hauf et al. (*J. Cell. Biol.* (2003) 161:281-294) identified the indolinone (Hesperadin) as an inhibitor of Aurora B, which causes cells to enter anaphase with monooriented chromosomes, having both sister kinetochores attached to a single spindle pole (a condition known as syntelic attachment).

Ditchfield et al. (*J. Cell. Biol.* (2003) 161:267-280) described ZM447-439 ((4-(4-(N-benzoylamino)anilino)-6-methoxy-7-(3-(1-morpholino)propoxy) quinazoline), an Aurora kinase inhibitor which interferes with chromosome alignment, segregation, and cytokinesis.

The present invention specifically relates to compounds of the formula I which inhibit, regulate and/or modulate signal transduction by Aurora kinase, to compositions which comprise these compounds, and to processes for the use thereof for the treatment of Aurora kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Aurora kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Aurora kinase for the prevention and/or treatment of diseases in connection with unregulated or disturbed Aurora kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Aurora kinase. In addition, they are particularly suitable for use in diagnostic methods for diseases in connection with unregulated or disturbed Aurora kinase activity.

It can be shown that the compounds of the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., *EMBO*, (1997), 16: 2783-93) and models of transgenic animals (for example White et al., *Oncogene*, (2001), 20: 7064-7072). For the determination of certain stages in the signal transduction cascade, interacting compounds can be utilised in order to modulate the signal (for example Stephens et al., *Biochemical J.*, (2000), 351:95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., *FEBS Lett.* (1996), 399(3): 333-338) or the basic myelin protein, are described in the literature (for example Campos-González, R. and Glenney, Jr., J. R., *J. Biol. Chem.* (1992), 267:14535).

For the identification of kinase inhibitors, various assay systems are available. In scintillation proximity assay (Sorg et al., *J. of. Biomolecular Screening*, (2002), 7:11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., *J. of Biomolecular Screening*, (2002) 191-214). Another possibility is the use of a caliper test as exemplified in example 151.

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, *Biochem. J.*).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

Accordingly, kinase inhibitors, particularly inhibitors of Aurora kinases, are of particular interest in treating certain disorders, including cancer and other proliferative diseases. Compounds exhibiting such inhibition are of particular value.

SUMMARY OF THE INVENTION

The present invention provides compounds or pharmaceutically usable derivatives, solvates, salts, tautomers and stereoisomers thereof, including mixtures thereof in all ratios, compositions comprising the compounds of the invention, and methods for treating diseases mediated by kinases. Such diseases include primary, secondary, and metastatic cancers such as melanoma, lymphoma, leukemia, colon, colorectal, breast, lung, kidney, pancreatic, renal, CNS, stomach, ovarian, prostate, cervical, and neuroblastoma and further proliferative diseases.

In one aspect the invention provides compounds according to formula I (I)

wherein
W is chosen from Hal, Ar-alk, Het-alk, O, OH, SH, $S(O)_mZ$, $S(O)_mAr$, $S(O)_mHet$, Z, OZ, OAr, OHet OAlk or NRR';
Q is N or NH depending upon valence requirements
X is chosen from N or $[N^+—O^-]$;
---------- denotes the presence of a single or a double bond;
$R^1$, $R^2$, $R^3$, $R^4$, $R^5$ and $R^6$ are independently chosen from hydrogen, Hal, Z, OZ, OAr, OHet, OH, NRR', Ar, Ar-alk, Het, Het-alk, $S(O)_mZ$, $S(O)_mAr$, $S(O)_mHet$, $C(O)_mOR$, $NRC(O)_mR'$, $NRSO_2R'$, $NRC(O)_mNR'$, $(CH_2)_nOZ$ or C(O)NRR';
R and R' are independently chosen from hydrogen, Z, Ar, Ar-alk, Het, Het-alk, OZ, OAr, $S(O)_mZ$, $S(O)_mAr$ or $S(O)_mHet$;
Z denotes unbranched or branched alkyl having 1-10 C atoms, in which 1-7H atoms may be replaced by F, Cl and/or Br, and/or in which one or two non adjacent $CH_2$ groups may be replaced by O, N, NH, S, SO, $SO_2$, and/or CH=CH groups, or cyclic alkyl having 3-7 C atoms;
Ar denotes phenyl, naphthyl or biphenyl, each of which is unsubstituted or mono-, di- or trisubstituted by Hal, Z, OR, $N(R)_2$, SR, $NO_2$, CN, COOR, $CON(R)_2$, NRCOZ, $NRSO_2Z$, $SO_2N(R)_2$, $S(O)_mZ$, CO-Het, Het, $O[C(R)_2]_nN(R)$, $O[C(R)_2]_nHet$, NHCOOZ, $NHCON(R)_2$, $NHCOO[C(R)_2]_nN(R)_2$, $NHCOO[C(R)_2]_pHet$, $NHCONH[C(R)_2]_nN(R)_2$, $NHCONH[C(R)_2]_pHet$, $OCONH[C(R)_2]_nN(R)_2$, $OCONH[C(R)_2]_nHet$, CHO and/or COZ;

Hal denotes halogen, preferably Cl, Br, I, or F
Het denotes independently a mono-, bi- or tricyclic saturated, unsaturated or aromatic heterocycle having 1 to 4 N, O and/or S atoms, which may be unsubstituted or mono-, di- or trisubstituted by Hal, Z, OR, $(CH_2)_pN(R)_2$, SR, $NO_2$, CN, COOR, $CON(R)_2$, $O[C(R)_2]_pN(R)$, $O[C(R)_2]_nHet^1$, NHCOOZ, $NHCON(R)_2$, $NHCOO[C(R)_2]_nN(R)_2$, $NHCOO[C(R)_2]_nHet$, $NHCONH[C(R)_2]_nN(R)_2$, $NHCONH[C(R)_2]_nHet$, $OCONH[C(R)_2]_nN(R)_2$, $OCONH[C(R)_2]_nHet$, NRCOZ, $NRSO_2Z$, $SO_2N(R)_2$, $S(O)_mZ$, CO-Het, CHO, COZ, =S, =NH, =NZ, oxy (—$O^-$) and/or =O (carbonyl oxygen);
alk denotes branched or unbranched alkylene with 1 to 10 C atoms, in which 1-7H atoms may be replaced by F, Cl and/or Br, and/or in which one or two non adjacent $CH_2$ groups may be replaced by O, S, SO, $SO_2$, NH, NZ, CH=CH and/or CC groups, and which may be substituted by Hal, OR, SR, Ar and/or =O;
m is 0, 1 or 2;
n is 0, 1, 2, 3, 4, 5 or 6;
p is 0, 1, 2, 3 or 4; and
a pharmaceutically acceptable prodrug, derivative, solvate, salt, tautomer and stereoisomer thereof, including mixtures thereof in all ratios.

Also included within the scope of the invention are compounds 1-506, and a pharmaceutically acceptable salt thereof.

Also encompassed by the present invention are methods of treating a subject in need of inhibition of a kinase protein comprising administering to a subject in need thereof an effective amount of a kinase inhibitor according to formula I.

Specially, the present invention provides methods of reducing cancer metastasis in a subject with cancer comprising administering to a subject in need thereof an effective amount of a kinase inhibitor according to formula I.

Furthermore, the present invention provides methods of curing proliferative diseases comprising administering to a subject in need thereof an effective amount of a kinase inhibitor according to formula I.

Further embodiments of the present invention include: a compound according to formula I for use as a medicament; use of the compound according to formula I for the preparation of a medicament for the treatment of a subject in need of inhibition of a kinase protein; and use of the compound according to formula I for the preparation of a medicament for the suppression (reduction) of cancer metastasis.

The present invention also encompasses a compound according to formula I, or pharmaceutically usable derivatives, solvates, salts, tautomers and stereoisomers thereof, including mixtures thereof in all ratios, for use in therapy, such as treating a subject in need of inhibition of a kinase protein, wherein the subject has a proliferative disease or an inflammatory disease.

Additionally, the present invention includes a pharmaceutical composition comprising an effective amount of a compound of formula I and a pharmaceutically acceptable carrier, excipient or diluent.

A method of synthesizing the compounds of the present invention is also encompassed.

Furthermore the present invention relates to a kit comprising a compound of formula I and a further medicament active ingredient.

The present invention is also related to the combined use of a compound of formula (I) together with further medicament active ingredient for the treatment of a subject in need of such treatment, specially for the afore and below mentioned diseases and conditions related to the inhibition of kinase proteins.

DETAILED DESCRIPTION OF THE INVENTION

One aspect of the present invention is to provide novel compounds according to formula I that are useful in the treatment of hyperproliferative diseases and inflammatory diseases.

In the following the description of the compounds of the invention in every case includes a pharmaceutically usable prodrug, derivative, solvate, salt, tautomer and stereoisomer thereof, including mixtures thereof in all ratios.

For the sake of clarity it is added here that if W is O and Q is NH in every case the tautomers NH/O and N/OH are comprised. At positions W and Q for the purpose of the present invention the term N comprises NH and O comprises OH and vice versa.

The compounds of the present invention are useful for the treatment of a subject in need of inhibition of a protein kinase. Specifically, the compounds of the present invention are protein kinase inhibitors. As a result, the invention provides in a first aspect novel compounds according to formula I. Values and particular values for the variables in formula I are provided in the following paragraphs.

Z denotes alkyl, is unbranched (linear) or branched, and has 1, 2, 3, 4, 5, 6, 7, 8, 9 or 10 C atoms. Z preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethyl-propyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

Z very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Z also encompasses cyclic alkyl(cycloalkyl), e.g. cyclopropyl, cyclobutyl, cyclopentyl, cyclohexyl or cycloheptyl.

One to seven H atoms in Z as defined above may be replaced by F, Cl and/or Br, and/or one or two $CH_2$ groups may be replaced by O, S, SO, $SO_2$ and/or CH=CH groups.

alk denotes alkylene, is unbranched (linear) or branched, and has 1, 2, 3, 4, 5, 6, 7, 8, 9 or 10 C atoms. alk preferably denotes methylene, furthermore ethylene, propylene, isopropylene, butylene, isobutylene, sec-butylene or tert-butylene, furthermore also pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, furthermore preferably, for example, difluoromethylene.

alk very particularly preferably denotes alkylene having 1, 2, 3, 4, 5 or 6 C atoms, preferably methylene, ethylene, propylene, isopropylene, butylene, isobutylene, sec-butylene, tert-butylene, pentylene, hexylene, difluoromethylene, tetrafluoroethylene or 1,1-difluoroethylene.

Cyclic alkylene (cycloalkylene) preferably denotes cyclopropylene, cyclobutylene, cyclopentylene, cyclohexylene or cycloheptylene.

In a further embodiment, Ar preferably denotes phenyl which is unsubstituted or mono-, di- or trisubstituted by Hal, alk, OR, $CF_3$, CN or $CONH_2$.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl, 2,5-dimethyl-4-chlorophenyl.

Most preferably, Ar denotes 4-, 3-, or 2-methoxy phenyl, 4-, 3-, or 2-fluoro phenyl, 4-, 3-, or 2-methyl phenyl, 4-, 3-, or 2-trifluoromethyl phenyl, 4-, 3-, or 2-cyano phenyl, 4-, 3-, or 2-bromo phenyl, 4-, 3-, or 2-chloro phenyl, 4-, 3-, or 2-amino phenyl, 4-isopropyl phenyl, 4-ethyl phenyl, 4-n-propyl phenyl, 2-ethoxy phenyl, 4-tert-butyl phenyl, 3-nitro phenyl, 3-alkynyl phenyl, 4-, 3-, or 2-carboxamide phenyl, 4-, 3-, or 2-methyl ester phenyl, 4-N,N-di-methylamino phenyl, 4-trifluoromethoxy phenyl, 4-,3-, or 2-acetamide phenyl, 4-N,N-dimethylsulfonamide phenyl, 4-sulfonamide phenyl, 4-N-methylsulfonamide phenyl, 4-methanesulfonyl morpholine, 3,4-di-fluoro phenyl, 2,4-di-fluoro phenyl, 3,5-di-fluoro phenyl, 2,6-di-fluoro phenyl, 2,3-di-fluoro phenyl, 2,3-di-chloro phenyl, 2,5-di-chloro phenyl, 2,4-di-chloro phenyl, 3,5-di-chloro phenyl, 2,6-di-chloro phenyl, 3,4-di-chlorophenyl, 2,5-di-methoxy phenyl, 3,-5-di-trifluoromethyl phenyl, 2,4-di-trifluoromethyl phenyl, 2,5-di-trifluoromethyl phenyl, 2-fluoro-6-chloro phenyl, 2-fluoro-5-chloro phenyl, 2-fluoro-4-chloro phenyl, 4-fluoro-3-chloro phenyl, 4-fluoro-2-trifluoromethyl phenyl, 2-fluoro-3-trifluoromethyl phenyl, 3-fluoro-5-trifluoromethyl phenyl, 2-fluoro-4-trifluoromethyl phenyl, 2-fluoro-6-trifluoromethyl phenyl, 2-fluoro-6-methoxy phenyl, 3-fluoro-4-methyl phenyl, 2-methyl-3-trifluoromethyl phenyl, 4-methyl-3-trifluoromethyl phenyl, 2-chloro-5-methoxy phenyl, 2-methyl-5-chloro phenyl, 2-cyano-3-methoxy phenyl, 2-fluoro-4-amino phenyl, 3-fluoro-4-amino phenyl, 5-chloro-benzo[1,3-dioxol], 2,4-di-chloro-5-methoxy phenyl or 4-chloro,2-5-di-methoxy phenyl.

Het denotes a monocyclic or polycyclic ring system of 3 to 20 atoms of which at least one atom is a heteroatom chosen from O, N and S which may be saturated, unsaturated or aromatic; wherein a —$CH_2$— group can optionally be replaced by a —C(O)—. Examples of Het include pyrrolidinyl, tetrahydrofuranyl, dihydrofuranyl, tetrahydrothienyl, tetrahydropyranyl, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, dibenzofuranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, azetidin-2-one-1-yl, pyrrolidin-2-one-1-yl, piperid-2-one-1-yl, azepan-2-one-1-yl, 3-azabicyco[3.1.0]hexanyl, 3-azabicyclo[4.1.0]heptanyl, azabicyclo[2.2.2]hexanyl, 3H-indolyl or quinolizinyl. Spiromoieties are also included within the scope of this definition. Other examples are piperidin-1-yl, pyrrolidin-1-yl, morpholin-4-yl, piperazin-1-yl, 1,3-oxazolidin-3-yl, imidazolidinyl, oxazolyl, thiazolyl, thienyl, furanyl or pyridyl. All the above defined radicals may also be mono- or disubstituted by Z.

The heterocyclic radicals may also be partially or fully hydrogenated.

Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxy-phenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydro-benzoxazolyl, 2,3-dihydrobenzimidazolyl, 1,3-dihydroindole, 2-oxo-1,3-dihydroindole or 2-oxo-2,3-dihydrobenzimidazolyl.

Preferably Het is morpholinyl, imidazolyl, dihydro-2H-benzo[1,4]oxazinyl, quinolinyl, piperazinyl, benzoylindolinyl, indazolyl, indolyl, oxazolyl, thiazolyl, azetidinyl, pyrrolidinyl, piperidinyl, 2,3-dihydro-benzofuranyl or pyrazolyl.

More preferably Het is morpholin-4-yl, imidazol-2-yl, dihydro-2H-benzo[1,4]oxazin-7-yl, quinolin-7-yl, piperazin-1-yl, benzoylindolin-6-yl, indazol-5-yl, indol-5-yl, oxazol-5-yl, thiazol-4-yl, azetidin-3-yl, pyrrolidin-3-yl, piperidin-1-yl, 2,3-dihydro-benzofuran-7-yl or pyrazol-1-yl.

W is chosen from Hal, Ar-alk, Het-alk, O, OH, SH, $S(O)_mZ$, $S(O)_mAr$, $S(O)_mHet$, Z, OZ, OAr, OHet, O-Alk, or NRR'. Preferably, W is preferably O, Hal or NRR'. It is preferred when W is Cl. In a further preferred embodiment, W is NRR', wherein R is H and R' is selected from the group consisting of Ar or Alk.

In a preferred embodiment the present invention relates to a compound according to formula (I), wherein Q is NH and W is O.

In a preferred embodiment the present invention relates to a compound according to formula (I), wherein X is N; Q is NH and W is O.

In a further preferred embodiment the present invention relates to a compound according to above formula (I), wherein X is N; Q is N and W is Hal, preferably Cl.

In a further preferred embodiment the present invention relates to a compound according to above formula (I), wherein W is NRR'.

In a further preferred embodiment the present invention relates to a compound according to above formula (I), wherein W is NRR' with R being H and R' being as shown in formula (II)

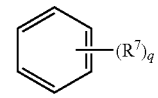

(II)

wherein $R^7$ denotes hydrogen, Hal, Z, OZ, OH, NRR', Ar, Het, sulfanyl, C(O)OR, NRC(O)R', $NRSO_2R'$, NRC(O)NR', or C(O)NRR' and q is an integer from 1 to 5.

In a further preferred embodiment the present invention relates to a compound according to formula (I), wherein W is O; Q is NH; X is N; and $R^1$, $R^2$, $R^3$, $R^4$, $R^5$ and $R^6$ denote independently hydrogen, Hal, Z, Ar, Het, NRR', $C(O)_mOR$, or OAr, and wherein m is 0 or 1. It is preferred when not more than two, and especially preferred that not more than one of $R^1$, $R^2$, $R^3$, $R^4$, $R^5$ or $R^6$ is other but hydrogen.

In a further preferred embodiment the present invention relates to a compound according to formula (I), wherein W is NRR', O, or Hal; Q is N or NH; X is N; and $R^1$, $R^2$, $R^3$, $R^4$, $R^5$ and $R^6$ denote independently hydrogen, Hal, Z, Ar, Het, NRR', $C(O)_mOR$, OZ, or OAr, and wherein m is 0 or 1. It is preferred when not more than two, specially preferred only one of $R^1$, $R^2$, $R^3$, $R^4$, $R^5$ or $R^6$ is other but hydrogen. If two of $R^1$, $R^2$, $R^3$, $R^4$, $R^5$ or $R^6$ are other than hydrogen, then these are preferably selected from the pairs $R^4/R^5$, $R^2/R^4$, $R^2/R^5$, R2/R6, and $R^1/R^4$, respectively.

In a further very preferred embodiment the present invention relates to a compound according to formula (I) wherein one of $R^1$, $R^2$ or $R^4$ is chosen from Hal, Z, Ar, Het, NRR', C(O)mOR, O—Z, OHet or OAr, and wherein only one $R^1$, $R^2$, $R^3$, $R^4$, $R^5$ and $R^6$ is other than hydrogen.

In a further preferred embodiment the present invention relates to a compound according to formula (I), wherein W is O; Q is NH; X is N; $R^1$, $R^2$, $R^3$, $R^5$ and $R^6$ denote independently hydrogen or Z; preferably hydrogen; and $R^4$ denotes Hal, Het, NRR', OAr or OZ.

In a very preferred embodiment the present invention relates to a compound according to formula (I), wherein W is O; Q is NH; X is N; $R^1$, $R^3$, $R^4$, $R^5$ and $R^6$ denote independently hydrogen or Z; preferably hydrogen; $R^2$ denotes Hal, NRR', OAr, Ar or OZ.

In a further preferred embodiment the present invention relates to a compound according to formula (I), wherein W is O; Q is NH; X is N; $R^2$, $R^3$, $R^4$, $R^5$ and $R^6$ denote independently hydrogen or Z; preferably hydrogen; and R' denotes Hal, Het, NRR', Ar or $C(O)_mOR$.

In a further preferred embodiment the present invention relates to a compound according to formula (I), wherein W is O; Q is NH; X is N; $R^1$, $R^2$, $R^3$, $R^4$, and $R^6$ denote independently hydrogen or Z; preferably hydrogen; and $R^5$ independently Hal, Het, NRR' or Ar.

In a further preferred embodiment the present invention relates to a compound according to formula (I), wherein W is O; Q is NH; X is N; $R^1$, $R^2$, $R^3$ and $R^6$ denote independently hydrogen or Z; preferably hydrogen; and $R^4$ and $R^5$ denote OZ.

In a further preferred embodiment the present invention relates to a compound according to formula (I), wherein W is O; Q is NH; X is N; $R^2$, $R^3$, $R^5$ and $R^6$ denote independently hydrogen or Z; preferably hydrogen; and $R^1$ and $R^4$ denote Hal.

In a further preferred embodiment the present invention relates to a compound according to formula (I), wherein W is Hal, OAlk, or NRR'; Q is N; X is N; and $R^1$, $R^2$, $R^3$, $R^5$ and $R^6$ denote independently hydrogen or Z, preferably hydrogen, and $R^4$ denotes hydrogen, Hal, Z, Ar, Het, NRR', or OAr; and wherein m is 0 or 1.

In a further preferred embodiment the present invention relates to a compound according to formula (I), wherein W denotes Hal, OAlk, or NRR'; $R^1$, $R^3$, $R^4$, $R^5$ and $R^6$ denote independently hydrogen or Z; preferably hydrogen, and $R^2$ denotes Hal, OAr or NRR'.

In a further preferred embodiment the present invention relates to a compound according to formula (I), wherein W denotes Hal, OAlk, or NRR'; Q is N; X is N; $R^2$, $R^3$, $R^4$, $R^5$ and $R^6$ denote independently hydrogen or Z; preferably hydrogen, and $R^1$ denotes Hal or NRR'.

In a further preferred embodiment the present invention relates to a compound according to formula (I), wherein W denotes Hal, OAlk, or NRR'; Q is N; X is N; $R^1$, $R^2$, $R^3$, $R^4$ and $R^6$ denote independently hydrogen or Z; preferably hydrogen, and $R^5$ denotes Hal or NRR'.

In a further preferred embodiment the present invention relates to a compound according to formula (I), wherein W denotes Hal, OAlk, or NRR'; Q is N; X is N; $R^1$, $R^2$, $R^3$, and $R^6$ denote independently hydrogen or Z; preferably hydrogen, and $R^4$ and $R^5$ denote independently Hal or OZ.

In an even more preferred embodiment the present invention relates to a compound according to formula (V)

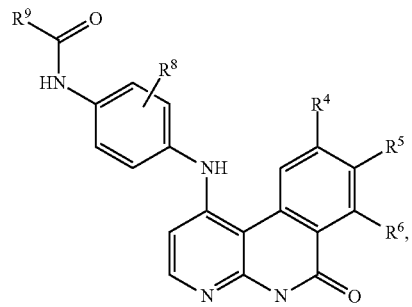

wherein
$R^4$, $R^5$ and $R^6$ are as defined above,
$R^9$ denotes Ar, Het or cyclic alkyl having 3-7 C atoms, all of which can be unsubstituted or substituted with $R^8$ and
$R^8$ denotes H, methyl, methoxy, ethyl, ethoxy, OH, CN, $NO_2$, trifluoromethyl or Hal, preferably H or F.
Preferably, $R^8$ denotes H or F.
Further preferred are compounds of subformulae A, B, C, D, E, F, G, H, J, K, L and M of formula (V), wherein
in Subformula A
$R^9$ is phenyl, unsubstituted, or monosubstituted or independently disubstituted, by methoxy, $CF_3$, F, $CH_3$ or Cl, $R^8$ is H or F,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
while the remaining two of $R^4$, $R^5$, $R^6$ are H,
in Subformula B
$R^9$ is phenyl, unsubstituted, or monosubstituted, or independently disubstituted, by methoxy, $CF_3$, F, $CH_3$ or Cl, $R^8$ is H,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
while the remaining two of $R^4$, $R^5$, $R^6$ are H,
in Subformula C
$R^9$ is phenyl, unsubstituted, or monosubstituted, or independently disubstituted, by methoxy, $CF_3$, F, $CH_3$ or Cl, $R^9$ is H,
$R^4$, $R^5$, $R^6$ are H,
in Subformula D
$R^9$ is phenyl,
$R^9$ is H,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, carboxylic acid 2-morpholin-4-yl-ethyl amidyl, N-(3-(dimethylamino)propyl)carbamoyl or $CF_3$,
while the remaining two of $R^4$, $R^5$, $R^6$ are H, in Subformula E
$R^9$ is phenyl, unsubstituted, or monosubstituted, or independently disubstituted, by methoxy, $CF_3$, F, $CH_3$ or Cl,
$R^8$ is H,
$R^4$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
$R^5$, $R^6$ are H,
in Subformula F
$R^9$ is phenyl, unsubstituted, or monosubstituted, or independently disubstituted, by methoxy, $CF_3$, F, $CH_3$ or Cl,
$R^8$ is H,
$R^5$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
$R^4$, $R^6$ are H,
in Subformula G
$R^9$ is phenyl, unsubstituted, or monosubstituted, or independently disubstituted, by methoxy, $CF_3$, F, $CH_3$ or Cl,
$R^8$ is H,
$R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
$R^4$, $R^5$ are H,
in Subformula H
$R^9$ is phenyl, substituted by $CF_3$ and F,
$R^8$ is H,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
while the remaining two of $R^4$, $R^5$, $R^6$ are H,
in Subformula J
$R^9$ is phenyl, substituted by $CF_3$ and F,
$R^8$ is H,
$R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
$R^4$, $R^5$ are H,
in Subformula K
$R^9$ is phenyl,
$R^8$ is H,
$R^5$, $R^6$ are independently hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
$R^4$ is H,
in Subformula L
$R^9$ is cyclohexyl, phenylamino, (trifluoromethyl)pyridyl,
$R^8$ is H,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$,
while the remaining two of $R^4$, $R^5$, $R^6$ are H,
in Subformula M
$R^9$ is phenyl, unsubstituted, or monosubstituted, or independently disubstituted, by methoxy, $CF_3$, F, $CH_3$ or Cl,
$R^8$ is H,
$R^4$, $R^5$ are methoxy,
$R^6$ is H.

Especially, the present invention relates to the compounds 1-506 contained herein.

In a further preferred embodiment the present invention relates to a process for the preparation of compounds of the formula (I), characterized in that a compound of formula (III)

$$\text{(III)}$$

wherein $R^1$ and $R^2$ have the meaning as set forth in formula (I); and X' is a leaving group, preferably Br, I, Cl or trifluoroacetate is reacted with a compound of formula (IV)

$$\text{IV}$$

wherein T is COOMethyl, COOEthyl or nitrile, $R^9$ is methyl or ethyl, and $R^3$, $R^4$, $R^5$ and $R^6$ have the meaning as set forth in formula (I).

In a further preferred embodiment the present invention relates to a medicament comprising at least one compound of formula (I) or a pharmaceutically usable prodrug, derivative, salt, solvate, tautomer or stereoisomer thereof, including mixtures thereof in all ratios and optionally including a pharmaceutically acceptable excipient, diluent and/or adjuvant.

In a further preferred embodiment the present invention relates to the use of compounds of formula (I) and pharmaceutically usable derivatives, salts, solvates, tautomers and stereoisomers thereof, including mixtures thereof in all ratios, for the preparation of a medicament for the treatment of diseases in which the inhibition, regulation and/or modulation of kinase signal transduction plays a role.

The medicaments preferably are for the treatment of diseases that are influenced by inhibition of serine/threonine kinases.

Preferably such medicaments are for the treatment of diseases which are influenced by inhibition of an enzyme selected from the group consisting of Aurora A kinase (EC 2.7.11.1), Aurora B kinase (EC 2.7.11.1), Aurora C kinase (EC 2.7.11.1), Src (EC 2.7.11.12), Abl (EC 2.7.11.12), Lck (EC 2.7.10.2), Lyn (EC 2.7.10.2), IKK (EC 2.7.11.10) and Fyn (EC 2.7.10.2), A very preferred medicament according to the invention is for the treatment of diseases which are influenced by inhibition of Aurora A kinase.

The disease which may be treated with the medicament according to the invention is selected from the group consisting of cancer, myocardial infarction, osteoporosis, stroke and inflammation.

The disease to be treated preferably is cancer.

It is equally preferred when the disease to be treated is inflammation.

If the disease to be treated is a tumour, the disease preferably originates from the group of cancers selected from the group consisting of melanoma, leukaemia, colon cancer, breast cancer, gastric cancer, ovarian cancer, renal cancer, prostrate cancer, lymphoma, neuroblastoma, pancreatic cancer, bladder cancer brain cancer and lung cancer.

In a further preferred embodiment the present invention relates to medicaments comprising at least one compound of the formula I, and at least one further medicament active ingredient.

In a further preferred embodiment the present invention relates to a set (kit) consisting of separate packs of (a) an effective amount of a compound of the formula I according to the invention, and (b) an effective amount of a further medicament active ingredient.

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The term "pharmaceutically usable derivative" or "pharmaceutically acceptable derivative" is taken to mean, for example, the salts of the compounds according to the invention and also so-called prodrug compounds.

The invention also relates to the optically active forms (stereoisomers), the enantiomers, the racemates, the diastereomers and the hydrates and solvates of these compounds.

The term solvates of the compounds is taken to mean adductions of inert solvent molecules onto the compounds which form owing to their mutual attractive force. Solvates are, for example, mono- or dihydrates or alkoxides.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in *Int. J. Pharm.*, (1995), 115:61-67.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

Pharmaceutical Salts and other Forms

The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2 hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2 naphthalenesulfonate, nicotinate, nitrate, oxalate, oleate, palmoate, pectinate, persulfate, phenylacetate, 3 phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2 diethylaminoethanol, 2 dimethylaminoethanol, ethanolamine, ethylenediamine, N ethylmorpholine, N ethylpiperidine, glucamine, glucosamine, histidine, hydrabamine, isopropylamine, lidocaine, lysine, meglumine, N methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as (C1 C4)alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, dodecyl, lauryl, myristyl and stearyl chloride, bromide and iodide; and aryl(C1-C4)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in *Pharmaceutical Research*, (1986) 3(6):318 .

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations that are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or a pharmaceutically acceptable prodrug, derivative, solvate or stereoisomer thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of serine/threonine kinase-induced diseases. These diseases include the proliferation of tumour cells, pathological neovascularisation (or angiogenesis) which promotes the growth of solid tumours and inflammation (e.g. psoriasis, rheumatoid arthritis and the like).

The present invention encompasses the use of the compounds of the formula I and/or a physiologically acceptable salt and/or solvate thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds of formula (I) according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or a physiologically acceptable salt or solvate thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or a physiologically acceptable salt and solvate thereof for the preparation of a medicament for the treatment or prevention of a tyrosine kinase-induced disease or a serine/threonine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "serine/threonine kinase-induced diseases or conditions" refers to pathological conditions that depend on the activity of one or more serine/threonine kinases. Serine/threonine kinases either directly or indirectly participate in the signal transduction pathways of a variety of cellular activities, including proliferation, adhesion and migration and differentiation. Diseases associated with serine/threonine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Aurora A kinase.

Preference is given to the use of compounds of the formula I, and pharmaceutically usable derivatives, solvates and stereoisomers thereof, including mixtures thereof in all ratios, for the preparation of a medicament for the treatment of diseases that are influenced by inhibition of kinases by the compounds according to the invention.

Particular preference is given to the use for the preparation of a medicament for the treatment of diseases that are influenced by inhibition of Aurora-kinase by the compounds according to formula (I).

Special preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myelotic leukaemia, chronic myelotic leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent that is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents, for example, cis-platin, carboplatin, cyclophosphamide, nitrogen mustard, melphalan, chlorambucil, busulphan and nitrosoureas; antimetabolites, for example, antifolates such as fluoropyrimidines like 5-fluorouracil and tegafur, raltitrexed, methotrexate, cytosine arabinoside, hydroxyurea and gemcitabine; antitumour antibiotics, for example, anthracyclines, like adriamycin, bleomycin, doxorubicin, daunomycin, epirubicin, idarubicin, mitomycin-C, dactinomycin and mithramycin; antimitotic agents, for example, vinca alkaloids, like vincristine, vinblastine, vindesine and vinorelbine, and taxoids, like taxol and taxotere; topoisomerase inhibitors, for example, epipodophyllotoxins, like etoposide and teniposide, amsacrine, topotecan, irinotecan and camptothecin; and cell-differentiating agents, for example, all-trans-retinoic acid, 13-cis-retinoic acid and fenretinide;

(ii) cytostatic agents, such as antioestrogens, for example, tamoxifen, toremifene, raloxifene, droloxifene and iodoxyfene; oestrogen receptor downregulators, for example, fulvestrant, antiandrogens, for example, bicalutamide, flutamide, nilutamide and cyproterone acetate, LHRH antagonists or LHRH agonists, for example, goserelin, leuprorelin and buserelin, progesterones, for example, megestrol acetate, aromatase inhibitors, for example, as anastrozole, letrozole, vorazole and exemestane; and inhibitors of 5'-reductase, such as finasteride;

(iii) agents which inhibit cancer cell invasion, for example, metalloproteinase inhibitors, like marimastat, and inhibitors of urokinase plasminogen activator receptor function;

(iv) inhibitors of growth factor function, for example, such inhibitors include growth factor antibodies, growth factor receptor antibodies, for example, the anti-erbb2 antibody trastuzumab [Herceptin™] and the anti-erbb1 antibody cetuximab [C225]; farnesyl transferase inhibitors, serine/threonine kinase inhibitors and serine/threonine kinase inhibitors, for example, inhibitors of the epidermal growth factor family, for example, EGFR family serine/threonine kinase inhibitors, such as N (3-chloro-4-fluorophenyl)-7-methoxy-6-(3-morpholinopropoxy) quinazolin-4-amine (gefitinib, AZD1839), N (3-ethynylphenyl)-6,7bis(2-methoxyethoxy)quinazolin-4-amine (erlotinib, OSI-774) and 6 acrylamido-N-(3-chloro-4-fluorophenyl)-7-(3-morpholinopropoxy)quinazolin-4-amine (CI 1033); inhibitors of the platelet-derived growth factor family; and inhibitors of the hepatocyte growth factor family;

(v) antiangiogenic agents, such as those which inhibit the effects of vascular endothelial growth factor, for example, the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms, (for example, linomide, inhibitors of integrin function and angiostatin;

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example, those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT; gene-directed enzyme pro-drug therapy approaches, such as those using cytosine deaminase, thymidine kinase or a bacterial nitroreductase enzyme; and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines like interleukin 2, interleukin 4 or granulocyte-macrophage colony stimulating factor; approaches for decreasing T cell energy; approaches using transfected immune cells, such as cytokine-transfected dendritic cells; approaches using cytokine-transfected tumour cell lines; and approaches using anti-idiotypic antibodies.

Medicaments that can be combined with the compounds of the formula (I) include, but are not limited to, those from Table 1 below.

| Category | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalato-platinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | | Diflomotecan (Beaufour-Ipsen) |
| | Irinotecan (CPT-11) | TAS-103 (Taiho) |
| | 7-Ethyl-10-hydroxycamptothecin | Elsamitrucin (Spectrum) |
| | Topotecan | J-107088 (Merck & Co) |
| | Dexrazoxanet (TopoTarget) | BNP-1350 (BioNumerik) |
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | | Oxantrazole |
| | Deoxyrubicin | Losoxantrone |
| | Valrubicin | Bleomycin sulfate (Blenoxan) |
| | Daunorubicin (Daunomycin) | Bleomycinic acid |
| | Epirubicin | Bleomycin A |
| | Therarubicin | Bleomycin B |
| | Idarubicin | Mitomycin C |
| | Rubidazon | MEN-10755 (Menarini) |
| | Plicamycinp | GPX-100 (Gem Pharmaceuticals) |
| | Porfiromycin | |
| | Cyanomorpholino-doxorubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | ZD 6126 (AstraZeneca) |
| | Epothilone B (Novartis) | PEG-Paclitaxel (Enzon) |
| | | AZ10992 (Asahi) |
| | T 900607 (Tularik) | IDN-5109 (Indena) |
| | T 138067 (Tularik) | AVLB (Prescient NeuroPharma) |
| | Cryptophycin 52 (Eli Lilly) | Azaepothilon B (BMS) |
| | | BNP-7787 (BioNumerik) |
| | Vinflunine (Fabre) | CA-4-Prodrug (OXiGENE) |
| | Auristatin PE (Teikoku Hormone) | Dolastatin-10 (NrH) |
| | BMS 247550 (BMS) | CA-4 (OXiGENE) |
| | BMS 184476 (BMS) | |
| | BMS 188797 (BMS) | |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenics) | JSF-154 (Tragen) |
| | Adenocarcinoma vaccine (Biomira) | Cancer vaccine (Intercell) |
| | | Norelin (Biostar) |
| | CTP-37 (AVI BioPharma) | BLP-25 (Biomira) |
| | | MGV (Progenics) |
| | JRX-2 (Immuno-Rx) | 3-Alethin (Dovetail) |
| | PEP-005 (Peplin Biotech) | CLL-Thera (Vasogen) |
| | Synchrovax vaccines (CTL Immuno) | |
| | Melanoma vaccine (CTL Immuno) | |
| | p21-RAS vaccine (GemVax) | |

| | | |
|---|---|---|
| Hormonal and antihormonal agents | Oestrogens<br>Conjugated oestrogens<br>Ethynyloestradiol chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide (Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>Cetuximab (Merck Serono, BMS))<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi-Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife)<br>SDX-101 (apoptosis promoter, Salmedix)<br>Ceflatonin (apoptosis promoter, ChemGenex) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol ™ (triclosan mouthwash, Endo)<br>Triacetyluridine (uridine prodrug, Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>Trans-retinic acid (differentiator, NIH)<br>MX6 (apoptosis promoter, MAXIA)<br>Apomine (apoptosis promoter, ILEX Oncology)<br>Urocidin (apoptosis promoter, Bioniche)<br>Ro-31-7453 (apoptosis promoter, La Roche)<br>Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

Synthesis Schematics

Scheme 1
The benzonapthiridinone scaffold can be synthesized via a two-step reaction sequence beginning with a Suzuki reaction followed by ring-closure amidation. A wide variety of 2-amino-3-halo pyridines can be combined with 2-carboxylic esters boronic acid to create a library of substituted benzonaphthiridinones.

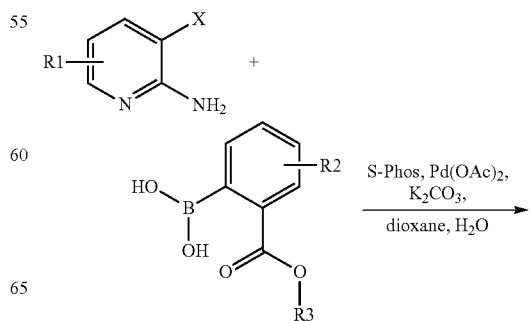

-continued

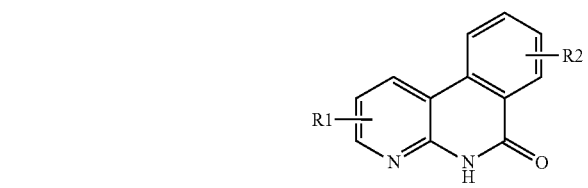

Scheme 2
An 8- or 9-position chlorine can be displaced with amines under Buchwald conditions.

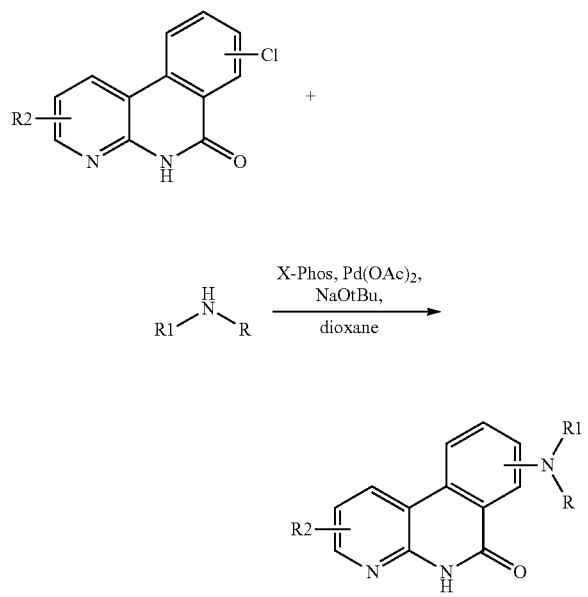

Scheme 3
A 1- or 2-position chlorine can be displaced under Buchwald conditions with a wide variety of alkyl or aryl amines.

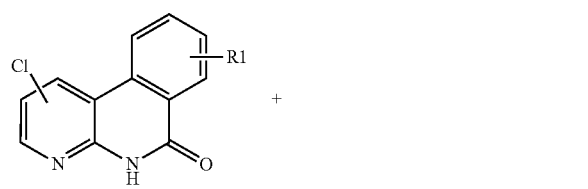

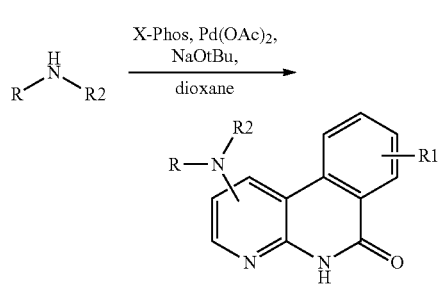

Scheme 4
The 6-position carbonyl can be reacted with POCl₃ to provide a 6-position chlorine.

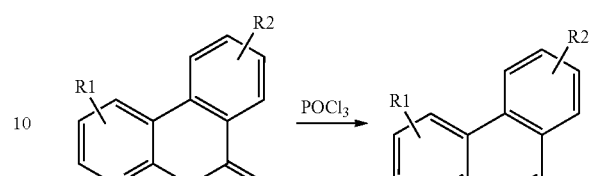

Scheme 5
This chlorine moiety can be displaced with either amines or alcohols.

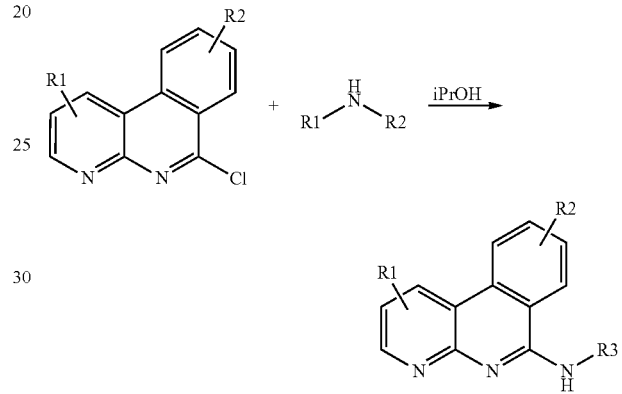

Scheme 6
Suitably substituted 2-carboxylic esters boronic esters could be synthesized from 2-carboxylic ester aryl bromides.

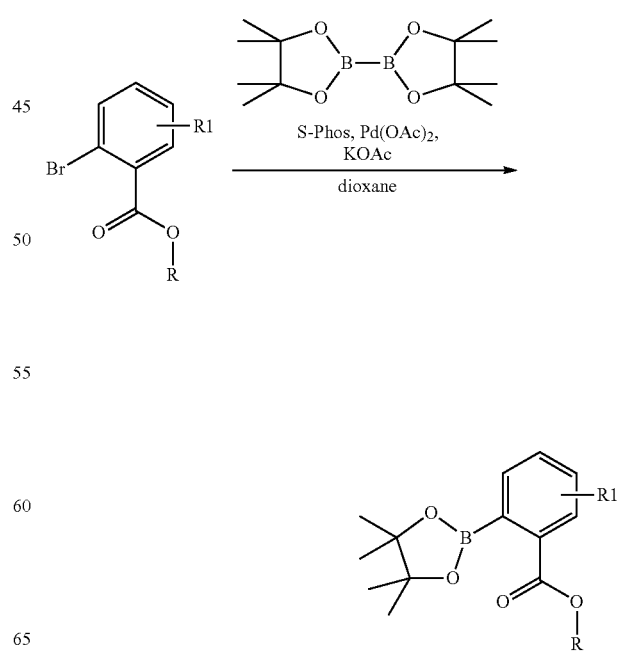

Scheme 7
A 9-position fluorine can be displaced with alcohols under basic conditions to provide ethers.

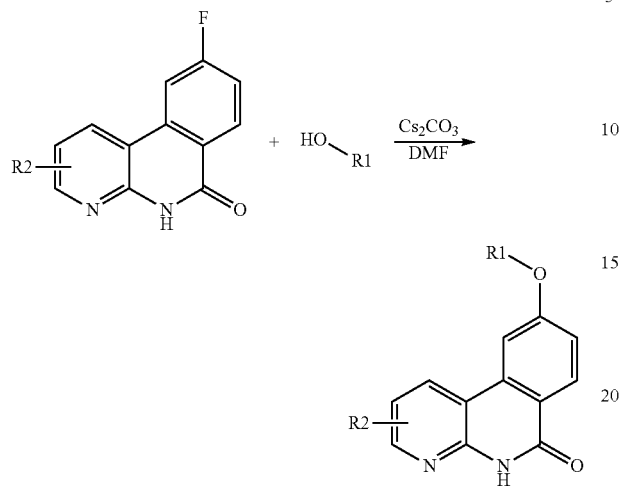

Scheme 8
An 8- or 9-position chlorine can be coupled with boronic acids under Suzuki conditions to provide bi-aryl compounds.

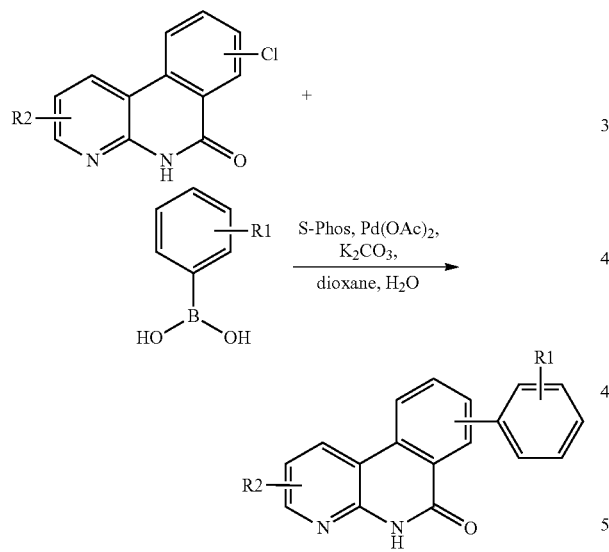

Scheme 9
An 8- or 9-position chlorine can be transformed to a primary amine under Buchwald conditions with LHMDS. The primary amine can subsequently be reacted with an alkyl halide under basic conditions to provide alkyl amines.

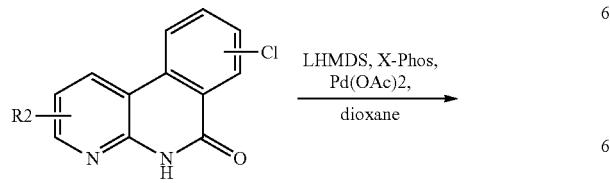

-continued

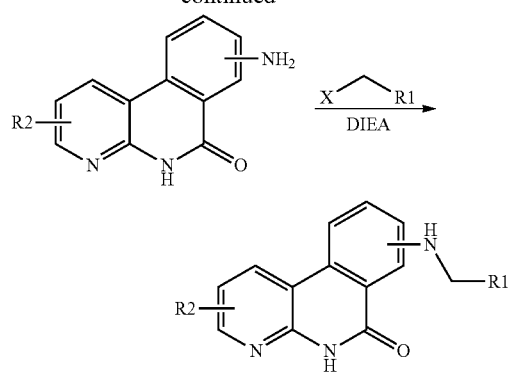

Scheme 10
An 8- or 9-position carboxylic ester can be hydrolyzed with lithium hydroxide to provide a carboxylic acid intermediate. The carboxylic acid can be reacted with a variety of amines under standard amide coupling conditions to provide an amide.

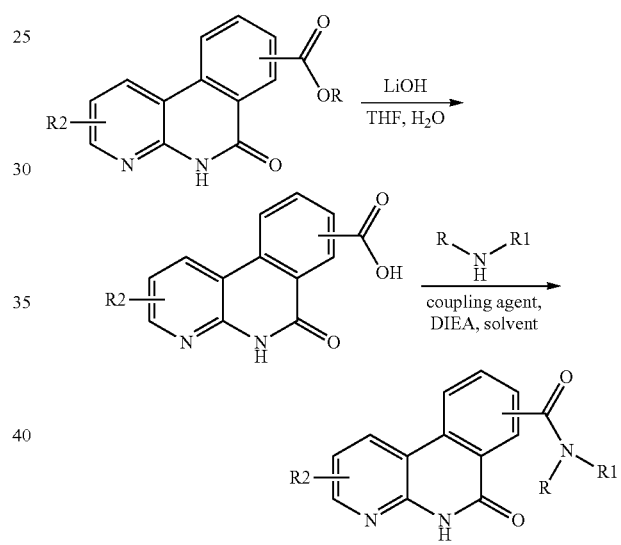

Scheme 11
An 8- or 9-position carboxylic ester can be reduced with a borohydride to provide a primary alcohol intermediate. The primary alcohol can be activated, and then displaced with amines.

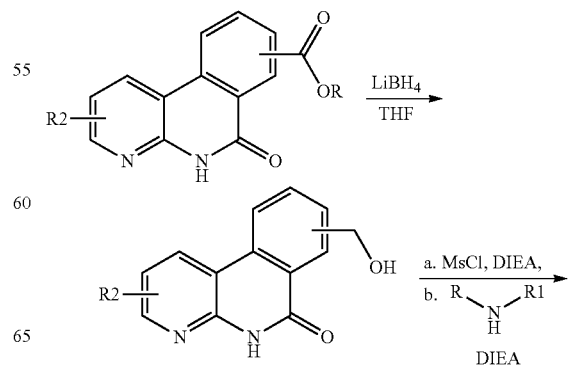

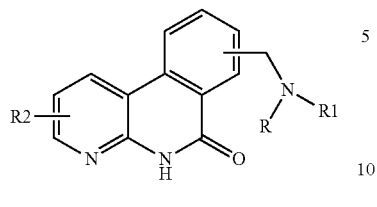

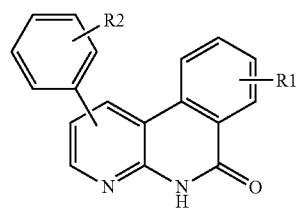

Scheme 12
A 1-position chlorine can be displaced with alcohols under basic conditions to provide ethers.

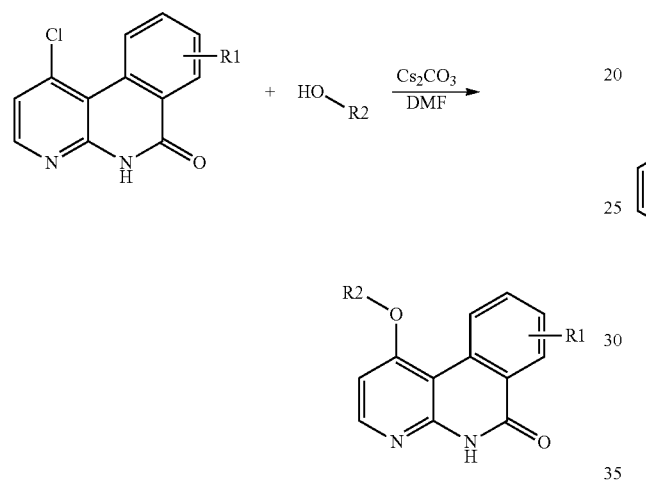

Scheme 14
A 1-position chlorine can be displaced with an amine under a variety of conditions; acidic, Buchwald, or basic.

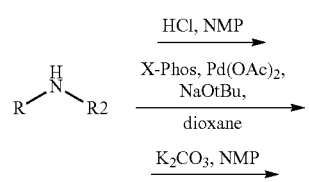

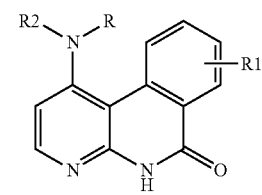

Scheme 13
A 1- or 2-position chlorine can be coupled with boronic acids under Suzuki conditions to provide bi-aryl compounds.

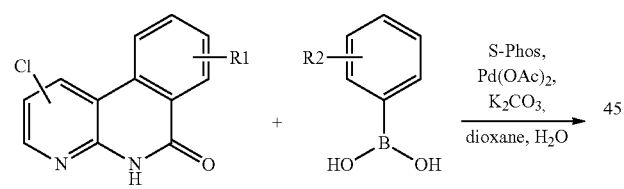

Scheme 15
An amine off of a 1-position di-aryl aniline or di-aryl ether can be reacted with either carboxylic acid or acid chlorides to provide amides, sulfonyl chlorides to provide sulfonamides, or isocyanates to provide ureas.

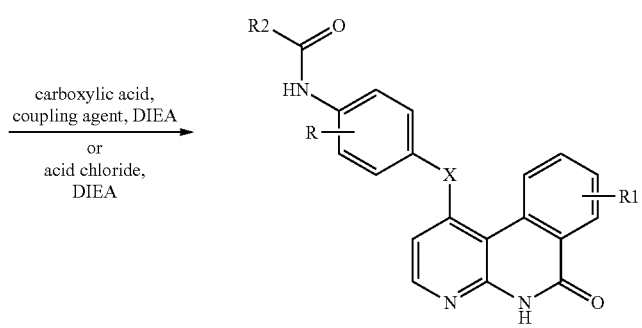

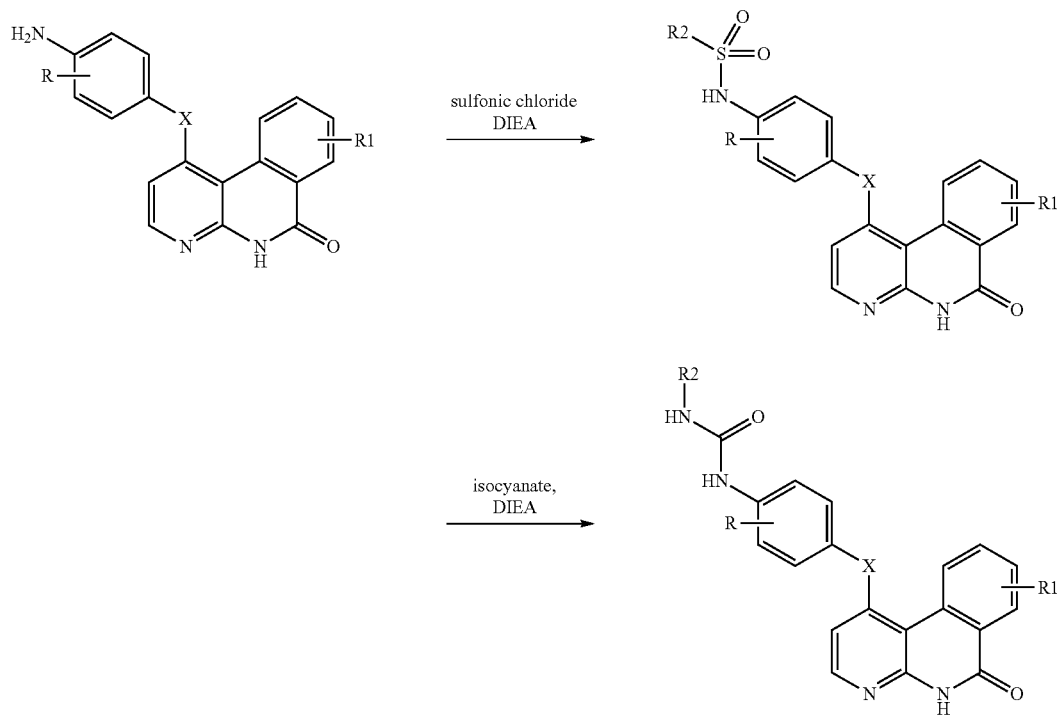

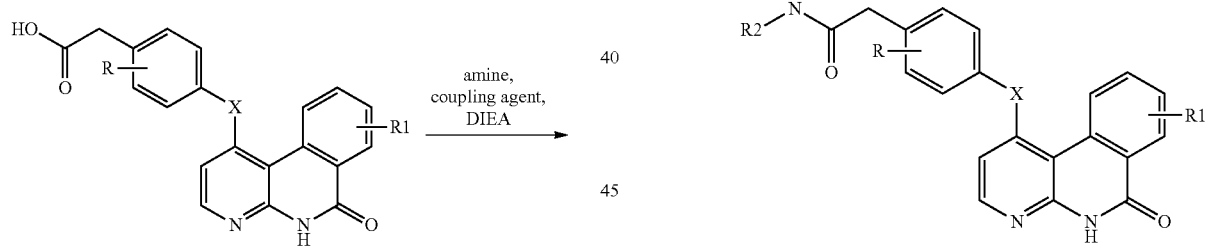

Scheme 16
A 4-substituted alkyl carboxylic acid moiety off a 1-position di-aryl aniline or di-aryl ether can be reacted with amines to provide amides.

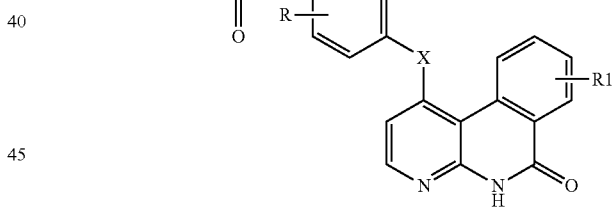

Scheme 17
A secondary amine off of a 1-position 4-substituted piperidine can be reacted with either carboxylic acids (acid chlorides) to provide amides, alkyl halides or aldehydes/reducing agents to provide alkyl amines, or isocyanates to provide ureas.

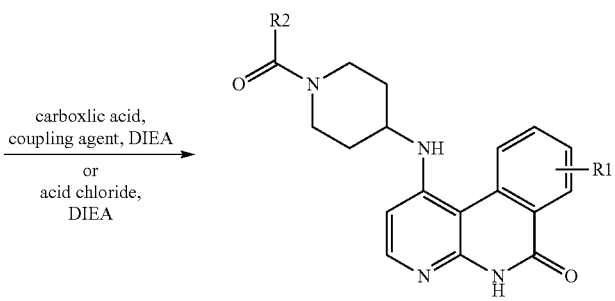

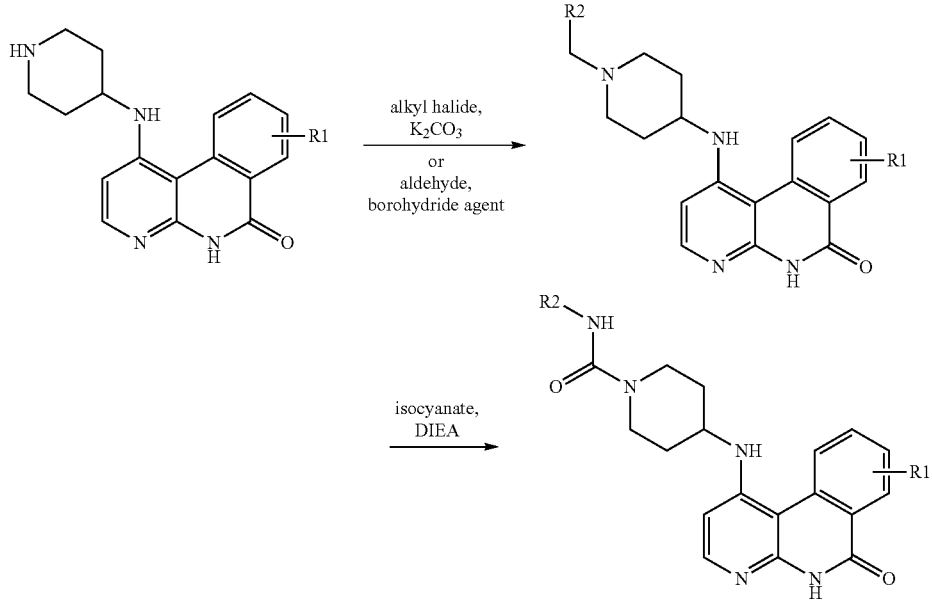

TABLE 2

| Abbreviations used: | |
| --- | --- |
| S-Phos | 2-dicyclohexylphosphino-2',6'-dimethoxybiphenyl |
| Pd(OAc)$_2$ | palladium(II) acetate |
| K$_2$CO$_3$ | Potassium carbonate |
| X-Phos | 2-dicyclohexylphosphino-2',4',6'-triisopropylbiphenyl |
| NaOtBu | Sodium tert-butoxide |
| POCl$_3$ | Phosphorus oxychloride |
| iPrOH | isopropanol |
| EtOAc | Ethyl acetate |
| MeOH | methanol |
| CH$_2$Cl$_2$, DCM | dichloromethane |
| HCl | Hydrochloric acid |
| MgSO$_4$ | Magnesium sulfate |
| NaOH | Sodium hydroxide |
| DIEA | N,N-Diisopropylethyl amine |
| DMF | dimethylformamide |
| TFA | Trifluoroacetic acid |
| BOP-Cl | Bis(2-oxo-3-oxazolidinyl)phosphinic chloride |

EXAMPLES

Example 1

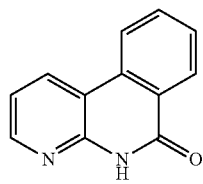 [SMILES: O=c1[nH]c2ncccc2c2ccccc12]

5H-Benzo[c][1,8]naphthyridin-6-one (1)

2-Amino-3-bromopyridine (173 mg, 1.00 mmol), 2-methoxycarbonyl-phenylboronic acid (225 mg, 1.25 mmol), Pd(OAc)$_2$ (9 mg, 0.04 mmol), S-Phos (33 mg, 0.08 mmol), and K$_2$CO$_3$ (414 mg, 3.00 mmol) were dissolved in dioxane/H$_2$O (2.0 mL, 10/1, v/v), and stirred overnight at 100° C. The reaction mixture was concentrated, suspended in EtOAc/H$_2$O, and filtered. The precipitate was washed with EtOAc/H$_2$O, and dried under vacuum to provide 1 (75 mg, 38% yield) as a solid. LC-MS (M+H=197, obsd.=197). $^1$H NMR (400 MHz, d6-DMSO): δ 12.08 (s, 1H), 8.83 (d, 1H), 8.55 (d, 1H), 8.49 (dd, 1H), 8.42 (d, 1H), 7.90 (t, 1H), 7.70 (t, 1H), 7.33 (dd, 1H).

Example 2

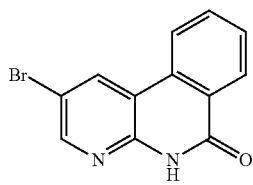

2-Bromo-5H-benzo[c][1,8]naphthyridin-6-one (2)

2-Amino-3-iodo-5-bromopyridine (299 mg, 1.00 mmol), 2-methoxycarbonylphenylboronic acid (189 mg, 1.05 mmol), palladium(II) acetate (9 mg, 0.04 mmol), 2-dicyclohexylphosphino-2',6'-dimethoxybiphenyl (33 mg, 0.08 mmol), and potassium carbonate (414 mg, 3.00 mmol) were dissolved in dioxane/H$_2$O (2.0 mL, 10/1, v/v), and stirred overnight at 100° C. The reaction mixture was concentrated, suspended in EtOAc/H$_2$O, and filtered. The precipitate was washed with EtOAc/H$_2$O, and dried under vacuum to provide 1 (6 mg, 7% yield) as a solid. LC-MS (M+H=275, obsd.=275). ¹H NMR (400 MHz, d6-DMSO): δ 12.22 (s, 1H), 9.11 (d, 1H), 8.64 (d, 1H), 8.61 (d, 1H), 8.33 (d, 1H), 7.91 (t, 1H), 7.73 (t, 1H).

Example 3

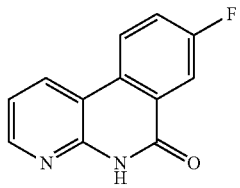 [SMILES: O=c1[nH]c2ncccc2c2ccc(F)cc12]

8-Fluoro-5H-benzo[c][1,8]naphthyridin-6-one (3)

2-Amino-3-bromopyridine (87 mg, 0.50 mmol), 4-fluoro-2-methoxycarbonylphenylboronic acid (149 mg, 0.75 mmol), palladium(II) acetate (5 mg, 0.02 mmol), 2-dicyclohexylphosphino-2',6'-dimethoxybiphenyl (16 mg, 0.04 mmol), and potassium carbonate (207 mg, 1.50 mmol) were dissolved in dioxane/H₂O (1.65 mL, 10/1, v/v), and stirred overnight at 100° C. The reaction mixture was concentrated, suspended in EtOAc/H₂O, and filtered. The precipitate was washed with EtOAc/H₂O, and dried under vacuum to provide 2 (34 mg, 32% yield) as a solid. LC-MS (M+H=215, obsd.=215). ¹H NMR (400 MHz, d6-DMSO): δ 12.22 (s, 1H), 8.82 (d, 1H), 8.66 (dd, 1H), 8.51 (d, 1H), 8.00 (d, 1H), 7.81 (t, 1H), 7.34 (dd, 1H).

Example 4

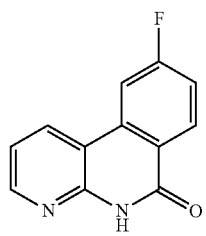 [SMILES: O=c1[nH]c2ncccc2c2cc(F)ccc12]

9-Fluoro-5H-benzo[c][1,8]naphthyridin-6-one (4)

2-Amino-3-bromopyridine (87 mg, 0.50 mmol), 5-fluoro-2-methoxycarbonylphenylboronic acid (149 mg, 0.75 mmol), palladium(II) acetate (5 mg, 0.02 mmol), 2-dicyclohexylphosphino-2',6'-dimethoxybiphenyl (16 mg, 0.04 mmol), and potassium carbonate (207 mg, 1.50 mmol) were dissolved in dioxane/H₂O (1.65 mL, 10/1, v/v), and stirred overnight at 100° C. The reaction mixture was concentrated, suspended in EtOAc/H₂O, and filtered. The precipitate was washed with EtOAc/H₂O, and dried under vacuum to provide 3 (35 mg, 33% yield) as a solid. LC-MS (M+H=215, obsd.=215). ¹H NMR (400 MHz, d6-DMSO): δ 12.12 (s, 1H), 8.84 (d, 1H), 8.53 (d, 1H), 8.43 (d, 1H), 8.38 (dd, 1H), 7.53 (t, 1H), 7.33 (dd, 1H).

Example 5

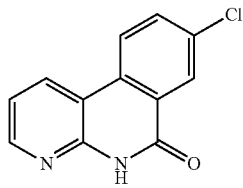 [SMILES: O=c1[nH]c2ncccc2c2ccc(Cl)cc12]

8-Chloro-5H-benzo[c][1,8]naphthyridin-6-one (5)

2-Amino-3-bromopyridine (87 mg, 0.50 mmol), 4-chloro-2-ethoxycarbonylphenylboronic acid (149 mg, 0.65 mmol), palladium(II) acetate (5 mg, 0.02 mmol), 2-dicyclohexylphosphino-2',6'-dimethoxybiphenyl (16 mg, 0.04 mmol), and potassium carbonate (207 mg, 1.50 mmol) were dissolved in dioxane/H₂O (1.65 mL, 10/1, v/v), and stirred overnight at 100° C. The reaction mixture was concentrated, suspended in EtOAc/H₂O, and filtered. The precipitate was washed with EtOAc/H₂O, and dried under vacuum to provide 4 (33 mg, 29% yield) as a solid. LC-MS (M+H=231, obsd.=231). ¹H NMR (400 MHz, d6-DMSO): δ 12.27 (s, 1H), 8.83 (d, 1H), 8.61 (d, 1H), 8.52 (dd, 1H), 8.27 (d, 1H), 7.96 (dd, 1H), 7.37 (dd, 1H).

Example 6

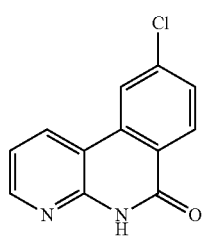 [SMILES: O=c1[nH]c2ncccc2c2cc(Cl)ccc12]

9-Chloro-5H-benzo[c][1,8]naphthyridin-6-one (6)

2-Amino-3-bromopyridine (87 mg, 0.50 mmol), 5-chloro-2-ethoxycarbonylphenylboronic acid (149 mg, 0.65 mmol), palladium(II) acetate (5 mg, 0.02 mmol), 2-dicyclohexylphosphino-2',6'-dimethoxybiphenyl (16 mg, 0.04 mmol), and potassium carbonate (207 mg, 1.50 mmol) were dissolved in dioxane/H₂O (1.65 mL, 10/1, v/v), and stirred overnight at 100° C. The reaction mixture was concentrated, suspended in EtOAc/H₂O, and filtered. The precipitate was washed with EtOAc/H₂O, and dried under vacuum to provide 5 (29 mg, 25% yield) as a solid. LC-MS (M+H=231, obsd.=231). ¹H NMR (400 MHz, d6-DMSO): δ 12.18 (s, 1H), 8.91 (dd, 1H), 8.68 (d, 1H), 8.54 (dd, 1H), 8.32 (d, 1H), 7.74 (dd, 1H), 7.34 (dd, 1H).

Example 7

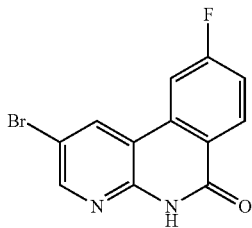 [SMILES: O=c1[nH]c2ncc(Br)cc2c2cc(F)ccc12]

2-Bromo-9-fluoro-5H-benzo[c][1,8]naphthyridin-6-one (7)

9-Fluoro-5H-benzo[c][1,8]naphthyridin-6-one (20 mg, 0.11 mmol) and N-bromosuccinimide (48 mg, 0.22 mmol) were suspended in dioxane and stirred for 2 days at 100° C. The reaction mixture was cooled to room temperature, diluted with $H_2O$/EtOAc, and filtered through an Extrelut column. The column was washed with EtOAc, and the filtrate was concentrated. The crude product was purified via Biotage eluting with a gradient of 0 to 85% EtOAc in hexanes to provide 6 (10 mg, 30% yield) as a white solid. LC-MS (M+H=293, obsd.=293). $^1$H NMR (400 MHz, d6-DMSO): δ 12.29 (s, 1H), 9.12 (d, 1H), 8.63 (d, 1H), 8.52 (dd, 1H), 8.38 (dd, 1H), 7.58 (dt, 1H).

Example 8

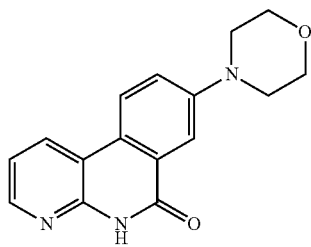 [SMILES: O=c1[nH]c2ncccc2c2ccc(N3CCOCC3)cc12]

8-Morpholin-4-yl-5H-benzo[c][1,8]naphthyridin-6-one (8)

8-Chloro-5H-benzo[c][1,8]naphthyridin-6-one (25 mg, 0.11 mmol), morpholine (14 mg, 0.16 mmol), palladium(II) acetate (1 mg, 0.005 mmol), 2-dicyclohexylphosphino-2',4',6'-triisopropylbiphenyl (4 mg, 0.01 mmol), and sodium tert-butoxide (21 mg, 0.22 mmol) were suspended in dioxane (2 mL) and stirred overnight at 100° C. The reaction mixture was diluted with $H_2O$/EtOAc, and filtered through an Extrelut column. The column was washed with EtOAc and the filtrate was concentrated. The crude product was purified via Biotage eluting with a gradient of 0 to 85% EtOAc in hexanes to provide 7 (5 mg, 16% yield) as a yellow solid. LC-MS (M+H=282, obsd.=282). $^1$H NMR (400 MHz, d6-DMSO): δ 11.93 (s, 1H), 8.69 (dd, 1H), 8.39 (m, 2H), 7.68 (d, 1H), 7.59 (dd, 1H), 7.28 (dd, 1H), 3.79 (m, 4H), 3.32 (m, 4H).

Example 9

2-Chloro-5H-benzo[c][1,8]naphthyridin-6-one (9)

2-Amino-3-bromo-5-chloropyridine (0.40 g, 1.93 mmol), 2-methoxycarbonylphenylboronic acid (0.42 g, 2.31 mmol), palladium(II) acetate (20 mg, 0.08 mmol), 2-dicyclohexylphosphino-2',6'-dimethoxybiphenyl (60 mg, 0.16 mmol), and potassium carbonate (0.80 g, 5.78 mmol) were dissolved in dioxane/$H_2O$ (3.3 mL, 10/1, v/v), and stirred overnight at 100° C. The reaction mixture was concentrated, suspended in EtOAc/$H_2O$, and filtered. The precipitate was washed with EtOAc/$H_2O$, and dried under vacuum to provide 8 (145 mg, 33% yield) as a brown solid. LC-MS (M+H=231, obsd.=231). $^1$H NMR (400 MHz, d6-DMSO): δ 8.94 (d, 1H), 8.59 (d, 1H), 8.51 (d, 1H), 8.33 (dd, 1H), 7.86 (dt, 1H), 7.71 (t, 1H).

Example 10

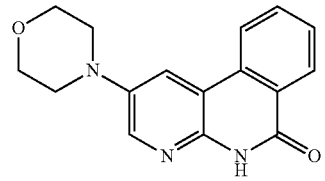 [SMILES: O=c1[nH]c2ncc(N3CCOCC3)cc2c2ccccc12]

2-Morpholin-4-yl-5H-benzo[c][1,8]naphthyridin-6-one (10)

2-Chloro-5H-benzo[c][1,8]naphthyridin-6-one (50 mg, 0.22 mmol), morpholine (28 mg, 0.33 mmol), palladium(II) acetate (2 mg, 0.01 mmol), 2-dicyclohexylphosphino-2',4',6'-triisopropylbiphenyl (8 mg, 0.02 mmol), and sodium tert-butoxide (42 mg, 0.43 mmol) were suspended in dioxane (2 mL), and stirred overnight at 100° C. The reaction mixture was diluted with $H_2O$/EtOAc, and filtered through an Extrelut column. The column was washed with EtOAc and the filtrate was concentrated. The crude product was purified via prep-LC-MS to provide 9 (6 mg, 10% yield) as a yellow solid. LC-MS (M+H=282, obsd.=282). $^1$H NMR (400 MHz, d6-DMSO): δ 11.84 (s, 1H), 8.64 (d, 1H), 8.31 (m, 3H), 7.88 (t, 1H), 7.68 (t, 1H), 3.81 (m, 4H), 3.26 (m, 4H).

Example 11

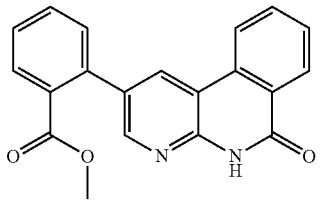 [SMILES: COC(=O)c1ccccc1-c1cnc2[nH]c(=O)c3ccccc3c2c1]

2-(6-Oxo-5,6-dihydro-benzo[c][1,8]naphthyridin-2-yl)-benzoic acid methyl ester (11)

2-Amino-3,5-dibromopyridine (252 mg, 1.00 mmol), 2-methoxycarbonylphenylboronic acid (216 mg, 1.2 mmol), palladium(II) acetate (9 mg, 0.04 mmol), 2-dicyclohexylphosphino-2',6'-dimethoxybiphenyl (33 mg, 0.08 mmol), and potassium carbonate (415 mg, 3.00 mmol) were dissolved in dioxane/$H_2O$ (2.2 mL, 10/1, v/v), and stirred overnight at 100° C. The reaction mixture was concentrated, suspended in EtOAc/$H_2O$, and filtered. The precipitate was washed with EtOAc/$H_2O$, dried under vacuum, and purified via prep-LC-MS to provide 10 (4 mg, 2% yield) as a white solid. LC-MS (M+H=331, obsd.=331). $^1$H NMR (400 MHz, d6-DMSO): δ 8.89 (d, 1H), 8.62 (d, 1H), 8.45 (m, 2H), 7.92 (d, 1H), 7.88 (t, 1H), 7.72 (m, 2H), 7.60 (m, 2H), 3.62 (s, 3H).

Example 12

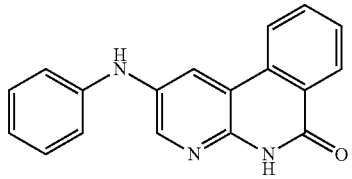 [SMILES: O=c1[nH]c2ncc(Nc3ccccc3)cc2c2ccccc12]

2-Phenylamino-5H-benzo[c][1,8]naphthyridin-6-one (12)

2-Chloro-5H-benzo[c][1,8]naphthyridin-6-one (50 mg, 0.22 mmol), aniline (40 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was diluted with MeOH, filtered through a membrane plug, and purified via prep-LC-MS to provide 11 (39 mg, 63% yield) as a white solid. LC-MS (M+H=288, obsd.=288). $^1$H NMR (400 MHz, d6-DMSO): δ 11.94 (s, 1H), 8.45 (d, 1H), 8.41 (d, 1H), 8.32 (m, 2H), 7.87 (dt, 1H), 7.69 (dt, 1H), 7.27 (dd, 2H), 7.09 (dd, 2H), 6.82 (t, 1H).

Example 13

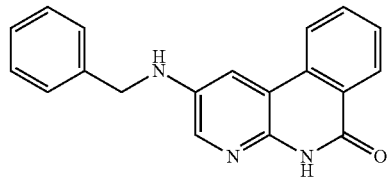 [SMILES: O=c1[nH]c2ncc(NCc3ccccc3)cc2c2ccccc12]

2-Benzylamino-5H-benzo[c][1,8]naphthyridin-6-one (13)

2-Chloro-5H-benzo[c][1,8]naphthyridin-6-one (50 mg, 0.22 mmol), benzylamine (46 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a membrane plug, and purified via prep-LC-MS to provide 12 (19 mg, 29% yield) as a white solid. LC-MS (M+H=302, obsd.=302). $^1$H NMR (400 MHz, d6-DMSO): δ 11.66 (s, 1H), 8.38 (d, 1H), 8.29 (dd, 1H), 8.04 (dd, 1H), 7.85 (m, 2H), 7.64 (dt, 1H), 7.45 (d, 2H), 7.33 (t, 2H), 7.22 (dd, 1H), 6.44 (t, 1H), 4.43 (d, 2H).

Example 14

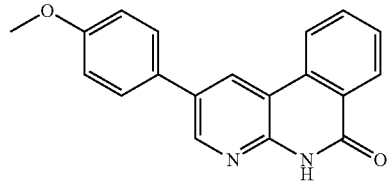 [SMILES: COc1ccc(-c2cnc3[nH]c(=O)c4ccccc4c3c2)cc1]

2-(4-Methoxy-phenyl)-5H-benzo[c][1,8]naphthyridin-6-one (14)

2-Chloro-5H-benzo[c][1,8]naphthyridin-6-one (50 mg, 0.22 mmol), 4-methoxyphenylboronic acid (66 mg, 0.43 mmol), palladium(II) acetate (2 mg, 0.01 mmol), 2-dicyclohexylphosphino-2',6'-dimethoxybiphenyl (9 mg, 0.02 mmol), and sodium tert-butoxide (63 mg, 0.65 mmol) were dissolved in dioxane/$H_2O$ (2.2 mL, 10/1, v/v), and stirred overnight at 100° C. The reaction mixture was diluted with MeOH, filtered through a membrane plug, and purified via prep-LC-MS to provide 13 (10 mg, 15% yield) as a white solid. LC-MS (M+H=303, obsd.=303). $^1$H NMR (400 MHz, d6-DMSO): δ 12.12 (s, 1H), 9.03 (d, 1H), 8.79 (m, 2H), 8.33 (d, 1H), 7.91 (t, 1H), 7.85 (d, 2H), 7.71 (t, 1H), 7.10 (d, 2H), 3.82 (s, 3H).

Example 15

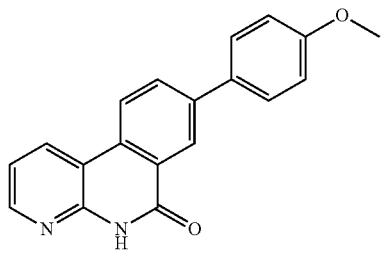 [SMILES: COc1ccc(-c2ccc3c(c2)c(=O)[nH]c2ncccc23)cc1]

8-(4-Methoxy-phenyl)-5H-benzo[c][1,8]naphthyridin-6-one (15)

8-Chloro-5H-benzo[c][1,8]naphthyridin-6-one (50 mg, 0.22 mmol), 4-methoxyphenylboronic acid (66 mg, 0.43 mmol), palladium(II) acetate (2 mg, 0.01 mmol), 2-dicyclohexylphosphino-2',6'-dimethoxybiphenyl (9 mg, 0.02 mmol), and sodium tert-butoxide (63 mg, 0.65 mmol) were dissolved in dioxane/H$_2$O (2.2 mL, 10/1, v/v), and stirred overnight at 100° C. The reaction mixture was diluted with MeOH, filtered through a membrane plug, and purified via prep-LC-MS to provide 14 (10 mg, 15% yield) as a white solid. LC-MS (M+H=303, obsd.=303). $^1$H NMR (400 MHz, d6-DMSO): δ 12.11 (s, 1H), 8.84 (d, 1H), 8.61 (d, 1H), 8.52 (dd, 1H), 8.18 (dd, 1H), 7.80 (d, 2H), 7.34 (dd, 1H), 7.10 (d, 2H), 6.93 (s, 1H), 3.83 (s, 3H).

Example 16

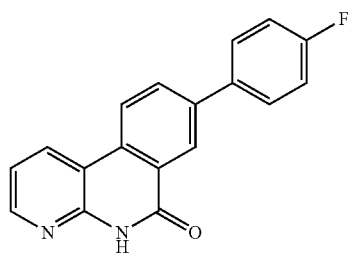 [SMILES: O=c1[nH]c2ncccc2c2ccc(-c3ccc(F)cc3)cc12]

8-(4-Fluoro-phenyl)-5H-benzo[c][1,8]naphthyridin-6-one (16)

8-Chloro-5H-benzo[c][1,8]naphthyridin-6-one (50 mg, 0.22 mmol), 4-fluorophenylboronic acid (61 mg, 0.43 mmol), palladium(II) acetate (2 mg, 0.01 mmol), 2-dicyclohexylphosphino-2',6'-dimethoxybiphenyl (7 mg, 0.02 mmol), and potassium carbonate (90 mg, 0.65 mmol) were dissolved in dioxane/H$_2$O (2.2 mL, 10/1, v/v), and stirred overnight at 100° C. The reaction mixture was diluted with MeOH, filtered through a membrane plug, and purified via prep-LC-MS to provide 15 (10 mg, 16% yield) as a white solid. LC-MS (M+H=291, obsd.=291). $^1$H NMR (400 MHz, d6-DMSO): δ 12.15 (s, 1H), 8.88 (dd, 1H), 8.64 (d, 1H), 8.54 (dd, 1H), 8.52 (dd, 1H), 8.22 (dd, 1H), 7.90 (m, 2H), 7.37 (m, 3H).

Example 17

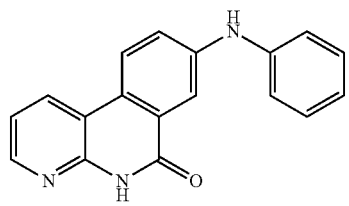 [SMILES: O=c1[nH]c2ncccc2c2ccc(Nc3ccccc3)cc12]

8-Phenylamino-5H-benzo[c][1,8]naphthyridin-6-one (17)

8-Chloro-5H-benzo[c][1,8]naphthyridin-6-one (50 mg, 0.22 mmol), aniline (40 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a membrane plug, and purified via prep-LC-MS to provide 16 (25 mg, 40% yield) as a tan solid. LC-MS (M+H=288, obsd.=288). $^1$H NMR (400 MHz, d6-DMSO): δ 11.91 (s, 1H), 8.78 (s, 1H), 8.62 (dd, 1H), 8.38 (m, 2H), 7.94 (d, 1H), 7.54 (dd, 1H), 7.35 (m, 2H), 7.27 (dd, 1H), 7.21 (m, 2H), 6.98 (t, 1H).

Example 18

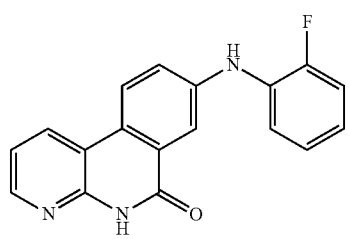 [SMILES: O=c1[nH]c2ncccc2c2ccc(Nc3ccccc3F)cc12]

8-(2-Fluoro-phenylamino)-5H-benzo[c][1,8]naphthyridin-6-one (18)

8-Chloro-5H-benzo[c][1,8]naphthyridin-6-one (50 mg, 0.22 mmol), 2-fluoroaniline (48 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a membrane plug, and purified via prep-LC-MS to provide 17 (25 mg, 38% yield) as a tan solid. LC-MS (M+H=306, obsd.=306). $^1$H NMR (400 MHz, d6-DMSO): δ 11.92 (s, 1H), 8.66 (dd, 1H), 8.58 (s, 1H), 8.39 (m, 2H), 7.75 (d, 1H), 7.44 (m, 2H), 7.32 (dd, 1H), 7.28 (dd, 1H), 7.21 (dt, 1H), 7.11 (m, 1H).

Example 19

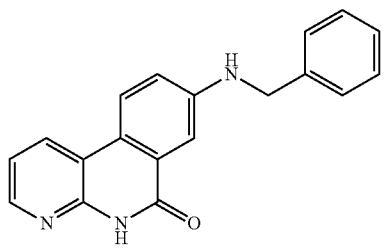 [SMILES: O=c1[nH]c2ncccc2c2ccc(NCc3ccccc3)cc12]

8-Benzylamino-5H-benzo[c][1,8]naphthyridin-6-one (19)

8-Chloro-5H-benzo[c][1,8]naphthyridin-6-one (50 mg, 0.22 mmol), benzylamine (46 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a membrane plug, and purified via prep-LC-MS to provide 18 (25 mg, 38% yield) as a tan solid. LC-MS (M+H=302, obsd.=302). $^1$H NMR (400 MHz, d6-DMSO): δ 11.79 (s, 1H), 8.55 (dd, 1H), 8.32 (dd, 1H), 821 (d, 1H), 7.37 (m, 5H), 7.22 (m, 3H), 7.05 (t, 1H), 4.42 (d, 2H).

Example 20

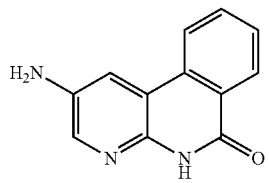 [SMILES: Nc1cnc2[nH]c(=O)c3ccccc3c2c1]

2-Amino-5H-benzo[c][1,8]naphthyridin-6-one (20)

2-Benzylamino-5H-benzo[c][1,8]naphthyridin-6-one (100 mg, 0.33 mmol), ammonium formate (209 mg, 3.30 mmol), and palladium/carbon (200 mg, 10% weight) were suspended in MeOH (6 mL) and stirred overnight at 60° C. The reaction mixture was filtered through celite, and the celite was washed with methanol. The filtrate was concentrated, and the crude product was purified via prep-LC-MS to provide 19 (10 mg, 14% yield) as a yellow solid. LC-MS (M+H=212, obsd.=212). $^1$H NMR (400 MHz, d6-DMSO): δ 11.63 (s, 1H), 8.31 (d, 1H), 8.28 (d, 1H), 7.96 (d, 1H), 7.85 (m, 2H), 7.64 (t, 1H), 7.31 (m, 1H), 7.24 (m, 1H).

Example 21

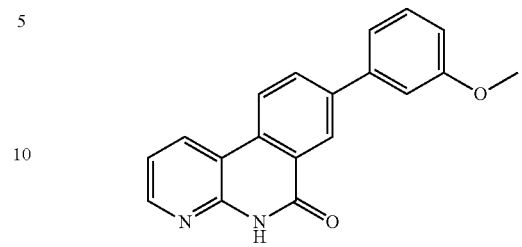

8-(3-Methoxy-phenyl)-5H-benzo[c][1,8]naphthyridin-6-one (21)

8-Chloro-5H-benzo[c][1,8]naphthyridin-6-one (50 mg, 0.22 mmol), 3-methoxyphenylboronic acid (49 mg, 0.33 mmol), palladium(II) acetate (2 mg, 0.01 mmol), 2-dicyclohexylphosphino-2',6'-dimethoxybiphenyl (7 mg, 0.02 mmol), and potassium carbonate (90 mg, 0.65 mmol) were dissolved in dioxane/H$_2$O (2.2 mL, 10/1, v/v), and stirred overnight at 100° C. The reaction mixture was diluted with MeOH, filtered through a membrane plug, and purified via prep-LC-MS to provide 20 (11 mg, 17% yield) as a white solid. LC-MS (M+H=303, obsd.=303). $^1$H NMR (400 MHz, d6-DMSO): δ 12.13 (s, 1H), 8.88 (d, 1H), 8.64 (d, 1H), 8.56 (d, 1H), 8.51 (d, 1H), 8.22 (dd, 1H), 7.41 (m, 4H), 7.02 (dd, 1H), 3.88 (s, 3H).

Example 22

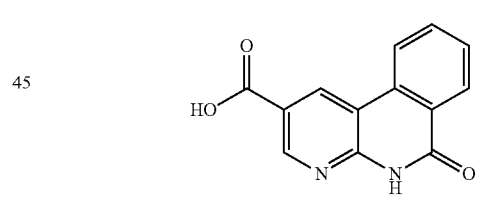

6-Oxo-5,6-dihydro-benzo[c][1,8]naphthyridine-2-carboxylic acid (22)

Methyl 6-amino-5-bromonicotinate (500 mg, 2.16 mmol), 2-methoxycarbonylphenylboronic acid (580 mg, 3.25 mmol), palladium(II) acetate (20 mg, 0.09 mmol), 2-dicyclohexylphosphino-2',6'-dimethoxybiphenyl (70 mg, 0.17 mmol), and potassium carbonate (900 mg, 6.50 mmol) were dissolved in dioxane/H$_2$O (11 mL, 10/1, v/v), and stirred overnight at 100° C. The reaction mixture was diluted with MeOH, filtered through a membrane plug, and purified via prep-LC-MS to provide 21 (60 mg, 11% yield) as a white solid. LC-MS (M+H=241, obsd.=241). $^1$H NMR (400 MHz, d6-DMSO): δ 8.98 (d, 1H), 8.87 (d, 1H), 8.48 (d, 1H), 8.32 (dd, 1H), 7.88 (t, 1H), 7.65 (t, 1H).

Example 23

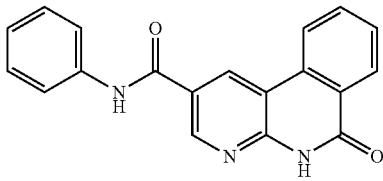 [SMILES: O=C(Nc1ccccc1)c1cnc2[nH]c(=O)c3ccccc3c2c1]

6-Oxo-5,6-dihydro-benzo[c][1,8]naphthyridine-2-carboxylic acid phenylamide (23)

6-Oxo-5,6-dihydro-benzo[c][1,8]naphthyridine-2-carboxylic acid (50 mg, 0.21 mmol), aniline (39 mg, 0.42 mmol), bis(2-oxo-3-oxazolidinyl)phosphinic chloride (106 mg, 0.42 mmol), and N,N-diisopropylethylamine (0.14 mL, 0.83 mmol) were dissolved in dioxane and stirred for 48 h at 100° C. The reaction mixture was added directly to a Biotage column. The crude product was purified via Biotage silica-gel chromatography eluting with a gradient of 0 to 10% MeOH in $CH_2Cl_2$ to provide 22 (10 mg, 15% yield) as a white solid. LC-MS (M+H=316, obsd.=316). $^1$H NMR (400 MHz, d6-DMSO): δ 10.45 (s, 1H), 9.32 (d, 1H), 9.04 (d, 1H), 8.68 (d, 1H), 8.38 (dd, 1H), 7.98 (dt, 1H), 7.80 (m, 3H), 7.41 (d, 2H), 7.14 (t, 1H).

Example 24

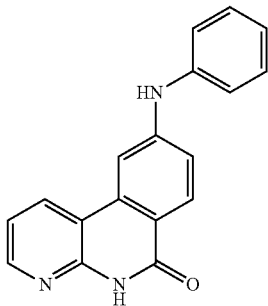 [SMILES: O=c1[nH]c2ncccc2c2cc(Nc3ccccc3)ccc12]

9-Phenylamino-5H-benzo[c][1,8]naphthyridin-6-one (24)

9-Chloro-5H-benzo[c][1,8]naphthyridin-6-one (50 mg, 0.22 mmol), aniline (30 mg, 0.33 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was added directly to a Biotage column. The crude product was purified via Biotage silica-gel chromatography eluting with a gradient of 0 to 10% MeOH in $CH_2Cl_2$ to provide 23 (20 mg, 32% yield) as a tan solid. LC-MS (M+H=288, obsd.=288). $^1$H NMR (400 MHz, d6-DMSO): δ 11.69 (s, 1H), 8.95 (s, 1H), 8.47 (m, 2H), 8.15 (d, 1H), 7.86 (d, 1H), 7.386 (m, 2H), 7.29 (m, 3H), 7.04 (t, 1H).

Example 25

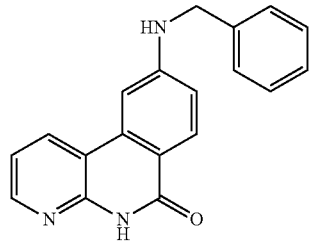 [SMILES: O=c1[nH]c2ncccc2c2cc(NCc3ccccc3)ccc12]

9-Benzylamino-5H-benzo[c][1,8]naphthyridin-6-one (25)

9-Chloro-5H-benzo[c][1,8]naphthyridin-6-one (50 mg, 0.22 mmol), benzylamine (35 mg, 0.33 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was added directly to a Biotage column. The crude product was purified via Biotage silica-gel chromatography eluting with a gradient of 0 to 10% MeOH in $CH_2Cl_2$ to provide 24 (15 mg, 23% yield) as a tan solid. LC-MS (M+H=302, obsd.=302). $^1$H NMR (400 MHz, d6-DMSO): δ 11.48 (s, 1H), 8.53 (dd, 1H), 8.41 (dd, 1H), 7.98 (d, 1H), 7.44 (m, 2H), 7.36 (m, 3H), 7.25 (m, 3H), 6.95 (dd, 1H), 4.51 (d, 2H).

Example 26

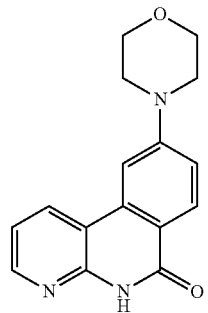 [SMILES: O=c1[nH]c2ncccc2c2cc(N3CCOCC3)ccc12]

9-Morpholin-4-yl-5H-benzo[c][1,8]naphthyridin-6-one (26)

9-Chloro-5H-benzo[c][1,8]naphthyridin-6-one (50 mg, 0.22 mmol), morpholine (28 mg, 0.33 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was added directly to a Biotage column. The crude product was purified via Biotage silica-gel chromatography eluting with a gradient of 0 to 10% MeOH in $CH_2Cl_2$ to provide 25 (20 mg, 33% yield) as a yellow solid. LC-MS (M+H=282, obsd.=282). $^1$H NMR (400 MHz, d6-DMSO): δ 11.65 (s, 1H), 8.88 (d, 1H), 8.44 (dd, 1H), 8.13 (d, 1H), 7.79 (d, 1H), 7.29 (m, 2H), 3.79 (m, 4H), 3.43 (m, 4H).

Example 27

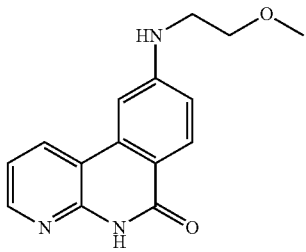 [SMILES: COCCNc1ccc2c(=O)[nH]c3ncccc3c2c1]

9-(2-Methoxy-ethylamino)-5H-benzo[c][1,8]naph-thyridin-6-one (27)

9-Chloro-5H-benzo[c][1,8]naphthyridin-6-one (50 mg, 0.22 mmol), 2-methoxy-ethylamine (24 mg, 0.33 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was added directly to a Biotage column. The crude product was purified via Biotage silica-gel chromatography eluting with a gradient of 0 to 10% MeOH in $CH_2Cl_2$ to provide 26 (20 mg, 34% yield) as a white solid. LC-MS (M+H=270, obsd.=270). $^1$H NMR (400 MHz, d6-DMSO): δ 11.48 (s, 1H), 8.67 (d, 1H), 8.42 (dd, 1H), 7.98 (d, 1H), 7.38 (d, 1H), 7.24 (dd, 1H), 6.95 (dd, 1H), 6.67 (t, 1H), 3.55 (t, 2H), 3.42 (t, 2H), 3.30 (s, 3H).

Example 28

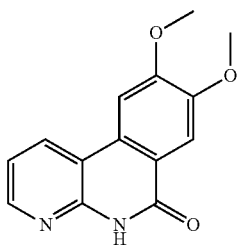 [SMILES: COc1cc2c(=O)[nH]c3ncccc3c2cc1OC]

8,9-Dimethoxy-5H-benzo[c][1,8]naphthyridin-6-one (28)

2-Amino-3-bromopyridine (500 mg, 2.89 mmol), 4,5-dimethoxy-2-methoxycarbonylphenylboronic acid (1.04 g, 4.33 mmol), palladium(II) acetate (30 mg, 0.12 mmol), 2-dicyclohexylphosphino-2',6'-dimethoxybiphenyl (90 mg, 0.23 mmol), and potassium carbonate (1.2 g, 8.67 mmol) were dissolved in dioxane/$H_2O$ (11 mL, 10/1, v/v), and stirred overnight at 100° C. The reaction mixture was concentrated, suspended in EtOAc/$H_2O$, and filtered. The precipitate was washed with EtOAc/$H_2O$, and dried under vacuum to provide 27 (600 mg, 81% yield) as a white solid. LC-MS (M+H=257, obsd.=257). $^1$H NMR (400 MHz, d6-DMSO): δ 8.83 (dd, 1H), 8.42 (dd, 1H), 7.92 (s, 1H), 7.71 (s, 1H), 7.29 (m, 1H), 4.04 (s, 3H), 3.91 (s, 3H).

Example 29

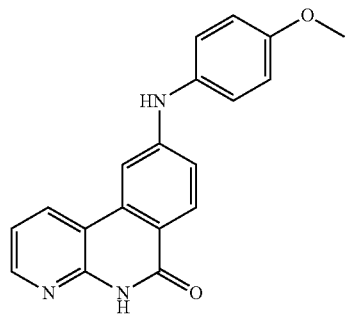 [SMILES: COc1ccc(Nc2ccc3c(=O)[nH]c4ncccc4c3c2)cc1]

9-(4-Methoxy-phenylamino)-5H-benzo[c][1,8]naph-thyridin-6-one (29)

9-Chloro-5H-benzo[c][1,8]naphthyridin-6-one (30 mg, 0.13 mmol), 4-methoxy-aniline (24 mg, 0.20 mmol), palladium(II) acetate (1 mg, 0.01 mmol), 2-dicyclohexylphosphino-2',4',6'-triisopropylbiphenyl (5 mg, 0.015 mmol), and sodium tert-butoxide (38 mg, 0.39 mmol) were suspended in dioxane (1 mL), and stirred overnight at 100° C. The reaction mixture was added directly to a Biotage column. The crude product was purified via Biotage silica-gel chromatography eluting with a gradient of 0 to 10% MeOH in $CH_2Cl_2$. The recovered product was converted to the HCl salt via suspending in $CH_2Cl_2$, addition of 2 M HCl/ether, filtering the resulting precipitate, and washing with $CH_2Cl_2$ to provide 28 (20 mg, 43% yield) as a yellow solid. LC-MS (M+H=318, obsd.=318). $^1$H NMR (400 MHz, d6-DMSO): δ 11.60 (s, 1H), 8.44 (dd, 1H), 8.39 (dd, 1H), 8.09 (d, 1H), 7.68 (d, 1H), 7.23 (m, 3H), 7.14 (dd, 1H), 6.97 (m, 2H), 3.77 (s, 3H).

Example 30

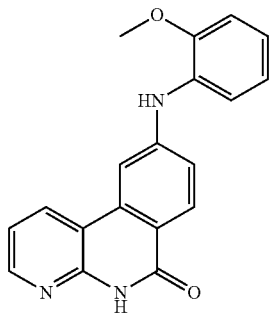 [SMILES: COc1ccccc1Nc1ccc2c(=O)[nH]c3ncccc3c2c1]

9-(2-Methoxy-phenylamino)-5H-benzo[c][1,8]naph-thyridin-6-one (30)

9-Chloro-5H-benzo[c][1,8]naphthyridin-6-one (30 mg, 0.13 mmol), 2-methoxy-aniline (24 mg, 0.20 mmol), palladium(II) acetate (1 mg, 0.01 mmol), 2-dicyclohexylphosphino-2',4',6'-triisopropylbiphenyl (5 mg, 0.015 mmol), and sodium tert-butoxide (38 mg, 0.39 mmol) were suspended in dioxane (1 mL), and stirred overnight at 100° C. The reaction mixture was added directly to a Biotage column. The crude product was purified via Biotage silica-gel chromatography eluting with a gradient of 0 to 10% MeOH in CH₂Cl₂. The recovered product was converted to the HCl salt via suspending in CH₂Cl₂, addition of 2 M HCl/ether, filtering the resulting precipitate, and washing with CH₂Cl₂ to provide 29 (21 mg, 46% yield) as a yellow solid. LC-MS (M+H=318, obsd.=318). ¹H NMR (400 MHz, d6-DMSO): δ 11.61 (s, 1H), 8.44 (dd, 1H), 8.38 (dd, 1H), 8.09 (d, 1H), 7.72 (d, 1H), 7.39 (d, 1H), 7.27 (dd, 1H), 7.20 (dd, 1H), 7.13 (m, 2H), 7.00 (m, 1H), 3.82 (s, 3H).

Example 31

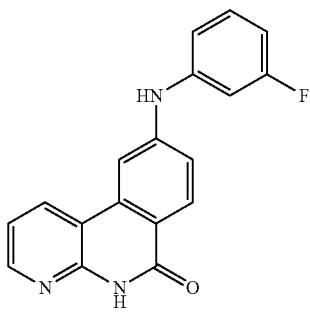 [SMILES: O=c1[nH]c2ncccc2c2cc(Nc3cccc(F)c3)ccc12]

9-(3-Fluoro-phenylamino)-5H-benzo[c][1,8]naphthyridin-6-one (31)

9-Chloro-5H-benzo[c][1,8]naphthyridin-6-one (30 mg, 0.13 mmol), 3-fluoro-aniline (22 mg, 0.20 mmol), palladium (II) acetate (1 mg, 0.01 mmol), 2-dicyclohexylphosphino-2',4',6'-triisopropylbiphenyl (5 mg, 0.015 mmol), and sodium tert-butoxide (38 mg, 0.39 mmol) were suspended in dioxane (1 mL), and stirred overnight at 100° C. The reaction mixture was added directly to a Biotage column. The crude product was purified via Biotage silica-gel chromatography eluting with a gradient of 0 to 10% MeOH in CH₂Cl₂. The recovered product was converted to the HCl salt via suspending in CH₂Cl₂, addition of 2 M HCl/ether, filtering the resulting precipitate, and washing with CH₂Cl₂ to provide 30 (17 mg, 38% yield) as a yellow solid. LC-MS (M+H=306, obsd.=306). ¹H NMR (400 MHz, d6-DMSO): δ 11.73 (s, 1H), 8.55 (dd, 1H), 8.47 (dd, 1H), 8.19 (d, 1H), 7.95 (d, 1H), 7.38 (m, 2H), 7.29 (dd, 1H), 7.12 (dd, 1H), 7.07 (m, 1H), 6.80 (dt, 1H).

Example 32

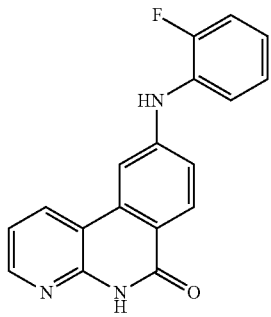 [SMILES: O=c1[nH]c2ncccc2c2cc(Nc3ccccc3F)ccc12]

9-(2-Fluoro-phenylamino)-5H-benzo[c][1,8]naphthyridin-6-one (32)

9-Chloro-5H-benzo[c][1,8]naphthyridin-6-one (30 mg, 0.13 mmol), 2-fluoro-aniline (22 mg, 0.20 mmol), palladium (II) acetate (1 mg, 0.01 mmol), 2-dicyclohexylphosphino-2',4',6'-triisopropylbiphenyl (5 mg, 0.015 mmol), and sodium tert-butoxide (38 mg, 0.39 mmol) were suspended in dioxane (1 mL), and stirred overnight at 100° C. The reaction mixture was added directly to a Biotage column. The crude product was purified via Biotage silica-gel chromatography eluting with a gradient of 0 to 10% MeOH in CH₂Cl₂. The recovered product was converted to the HCl salt via suspending in CH₂Cl₂, addition of 2 M HCl/ether, filtering the resulting precipitate, and washing with CH₂Cl₂ to provide 31 (18 mg, 45% yield) as a yellow solid. LC-MS (M+H=306, obsd.=306). ¹H NMR (400 MHz, d6-DMSO): δ 11.70 (s, 1H), 8.79 (s, 1H), 8.44 (m, 2H), 8.12 (d, 1H), 7.72 (d, 1H), 7.49 (dt, 1H), 7.22 (m, 5H).

Example 33

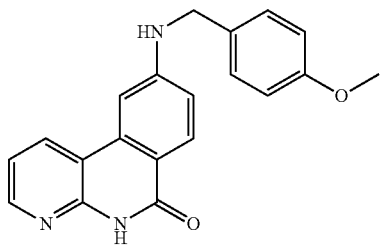 [SMILES: COc1ccc(CNc2ccc3c(=O)[nH]c4ncccc4c3c2)cc1]

9-(4-Methoxy-benzylamino)-5H-benzo[c][1,8]naphthyridin-6-one (33)

9-Chloro-5H-benzo[c][1,8]naphthyridin-6-one (40 mg, 0.17 mmol), 4-methoxy-benzylamine (36 mg, 0.26 mmol), palladium(II) acetate (2 mg, 0.01 mmol), 2-dicyclohexylphosphino-2',4',6'-triisopropylbiphenyl (7 mg, 0.02 mmol), and sodium tert-butoxide (50 mg, 0.52 mmol) were suspended in dioxane (1 mL), and stirred overnight at 100° C. The reaction mixture was added directly to a Biotage column. The crude product was purified via Biotage silica-gel chromatography eluting with a gradient of 0 to 10% MeOH in CH₂Cl₂. The recovered product was converted to the HCl salt via suspending in CH₂Cl₂, addition of 2 M HCl/ether, filtering the resulting precipitate, and washing with CH₂Cl₂ to provide 32 (5 mg, 8% yield) as a yellow solid. LC-MS (M+H=332, obsd.=332). ¹H NMR (400 MHz, d6-DMSO): δ 11.49 (s, 1H), 8.58 (dd, 1H), 8.42 (dd, 1H), 7.98 (d, 1H), 7.38 (m, 3H), 7.25 (dd, 1H), 6.95 (m, 3H), 4.41 (s, 2H), 3.72 (s, 3H).

Example 34

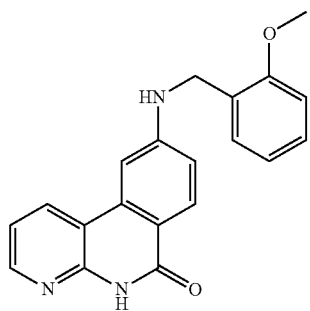 [SMILES: COc1ccccc1CNc1ccc2c(=O)[nH]c3ncccc3c2c1]

9-(2-Methoxy-benzylamino)-5H-benzo[c][1,8]naph-thyridin-6-one (34)

9-Chloro-5H-benzo[c][1,8]naphthyridin-6-one (40 mg, 0.17 mmol), 2-methoxy-benzylamine (36 mg, 0.26 mmol), palladium(II) acetate (2 mg, 0.01 mmol), 2-dicyclohexylphosphino-2',4',6'-triisopropylbiphenyl (7 mg, 0.02 mmol), and sodium tert-butoxide (50 mg, 0.52 mmol) were suspended in dioxane (1 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 33 (10 mg, 16% yield) as a yellow solid. LC-MS (M+H=332, obsd.=332). $^1$H NMR (400 MHz, d6-DMSO): δ 11.48 (s, 1H), 8.53 (dd, 1H), 8.42 (dd, 1H), 7.98 (d, 1H), 7.39 (d, 1H), 7.32 (dd, 1H), 7.25 (m, 2H), 7.03 (d, 1H), 6.91 (m, 2H), 4.43 (s, 2H), 3.88 (s, 3H).

Example 35

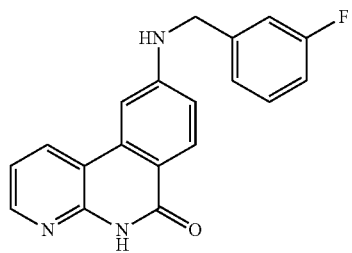 [SMILES: O=c1[nH]c2ncccc2c2cc(NCc3cccc(F)c3)ccc12]

9-(3-Fluoro-benzylamino)-5H-benzo[c][1,8]naph-thyridin-6-one (35)

9-Chloro-5H-benzo[c][1,8]naphthyridin-6-one (40 mg, 0.17 mmol), 3-fluoro-benzylamine (33 mg, 0.26 mmol), palladium(II) acetate (2 mg, 0.01 mmol), 2-dicyclohexylphosphino-2',4',6'-triisopropylbiphenyl (7 mg, 0.02 mmol), and sodium tert-butoxide (50 mg, 0.52 mmol) were suspended in dioxane (1 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 34 (10 mg, 16% yield) as a yellow solid. LC-MS (M+H=320, obsd.=320). $^1$H NMR (400 MHz, d6-DMSO): δ 11.48 (s, 1H), 8.57 (dd, 1H), 8.41 (dd, 1H), 7.99 (d, 1H), 7.39 (m, 2H), 7.25 (m, 3H), 7.08 (m, 1H), 6.93 (m, 1H), 4.52 (s, 2H).

Example 36

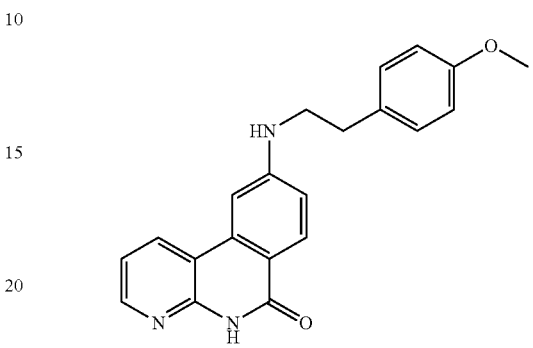

9-[2-(4-Methoxy-phenyl)-ethylamino]-5H-benzo[c][1,8]naphthyridin-6-one (36)

9-Chloro-5H-benzo[c][1,8]naphthyridin-6-one (40 mg, 0.17 mmol), 4-methoxy-phenethylamine (40 mg, 0.26 mmol), palladium(II) acetate (2 mg, 0.01 mmol), 2-dicyclohexylphosphino-2',4',6'-triisopropylbiphenyl (7 mg, 0.02 mmol), and sodium tert-butoxide (50 mg, 0.52 mmol) were suspended in dioxane (1 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 35 (11 mg, 17% yield) as a yellow solid. LC-MS (M+H=346, obsd.=346). $^1$H NMR (400 MHz, d6-DMSO): δ 11.47 (s, 1H), 8.66 (dd, 1H), 8.42 (dd, 1H), 7.99 (d, 1H), 7.33 (d, 1H), 7.24 (m, 3H), 6.91 (dd, 1H), 6.88 (m, 2H), 3.71 (s, 3H), 3.43 (t, 2H), 2.87 (t, 2H).

Example 37

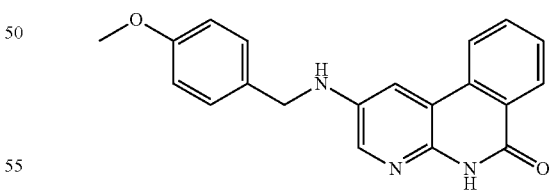

2-(4-Methoxy-benzylamino)-5H-benzo[c][1,8]naph-thyridin-6-one (37)

2-Chloro-5H-benzo[c][1,8]naphthyridin-6-one (50 mg, 0.22 mmol), 4-methoxy-benzylamine (59 mg, 0.43 mmol), palladium(II) acetate (2 mg, 0.01 mmol), 2-dicyclohexylphosphino-2',4',6'-triisopropylbiphenyl (8 mg, 0.02 mmol), and sodium ted-butoxide (63 mg, 0.65 mmol) were suspended in dioxane (2 mL), and stirred overnight at 100° C.

The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 36 (10 mg, 14% yield) as a yellow solid. LC-MS (M+H=332, obsd.=332). $^1$H NMR (400 MHz, d6-DMSO): δ 8.38 (d, 1H), 8.29 (d, 1H), 8.10 (d, 1H), 7.88 (d, 1H), 7.39 (m, 3H), 6.99 (m, 2H), 6.89 (d, 1H), 3.75 (s, 3H), 3.71 (s, 2H).

Example 38

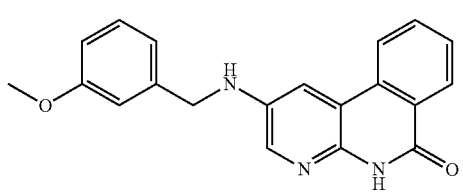 [SMILES: COc1cccc(CNc2cnc3[nH]c(=O)c4ccccc4c3c2)c1]

2-(3-Methoxy-benzylamino)-5H-benzo[c][1,8]naphthyridin-6-one (38)

2-Chloro-5H-benzo[c][1,8]naphthyridin-6-one (50 mg, 0.22 mmol), 3-methoxy-benzylamine (59 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 37 (10 mg, 12% yield) as a yellow solid. LC-MS (M+H=332, obsd.=332). $^1$H NMR (400 MHz, d6-DMSO): δ 11.68 (s, 1H), 8.38 (d, 1H), 8.29 (dd, 1H), 8.05 (d, 1H), 7.91 (d, 1H), 7.84 (dt, 1H), 7.63 (t, 1H), 7.25 (t, 1H), 7.05 (m, 2H), 6.80 (d, 1H), 3.78 (s, 2H), 3.71 (s, 3H).

Example 39

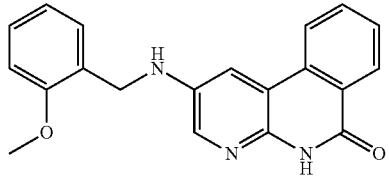 [SMILES: COc1ccccc1CNc1cnc2[nH]c(=O)c3ccccc3c2c1]

2-(2-Methoxy-benzylamino)-5H-benzo[c][1,8]naphthyridin-6-one (39)

2-Chloro-5H-benzo[c][1,8]naphthyridin-6-one (50 mg, 0.22 mmol), 2-methoxy-benzylamine (59 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 38 (6 mg, 8% yield) as a yellow solid. LC-MS (M+H=332, obsd.=332). $^1$H NMR (400 MHz, d6-DMSO): δ 11.68 (s, 1H), 8.37 (d, 1H), 8.31 (d, 1H), 8.05 (d, 1H), 7.91 (d, 1H), 7.85 (t, 1H), 7.64 (t, 1H), 7.36 (m, 1H), 7.24 (m, 1H), 7.02 (m, 1H), 6.89 (t, 1H), 4.32 (s, 2H), 3.88 (s, 3H).

Example 40

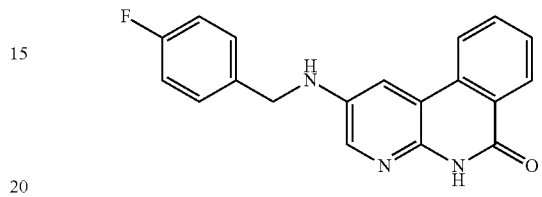

2-(4-Fluoro-benzylamino)-5H-benzo[c][1,8]naphthyridin-6-one (40)

2-Chloro-5H-benzo[c][1,8]naphthyridin-6-one (50 mg, 0.22 mmol), 4-fluoro-benzylamine (54 mg, 0.43 mmol), palladium(II) acetate (2 mg, 0.01 mmol), 2-dicyclohexylphosphino-2',4',6'-triisopropylbiphenyl (8 mg, 0.02 mmol), and sodium tert-butoxide (63 mg, 0.65 mmol) were suspended in dioxane (2 mL), and stirred overnight at 100° C. The reaction mixture was diluted with MeOH, filtered through a filter membrane, and purified via prep-LC-MS. The recovered product was converted to the HCl salt via suspending in CH$_2$Cl$_2$, addition of 2 M HCl/ether, filtering the resulting precipitate, and washing with CH$_2$Cl$_2$ to provide 39 (5 mg, 6% yield) as a yellow solid. LC-MS (M+H=320, obsd.=320). $^1$H NMR (400 MHz, d6-DMSO): δ 11.65 (s, 1H), 8.38 (d, 1H), 8.29 (d, 1H), 8.04 (d, 1H), 7.88 (m, 2H), 7.64 (m, 1H), 7.49 (m, 2H), 7.14 (m, 2H), 4.42 (s, 2H).

Example 41

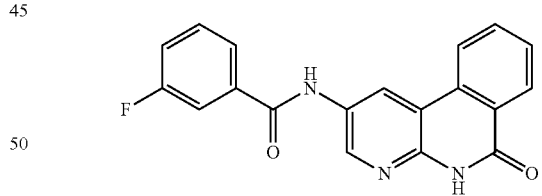

3-Fluoro-N-(6-oxo-5,6-dihydro-benzo[c][1,8]naphthyridin-2-yl)-benzamide (41)

2-Amino-3-bromo-5-nitropyridine (1.00 g, 4.59 mmol), 4-dimethylaminopyridine (1.12 g, 9.17 mmol), and di-tert-butyl dicarbonate (1.20 g, 5.50 mmol) were dissolved in CH$_2$Cl$_2$ (22 mL), and stirred for 48 h at room temperature. The reaction mixture was washed with 0.1 M HCl and brine. The organic extracts were dried over MgSO$_4$, filtered, and concentrated. The crude product was purified via Biotage eluting with a gradient of 0 to 65% EtOAc in hexanes to provide (3-bromo-5-nitro-pyridin2-yl)-carbamic acid tert-butyl ester (600 mg, 41% yield) as a white solid.

(3-Bromo-5-nitro-pyridin2-yl)-carbamic acid tert-butyl ester (100 mg, 0.31 mmol) and tin chloride (298 mg, 1.57 mmol) were dissolved in EtOH (3 mL), and stirred for 2 h at 40° C. The reaction solution was quenched with 2M NaOH, diluted with EtOAc, and filtered through an Extrelut column. The column was washed with EtOAc, and the filtrate was concentrated to provide (5-amino-3-bromo-pyridin-2-yl)-carbamic acid tert-butyl ester (85 mg, 94% yield) as a brown solid.

(5-Amino-3-bromo-pyridin-2-yl)-carbamic acid tert-butyl ester (50 mg, 0.17 mmol), 3-fluoro-benzoyl chloride (28 mg, 0.17 mmol), and N,N-diisopropylethylamine (0.03 mL, 0.19 mmol) were dissolved in CH$_2$Cl$_2$ (2 mL), and stirred or 1 h at 0° C. The reaction solution was diluted with 1 M HCl/CH$_2$Cl$_2$, and filtered through an Extrelut column. The column was washed with CH$_2$Cl$_2$, and the filtrate was concentrated. The crude product was purified via Biotage eluting with a gradient of 20 to 70% EtOAc/hexanes to provide of [3-bromo-5-(3-fluoro-benzoylamino)-pyridin-2-yl]-carbamic acid tert-butyl ester (47 mg, 66% yield) as a solid.

[3-bromo-5-(3-fluoro-benzoylamino)-pyridin-2-yl]-carbamic acid tert-butyl ester (47 mg, 0.11 mmol), 2-methoxycarbonylphenylboronic acid (23 mg, 0.13 mmol), palladium (II) acetate (1 mg, 0.01 mmol), 2-dicyclohexylphosphino-2', 6'-dimethoxybiphenyl (5 mg, 0.02 mmol), and potassium carbonate (48 mg, 0.34 mmol) were dissolved in dioxane/H$_2$O (1.65 mL, 10/1, v/v), and stirred overnight at 100° C. The reaction mixture was concentrated, suspended in EtOAc/H$_2$O, and filtered. The precipitate was washed with EtOAc/H$_2$O, and dried under vacuum to provide 40 (12 mg, 32% yield) as a off-white solid. LC-MS (M+H=334, obsd.=334). $^1$H NMR (400 MHz, d6-DMSO): δ 12.11 (s, 1H), 10.63 (s, 1H), 9.11 (d, 1H), 8.81 (d, 1H), 8.38 (m, 2H), 7.90 (m, 3H), 7.71 (m, 1H), 7.64 (m, 1H), 7.51 (m, 1H).

Example 42

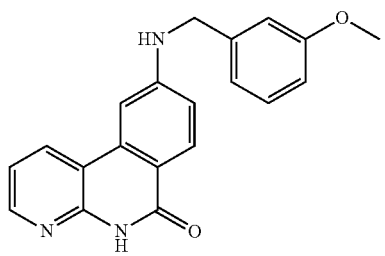 [SMILES: COc1cccc(CNc2ccc3c(=O)[nH]c4ncccc4c3c2)c1]

9-(3-Methoxy-benzylamino)-5H-benzo[c][1,8]naphthyridin-6-one (42)

9-Chloro-5H-benzo[c][1,8]naphthyridin-6-one (50 mg, 0.22 mmol), 3-methoxy-benzylamine (60 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H$_2$O/EtOAc, and filtered. The precipitate was washed with EtOAc/H$_2$O and purified via prep-LC-MS. The purified product was converted to the HCl salt via dissolving in MeOH, addition of 1 M HCl/ether, and concentration. The HCl salt was triturated in CH$_2$Cl$_2$, filtered, washed with CH$_2$Cl$_2$, and dried under vacuum to provide 41 (15 mg, 19% yield) as a yellow solid. LC-MS (M+H=332, obsd.=332). $^1$H NMR (400 MHz, d6-DMSO): δ 11.48 (s, 1H), 8.58 (d, 1H), 8.41 (dd, 1H), 7.99 (d, 1H), 7.39 (d, 1H), 7.33 (t, 1H), 7.25 (m, 2H), 7.09 (m, 1H), 7.03 (m, 2H), 6.95 (dd, 1H), 6.81 (m, 1H), 4.47 (s, 2H), 3.75 (s, 3H).

Example 43

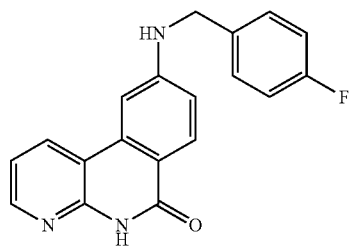 [SMILES: O=c1[nH]c2ncccc2c2cc(NCc3ccc(F)cc3)ccc12]

9-(4-Fluoro-benzylamino)-5H-benzo[c][1,8]naphthyridin-6-one (43)

9-Chloro-5H-benzo[c][1,8]naphthyridin-6-one (50 mg, 0.22 mmol), 4-fluoro-benzylamine (54 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H$_2$O/EtOAc, and filtered. The precipitate was washed with EtOAc/H$_2$O and purified via prep-LC-MS. The purified product was converted to the HCl salt via dissolving in MeOH, addition of 1 M HCl/ether, and concentration. The HCl salt was triturated in CH$_2$Cl$_2$, filtered, washed with CH$_2$Cl$_2$, and dried under vacuum to provide 42 (20 mg, 26% yield) as a yellow solid. LC-MS (M+H=320, obsd.=320). $^1$H NMR (400 MHz, d6-DMSO): δ 11.48 (s, 1H), 8.58 (d, 1H), 8.42 (dd, 1H), 7.99 (d, 1H), 7.48 (m, 3H), 7.38 (d, 1H), 7.24 (m, 2H), 7.18 (m, 2H), 6.94 (d, 1H), 4.49 (s, 2H).

Example 44

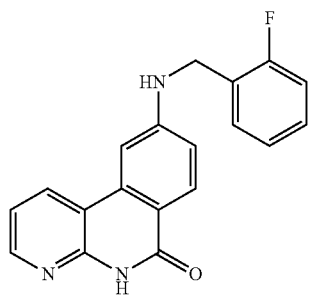 [SMILES: O=c1[nH]c2ncccc2c2cc(NCc3ccccc3F)ccc12]

9-(2-Fluoro-benzylamino)-5H-benzo[c][1,8]naphthyridin-6-one (44)

9-Chloro-5H-benzo[c][1,8]naphthyridin-6-one (50 mg, 0.22 mmol), 2-fluoro-benzylamine (54 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H$_2$O/EtOAc, and filtered. The precipitate was washed with EtOAc/H₂O and purified via prep-LC-MS. The purified product was converted to the HCl salt via dissolving in MeOH, addition of 1 M HCl/ether, and concentration. The HCl salt was triturated in CH₂Cl₂, filtered, washed with CH₂Cl₂, and dried under vacuum to provide 43 (19 mg, 25% yield) as a yellow solid. LC-MS (M+H=320, obsd.=320). ¹H NMR (400 MHz, d6-DMSO): δ 11.48 (s, 1H), 8.59 (d, 1H), 8.42 (dd, 1H), 8.00 (d, 1H), 7.48 (m, 1H), 7.42 (d, 1H), 7.32 (m, 1H), 7.22 (m, 2H), 7.19 (m, 2H), 6.98 (d, 1H), 4.55 (s, 2H).

Example 45

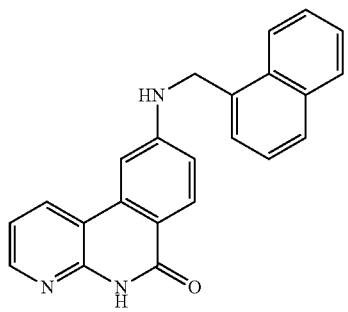 [SMILES: O=c1[nH]c2ncccc2c2cc(NCc3cccc4ccccc34)ccc12]

9-[(Naphthalen-1-ylmethyl)-amino]-5H-benzo[c][1,8]naphthyridin-6-one (45)

9-Chloro-5H-benzo[c][1,8]naphthyridin-6-one (50 mg, 0.22 mmol), 1-naphthelnemethylamine (68 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H₂O/EtOAc, and filtered. The precipitate was washed with EtOAc/H₂O and purified via prep-LC-MS. The purified product was converted to the HCl salt via dissolving in MeOH, addition of 1 M HCl/ether, and concentration. The HCl salt was triturated in CH₂Cl₂, filtered, washed with CH₂Cl₂, and dried under vacuum to provide 44 (19 mg, 25% yield) as a yellow solid. LC-MS (M+H=352, obsd.=352). ¹H NMR (400 MHz, d6-DMSO): δ 11.50 (s, 1H), 8.60 (d, 1H), 8.42 (m, 2H), 8.20 (d, 1H), 7.99 (m, 2H), 7.88 (d, 1H), 7.61 (m, 3H), 7.51 (m, 2H), 7.23 (dd, 1H), 7.01 (dd, 1H), 4.97 (s, 2H).

Example 46

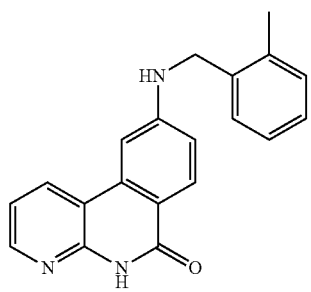 [SMILES: Cc1ccccc1CNc1ccc2c(=O)[nH]c3ncccc3c2c1]

9-(2-Methyl-benzylamino)-5H-benzo[c][1,8]naphthyridin-6-one (46)

9-Chloro-5H-benzo[c][1,8]naphthyridin-6-one (50 mg, 0.22 mmol), 2-methylbenzylamine (53 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H₂O/EtOAc, and filtered. The precipitate was washed with EtOAc/H₂O and purified via prep-LC-MS. The purified product was converted to the HCl salt via dissolving in MeOH, addition of 1 M HCl/ether, and concentration. The HCl salt was triturated in CH₂Cl₂, filtered, washed with CH₂Cl₂, and dried under vacuum to provide 45 (25 mg, 33% yield) as a yellow solid. LC-MS (M+H=316, obsd.=316). ¹H NMR (400 MHz, d6-DMSO): δ 11.50 (s, 1H), 8.59 (dd, 1H), 8.42 (dd, 1H), 8.00 (d, 1H), 7.41 (d, 1H), 7.33 (dd, 1H), 7.22 (m, 4H), 6.98 (dd, 1H), 4.45 (s, 2H), 2.37 (s, 3H).

Example 47

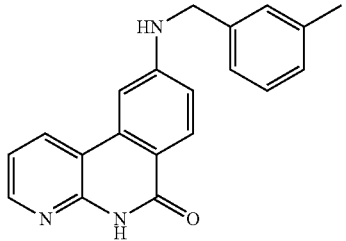 [SMILES: Cc1cccc(CNc2ccc3c(=O)[nH]c4ncccc4c3c2)c1]

9-(3-Methyl-benzylamino)-5H-benzo[c][1,8]naphthyridin-6-one (47)

9-Chloro-5H-benzo[c][1,8]naphthyridin-6-one (50 mg, 0.22 mmol), 3-methylbenzylamine (53 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with H₂O/EtOAc, and filtered. The precipitate was washed with EtOAc/H₂O and purified via prep-LC-MS. The purified product was converted to the HCl salt via dissolving in MeOH, addition of 1 M HCl/ether, and concentration. The HCl salt was triturated in CH₂Cl₂, filtered, washed with CH₂Cl₂, and dried under vacuum to provide 46 (18 mg, 24% yield) as a yellow solid. LC-MS (M+H=316, obsd.=316). ¹H NMR (400 MHz, d6-DMSO): δ 11.48 (s, 1H), 8.58 (dd, 1H), 8.41 (m, 1H), 7.99 (d, 1H), 7.38 (m, 1H), 7.22 (m, 4H), 7.08 (m, 1H), 6.95 (dd, 1H), 4.45 (s, 2H), 2.28 (s, 3H).

Example 48

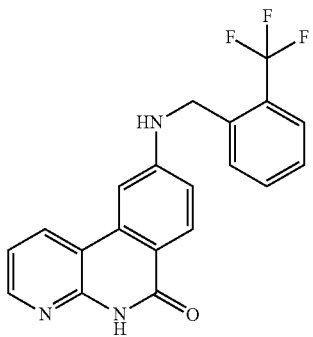 [SMILES: O=c1[nH]c2ncccc2c2cc(NCc3ccccc3C(F)(F)F)ccc12]

9-(2-Trifluoromethyl-benzylamino)-5H-benzo[c][1,8]naphthyridin-6-one (48)

9-Chloro-5H-benzo[c][1,8]naphthyridin-6-one (50 mg, 0.22 mmol), 2-trifluoromethylbenzylamine (76 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, diluted with $H_2O$/EtOAc, and filtered. The precipitate was washed with EtOAc/$H_2O$ and purified via prep-LC-MS. The purified product was converted to the HCl salt via dissolving in MeOH, addition of 1 M HCl/ether, and concentration. The HCl salt was triturated in $CH_2Cl_2$, filtered, washed with $CH_2Cl_2$, and dried under vacuum to provide 47 (22 mg, 25% yield) as a yellow solid. LC-MS (M+H=370, obsd.=370). $^1$H NMR (400 MHz, d6-DMSO): δ 11.52 (s, 1H), 8.46 (dd, 1H), 8.41 (m, 1H), 8.02 (d, 1H), 7.79 (d, 1H), 7.64 (m, 3H), 7.50 (m, 1H), 7.33 (d, 1H), 7.24 (dd, 1H), 6.95 (dd, 1H), 4.67 (s, 2H).

Example 49

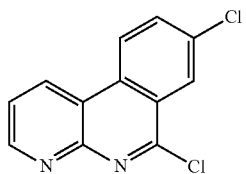 [SMILES: Clc1ccc2c(c1)c(Cl)nc1ncccc12]

6,8-Dichloro-benzo[c][1,8]naphthyridine (49)

8-Chloro-5H-benzo[c][1,8]naphthyridin-6-one (100 mg, 0.43 mmol) was suspended in phosphorus oxychloride (2 mL) and stirred overnight at 100° C. The reaction solution was concentrated via rotary evaporation to provide a white solid. The solid was washed with $H_2O$, filtered, and dried under vacuum to provide 48 (25 mg, 23% yield) as a white solid. LC-MS (M+H=249, obsd.=249). $^1$H NMR (400 MHz, d6-DMSO): δ 9.38 (dd, 1H), 9.10 (dd, 1H), 9.06 (d, 1H), 8.49 (d, 1H), 8.21 (dd, 1H), 7.88 (dd, 1H).

Example 50

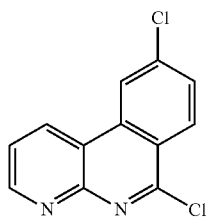 [SMILES: Clc1ccc2c(Cl)nc3ncccc3c2c1]

6,9-Dichloro-benzo[c][1,8]naphthyridine (50)

9-Chloro-5H-benzo[c][1,8]naphthyridin-6-one (100 mg, 0.43 mmol) was suspended in phosphorus oxychloride (2 mL) and stirred overnight at 100° C. The reaction solution was concentrated via rotary evaporation to provide a white solid. The solid was washed with $H_2O$, filtered, and dried under vacuum to provide 49 (105 mg, 97% yield) as a white solid. LC-MS (M+H=249, obsd.=249). $^1$H NMR (400 MHz, d6-DMSO): δ 9.42 (dd, 1H), 9.17 (d, 1H), 9.09 (dd, 1H), 8.51 (d, 1H), 8.03 (dd, 1H), 7.88 (dd, 1H).

Example 51

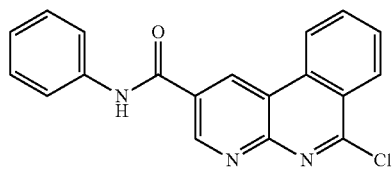 [SMILES: O=C(Nc1ccccc1)c1cnc2nc(Cl)c3ccccc3c2c1]

6-Chloro-benzo[c][1,8]naphthyridine-2-carboxylic acid phenylamide (51)

6-Oxo-5,6-dihydro-benzo[c][1,8]naphthyridine-2-carboxylic acid phenylamide (40 mg, 0.13 mmol) was suspended in phosphorus oxychloride (2 mL) and stirred overnight at 100° C. The reaction solution was concentrated via rotary evaporation to provide a white solid. The solid was washed with $H_2O$, filtered, and dried under vacuum to provide 50 (18 mg, 43% yield) as a white solid. LC-MS (M+H=334, obsd.=334). $^1$H NMR (400 MHz, d6-DMSO): δ 10.82 (s, 1H), 9.88 (d, 1H), 9.50 (d, 1H), 9.15 (d, 1H), 8.56 (d, 1H), 8.22 (dt, 1H), 8.07 (dt, 1H), 7.88 (d, 2H), 7.42 (d, 2H), 7.18 (t, 1H).

Example 52

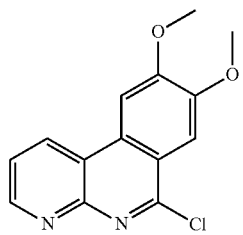 [SMILES: COc1cc2c(Cl)nc3ncccc3c2cc1OC]

6-Chloro-8,9-dimethoxy-benzo[c][1,8]naphthyridine (52)

8,9-Dimethoxy-5H-benzo[c][1,8]naphthyridin-6-one (200 mg, 0.78 mmol) was suspended in phosphorus oxychloride (4 mL) and stirred overnight at 100° C. The reaction solution was concentrated via rotary evaporation to provide a white solid. The solid was washed with H$_2$O, filtered, and dried under vacuum to provide 51 (219 mg, 98% yield) as a white solid. LC-MS (M+H=275, obsd.=275). $^1$H NMR (400 MHz, d6-DMSO): δ 9.51 (dd, 1H), 9.08 (dd, 1H), 8.34 (s, 1H), 7.89 (dd, 1H), 7.73 (s, 1H), 4.13 (s, 3H), 4.05 (s, 3H).

Example 53

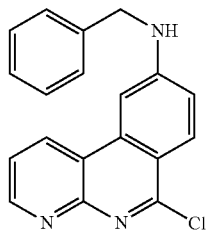 [SMILES: Clc1nc2ncccc2c2cc(NCc3ccccc3)ccc12]

Benzyl-(6-chloro-benzo[c][1,8]naphthyridin-9-yl)-amine (53)

9-Benzylamino-5H-benzo[c][1,8]naphthyridin-6-one (100 mg, 0.33 mmol) was suspended in phosphorus oxychloride (4 mL) and stirred overnight at 100° C. The reaction solution was concentrated via rotary evaporation to provide a white solid. The solid was washed with H$_2$O, filtered, and dried under vacuum to provide 52 (100 mg, 94% yield) as a orange solid. LC-MS (M+H=320, obsd.=320). $^1$H NMR (400 MHz, d6-DMSO): δ 9.28 (d, 1H), 9.00 (d, 1H), 8.18 (d, 1H), 7.82 (m, 2H), 7.77 (d, 1H), 7.47 (d, 2H), 7.35 (m, 3H), 7.28 (m, 1H), 4.62 (s, 2H).

Example 54

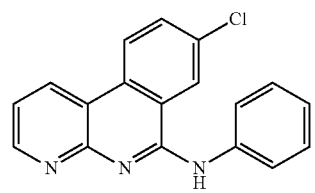 [SMILES: Clc1ccc2c(c1)c(Nc1ccccc1)nc1ncccc12]

(8-Chloro-benzo[c][1,8]naphthyridin-6-yl)-phenyl-amine (54)

6,8-Dichloro-benzo[c][1,8]naphthyridine (25 mg, 0.10 mmol), and aniline (11 mg, 0.12 mmol) were suspended in isopropanol (2 mL) and stirred overnight at 120° C. The reaction solution was cooled to room temperature, and the resulting precipitate was filtered, washed with isopropanol, and dried under vacuum to provide 53 (10 mg, 33% yield) as a white solid. LC-MS (M+H=306, obsd.=306). $^1$H NMR (400 MHz, d6-DMSO): δ 10.11 (s, 1H), 9.32 (d, 1H), 9.01 (d, 1H), 8.89 (d, 1H), 8.78 (d, 1H), 8.10 (dd, 1H), 8.04 (d, 2H), 7.62 (m, 1H), 7.46 (m, 2H), 7.21 (t, 1H).

Example 55

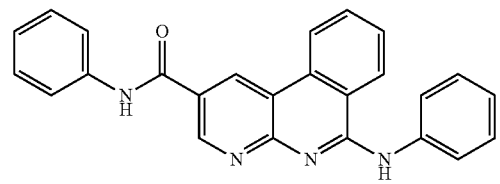 [SMILES: O=C(Nc1ccccc1)c1cnc2nc(Nc3ccccc3)c3ccccc3c2c1]

6-Phenylamino-benzo[c][1,8]naphthyridine-2-carboxylic acid phenylamide (55)

6-Chloro-benzo[c][1,8]naphthyridine-2-carboxylic acid phenylamide (15 mg, 0.04 mmol), and aniline (8 mg, 0.09 mmol) were suspended in isopropanol (2 mL) and stirred overnight at 120° C. The reaction solution was cooled to room temperature, and the resulting precipitate was filtered, washed with isopropanol, and dried under vacuum to provide 54 (5 mg, 29% yield) as a yellow solid. LC-MS (M+H=391, obsd.=391).

Example 56

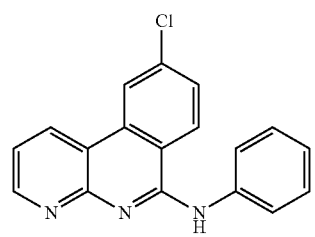 [SMILES: Clc1ccc2c(Nc3ccccc3)nc3ncccc3c2c1]

19-Chloro-benzo[c][1,8]naphthyridin-6-yl)-phenyl-amine (56)

6,9-Dichloro-benzo[c][1,8]naphthyridine (20 mg, 0.08 mmol), and aniline (15 mg, 0.16 mmol) were suspended in isopropanol (2 mL) and stirred overnight at 120° C. The reaction solution was cooled to room temperature, and the resulting precipitate was filtered, washed with isopropanol, and dried under vacuum to provide 55 (12 mg, 49% yield) as a yellow solid. LC-MS (M+H=306, obsd.=306). $^1$H NMR (400 MHz, d6-DMSO): δ 10.08 (s, 1H), 9.33 (d, 1H), 8.98 (d, 1H), 8.85 (d, 1H), 8.78 (dd, 1H), 8.02 (m, 3H), 7.59 (m, 1H), 7.46 (m, 2H), 7.20 (t, 1H).

Example 57

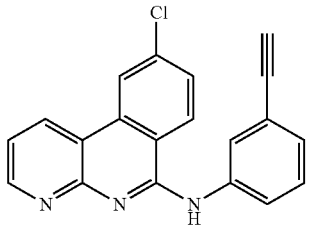 [SMILES: C#Cc1cccc(Nc2nc3ncccc3c3cc(Cl)ccc23)c1]

(9-Chloro-benzo[c][1,8]naphthyridin-6-yl)-(3-ethynyl-phenyl)-amine (57)

6,9-Dichloro-benzo[c][1,8]naphthyridine (20 mg, 0.08 mmol), and 3-ethynylaniline (19 mg, 0.16 mmol) were suspended in isopropanol (2 mL) and stirred overnight at 120° C. The reaction solution was cooled to room temperature, and the resulting precipitate was filtered, washed with isopropanol, and dried under vacuum to provide 56 (15 mg, 57% yield) as a yellow solid. LC-MS (M+H=330, obsd.=330). $^1$H NMR (400 MHz, d6-DMSO): δ 10.40 (s, 1H), 9.48 (d, 1H), 9.04 (d, 1H), 8.92 (d, 1H), 8.81 (d, 1H), 8.14 (d, 1H), 8.09 (d, 1H), 8.05 (dd, 1H), 7.70 (dd, 1H), 7.48 (t, 1H), 7.33 (dd, 1H), 4.28 (s, 1H).

Example 58

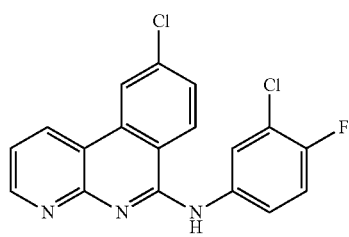 [SMILES: Fc1ccc(Nc2nc3ncccc3c3cc(Cl)ccc23)cc1Cl]

(9-Chloro-benzo[c][1,8]naphthyridin-6-yl)-(3-chloro-4-fluoro-phenyl)-amine (58)

6,9-Dichloro-benzo[c][1,8]naphthyridine (20 mg, 0.08 mmol), and 3-chloro-4-fluoroaniline (24 mg, 0.16 mmol) were suspended in isopropanol (2 mL) and stirred overnight at 120° C. The reaction solution was cooled to room temperature, and the resulting precipitate was filtered, washed with isopropanol, and dried under vacuum to provide 57 (18 mg, 63% yield) as a yellow solid. LC-MS (M+H=358, obsd.=358). $^1$H NMR (400 MHz, d6-DMSO): δ 10.75 (s, 1H), 9.63 (dd, 1H), 9.07 (d, 1H), 8.99 (d, 1H), 8.86 (dd, 1H), 8.33 (dd, 1H), 8.09 (dd, 1H), 8.04 (m, 1H), 7.80 (dd, 1H), 7.52 (t, 1H).

Example 59

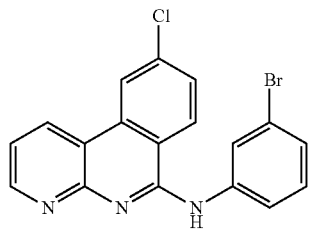 [SMILES: Clc1ccc2c(Nc3cccc(Br)c3)nc3ncccc3c2c1]

(3-Bromo-phenyl)-(9-chloro-benzo[c][1,8]naphthyridin-6-yl)-amine (59)

6,9-Dichloro-benzo[c][1,8]naphthyridine (20 mg, 0.08 mmol), and 3-bromoaniline (24 mg, 0.16 mmol) were suspended in isopropanol (2 mL) and stirred overnight at 120° C. The reaction solution was cooled to room temperature, and the resulting precipitate was filtered, washed with isopropanol, and dried under vacuum to provide 58 (18 mg, 63% yield) as a yellow solid. LC-MS (M+H=384, obsd.=384). $^1$H NMR (400 MHz, d6-DMSO): δ 10.63 (s, 1H), 9.61 (d, 1H), 9.08 (d, 1H), 8.95 (d, 1H), 8.84 (dd, 1H), 8.25 (d, 1H), 8.09 (m, 2H), 7.79 (dd, 1H), 7.43 (m, 2H).

Example 60

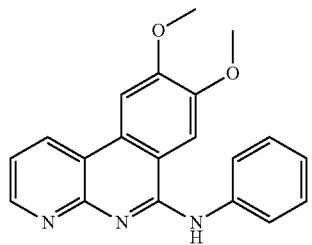 [SMILES: COc1cc2c(Nc3ccccc3)nc3ncccc3c2cc1OC]

(8,9-Dimethoxy-benzo[c][1,8]naphthyridin-6-yl)-phenyl-amine (60)

6-Chloro-8,9-dimethoxy-benzo[c][1,8]naphthyridine (15 mg, 0.05 mmol), and aniline (10 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 59 (8 mg, 40% yield) as a yellow solid. LC-MS (M+H=332, obsd.=332). $^1$H NMR (400 MHz, d6-DMSO): δ 10.47 (s, 1H), 9.65 (d, 1H), 8.70 (d, 1H), 8.28 (s, 1H), 8.22 (s, 1H), 7.85 (d, 2H), 7.75 (dd, 1H), 7.52 (m, 2H), 7.31 (t, 1H), 4.11 (s, 3H), 4.08 (s, 3H).

Example 61

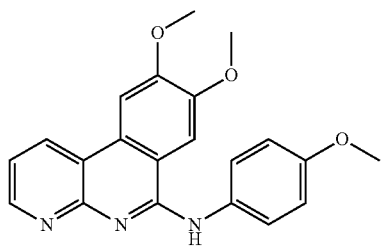 [SMILES: COc1ccc(Nc2nc3ncccc3c3cc(OC)c(OC)cc23)cc1]

8,9-Dimethoxy-benzo[c][1,8]naphthyridin-6-yl)-(4-methoxy-phenyl)-amine (61)

6-Chloro-8,9-dimethoxy-benzo[c][1,8]naphthyridine (15 mg, 0.05 mmol), and 4-methoxyaniline (14 mg, 0.11 mmol) were suspended in isopropanol (2 mL) and stirred overnight at 110° C. The reaction solution was concentrated and purified via prep-LC-MS. The recovered product was converted to the HCl salt via dissolving in $CH_2Cl_2$, addition of 2 M HCl/ether. The resulting precipitate was filtered, washed with $CH_2Cl_2$, and dried under vacuum to provide 60 (10 mg, 46% yield) as a yellow solid. LC-MS (M+H=362, obsd.=362). $^1$H NMR (400 MHz, d6-DMSO): δ 10.48 (s, 1H), 9.60 (dd, 1H), 8.66 (d, 1H), 8.26 (s, 1H), 8.22 (s, 1H), 7.71 (m, 3H), 7.09 (m, 2H), 4.11 (s, 3H), 4.08 (s, 3H), 3.81 (s, 3H).

Example 62

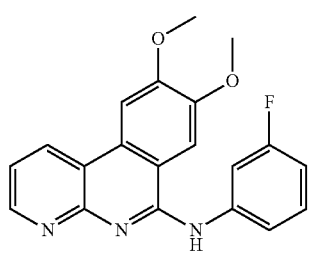 [SMILES: COc1cc2c(Nc3cccc(F)c3)nc3ncccc3c2cc1OC]

(8,9-Dimethoxy-benzo[c][1,8]naphthyridin-6-yl)-(3-fluoro-phenyl)-amine (62)

6-Chloro-8,9-dimethoxy-benzo[c][1,8]naphthyridine (15 mg, 0.05 mmol), and 3-fluoroaniline (12 mg, 0.11 mmol) were suspended in isopropanol (2 mL) and stirred overnight at 110° C. The reaction solution was concentrated and purified via prep-LC-MS. The recovered product was converted to the HCl salt via dissolving in $CH_2Cl_2$, addition of 2 M HCl/ether. The resulting precipitate was filtered, washed with $CH_2Cl_2$, and dried under vacuum to provide 61 (16 mg, 76% yield) as a yellow solid. LC-MS (M+H=350, obsd.=350). $^1$H NMR (400 MHz, d6-DMSO): δ 10.52 (s, 1H), 9.69 (dd, 1H), 8.79 (dd, 1H), 8.30 (s, 1H), 8.28 (s, 1H), 8.03 (m, 1H), 7.81 (dd, 1H), 7.72 (dd, 1H), 7.52 (m, 1H), 7.10 (dt, 1H), 4.11 (s, 3H), 4.08 (s, 3H).

Example 63

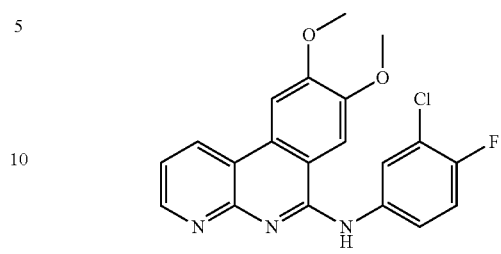

(3-Chloro-4-fluoro-phenyl)-(8,9-dimethoxy-benzo[c][1,8]naphthyridin-6-yl)-amine (63)

6-Chloro-8,9-dimethoxy-benzo[c][1,8]naphthyridine (15 mg, 0.05 mmol), and 3-chloro-4-fluoroaniline (16 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 62 (19 mg, 91% yield) as a yellow solid. LC-MS (M+H=384, obsd.=384). $^1$H NMR (400 MHz, d6-DMSO): δ 10.69 (s, 1H), 9.68 (dd, 1H), 8.76 (dd, 1H), 8.33 (s, 1H), 8.27 (s, 1H), 8.23 (dd, 1H), 7.98 (m, 1H), 7.79 (dd, 1H), 7.54 (t, 1H), 7.21 (t, 1H), 4.11 (s, 3H), 4.08 (s, 3H).

Example 64

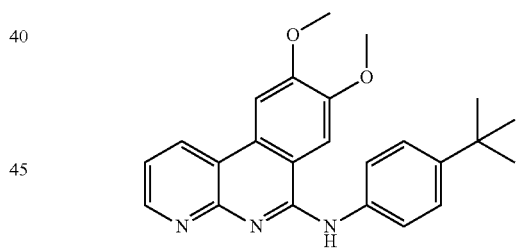

(4-tert-Butyl-phenyl)-(8,9-dimethoxy-benzo[c][1,8]naphthyridin-6-yl)-amine (64)

6-Chloro-8,9-dimethoxy-benzo[c][1,8]naphthyridine (15 mg, 0.05 mmol), and 4-tert-butylaniline (16 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 63 (13 mg, 61% yield) as a yellow solid. LC-MS (M+H=388, obsd.=388). $^1$H NMR (400 MHz, d6-DMSO): δ 10.52 (s, 1H), 9.63 (dd, 1H), 8.68 (dd, 1H), 8.29 (m, 2H), 7.76 (m, 3H), 7.52 (m, 2H), 4.11 (s, 3H), 4.08 (s, 3H), 1.35 (s, 9H).

Example 65

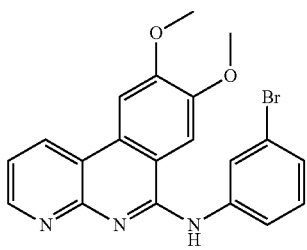 [SMILES: COc1cc2c(Nc3cccc(Br)c3)nc3ncccc3c2cc1OC]

13-Bromo-phenyl)-(8,9-dimethoxy-benzo[c][1,8] naphthyridin-6-yl)-amine (65)

6-Chloro-8,9-dimethoxy-benzo[c][1,8]naphthyridine (15 mg, 0.05 mmol), and 3-bromoaniline (19 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 64 (23 mg, 94% yield) as a yellow solid. LC-MS (M+H=410, obsd.=410). $^1$H NMR (400 MHz, d6-DMSO): δ 10.68 (s, 1H), 9.68 (dd, 1H), 8.78 (dd, 1H), 8.33 (s, 1H), 8.28 (s, 1H), 8.15 (m, 1H), 8.08 (m, 1H), 7.80 (dd, 1H), 7.46 (m, 1H), 7.18 (m, 2H), 6.99 (m, 1H), 4.11 (s, 3H), 4.08 (s, 3H).

Example 66

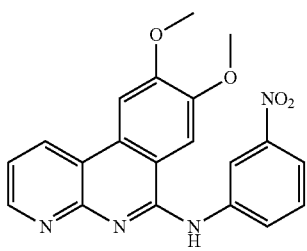 [SMILES: COc1cc2c(Nc3cccc([N+](=O)[O-])c3)nc3ncccc3c2cc1OC]

(8,9-Dimethoxy-benzo[c][1,8]naphthyridin-6-yl)-(3-nitro-phenyl)-amine (66)

6-Chloro-8,9-dimethoxy-benzo[c][1,8]naphthyridine (15 mg, 0.05 mmol), and 3-nitroaniline (15 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 65 (22 mg, 98% yield) as a yellow solid. LC-MS (M+H=377, obsd.=377). $^1$H NMR (400 MHz, d6-DMSO): δ 10.91 (s, 1H), 9.69 (d, 1H), 8.81 (d, 1H), 8.73 (d, 1H), 8.63 (d, 1H), 8.38 (s, 1H), 8.28 (s, 1H), 8.09 (dd, 1H), 7.81 (m, 2H), 4.11 (s, 3H), 4.08 (s, 3H).

Example 67

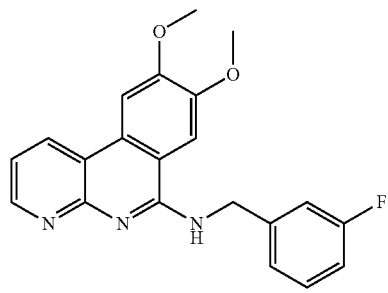 [SMILES: COc1cc2c(NCc3cccc(F)c3)nc3ncccc3c2cc1OC]

(8,9-Dimethoxy-benzo[c][1,8]naphthyridin-6-yl)-(3-fluoro-benzyl)-amine (67)

6-Chloro-8,9-dimethoxy-benzo[c][1,8]naphthyridine (15 mg, 0.05 mmol), and 3-fluorobenzylamine (14 mg, 0.11 mmol) were suspended in isopropanol (2 mL) and stirred overnight at 110° C. The reaction solution was concentrated and purified via Biotage eluting with $CH_2Cl_2$/MeOH (9/1). The recovered product was converted to the HCl salt via dissolving in $CH_2Cl_2$, addition of 2 M HCl/ether. The resulting precipitate was filtered, washed with $CH_2Cl_2$, and dried under vacuum to provide 66 (21 mg, 96% yield) as a yellow solid. LC-MS (M+H=364, obsd.=364). $^1$H NMR (400 MHz, d6-DMSO): δ 10.02 (m, 1H), 9.53 (dd, 1H), 8.62 (dd, 1H), 8.18 (s, 2H), 7.64 (dd, 1H), 7.40 (m, 3H), 7.21 (m, 1H), 7.11 (m, 1H), 4.96 (d, 2H), 4.11 (s, 3H), 4.08 (s, 3H).

Example 68

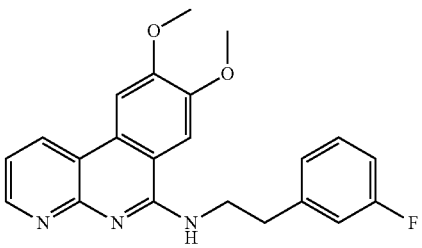 [SMILES: COc1cc2c(NCCc3cccc(F)c3)nc3ncccc3c2cc1OC]

(8,9-Dimethoxy-benzo[c][1,8]naphthyridin-6-yl)-[2-(3-fluoro-phenyl)-ethyl]-amine (68)

6-Chloro-8,9-dimethoxy-benzo[c][1,8]naphthyridine (15 mg, 0.05 mmol), and 3-fluorophenethylamine (14 mg, 0.11 mmol) were suspended in isopropanol (2 mL) and stirred overnight at 110° C. The reaction solution was purified via prep-LC-MS. The recovered product was converted to the HCl salt via dissolving in $CH_2Cl_2$, addition of 2 M HCl/ether. The resulting precipitate was filtered, washed with $CH_2Cl_2$, and dried under vacuum to provide 67 (17 mg, 75% yield) as a yellow solid. LC-MS (M+H=378, obsd.=378). $^1$H NMR (400 MHz, d6-DMSO): δ 9.50 (d, 2H), 8.66 (d, 1H), 8.18 (s, 1H), 8.06 (s, 1H), 7.62 (dd, 1H), 7.38 (m, 1H), 7.22 (m, 2H), 7.08 (m, 1H), 4.08 (s, 3H), 3.99 (s, 3H), 3.91 (m, 2H), 3.11 (m, 2H).

Example 69

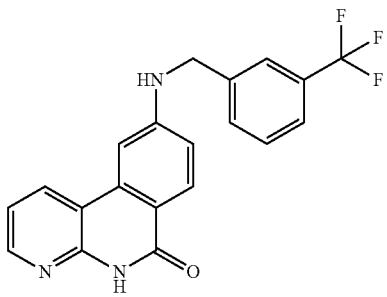 [SMILES: O=c1[nH]c2ncccc2c2cc(NCc3cccc(C(F)(F)F)c3)ccc12]

9-(3-Trifluoromethyl-benzylamino)-5H-benzo[c][1,8]naphthyridin-6-one (69)

9-Chloro-5H-benzo[c][1,8]naphthyridin-6-one (50 mg, 0.22 mmol), 3-trifluoromethylbenzylamine (76 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was diluted with MeOH, filtered, and purified via prep-LC-MS. The purified product was converted to the HCl salt via dissolving in MeOH, addition of 1 M HCl/ether, and concentration. The HCl salt was triturated in CH$_2$Cl$_2$, filtered, washed with CH$_2$Cl$_2$, and dried under vacuum to provide 68 (20 mg, 23% yield) as a yellow solid. LC-MS (M+H=370, obsd.=370). $^1$H NMR (400 MHz, d6-DMSO): δ 11.49 (s, 1H), 8.58 (dd, 1H), 8.41 (dd, 1H), 8.01 (d, 1H), 7.83 (s, 1H), 7.74 (d, 1H), 7.60 (m, 3H), 7.42 (d, 1H), 7.25 (dd, 1H), 6.97 (dd, 1H), 4.62 (s, 2H).

Example 70

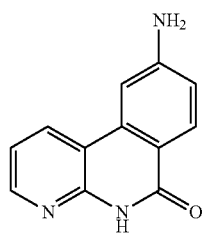

9-Amino-5H-benzo[c][1,8]naphthyridin-6-one (70)

9-Chloro-5H-benzo[c][1,8]naphthyridin-6-one (150 mg, 0.65 mmol), lithium bis(trimethylsilylamide) (1.3 mL, 1.3 mmol, 1M in THF), palladium(II) acetate (6 mg, 0.03 mmol), and 2-dicyclohexylphosphino-2',4',6'-triisopropylbiphenyl (25 mg, 0.06 mmol) were suspended in dioxane (3 mL), and stirred for 48 h at 100° C. The reaction mixture was concentrated. The resulting precipitate was suspended in 1M HCl/EtOAc, and filtered to provide 69 9-amino-5H-benzo[c][1,8]naphthyridin-6-one. LC-MS (M+H=212, obsd.=212).

Example 71

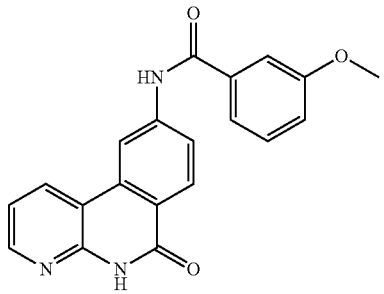 [SMILES: COc1cccc(C(=O)Nc2ccc3c(=O)[nH]c4ncccc4c3c2)c1]

3-Methoxy-N-(6-oxo-5,6-dihydro-benzo[c][1,8]naphthyridin-9-yl)-benzamide (71)

9-Amino-5H-benzo[c][1,8]naphthyridin-6-one (15 mg, 0.07 mmol), 3-methoxybenzoyl chloride (18 mg, 0.11 mmol), and DIEA (40 μL, 0.21 mmol) were suspended in dioxane (2 mL), and stirred overnight at 60° C. The reaction was quenched with MeOH, and purified directly via prep-LC-MS to provide 70 (5 mg, 20% yield) as a white solid. LC-MS (M+H=346, obsd.=346). $^1$H NMR (400 MHz, d6-DMSO): δ 10.71 (s, 1H), 8.93 (d, 1H), 8.57 (d, 1H), 8.52 (m, 1H), 8.31 (d, 1H), 8.06 (dd, 1H), 7.62 (dd, 1H), 7.58 (m, 1H), 7.51 (t, 1H), 7.37 (dd, 1H), 7.21 (dd, 1H), 3.88 (s, 3H).

Example 72

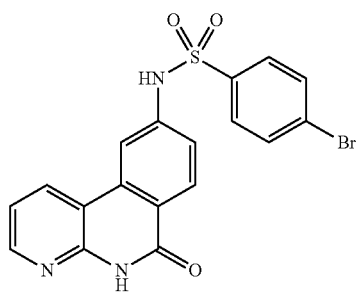 [SMILES: O=c1[nH]c2ncccc2c2cc(NS(=O)(=O)c3ccc(Br)cc3)ccc12]

4-Bromo-N-(6-oxo-5,6-dihydro-benzo[c][1,8]naphthyridin-9-yl)-benzenesulfonamide (72)

9-Amino-5H-benzo[c][1,8]naphthyridin-6-one (15 mg, 0.07 mmol), 4-bromobenzenesulfonyl chloride (27 mg, 0.11 mmol), and DIEA (40 μL, 0.21 mmol) were suspended in dioxane (2 mL), and stirred overnight at 60° C. The reaction was quenched with MeOH, and purified directly via prep-LC-MS to provide 71 (10 mg, 33% yield) as a white solid. LC-MS (M+H=430, obsd.=430). $^1$H NMR (400 MHz, d6-DMSO): δ 11.81 (s, 1H), 8.44 (m, 2H), 8.12 (d, 1H), 7.95 (s, 1H), 7.75 (m, 4H), 7.33 (m, 2H), 6.52 (s, 1H).

Example 73

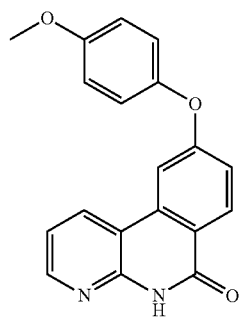 [SMILES: COc1ccc(Oc2ccc3c(=O)[nH]c4ncccc4c3c2)cc1]

9-(4-Methoxy-phenoxy)-5H-benzo[c][1,8]naphthyridin-6-one (73)

9-Fluoro-5H-benzo[c][1,8]naphthyridin-6-one (50 mg, 0.23 mmol), 4-methoxyphenol (87 mg, 0.70 mmol), and potassium carbonate (161 mg, 1.17 mmol) were suspended in dioxane (2 mL), and stirred for 20 minutes at 180° C. in the microwave. The reaction mixture was quenched with $H_2O$. The resulting precipitate was filtered, washed with $H_2O$, and dried under vacuum to provide 72 (40 mg, 54% yield) as a tan solid. LC-MS (M+H=319, obsd.=319). $^1$H NMR (400 MHz, d6-DMSO): δ 11.92 (s, 1H), 8.68 (dd, 1H), 8.49 (dd, 1H), 8.29 (d, 1H), 8.03 (d, 1H), 7.28 (dd, 1H), 7.16 (m, 3H), 7.05 (m, 2H), 3.79 (s, 3H).

Example 74

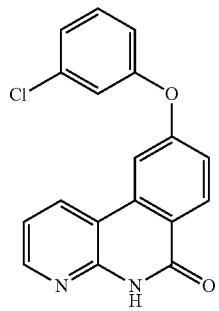 [SMILES: O=c1[nH]c2ncccc2c2cc(Oc3cccc(Cl)c3)ccc12]

9-(3-Chloro-phenoxy)-5H-benzo[c][1,8]naphthyridin-6-one (74)

9-Fluoro-5H-benzo[c][1,8]naphthyridin-6-one (40 mg, 0.19 mmol), 3-chlorophenol (72 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered, washed with $H_2O$, and dried under vacuum to provide 73 (50 mg, 83% yield) as a tan solid. LC-MS (M+H=323, obsd.=323). $^1$H NMR (400 MHz, d6-DMSO): δ 12.05 (s, 1H), 8.78 (dd, 1H), 8.51 (dd, 1H), 8.35 (d, 1H), 8.19 (d, 1H), 7.49 (t, 1H), 7.29 (m, 4H), 7.12 (dd, 1H).

Example 75

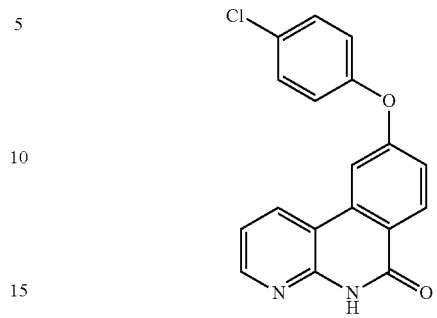

9-(4-Chloro-phenoxy)-5H-benzo[c][1,8]naphthyridin-6-one (75)

9-Fluoro-5H-benzo[c][1,8]naphthyridin-6-one (40 mg, 0.19 mmol), 4-chlorophenol (72 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered, washed with $H_2O$, and dried under vacuum to provide 74 (59 mg, 98% yield) as a tan solid. LC-MS (M+H=323, obsd.=323). $^1$H NMR (400 MHz, d6-DMSO): δ 12.02 (s, 1H), 8.77 (dd, 1H), 8.51 (dd, 1H), 8.33 (d, 1H), 8.15 (d, 1H), 7.52 (m, 2H), 7.23 (m, 4H).

Example 76

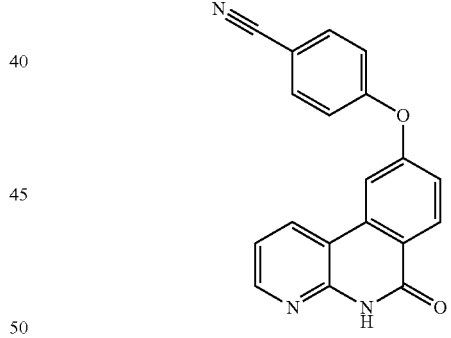

4-(6-Oxo-5,6-dihydro-benzo[c][1,8]naphthyridin-9-yloxy)-benzonitrile (76)

9-Fluoro-5H-benzo[c][1,8]naphthyridin-6-one (40 mg, 0.19 mmol), 4-cyanophenol (67 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered, washed with $H_2O$, and dried under vacuum to provide 75 (47 mg, 80% yield) as a tan solid. LC-MS (M+H=314, obsd.=314). $^1$H NMR (400 MHz, d6-DMSO): δ 12.05 (s, 1H), 8.79 (dd, 1H), 8.52 (dd, 1H), 8.39 (d, 1H), 8.30 (d, 1H), 7.92 (m, 2H), 7.39 (dd, 1H), 7.28 (m, 3H).

Example 77

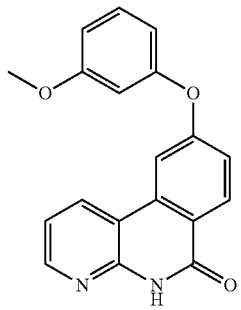 [SMILES: COc1cccc(Oc2ccc3c(=O)[nH]c4ncccc4c3c2)c1]

9-(3-Methoxy-phenoxy)-5H-benzo[c][1,8]naphthyridin-6-one (77)

9-Fluoro-5H-benzo[c][1,8]naphthyridin-6-one (40 mg, 0.19 mmol), 3-methoxyphenol (70 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered and washed with $H_2O$. The precipitate was triturated with MeOH, filtered, washed with MeOH, and dried under vacuum to provide 76 (22 mg, 37% yield) as a brown solid. LC-MS (M+H=319, obsd.=319). $^1$H NMR (400 MHz, d6-DMSO): δ 11.99 (s, 1H), 8.73 (dd, 1H), 8.50 (dd, 1H), 8.32 (d, 1H), 8.14 (d, 1H), 7.38 (t, 1H), 7.30 (dd, 1H), 7.22 (dd, 1H), 6.83 (dd, 1H), 6.77 (t, 1H), 6.71 (dd, 1H), 3.77 (s, 3H).

Example 78

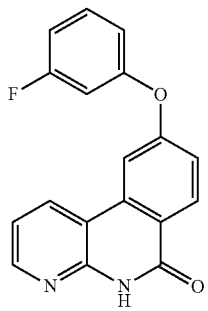

9-(3-Fluoro-phenoxy)-5H-benzo[c][1,8]naphthyridin-6-one (78)

9-Fluoro-5H-benzo[c][1,8]naphthyridin-6-one (40 mg, 0.19 mmol), 3-fluorophenol (63 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered, washed with $H_2O$, and dried under vacuum to provide 77 (52 mg, 91% yield) as a tan solid. LC-MS (M+H=307, obsd.=307). $^1$H NMR (400 MHz, d6-DMSO): δ 12.00 (s, 1H), 8.77 (dd, 1H), 8.51 (dd, 1H), 8.36 (d, 1H), 8.21 (d, 1H), 7.50 (t, 1H), 7.30 (m, 2H), 7.09 (m, 2H), 7.02 (dd, 1H).

Example 79

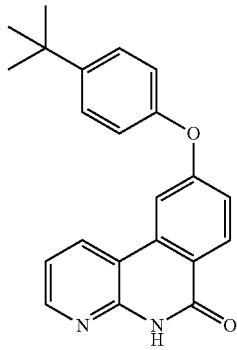 [SMILES: CC(C)(C)c1ccc(Oc2ccc3c(=O)[nH]c4ncccc4c3c2)cc1]

9-(4-tert-Butyl-phenoxy)-5H-benzo[c][1,8]naphthyridin-6-one (79)

9-Fluoro-5H-benzo[c][1,8]naphthyridin-6-one (40 mg, 0.19 mmol), 4-tert-butylphenol (84 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered and washed with $H_2O$. The precipitate was triturated with MeOH, filtered, washed with MeOH, and dried under vacuum to provide 78 (32 mg, 50% yield) as a tan solid. LC-MS (M+H=345, obsd.=345). $^1$H NMR (400 MHz, d6-DMSO): δ 11.98 (s, 1H), 8.75 (dd, 1H), 8.50 (dd, 1H), 8.32 (d, 1H), 8.18 (d, 1H), 7.50 (m, 2H), 7.31 (dd, 1H), 7.16 (dd, 1H), 7.11 (m, 2H), 1.32 (s, 9H).

Example 80

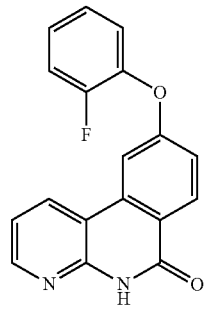 [SMILES: O=c1[nH]c2ncccc2c2cc(Oc3ccccc3F)ccc12]

9-(2-Fluoro-phenoxy)-5H-benzo[c][1,8]naphthyridin-6-one (80)

9-Fluoro-5H-benzo[c][1,8]naphthyridin-6-one (40 mg, 0.19 mmol), 2-fluorophenol (63 mg, 0.56 mmol), and potassium carbonate (129 mg, 0.93 mmol) were suspended in DMF (1.5 mL), and stirred for 20 minutes at 180° C. in the microwave. The reaction mixture was quenched with $H_2O$. The resulting precipitate was filtered, and washed with $H_2O$. The precipitate was triturated with MeOH, filtered, washed with MeOH, and dried under vacuum to provide 79 (23 mg, 40% yield) as a tan solid. LC-MS (M+H=307, obsd.=307). $^1$H NMR (400 MHz, d6-DMSO): δ 11.99 (s, 1H), 8.74 (dd, 1H), 8.50 (dd, 1H), 8.32 (d, 1H), 8.14 (d, 1H), 7.49 (m, 1H), 7.33 (m, 4H), 7.18 (dd, 1H).

Example 81

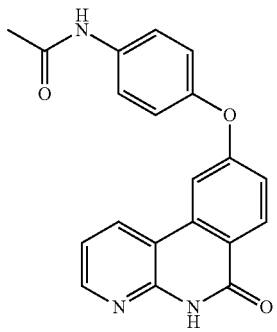 [SMILES: CC(=O)Nc1ccc(Oc2ccc3c(=O)[nH]c4ncccc4c3c2)cc1]

N-[4-(6-Oxo-5,6-dihydro-benzo[c][1,8]naphthyridin-9-yloxy)-phenyl]-acetamide (81)

9-Fluoro-5H-benzo[c][1,8]naphthyridin-6-one (40 mg, 0.19 mmol), N-(4-hydroxyphenyl)acetamide (85 mg, 0.56 mmol), and potassium carbonate (129 mg, 0.93 mmol) were suspended in DMF (1.5 mL), and stirred for 20 minutes at 180° C. in the microwave. The reaction mixture was quenched with H$_2$O. The resulting precipitate was filtered, and washed with H$_2$O. The precipitate was triturated with MeOH, filtered, washed with MeOH, and dried under vacuum to provide 81 (48 mg, 74% yield) as a tan solid. LC-MS (M+H=346, obsd.=346). $^1$H NMR (400 MHz, d6-DMSO): δ 11.92 (s, 1H), 10.04 (s, 1H), 8.69 (dd, 1H), 8.50 (dd, 1H), 8.30 (d, 1H), 8.05 (d, 1H), 7.68 (m, 2H), 7.29 (dd, 1H), 7.16 (m, 3H), 2.08 (s, 3H).

Example 82

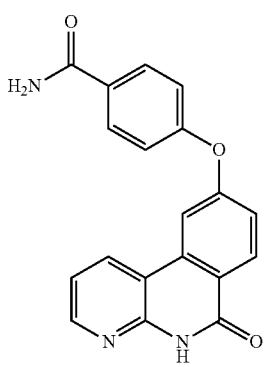 [SMILES: NC(=O)c1ccc(Oc2ccc3c(=O)[nH]c4ncccc4c3c2)cc1]

N-[4-(6-Oxo-5,6-dihydro-benzo[c][1,8]naphthyridin-9-yloxy)-phenyl]-acetamide (82)

9-Fluoro-5H-benzo[c][1,8]naphthyridin-6-one (40 mg, 0.19 mmol), 4-hydroxybenzamide (77 mg, 0.56 mmol), and potassium carbonate (129 mg, 0.93 mmol) were suspended in DMF (1.5 mL), and stirred for 20 minutes at 180° C. in the microwave. The reaction mixture was quenched with H$_2$O. The resulting precipitate was filtered, and washed with H$_2$O. The precipitate was triturated with MeOH, filtered, washed with MeOH, and dried under vacuum to provide 81 (41 mg, 66% yield) as a tan solid. LC-MS (M+H=332, obsd.=332). $^1$H NMR (400 MHz, d6-DMSO): δ 12.00 (s, 1H), 10.04 (s, 1H), 8.77 (dd, 1H), 8.51 (dd, 1H), 8.37 (d, 1H), 8.21 (d, 1H), 7.98 (m, 2H), 7.33 (s, 1H), 7.30 (m, 2H), 7.21 (m, 2H).

Example 83

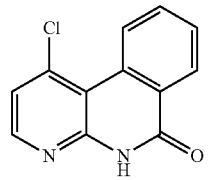 [SMILES: O=c1[nH]c2nccc(Cl)c2c2ccccc12]

1-Chloro-5H-benzo[c][1,8]naphthyridin-6-one (83)

4-Chloro-3-iodopyridin-2-amine (500 mg, 1.96 mmol), 2-methoxycarbonylphenylboronic acid (442 mg, 2.46 mmol), palladium(II) acetate (18 mg, 0.08 mmol), 2-dicyclohexylphosphino-2',6'-dimethoxybiphenyl (65 mg, 0.16 mmol), and potassium carbonate (814 mg, 5.89 mmol) were dissolved in dioxane/H$_2$O (11.0 mL, 10/1, v/v), and stirred overnight at 100° C. The reaction mixture was concentrated, suspended in EtOAc/H$_2$O, and filtered. The precipitate was washed with EtOAc/H$_2$O, and dried under vacuum to provide 82 (44 mg, 10% yield) as a white solid. LC-MS (M+H=231, obsd.=231). $^1$H NMR (400 MHz, d6-DMSO): δ 12.29 (s, 1H), 9.34 (d, 1H), 8.45 (d, 1H), 8.40 (d, 1H), 8.93 (dt, 1H), 7.79 (t, 1H), 7.48 (d, 1H).

Example 84

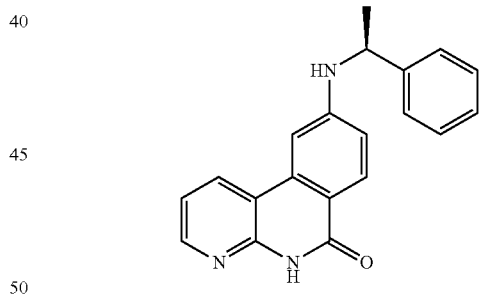

9-((S)-1-Phenyl-ethylamino)-5H-benzo[c][1,8]naphthyridin-6-one (84)

9-Chloro-5H-benzo[c][1,8]naphthyridin-6-one (50 mg, 0.22 mmol), (s)-(−)-alpha-methylbenzylamine (53 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was diluted with MeOH, filtered, and purified via prep-LC-MS to provide 83 (3 mg, 5% yield) as an oil. LC-MS (M+H=316, obsd.=316). $^1$H NMR (400 MHz, d6-DMSO): δ 12.08 (s, 1H), 8.83 (dd, 1H), 8.57 (d, 1H), 8.51 (dd, 1H), 8.34 (dd, 1H), 7.91 (dt, 1H), 7.69 (m, 3H), 7.35 (m, 2H), 7.25 (m, 1H), 4.14 (q, 1H), 0.87 (d, 3H).

Example 85

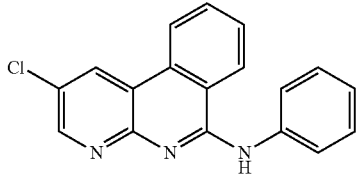 [SMILES: Clc1cnc2nc(Nc3ccccc3)c3ccccc3c2c1]

(2-Chloro-benzo[c][1,8]naphthyridin-6-yl)-phenyl-amine (85)

2,6-Dichloro-benzo[c][1,8]naphthyridine (25 mg, 0.10 mmol) and aniline (19 mg, 0.20 mmol) were suspended in isopropanol (2 mL), and stirred overnight at 110° C. The reaction solution was purified directly via prep-LC-MS. The purified product was converted to the TFA salt via dissolving in MeOH, addition of TFA, and concentration on the Genevac. The reaction mixture was diluted with MeOH, filtered, and purified via prep-LC-MS to provide 84 (7 mg, 42% yield) as a solid. LC-MS (M+H=306, obsd.=306). $^1$H NMR (400 MHz, d6-DMSO): δ 9.92 (s, 1H), 9.25 (d, 1H), 8.88 (d, 1H), 8.79 (m, 2H), 8.04 (m, 3H), 7.92 (dt, 1H), 7.43 (m, 2H), 7.19 (t, 1H).

Example 86

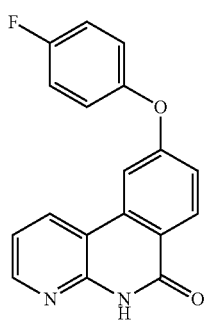

9-(4-Fluoro-phenoxy)-5H-benzo[c][1,8]naphthyridin-6-one (86)

4-Fluoro phenol (58 mg, 0.5 mmol) and sodium hydride (17 mg, 0.70 mmol) were suspended in dioxane and stirred for 30 minutes at room temperature. 9-Fluoro-5H-benzo[c][1,8] naphthyridin-6-one (50 mg, 0.23 mmol) was added, and the reaction mixture was stirred for 2 h at room temperature. The reaction mixture was diluted with MeOH, filtered, and purified directly via prep-LC-MS to provide 85 (5 mg, 7% yield) as a tan solid. LC-MS (M+H=307, obsd.=307). $^1$H NMR (400 MHz, d6-DMSO): δ 8.72 (dd, 1H), 8.50 (dd, 1H), 8.32 (d, 1H), 8.09 (d, 1H), 7.30 (m, 5H), 7.21 (s, 1H).

Example 87

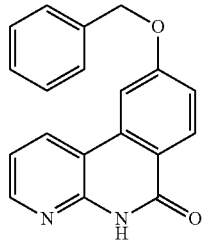 [SMILES: O=c1[nH]c2ncccc2c2cc(OCc3ccccc3)ccc12]

9-Benzyloxy-5H-benzo[c][1,8]naphthyridin-6-one (87)

Benzyl alcohol (50 mg, 0.47 mmol) and sodium hydride (17 mg, 0.70 mmol) were suspended in dioxane and stirred for 30 minutes at room temperature. 9-Fluoro-5H-benzo[c][1,8] naphthyridin-6-one (50 mg, 0.23 mmol) was added, and the reaction mixture was stirred overnight at 100° C. The reaction mixture was diluted with MeOH, and purified directly via prep-LC-MS to provide 86 (15 mg, 21% yield) as a solid. LC-MS (M+H=303, obsd.=303). $^1$H NMR (400 MHz, d6-DMSO): δ 8.86 (dd, 1H), 8.83 (dd, 1H), 8.52 (d, 1H), 8.49 (dd, 1H), 8.43 (dd, 1H), 8.38 (dd, 1H), 8.25 (d, 1H), 8.09 (d, 1H), 7.55 (m, 2H), 7.43 (m, 1H), 7.33 (m, 2H), 5.36 (s, 2H).

Example 88

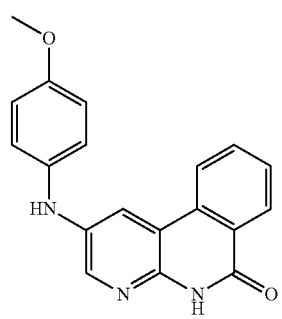 [SMILES: COc1ccc(Nc2cnc3[nH]c(=O)c4ccccc4c3c2)cc1]

2-(4-Methoxy-phenylamino)-5H-benzo[c][1,8]naphthyridin-6-one (88)

2-Chloro-5H-benzo[c][1,8]naphthyridin-6-one (30 mg, 0.13 mmol), 4-methoxy aniline (32 mg, 0.26 mmol), palladium(II) acetate (2 mg, 0.01 mmol), 2-dicyclohexylphosphino-2',4',6'-triisopropylbiphenyl (6 mg, 0.02 mmol), and sodium tert-butoxide (38 mg, 0.39 mmol) were suspended in dioxane (2 mL), and stirred overnight at 100° C. The reaction mixture was diluted with MeOH, filtered, and purified via prep-LC-MS to provide 87 (15 mg, 36% yield) as a solid. LC-MS (M+H=318, obsd.=318). $^1$H NMR (400 MHz, d6-DMSO): δ 11.86 (s, 1H), 8.33 (dd, 2H), 8.22 (m, 2H), 7.88 (dt, 1H), 7.68 (m, 1H), 7.11 (d, 2H), 6.91 (d, 2H), 3.73 (s, 3H).

Example 89

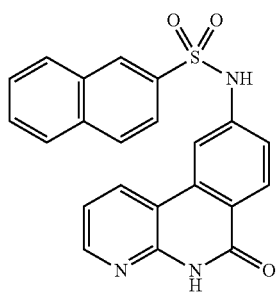 [SMILES: O=c1[nH]c2ncccc2c2cc(NS(=O)(=O)c3ccc4ccccc4c3)ccc12]

Naphthalene-2-sulfonic acid (6-oxo-5,6-dihydro-benzo[c][1,8]naphthyridin-9-yl)-amide (89)

9-Amino-5H-benzo[c][1,8]naphthyridin-6-one (15 mg, 0.07 mmol), 2-napthylsulfonyl chloride (24 mg, 0.11 mmol), and N,N-diisopropylethylamine (0.04 mL, 0.21 mmol) were suspended in dioxane (2 mL), and stirred overnight at 60° C. The reaction mixture was diluted with MeOH, filtered, and purified via prep-LC-MS to provide 88 (5 mg, 17% yield) as a solid. LC-MS (M+H=402, obsd.=402). $^1$H NMR (400 MHz, d6-DMSO): δ 11.89 (s, 1H), 11.22 (s, 1H), 8.72 (d, 1H), 8.47 (d, 2H), 8.19 (d, 1H), 8.16 (dd, 1H), 8.12 (dd, 1H), 8.08 (dd, 1H), 7.99 (dd, 1H), 7.78 (dd, 1H), 7.65 (m, 2H), 7.42 (dd, 1H), 7.32 (m, 1H).

Example 90

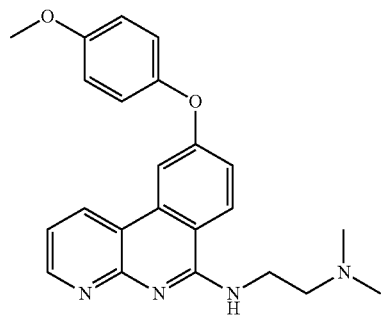

9-tert-Butoxy-5H-benzo[c][1,8]naphthyridin-6-one (90)

9-Fluoro-5H-benzo[c][1,8]naphthyridin-6-one (50 mg, 0.23 mmol), and sodium tert-butoxide (112 mg, 1.17 mmol) were suspended in dioxane (2 mL), and stirred for 15 minutes at 150° C. in the microwave. The reaction mixture was diluted with MeOH, filtered, and purified via prep-LC-MS to provide 89 (10 mg, 16% yield) as a solid. LC-MS (M+H=269, obsd.=269). $^1$H NMR (400 MHz, d6-DMSO): δ 11.91 (s, 1H), 8.82 (d, 1H), 8.49 (d, 1H), 8.23 (d, 1H), 7.98 (d, 1H), 7.30 (m, 2H), 1.43 (s, 9H).

Example 91

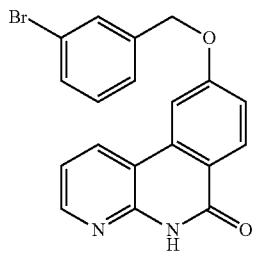 [SMILES: O=c1[nH]c2ncccc2c2cc(OCc3cccc(Br)c3)ccc12]

9-(3-Bromo-benzyloxy)-5H-benzo[c][1,8]naphthyridin-6-one (91)

9-Fluoro-5H-benzo[c][1,8]naphthyridin-6-one (40 mg, 0.19 mmol), 3-bromobenzyl alcohol (105 mg, 0.56 mmol), and potassium carbonate (129 mg, 0.93 mmol) were suspended in DMF (1 mL), and stirred for 20 minutes at 150° C. in the microwave. The reaction mixture was diluted with MeOH, filtered, and purified via prep-LC-MS to provide 90 (2 mg, 3% yield) as a solid. LC-MS (M+H=381, obsd.=381). $^1$H NMR (400 MHz, d6-DMSO): δ 11.88 (s, 1H), 8.88 (dd, 1H), 8.50 (dd, 1H), 8.26 (d, 1H), 8.10 (d, 1H), 7.77 (m, 1H), 7.56 (m, 2H), 7.38 (m, 3H), 5.38 (s, 2H).

Example 92

N'-[9-(4-Methoxy-phenoxy)-benzo[c][1,8]naphthyridin-6-yl]-N,N-dimethyl-ethane-1,2-diamine (92)

6-Chloro-9-(4-methoxy-phenoxy)-benzo[c][1,8]naphthyridine (21 mg, 0.06 mmol) and N,N-dimethylethylenediamine (8 mg, 0.09 mmol) were suspended in isopropanol (1 mL), and stirred for 4 h at 100° C. The crude reaction solution was purified directly via prep-LC-MS. The purified product was converted to the TFA salt via dissolving in MeOH, addition of TFA, and concentration on the Genevac to provide 91 (8 mg, 25% yield) as an oil. LC-MS (M+H=389, obsd.=389). $^1$H NMR (400 MHz, d6-DMSO): δ 9.23 (d, 1H), 9.13 (s, 1H), 8.76 (dd, 1H), 8.44 (d, 1H), 8.28 (d, 1H), 7.58 (m, 1H), 7.43 (dd, 2H), 7.16 (d, 2H), 7.07 (d, 2H), 4.00 (m, 2H), 3.81 (s, 3H), 3.49 (m, 2H), 2.95 (s, 6H).

Example 93

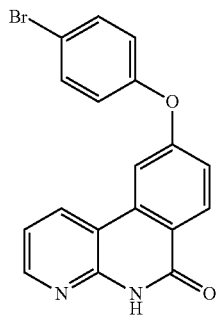 [SMILES: O=c1[nH]c2ncccc2c2cc(Oc3ccc(Br)cc3)ccc12]

9-(4-Bromo-phenoxy)-5H-benzo[c][1,8]naphthyridin-6-one (93)

9-Fluoro-5H-benzo[c][1,8]naphthyridin-6-one (40 mg, 0.19 mmol), 4-bromophenol (97 mg, 0.56 mmol), and potassium carbonate (129 mg, 0.93 mmol) were suspended in dimethylacetamide (2 mL), and stirred for 30 minutes at 200° C. in the microwave. The reaction mixture was quenched with $H_2O$. The resulting precipitate was filtered, washed with $H_2O$, and dried under vacuum to provide 92 (2 mg, 3% yield) as a tan solid. LC-MS (M+H=367, obsd.=367). $^1H$ NMR (400 MHz, d6-DMSO): δ 12.02 (s, 1H), 8.75 (dd, 1H), 8.51 (dd, 1H), 8.33 (d, 1H), 8.18 (d, 1H), 7.65 (d, 2H), 7.28 (m, 2H), 7.18 (d, 2H).

Example 94

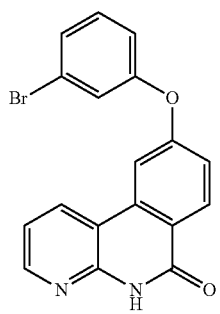

9-(3-Bromo-phenoxy)-5H-benzo[c][1,8]naphthyridin-6-one (94)

9-Fluoro-5H-benzo[c][1,8]naphthyridin-6-one (40 mg, 0.19 mmol), 3-bromophenol (97 mg, 0.56 mmol), and potassium carbonate (129 mg, 0.93 mmol) were suspended in dimethylacetamide (2 mL), and stirred for 30 minutes at 200° C. in the microwave. The reaction mixture was quenched with $H_2O$. The resulting precipitate was filtered, washed with $H_2O$, and dried under vacuum to provide 93 (2 mg, 3% yield) as a solid. LC-MS (M+H=367, obsd.=367). $^1H$ NMR (400 MHz, d6-DMSO): δ 12.01 (s, 1H), 8.78 (d, 1H), 8.52 (d, 1H), 8.35 (d, 1H), 8.22 (d, 1H), 7.43 (m, 3H), 7.29 (m, 2H), 7.18 (m, 1H).

Example 95

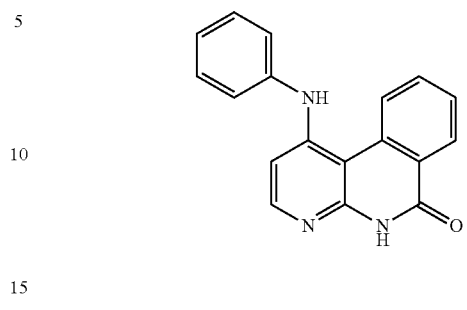

1-Phenylamino-5H-benzo[c][1,8]naphthyridin-6-one (95)

1-Chloro-5H-benzo[c][1,8]naphthyridin-6-one (50 mg, 0.22 mmol), aniline (40 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction mixture was concentrated, partitioned between $H_2O$/EtOAc, and filtered. The precipitate was washed with $H_2O$/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2 M HCl/ether, and concentration on the Genevac to provide 94 (8 mg, 11% yield) as an oil. LC-MS (M+H=288, obsd.=288). $^1H$ NMR (400 MHz, d6-DMSO): δ 9.66 (s, 1H), 8.75 (d, 1H), 8.33 (dd, 1H), 8.12 (d, 1H), 7.80 (dt, 1H), 7.66 (m, 1H), 7.40 (m, 2H), 7.28 (d, 2H), 7.18 (t, 1H), 6.97 (d, 1H).

Example 96

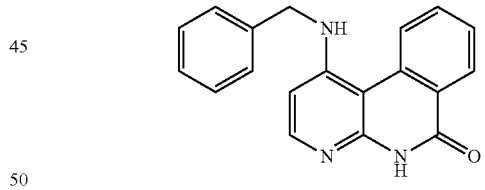

1-Benzylamino-5H-benzo[c][1,8]naphthyridin-6-one (96)

1-Chloro-5H-benzo[c][1,8]naphthyridin-6-one (50 mg, 0.22 mmol), benzylamine (46 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction mixture was cooled to room temperature, partitioned between $H_2O$/EtOAc, and filtered. The precipitate was washed with $H_2O$/EtOAc, and suspended in MeOH. 2M HCl/ether was added and the resulting mixture was filtered. The precipitate (Pd salts) was washed with MeOH, and the filtrate was concentrated to provide 95 (35 mg, 48% yield) as a tan solid. LC-MS (M+H=302, obsd.=302). ¹H NMR (400 MHz, d6-DMSO): δ 8.86 (s, 1H), 8.66 (d, 1H), 8.38 (dd, 1H), 8.04 (dd, 1H), 7.96 (dt, 1H), 7.72 (t, 1H), 7.44 (m, 2H), 7.38 (m, 2H), 7.28 (m, 1H), 6.71 (d, 1H), 4.73 (d, 2H).

Example 97

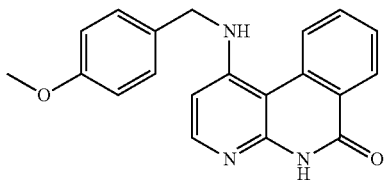 [SMILES: COc1ccc(CNc2ccnc3[nH]c(=O)c4ccccc4c23)cc1]

1-(4-Methoxy-benzylamino)-5H-benzo[c][1,8]naphthyridin-6-one (97)

1-Chloro-5H-benzo[c][1,8]naphthyridin-6-one (50 mg, 0.22 mmol), 4-methoxybenzylamine (60 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS to provide 06 (15 mg, 20% yield) as a yellow solid. LC-MS (M+H=332, obsd.=332). ¹H NMR (400 MHz, d6-DMSO): δ 9.02 (s, 1H), 8.62 (d, 1H), 8.38 (dd, 1H), 8.09 (d, 1H), 7.96 (dt, 1H), 7.70 (m, 1H), 7.40 (d, 2H), 6.92 (d, 2H), 6.77 (m, 1H), 4.69 (d, 2H), 3.73 (s, 3H).

Example 98

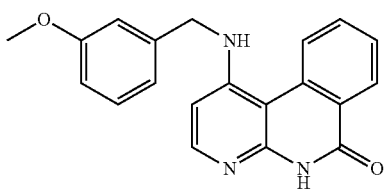 [SMILES: COc1cccc(CNc2ccnc3[nH]c(=O)c4ccccc4c23)c1]

1-(3-Methoxy-benzylamino)-5H-benzo[c][1,8]naphthyridin-6-one (98)

1-Chloro-5H-benzo[c][1,8]naphthyridin-6-one (40 mg, 0.22 mmol), 3-methoxybenzylamine (48 mg, 0.35 mmol), palladium(II) acetate (2 mg, 0.01 mmol), 2-dicyclohexylphosphino-2',4',6'-triisopropylbiphenyl (7 mg, 0.02 mmol), and sodium tert-butoxide (67 mg, 0.69 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2 M HCl, and evaporation. The resulting precipitate was triturated from CH₂Cl₂, filtered, and dried under vacuum to provide 97 (10 mg, 16% yield) as a yellow solid. LC-MS (M+H=332, obsd.=332). ¹H NMR (400 MHz, d6-DMSO): δ 9.10 (s, 1H), 8.63 (d, 1H), 8.38 (d, 1H), 8.08 (d, 1H), 7.98 (t, 1H), 7.71 (m, 2H), 7.29 (t, 1H), 7.05 (m, 2H), 6.87 (dd, 1H), 6.74 (d, 1H), 4.76 (d, 2H), 3.72 (s, 3H).

Example 99

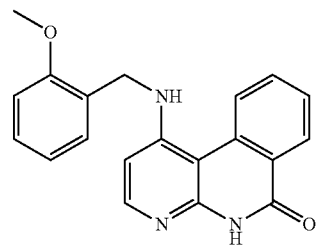 [SMILES: COc1ccccc1CNc1ccnc2[nH]c(=O)c3ccccc3c12]

1-(2-Methoxy-benzylamino)-5H-benzo[c][1,8]naphthyridin-6-one (99)

1-Chloro-5H-benzo[c][1,8]naphthyridin-6-one (40 mg, 0.22 mmol), 2-methoxybenzylamine (48 mg, 0.35 mmol), palladium(II) acetate (2 mg, 0.01 mmol), 2-dicyclohexylphosphino-2',4',6'-triisopropylbiphenyl (7 mg, 0.02 mmol), and sodium tert-butoxide (67 mg, 0.69 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2 M HCl, and evaporation. The resulting precipitate was triturated from CH₂Cl₂, filtered, and dried under vacuum to provide 98 (20 mg, 32% yield) as a yellow solid. LC-MS (M+H=332, obsd.=332). ¹H NMR (400 MHz, d6-DMSO): δ 9.08 (s, 1H), 8.61 (d, 1H), 8.38 (dd, 1H), 8.09 (d, 1H), 7.97 (dt, 1H), 7.71 (t, 1H), 7.32 (m, 2H), 7.10 (d, 1H), 6.92 (dt, 1H), 6.72 (d, 1H), 4.68 (d, 2H), 3.93 (s, 3H).

Example 100

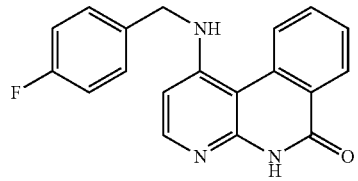 [SMILES: O=c1[nH]c2nccc(NCc3ccc(F)cc3)c2c2ccccc12]

1-(4-Fluoro-benzylamino)-5H-benzo[c][1,8]naphthyridin-6-one (100)

1-Chloro-5H-benzo[c][1,8]naphthyridin-6-one (40 mg, 0.22 mmol), 4-fluorobenzylamine (43 mg, 0.35 mmol), palladium(II) acetate (2 mg, 0.01 mmol), 2-dicyclohexylphosphino-2',4',6'-triisopropylbiphenyl (7 mg, 0.02 mmol), and sodium tert-butoxide (67 mg, 0.69 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2 M HCl, and evaporation. The resulting precipitate was triturated from CH₂Cl₂, filtered, and dried under vacuum to provide 99 (13 mg, 22% yield) as a yellow solid. LC-MS (M+H=320, obsd.=320). ¹H NMR (400 MHz, d6-DMSO): δ 8.88 (s, 1H), 8.66 (d, 1H), 8.38 (dd, 1H), 8.05 (d, 1H), 7.96 (dt, 1H), 7.71 (m, 2H), 7.50 (m, 2H), 7.20 (m, 2H), 6.71 (d, 1H), 4.72 (d, 2H).

Example 101

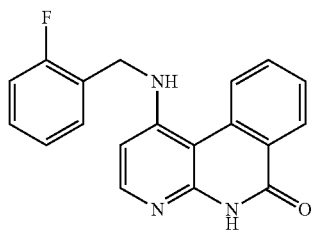 [SMILES: O=c1[nH]c2nccc(NCc3ccccc3F)c2c2ccccc12]

1-(4-Fluoro-benzylamino)-5H-benzo[c][1,8]naphthyridin-6-one (101)

1-Chloro-5H-benzo[c][1,8]naphthyridin-6-one (40 mg, 0.22 mmol), 2-fluorobenzylamine (43 mg, 0.35 mmol), palladium(II) acetate (2 mg, 0.01 mmol), 2-dicyclohexylphosphino-2',4',6'-triisopropylbiphenyl (7 mg, 0.02 mmol), and sodium tert-butoxide (67 mg, 0.69 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2 M HCl, and evaporation. The resulting precipitate was triturated from CH₂Cl₂, filtered, and dried under vacuum to provide 100 (28 mg, 48% yield) as a yellow solid. LC-MS (M+H=320, obsd.=320). ¹H NMR (400 MHz, d6-DMSO): δ 9.04 (s, 1H), 8.61 (d, 1H), 8.38 (dd, 1H), 8.12 (d, 1H), 7.95 (dt, 1H), 7.70 (m, 2H), 7.40 (m, 2H), 7.28 (m, 1H), 7.19 (dt, 1H), 6.79 (d, 1H), 4.81 (d, 2H).

Example 102

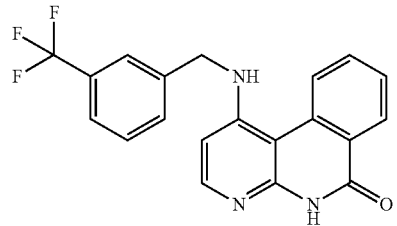 [SMILES: O=c1[nH]c2nccc(NCc3cccc(C(F)(F)F)c3)c2c2ccccc12]

1-(3-Trifluoromethyl-benzylamino)-5H-benzo[c][1,8]naphthyridin-6-one (102)

1-Chloro-5H-benzo[c][1,8]naphthyridin-6-one (40 mg, 0.22 mmol), 3-trifluoromethylbenzylamine (61 mg, 0.35 mmol), palladium(II) acetate (2 mg, 0.01 mmol), 2-dicyclohexylphosphino-2',4',6'-triisopropylbiphenyl (7 mg, 0.02 mmol), and sodium tert-butoxide (67 mg, 0.69 mmol) were suspended in dioxane (2 mL), and stirred overnight at 100° C. The reaction mixture was concentrated, partitioned between H₂O/EtOAc, and filtered. The precipitate was washed with H₂O/EtOAc, and suspended in MeOH. 2M HCl/ether was added and the resulting mixture was filtered. The precipitate (Pd salts) was washed with MeOH, and the filtrate was concentrated. The crude product was purified via prep-LC-MS. The purified product was converted to the HCl salt via dissolving in MeOH, addition of 2M HCl/ether, and concentration on the Genevac to provide 101 (9 mg, 13% yield) as an oil. LC-MS (M+H=370, obsd.=370). ¹H NMR (400 MHz, d6-DMSO): δ 8.91 (s, 1H), 8.68 (d, 1H), 8.39 (d, 1H), 8.08 (d, 1H), 7.96 (dt, 1H), 7.85 (s, 1H), 7.70 (m, 4H), 6.73 (d, 1H), 4.88 (d, 2H).

Example 103

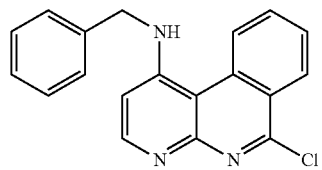 [SMILES: Clc1nc2nccc(NCc3ccccc3)c2c2ccccc12]

Benzyl-(6-chloro-benzo[c][1,8]naphthyridin-1-yl)-amine (103)

1-Benzylamino-5H-benzo[c][1,8]naphthyridin-6-one (18 mg, 0.06 mmol) was suspended in POCl₃ (2 mL), and stirred overnight at 120° C. The reaction solution was concentrated, and the resulting material was triturated with H₂O. The resulting precipitate was filtered, washed with H₂O, and dried under vacuum to provide 102 (8 mg, 38% yield) as a yellow solid. LC-MS (M+H=320, obsd.=320). ¹H NMR (400 MHz, d6-DMSO): δ 9.71 (s, 1H), 9.08 (m, 1H), 8.64 (d, 1H), 8.25 (d, 1H), 8.05 (m, 1H), 7.70 (m, 1H), 7.50 (m, 2H), 7.39 (m, 2H), 7.31 (m, 1H), 7.04 (m, 1H), 4.90 (d, 2H).

Example 104

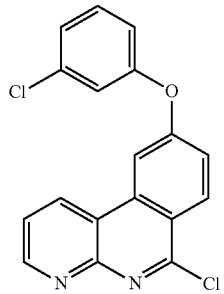 [SMILES: Clc1cccc(Oc2ccc3c(Cl)nc4ncccc4c3c2)c1]

6-Chloro-9-(3-chloro-phenoxy)-benzo[c][1,8]naphthyridine (104)

9-(3-Chloro-phenoxy)-5H-benzo[c][1,8]naphthyridin-6-one (36 mg, 0.11 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 103 (36 mg, 95% yield) as a tan solid. LC-MS (M+H=341, obsd.=341). $^1$H NMR (400 MHz, d6-DMSO): δ 9.28 (dd, 1H), 9.06 (dd, 1H), 8.63 (d, 1H), 8.53 (d, 1H), 7.79 (dd, 1H), 7.62 (dd, 1H), 7.52 (m, 1H), 7.36 (m, 2H), 7.21 (m, 1H).

Example 105

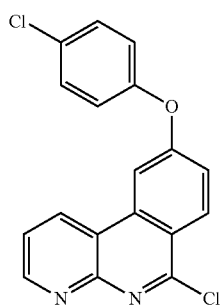 [SMILES: Clc1ccc(Oc2ccc3c(Cl)nc4ncccc4c3c2)cc1]

6-Chloro-9-(4-chloro-phenoxy)-benzo[c][1,8]naphthyridine (105)

9-(4-Chloro-phenoxy)-5H-benzo[c][1,8]naphthyridin-6-one (47 mg, 0.15 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 104 (43 mg, 87% yield) as a tan solid. LC-MS (M+H=341, obsd.=341). $^1$H NMR (400 MHz, d6-DMSO): δ 9.25 (dd, 1H), 9.06 (dd, 1H), 8.58 (d, 1H), 8.52 (d, 1H), 7.78 (dd, 1H), 7.59 (dd, 1H), 7.56 (d, 2H), 7.29 (d, 2H).

Example 106

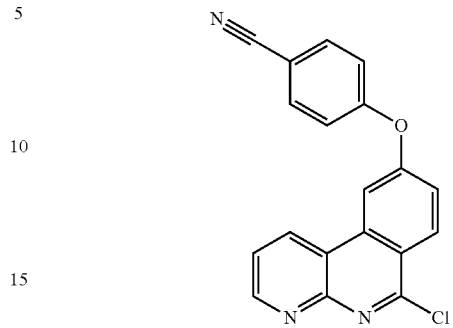

6-Chloro-9-(4-cyano-phenoxy)-benzo[c][1,8]naphthyridine (106)

9-(4-Cyano-phenoxy)-5H-benzo[c][1,8]naphthyridin-6-one (37 mg, 0.12 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 105 (28 mg, 71% yield) as a tan solid. LC-MS (M+H=332, obsd.=332). $^1$H NMR (400 MHz, d6-DMSO): δ 9.29 (dd, 1H), 9.08 (dd, 1H), 8.72 (d, 1H), 8.58 (d, 1H), 7.96 (d, 2H), 7.79 (dd, 1H), 7.71 (d, 1H), 7.38 (d, 2H).

Example 107

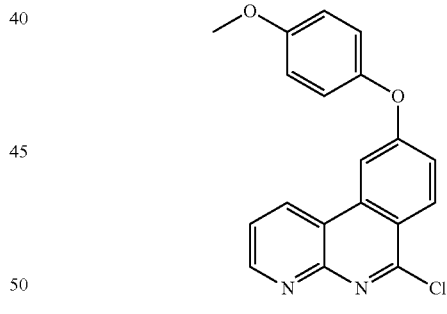

6-Chloro-9-(4-methoxy-phenoxy)-benzo[c][1,8]naphthyridine (107)

9-(4-Methoxy-phenoxy)-5H-benzo[c][1,8]naphthyridin-6-one (18 mg, 0.06 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 106 (13 mg, 68% yield) as a tan solid. LC-MS (M+H=337, obsd.=337). $^1$H NMR (400 MHz, d6-DMSO): δ 9.16 (dd, 1H), 9.05 (dd, 1H), 8.49 (d, 1H), 8.42 (d, 1H), 7.77 (dd, 1H), 7.48 (dd, 1H), 7.22 (d, 2H), 7.09 (d, 2H), 3.81 (s, 3H).

Example 108

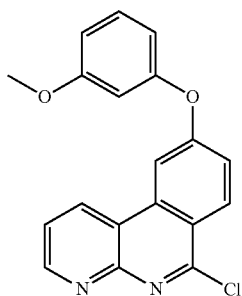 [SMILES: COc1cccc(Oc2ccc3c(Cl)nc4ncccc4c3c2)c1]

6-Chloro-9-(3-methoxy-phenoxy)-benzo[c][1,8]naphthyridine (108)

9-(3-Methoxy-phenoxy)-5H-benzo[c][1,8]naphthyridin-6-one (18 mg, 0.06 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 107 (13 mg, 68% yield) as a tan solid. LC-MS (M+H=337, obsd.=337). $^1$H NMR (400 MHz, d6-DMSO): δ 9.22 (dd, 1H), 9.05 (dd, 1H), 8.54 (d, 1H), 8.52 (d, 1H), 7.78 (dd, 1H), 7.53 (dd, 1H), 7.41 (t, 1H), 6.89 (dd, 1H), 6.84 (dd, 1H), 6.77 (dd, 1H), 3.78 (s, 3H).

Example 109

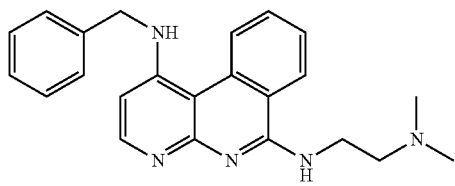 [SMILES: CN(C)CCNc1nc2nccc(NCc3ccccc3)c2c2ccccc12]

N-1-Benzyl-N-6-(2-dimethylamino-ethyl)-benzo[c][1,8]naphthyridine-1,6-diamine (109)

Benzyl-(6-chloro-benzo[c][1,8]naphthyridin-1-yl)-amine (5 mg, 0.02 mmol), and N,N-dimethylethan-1,2-diamine (4 mg, 0.05 mmol) were dissolved in isopropanol (2 mL), and stirred overnight at 110° C. The crude product was purified directly via prep-LC-MS. The purified product was converted to the TFA salt via dissolving in MeOH, addition of TFA, and concentration on the Genevac to provide 108 (3 mg, 27% yield) as an oil. LC-MS (M+H=372, obsd.=372). $^1$H NMR (400 MHz, d6-DMSO): δ 9.19 (t, 1H), 9.12 (t, 1H), 8.82 (d, 1H), 8.52 (d, 1H), 8.12 (m, 1H), 8.00 (m, 1H), 7.82 (t, 1H), 7.47 (d, 2H), 7.39 (t, 2H), 7.30 (m, 1H), 6.72 (d, 1H), 4.81 (d, 2H), 3.95 (m, 2H), 2.90 (m, 2H), 2.82 (s, 6H).

Example 110

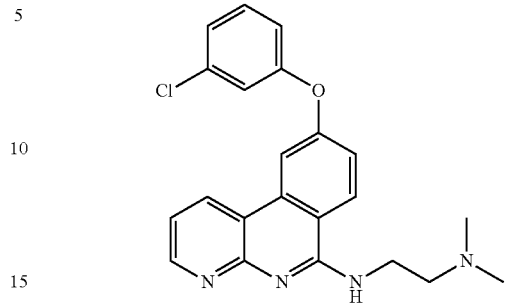

N'-[9-(3-Chloro-phenoxy)-benzo[c][1,8]naphthyridin-6-yl]-N,N-dimethyl-ethane-1,2-diamine (110)

6-Chloro-9-(3-chloro-phenoxy)-benzo[c][1,8]naphthyridine (25 mg, 0.07 mmol), and N,N-dimethylethan-1,2-diamine (19 mg, 0.22 mmol) were dissolved in isopropanol (2 mL), and stirred overnight at 110° C. The crude product was purified directly via prep-LC-MS. The purified product was converted to the TFA salt via dissolving in MeOH, addition of TFA, and concentration on the Genevac to provide 109 (39 mg, 86% yield) as an oil. LC-MS (M+H=393, obsd.=393). $^1$H NMR (400 MHz, d6-DMSO): δ 10.48 (s, 1H), 9.82 (t, 1H), 9.43 (d, 1H), 8.82 (d, 1H), 8.74 (d, 1H), 8.44 (d, 1H), 7.67 (dd, 1H), 7.57 (dd, 1H), 7.51 (t, 1H), 7.34 (dd, 1H), 7.28 (d, 1H), 7.14 (dd, 1H), 4.05 (m, 2H), 3.55 (m, 2H), 2.92 (s, 6H).

Example 111

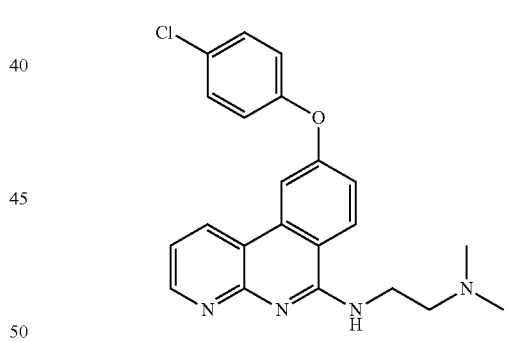

N'-[9-(4-Chloro-phenoxy)-benzo[c][1,8]naphthyridin-6-yl]-N,N-dimethyl-ethane-1,2-diamine (111)

6-Chloro-9-(4-chloro-phenoxy)-benzo[c][1,8]naphthyridine (25 mg, 0.07 mmol), and N,N-dimethylethan-1,2-diamine (19 mg, 0.22 mmol) were dissolved in isopropanol (2 mL), and stirred overnight at 110° C. The crude product was purified directly via prep-LC-MS. The purified product was converted to the TFA salt via dissolving in MeOH, addition of TFA, and concentration on the Genevac to provide 110 (25 mg, 55% yield) as an oil. LC-MS (M+H=393, obsd.=393). $^1$H NMR (400 MHz, d6-DMSO): δ 10.38 (s, 1H), 9.72 (t, 1H), 9.43 (dd, 1H), 8.76 (d, 2H), 8.41 (d, 1H), 7.66 (dd, 1H), 7.54 (m, 3H), 7.22 (d, 2H), 4.05 (m, 2H), 3.55 (m, 2H), 2.91 (s, 6H).

Example 112

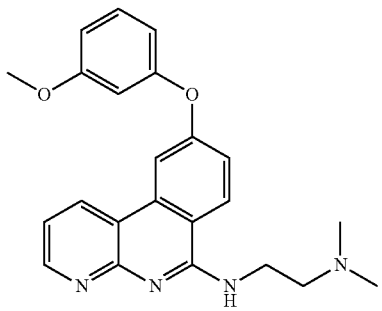

N'-[9-(3-Methoxy-phenoxy)-benzo[c][1,8]naphthyridin-6-yl]-N,N-dimethyl-ethane-1,2-diamine (112)

6-Chloro-9-(3-methoxy-phenoxy)-benzo[c][1,8]naphthyridine (10 mg, 0.03 mmol), and N,N-dimethylethan-1,2-diamine (8 mg, 0.09 mmol) were dissolved in isopropanol (2 mL), and stirred overnight at 110° C. The crude product was purified directly via prep-LC-MS. The purified product was converted to the TFA salt via dissolving in MeOH, addition of TFA, and concentration on the Genevac to provide 111 (18 mg, 98% yield) as an oil. LC-MS (M+H=389, obsd.=389). $^1$H NMR (400 MHz, d6-DMSO): δ 10.40 (s, 1H), 9.73 (t, 1H), 9.42 (d, 1H), 8.75 (d, 1H), 8.41 (d, 1H), 7.67 (dd, 1H), 7.50 (dd, 1H), 7.39 (t, 1H), 6.88 (dd, 1H), 6.77 (dd, 1H), 6.74 (dd, 1H), 4.05 (m, 2H), 3.77 (s, 3H), 3.54 (m, 2H), 2.90 (s, 6H).

Example 113

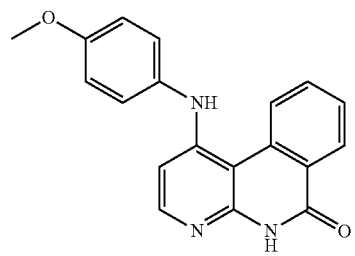 [SMILES: COc1ccc(Nc2ccnc3[nH]c(=O)c4ccccc4c23)cc1]

1-(4-Methoxy-phenylamino)-5H-benzo[c][1,8]naphthyridin-6-one (113)

1-Chloro-5H-benzo[c][1,8]naphthyridin-6-one (50 mg, 0.22 mmol), 4-methoxyaniline (53 mg, 0.43 mmol), palladium(II) acetate (2 mg, 0.01 mmol), 2-dicyclohexylphosphino-2',4',6'-triisopropylbiphenyl (10 mg, 0.02 mmol), and sodium ted-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 112 (16 mg, 21% yield) as an oil. LC-MS (M+H=318, obsd.=318). $^1$H NMR (400 MHz, d6-DMSO): δ 10.02 (s, 1H), 8.71 (d, 1H), 8.35 (dd, 1H), 8.04 (d, 1H), 7.88 (dt, 1H), 7.70 (m, 1H), 7.30 (d, 2H), 7.06 (d, 2H), 6.74 (d, 1H), 3.78 (s, 3H).

Example 114

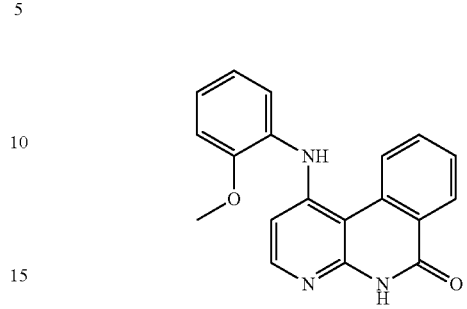

1-(2-Methoxy-phenylamino)-5H-benzo[c][1,8]naphthyridin-6-one (114)

1-Chloro-5H-benzo[c][1,8]naphthyridin-6-one (50 mg, 0.22 mmol), 2-methoxyaniline (53 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 113 (38 mg, 50% yield) as an oil. LC-MS (M+H=318, obsd.=318). $^1$H NMR (400 MHz, d6-DMSO): δ 9.71 (s, 1H), 8.68 (d, 1H), 8.36 (d, 1H), 8.05 (d, 1H), 7.86 (t, 1H), 7.69 (t, 1H), 7.34 (m, 1H), 7.24 (d, 2H), 7.04 (t, 1H), 6.46 (d, 1H), 3.83 (s, 3H).

Example 115

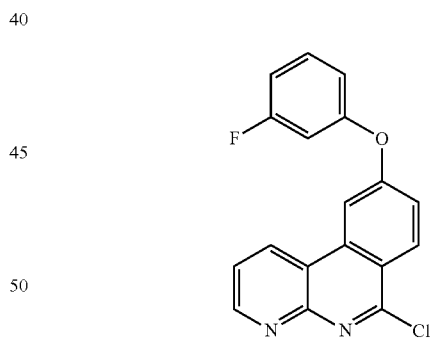

6-Chloro-9-(3-fluoro-phenoxy)-benzo[c][1,8]naphthyridine (115)

9-(3-Fluoro-phenoxy)-5H-benzo[c][1,8]naphthyridin-6-one (40 mg, 0.13 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 114 (38 mg, 90% yield) as a tan solid. LC-MS (M+H=325, obsd.=325). $^1$H NMR (400 MHz, d6-DMSO): δ 9.26 (dd, 1H), 9.05 (d, 1H), 8.61 (d, 1H), 8.53 (d, 1H), 7.77 (dd, 1H), 7.63 (dd, 1H), 7.54 (m, 1H), 7.16 (m, 2H), 7.08 (dd, 1H).

Example 116

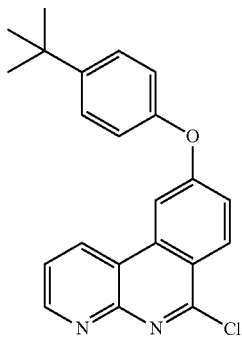 [SMILES: CC(C)(C)c1ccc(Oc2ccc3c(Cl)nc4ncccc4c3c2)cc1]

6-Chloro-9-(4-tert-butyl-phenoxy)-benzo[c][1,8]naphthyridine (116)

9-(4-tert-Butyl-phenoxy)-5H-benzo[c][1,8]naphthyridin-6-one (25 mg, 0.07 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 115 (24 mg, 91% yield) as a tan solid. LC-MS (M+H=363, obsd.=363). $^1$H NMR (400 MHz, d6-DMSO): δ 9.25 (dd, 1H), 9.05 (d, 1H), 8.57 (d, 1H), 8.50 (d, 1H), 7.79 (dd, 1H), 7.50 (m, 3H), 7.17 (d, 2H), 1.30 (s, 9H).

Example 117

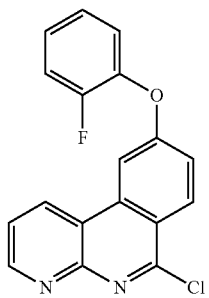 [SMILES: Fc1ccccc1Oc1ccc2c(Cl)nc3ncccc3c2c1]

6-Chloro-9-(2-fluoro-phenoxy)-benzo[c][1,8]naphthyridine (117)

9-(2-Fluoro-phenoxy)-5H-benzo[c][1,8]naphthyridin-6-one (15 mg, 0.05 mmol) was suspended in POCl$_3$ (2 mL), and stirred overnight at 120° C. The reaction solution was concentrated, and the resulting material was triturated with H$_2$O. The resulting precipitate was filtered, washed with H$_2$O, and dried under vacuum to provide 116 (11 mg, 69% yield) as a tan solid. LC-MS (M+H=325, obsd.=325). $^1$H NMR (400 MHz, d6-DMSO): δ 9.23 (dd, 1H), 9.05 (dd, 1H), 8.54 (d, 1H), 8.51 (d, 1H), 7.78 (dd, 1H), 7.48 (m, 5H).

Example 118

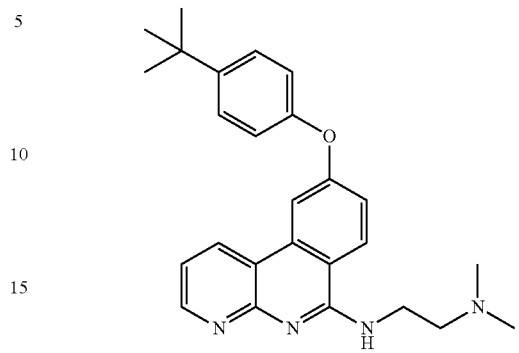

N'-[9-(4-tert-Butyl-phenoxy)-benzo[c][1,8]naphthyridin-6-yl]-N,N-dimethyl-ethane-1,2-diamine (118)

6-Chloro-9-(4-tert-butyl-phenoxy)-benzo[c][1,8]naphthyridine (15 mg, 0.04 mmol), and N,N-dimethylethan-1,2-diamine (11 mg, 0.12 mmol) were dissolved in isopropanol (2 mL), and stirred overnight at 110° C. The crude product was purified directly via prep-LC-MS. The purified product was converted to the TFA salt via dissolving in MeOH, addition of TFA, and concentration on the Genevac to provide 117 (5 mg, 19% yield) as a solid. LC-MS (M+H=415, obsd.=415). $^1$H NMR (400 MHz, d6-DMSO): δ 9.78 (t, 1H), 9.43 (d, 1H), 8.81 (d, 1H), 8.74 (d, 1H), 8.46 (d, 1H), 7.68 (dd, 1H), 7.51 (d, 2H), 7.43 (dd, 1H), 7.11 (d, 2H), 4.05 (m, 2H), 3.55 (m, 2H), 2.81 (s, 6H), 1.32 (s, 9H).

Example 119

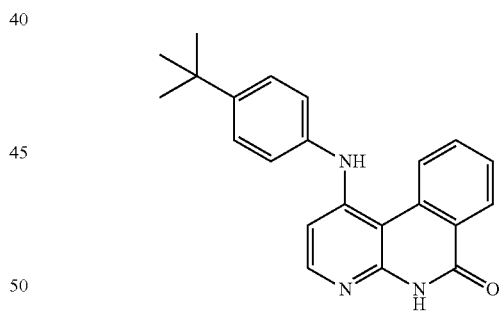

1-(4-tert-Butyl-phenylamino)-5H-benzo[c][1,8]naphthyridin-6-one (119)

1-Chloro-5H-benzo[c][1,8]naphthyridin-6-one (50 mg, 0.22 mmol), 4-tert-butylaniline (65 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 118 (7 mg, 9% yield)

as a dark solid. LC-MS (M+H=344, obsd.=344). $^1$H NMR (400 MHz, d6-DMSO): δ 9.65 (s, 1H), 8.77 (d, 1H), 8.36 (d, 1H), 8.07 (d, 1H), 7.82 (t, 1H), 7.68 (m, 2H), 7.45 (d, 2H), 7.25 (d, 2H), 6.93 (d, 1H), 1.25 (s, 9H).

Example 120

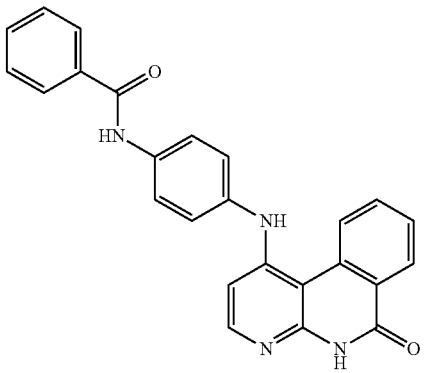 [SMILES: O=C(Nc1ccc(Nc2ccnc3[nH]c(=O)c4ccccc4c23)cc1)c1ccccc1]

N-[4-(6-Oxo-5,6-dihydro-benzo[c][1,8]naphthyridin-1-ylamino)-phenyl]-benzamide (120)

1-Chloro-5H-benzo[c][1,8]naphthyridin-6-one (50 mg, 0.22 mmol), 4'-aminobenzanilide (92 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 119 (22 mg, 23% yield) as a dark solid. LC-MS (M+H=407, obsd.=407). $^1$H NMR (400 MHz, d6-DMSO): δ 10.33 (s, 1H), 9.52 (s, 1H), 8.78 (d, 1H), 8.36 (d, 1H), 8.09 (d, 1H), 7.96 (d, 2H), 7.81 (d, 2H), 7.55 (m, 5H), 7.26 (d, 2H), 6.93 (d, 1H).

Example 121

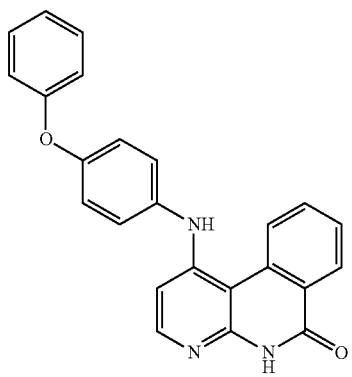 [SMILES: O=c1[nH]c2nccc(Nc3ccc(Oc4ccccc4)cc3)c2c2ccccc12]

1-(4-Phenoxy-phenylamino)-5H-benzo[c][1,8]naphthyridin-6-one (121)

1-Chloro-5H-benzo[c][1,8]naphthyridin-6-one (50 mg, 0.22 mmol), 4-phenoxyaniline (80 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 120 (45 mg, 50% yield) as a dark solid. LC-MS (M+H=380, obsd.=380). $^1$H NMR (400 MHz, d6-DMSO): δ 10.20 (s, 1H), 8.66 (d, 1H), 8.35 (d, 1H), 8.14 (d, 1H), 7.84 (t, 1H), 7.68 (m, 2H), 7.40 (m, 4H), 7.15 (m, 5H), 6.92 (d, 1H).

Example 122

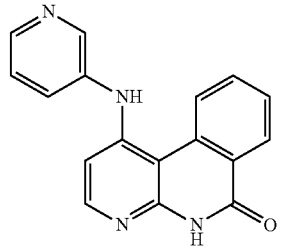 [SMILES: O=c1[nH]c2nccc(Nc3cccnc3)c2c2ccccc12]

1-(Pyridin-3-ylamino)-5H-benzo[c][1,8]naphthyridin-6-one (122)

1-Chloro-5H-benzo[c][1,8]naphthyridin-6-one (50 mg, 0.22 mmol), 3-aminopyridine (41 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction solution was concentrated, diluted with MeOH/2M HCl/ether, and filtered. The crude product was purified directly via prep-LC-MS. The purified product was converted to the HCl salt via dissolving in MeOH, addition of 2M HCl/ether, and concentration on the Genevac to provide 121 (14 mg, 20% yield) as a tan solid. LC-MS (M+H=289, obsd.=289). $^1$H NMR (400 MHz, d6-DMSO): δ 12.13 (s, 1H), 10.02 (s, 1H), 8.70 (d, 1H), 8.52 (d, 1H), 8.36 (m, 3H), 8.08 (dd, 1H), 7.83 (dd, 1H), 7.72 (dt, 1H), 7.66 (dt, 1H), 7.23 (d, 1H).

Example 123

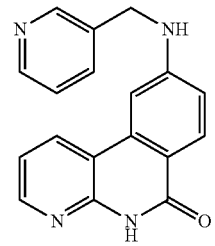 [SMILES: O=c1[nH]c2ncccc2c2cc(NCc3cccnc3)ccc12]

9-[(Pyridin-3-ylmethyl)-amino]-5H-benzo[c][1,8]naphthyridin-6-one (123)

9-Chloro-5H-benzo[c][1,8]naphthyridin-6-one (50 mg, 0.22 mmol), 1-pyridin-3-ylmethanamine (47 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction mixture was diluted with MeOH, filtered through a membrane, and purified via prep-LC-MS to provide 122 (8 mg, 12% yield) as a tan solid. LC-MS (M+H=303, obsd.=303). $^1$H NMR (400 MHz, d6-DMSO): δ 11.50 (s, 1H), 8.68 (d, 1H), 8.61 (dd, 1H), 8.47 (dd, 1H), 8.41 (dd, 1H), 8.02 (d, 1H), 7.83 (dt, 1H), 7.41 (dt, 1H), 7.38 (dd, 1H), 7.26 (m, 2H), 6.98 (d, 1H), 4.55 (d, 2H).

Example 124

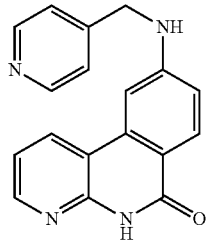 [SMILES: O=c1[nH]c2ncccc2c2cc(NCc3ccncc3)ccc12]

9-[(Pyridin-4-ylmethyl)-amino]-5H-benzo[c][1,8]naphthyridin-6-one (124)

9-Chloro-5H-benzo[c][1,8]naphthyridin-6-one (50 mg, 0.22 mmol), 1-pyridin-4-ylmethanamine (47 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (83 mg, 0.87 mmol) were suspended in dioxane (2 mL), and stirred overnight at 100° C. The reaction mixture was diluted with MeOH, filtered through a membrane, and purified via prep-LC-MS to provide 124 (10 mg, 15% yield) as a tan solid. LC-MS (M+H=303, obsd.=303). $^1$H NMR (400 MHz, d6-DMSO): δ 11.50 (s, 1H), 8.52 (m, 3H), 8.41 (d, 1H), 8.01 (dd, 1H), 7.42 (d, 2H), 7.35 (m, 2H), 7.24 (m, 1H), 6.95 (d, 1H), 4.58 (d, 2H).

Example 125

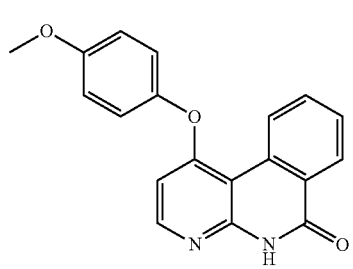 [SMILES: COc1ccc(Oc2ccnc3[nH]c(=O)c4ccccc4c23)cc1]

1-(4-Methoxy-phenoxy)-5H-benzo[c][1,8]naphthyridin-6-one (125)

1-Chloro-5H-benzo[c][1,8]naphthyridin-6-one (30 mg, 0.13 mmol), 4-methoxyphenol (48 mg, 0.39 mmol), and potassium carbonate (90 mg, 0.65 mmol) were suspended in DMF (2 mL), and stirred overnight at 100° C. The reaction mixture was diluted with H$_2$O, and extracted with EtOAc. The organic extracts were washed with brine, dried over MgSO$_4$, filtered, and concentrated. The crude product was purified via Biotage eluting with a gradient of 25 to 75% EtOAc in hexanes to provide 124 (3 mg, 7% yield) as a solid. LC-MS (M+H=319, obsd.=319). $^1$H NMR (400 MHz, d6-DMSO): δ 12.11 (s, 1H), 9.09 (d, 1H), 8.41 (dd, 1H), 8.27 (d, 1H), 7.89 (dt, 1H), 7.71 (t, 1H), 7.29 (d, 2H), 7.10 (d, 2H), 6.48 (d, 1H), 3.80 (s, 3H).

Example 126

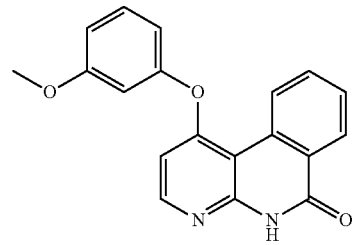 [SMILES: COc1cccc(Oc2ccnc3[nH]c(=O)c4ccccc4c23)c1]

1-(3-Methoxy-phenoxy)-5H-benzo[c][1,8]naphthyridin-6-one (126)

1-Chloro-5H-benzo[c][1,8]naphthyridin-6-one (30 mg, 0.13 mmol), 3-methoxyphenol (48 mg, 0.39 mmol), and potassium carbonate (90 mg, 0.65 mmol) were suspended in DMF (2 mL), and stirred overnight at 100° C. The reaction mixture was diluted with H$_2$O, and extracted with EtOAc. The organic extracts were washed with brine, dried over MgSO$_4$, filtered, and concentrated. The crude product was purified via Biotage eluting with a gradient of 25 to 75% EtOAc in hexanes to provide 125 (4 mg, 10% yield) as a solid. LC-MS (M+H=319, obsd.=319). $^1$H NMR (400 MHz, d6-DMSO): δ 12.14 (s, 1H), 9.04 (d, 1H), 8.42 (dd, 1H), 8.30 (d, 1H), 7.87 (dt, 1H), 7.71 (t, 1H), 7.45 (t, 1H), 6.94 (m, 2H), 6.87 (dd, 1H), 6.58 (d, 1H), 3.79 (s, 3H).

Example 127

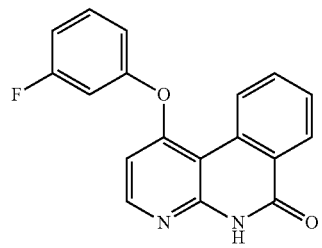 [SMILES: O=c1[nH]c2nccc(Oc3cccc(F)c3)c2c2ccccc12]

1-(3-Fluoro-phenoxy)-5H-benzo[a-1,8]naphthyridin-6-one (127)

1-Chloro-5H-benzo[c][1,8]naphthyridin-6-one (30 mg, 0.13 mmol), 3-fluorophenol (44 mg, 0.39 mmol), and potassium carbonate (90 mg, 0.65 mmol) were suspended in DMF (2 mL), and stirred overnight at 100° C. The reaction mixture was diluted with H₂O, and extracted with EtOAc. The organic extracts were washed with brine, dried over MgSO₄, filtered, and concentrated. The crude product was purified via Biotage eluting with a gradient of 25 to 75% EtOAc in hexanes to provide 126 (4 mg, 10% yield) as a solid. LC-MS (M+H=307, obsd.=307). ¹H NMR (400 MHz, d6-DMSO): δ 12.17 (s, 1H), 9.00 (d, 1H), 8.43 (dd, 1H), 8.33 (d, 1H), 7.88 (dt, 1H), 7.71 (t, 1H), 7.58 (t, 1H), 7.36 (dt, 1H), 7.20 (m, 2H), 6.64 (d, 1H).

Example 128

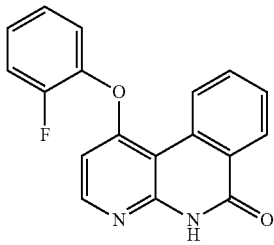 [SMILES: O=c1[nH]c2nccc(Oc3ccccc3F)c2c2ccccc12]

1-(2-Fluoro-phenoxy)-5H-benzo[c][1,8]naphthyridin-6-one (128)

1-Chloro-5H-benzo[c][1,8]naphthyridin-6-one (30 mg, 0.13 mmol), 2-fluorophenol (44 mg, 0.39 mmol), and potassium carbonate (90 mg, 0.65 mmol) were suspended in DMF (2 mL), and stirred overnight at 100° C. The reaction mixture was diluted with H₂O, and extracted with EtOAc. The organic extracts were washed with brine, dried over MgSO₄, filtered, and concentrated. The crude product was purified via Biotage eluting with a gradient of 25 to 75% EtOAc in hexanes to provide 127 (2 mg, 5% yield) as a solid. LC-MS (M+H=307, obsd.=307). ¹H NMR (400 MHz, d6-DMSO): δ 12.18 (s, 1H), 9.05 (d, 1H), 8.42 (dd, 1H), 8.31 (d, 1H), 7.90 (m, 2H), 7.72 (t, 1H), 7.55 (m, 2H), 7.42 (m, 2H).

Example 129

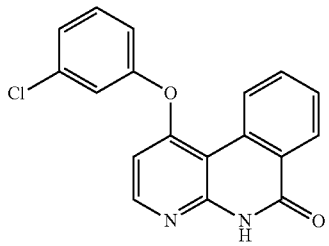 [SMILES: O=c1[nH]c2nccc(Oc3cccc(Cl)c3)c2c2ccccc12]

1-(3-Chloro-phenoxy)-5H-benzo[c][1,8]naphthyridin-6-one (129)

1-Chloro-5H-benzo[c][1,8]naphthyridin-6-one (30 mg, 0.13 mmol), 3-chlorophenol (50 mg, 0.39 mmol), and potassium carbonate (90 mg, 0.65 mmol) were suspended in DMF (2 mL), and stirred overnight at 100° C. The reaction mixture was diluted with H₂O, and extracted with EtOAc. The organic extracts were washed with brine, dried over MgSO₄, filtered, and concentrated. The crude product was purified via Biotage eluting with a gradient of 25 to 75% EtOAc in hexanes to provide 128 (5 mg, 12% yield) as a solid. LC-MS (M+H=323, obsd.=323). ¹H NMR (400 MHz, d6-DMSO): δ 12.18 (s, 1H), 8.98 (d, 1H), 8.41 (dd, 1H), 8.33 (d, 1H), 7.87 (dt, 1H), 7.71 (t, 1H), 7.54 (m, 2H), 7.42 (dd, 1H), 7.33 (dd, 1H), 6.63 (d, 1H).

Example 130

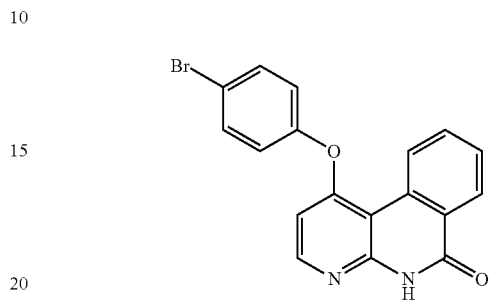

1-(4-Bromo-phenoxy)-5H-benzo[c][1,8]naphthyridin-6-one (130)

1-Chloro-5H-benzo[c][1,8]naphthyridin-6-one (30 mg, 0.13 mmol), 4-bromophenol (68 mg, 0.39 mmol), and potassium carbonate (90 mg, 0.65 mmol) were suspended in DMF (2 mL), and stirred overnight at 100° C. The reaction mixture was diluted with H₂O, and extracted with EtOAc. The organic extracts were washed with brine, dried over MgSO₄, filtered, and concentrated. The crude product was purified via Biotage eluting with a gradient of 25 to 75% EtOAc in hexanes to provide 129 (5 mg, 11% yield) as a solid. LC-MS (M+H=367, obsd.=367). ¹H NMR (400 MHz, d6-DMSO): δ 12.17 (s, 1H), 8.99 (d, 1H), 8.41 (dd, 1H), 8.31 (d, 1H), 7.88 (dt, 1H), 7.72 (m, 3H), 7.33 (d, 2H), 6.60 (d, 1H).

Example 131

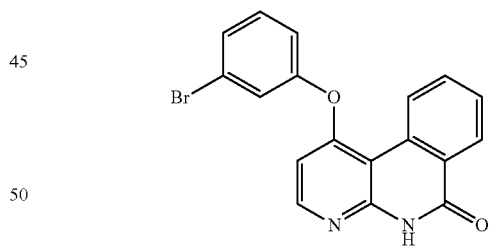

1-(3-Bromo-phenoxy)-5H-benzo[c][1,8]naphthyridin-6-one (131)

1-Chloro-5H-benzo[c][1,8]naphthyridin-6-one (30 mg, 0.13 mmol), 3-bromophenol (68 mg, 0.39 mmol), and potassium carbonate (90 mg, 0.65 mmol) were suspended in DMF (2 mL), and stirred overnight at 100° C. The reaction mixture was diluted with H₂O, and extracted with EtOAc. The organic extracts were washed with brine, dried over MgSO₄, filtered, and concentrated. The crude product was purified via Biotage eluting with a gradient of 25 to 75% EtOAc in hexanes to provide 130 (5 mg, 11% yield) as a solid. LC-MS (M+H=367, obsd.=367). ¹H NMR (400 MHz, d6-DMSO): δ 12.15 (s, 1H), 8.99 (d, 1H), 8.42 (dd, 1H), 8.33 (d, 1H), 7.87 (dt, 1H), 7.71 (t, 1H), 7.66 (d, 1H), 7.56 (dd, 1H), 7.51 (t, 1H), 7.38 (dd, 1H), 6.63 (d, 1H).

Example 132

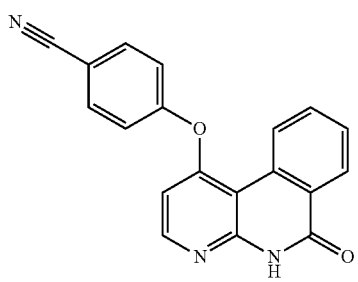 [SMILES: N#Cc1ccc(Oc2ccnc3[nH]c(=O)c4ccccc4c23)cc1]

1-(4-Cyano-phenoxy)-5H-benzo[c][1,8]naphthyridin-6-one (132)

1-Chloro-5H-benzo[c][1,8]naphthyridin-6-one (30 mg, 0.13 mmol), 4-cyanophenol (47 mg, 0.39 mmol), and potassium carbonate (90 mg, 0.65 mmol) were suspended in DMF (2 mL), and stirred overnight at 100° C. The reaction mixture was diluted with H$_2$O, and extracted with EtOAc. The organic extracts were washed with brine, dried over MgSO$_4$, filtered, and concentrated. The crude product was purified via Biotage eluting with a gradient of 25 to 75% EtOAc in hexanes to provide 131 (5 mg, 12% yield) as a solid. LC-MS (M+H=314, obsd.=314). $^1$H NMR (400 MHz, d6-DMSO): δ 12.23 (s, 1H), 8.89 (d, 1H), 8.41 (dd, 1H), 8.38 (d, 1H), 8.01 (d, 2H), 7.85 (dt, 1H), 7.71 (t, 1H), 7.52 (d, 2H), 6.74 (d, 1H).

Example 133

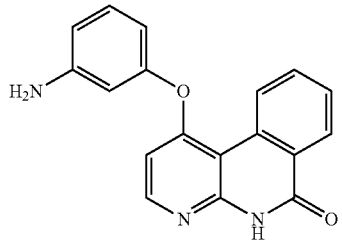 [SMILES: Nc1cccc(Oc2ccnc3[nH]c(=O)c4ccccc4c23)c1]

1-(3-Amino-phenoxy)-5H-benzo[c][1,8]naphthyridin-6-one (133)

1-Chloro-5H-benzo[c][1,8]naphthyridin-6-one (30 mg, 0.13 mmol), 3-aminophenol (43 mg, 0.39 mmol), and potassium carbonate (90 mg, 0.65 mmol) were suspended in DMF (2 mL), and stirred overnight at 100° C. The reaction mixture was diluted with MeOH, and filtered through a membrane. The crude product was purified via prep-LC-MS to provide 132 (3 mg, 8% yield) as a solid. LC-MS (M+H=304, obsd.=304). $^1$H NMR (400 MHz, d6-DMSO): δ 12.09 (s, 1H), 9.04 (d, 1H), 8.42 (dd, 1H), 8.28 (d, 1H), 7.78 (dt, 1H), 7.69 (t, 1H), 7.13 (t, 1H), 6.63 (d, 1H), 6.52 (dd, 1H), 6.39 (m, 2H), 5.54 (s, 2H).

Example 134

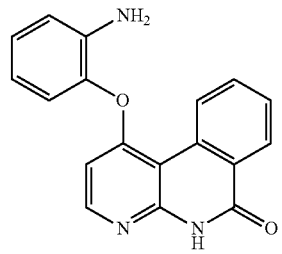 [SMILES: Nc1ccccc1Oc1ccnc2[nH]c(=O)c3ccccc3c12]

1-(2-Amino-phenoxy)-5H-benzo[a-1,8]naphthyridin-6-one (134)

1-Chloro-5H-benzo[c][1,8]naphthyridin-6-one (30 mg, 0.13 mmol), 2-aminophenol (43 mg, 0.39 mmol), and potassium carbonate (90 mg, 0.65 mmol) were suspended in DMF (2 mL), and stirred overnight at 100° C. The reaction mixture was diluted with MeOH, and filtered through a membrane. The crude product was purified via prep-LC-MS to provide 133 (5 mg, 12% yield) as a solid. LC-MS (M+H=304, obsd.=304). $^1$H NMR (400 MHz, d6-DMSO): δ 11.72 (s, 1H), 9.68 (s, 2H), 8.88 (d, 1H), 8.35 (d, 1H), 8.18 (m, 1H), 8.01 (d, 1H), 7.76 (t, 1H), 7.58 (t, 1H), 7.02 (m, 2H), 6.78 (t, 1H), 6.48 (d, 1H).

Example 135

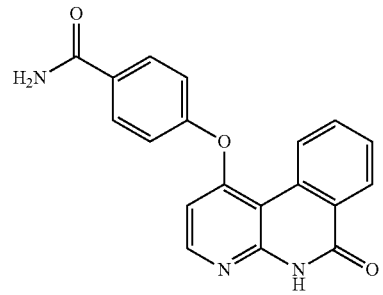 [SMILES: NC(=O)c1ccc(Oc2ccnc3[nH]c(=O)c4ccccc4c23)cc1]

4-(6-Oxo-5,6-dihydro-benzo[c][1,8]naphthyridin-1-yloxy)-benzamide (135)

1-Chloro-5H-benzo[c][1,8]naphthyridin-6-one (30 mg, 0.13 mmol), 4-hydroxybenzamide (54 mg, 0.39 mmol), and potassium carbonate (90 mg, 0.65 mmol) were suspended in DMF (2 mL), and stirred overnight at 100° C. The reaction mixture was diluted with MeOH, and filtered through a membrane. The crude product was purified via prep-LC-MS to provide 134 (2 mg, 5% yield) as a solid. LC-MS (M+H=332, obsd.=332). $^1$H NMR (400 MHz, d6-DMSO): δ 12.18 (s, 1H), 9.00 (d, 1H), 8.48 (s, 1H), 8.42 (d, 1H), 8.18 (m, 1H), 8.05 (m, 2H), 7.88 (dt, 1H), 7.70 (t, 1H), 7.44 (s, 1H), 7.38 (d, 2H), 6.63 (d, 1H).

Example 136

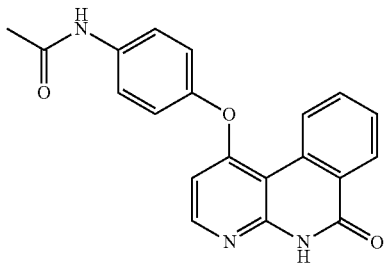 [SMILES: CC(=O)Nc1ccc(Oc2ccnc3[nH]c(=O)c4ccccc4c23)cc1]

N-[4-(6-Oxo-5,6-dihydro-benzo[c][1,8]naphthyridin-1-yloxy)-phenyl]-acetamide (136)

1-Chloro-5H-benzo[c][1,8]naphthyridin-6-one (30 mg, 0.13 mmol), N-(4-hydroxyphenyl)acetamide (59 mg, 0.39 mmol), and potassium carbonate (90 mg, 0.65 mmol) were suspended in DMF (2 mL), and stirred overnight at 100° C. The reaction mixture was diluted with MeOH, and filtered through a membrane. The crude product was purified via prep-LC-MS to provide 135 (3 mg, 7% yield) as a solid. LC-MS (M+H=346, obsd.=346). $^1$H NMR (400 MHz, d6-DMSO): δ 12.14 (s, 1H), 10.15 (s, 1H), 9.08 (d, 1H), 8.42 (d, 1H), 8.29 (d, 1H), 7.88 (t, 1H), 7.73 (m, 3H), 7.28 (d, 2H), 6.52 (d, 1H), 2.09 (s, 3H).

Example 137

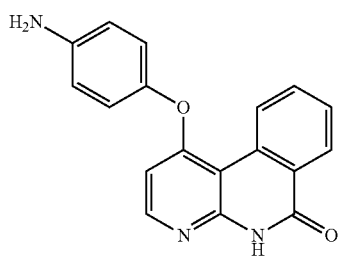 [SMILES: Nc1ccc(Oc2ccnc3[nH]c(=O)c4ccccc4c23)cc1]

1-(4-Amino-phenoxy)-5H-benzo[c][1,8]naphthyridin-6-one (137)

1-Chloro-5H-benzo[c][1,8]naphthyridin-6-one (30 mg, 0.13 mmol), 4-(benzylamino)phenol (78 mg, 0.39 mmol), and potassium carbonate (90 mg, 0.65 mmol) were suspended in DMF (2 mL), and stirred overnight at 100° C. The reaction mixture was diluted with MeOH, and filtered through a membrane. The crude product was purified via prep-LC-MS to provide 136 (8 mg, 20% yield) as a solid. LC-MS (M+H=304, obsd.=304). $^1$H NMR (400 MHz, d6-DMSO): δ 12.06 (s, 1H), 9.11 (d, 1H), 8.42 (dd, 1H), 8.26 (d, 1H), 7.82 (d, 1H), 6.99 (d, 2H), 6.70 (m, 3H), 6.48 (d, 1H), 6.42 (s, 2H).

Example 138

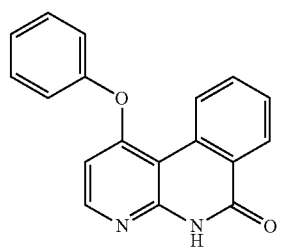 [SMILES: O=c1[nH]c2nccc(Oc3ccccc3)c2c2ccccc12]

1-Phenoxy-5H-benzo[c][1,8]naphthyridin-6-one (138)

1-Chloro-5H-benzo[c][1,8]naphthyridin-6-one (80 mg, 0.35 mmol), and lithium phenoxide (1 mL, 1.04 mmol, 1M solution in THF) were suspended in DMAC (2 mL), and stirred for 4 h at 100° C. The reaction mixture was cooled to room temperature, and diluted with H$_2$O. The resulting precipitate was filtered, washed with H$_2$O, and dried under vacuum to provide 137 (22 mg, 22% yield) as a tan solid. LC-MS (M+H=289, obsd.=289). $^1$H NMR (400 MHz, d6-DMSO): δ 12.12 (s, 1H), 9.08 (d, 1H), 8.42 (dd, 1H), 8.28 (d, 1H), 7.88 (td, 1H), 7.70 (t, 1H), 7.55 (m, 2H), 7.35 (m, 3H), 6.55 (d, 1H).

Example 139

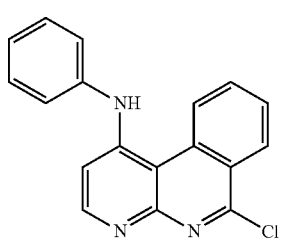 [SMILES: Clc1nc2nccc(Nc3ccccc3)c2c2ccccc12]

(6-Chloro-benzo[c][1,8]naphthyridin-1-yl)-phenyl-amine (139)

1-Phenylamino-5H-benzo[c][1,8]naphthyridin-6-one (240 mg, 0.84 mmol) was suspended in POCl$_3$ (4 mL), and stirred overnight at 120° C. The reaction solution was concentrated, and the resulting material was triturated with H$_2$O. The resulting precipitate was filtered, washed with H$_2$O, and dried under vacuum to provide 138 (250 mg, 87% yield) as a yellow solid. LC-MS (M+H=306, obsd.=306). $^1$H NMR (400 MHz, d6-DMSO): δ 9.18 (d, 1H), 8.64 (dd, 1H), 8.48 (d, 1H), 8.19 (dt, 1H), 8.06 (t, 1H), 7.58 (m, 2H), 7.49 (m, 2H), 7.40 (t, 1H), 7.20 (d, 1H), 6.92 (s, 1H).

Example 140

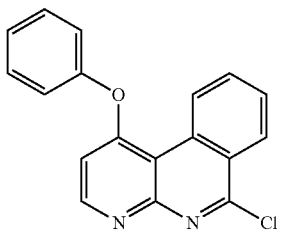 [SMILES: Clc1nc2nccc(Oc3ccccc3)c2c2ccccc12]

6-Chloro-1-phenoxy-benzo[c][1,8]naphthyridine (140)

1-Phenoxy-5H-benzo[c][1,8]naphthyridin-6-one (17 mg, 0.06 mmol) was suspended in POCl₃ (2 mL), and stirred overnight at 120° C. The reaction solution was concentrated, and the resulting material was triturated with H₂O. The resulting precipitate was filtered, washed with H₂O, and dried under vacuum to provide 139 (17 mg, 94% yield) as a tan solid. LC-MS (M+H=307, obsd.=307). $^1$H NMR (400 MHz, d6-DMSO): δ 9.51 (d, 1H), 8.82 (d, 1H), 8.62 (dd, 1H), 8.16 (dt, 1H), 8.04 (t, 1H), 7.64 (m, 2H), 7.44 (m, 3H), 6.99 (d, 1H).

Example 141

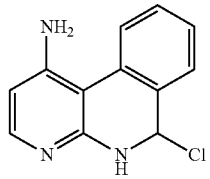 [SMILES: Nc1ccnc2c1-c1ccccc1C(Cl)N2]

1-Amino-5H-benzo[c][1,8]naphthyridin-6-one (141)

1-Benzylamino-5H-benzo[c][1,8]naphthyridin-6-one (170 mg, 0.51 mmol) was dissolved in TFA (3 mL) and stirred at room temperature overnight. The reaction solution was concentrated, and the product was triturated in MeOH. The resulting precipitate was filtered, washed with MeOH, and dried under vacuum to provide 140 (130 mg, 78% yield) as a dark solid. LC-MS (M+H=212, obsd.=212). $^1$H NMR (400 MHz, d6-DMSO): δ 8.48 (d, 1H), 8.34 (dd, 1H), 7.94 (d, 2H), 7.88 (dt, 1H), 7.68 (t, 1H), 6.76 (d, 1H).

Example 142

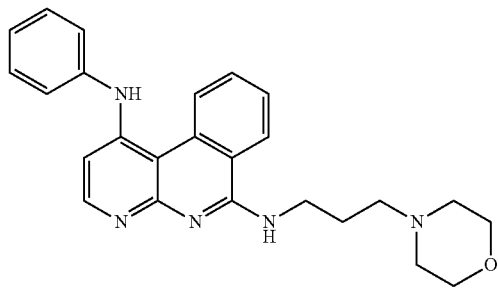 [SMILES: c1ccc(Nc2ccnc3nc(NCCCN4CCOCC4)c4ccccc4c23)cc1]

N'6'-(3-Morpholin-4-yl-propyl)-N'1'-phenyl-benzo[a-1,8]naphthyridine-1,6-diamine (142)

(6-Chloro-benzo[c][1,8]naphthyridin-1-yl)-phenyl-amine (25 mg, 0.08 mmol) and N-(3-aminopropyl)morpholine (18 mg, 0.12 mmol) were dissolved in iPrOH (2 mL), and stirred overnight at 100° C. The reaction mixture was diluted with MeOH, filtered through a membrane, and purified via prep-LC-MS. The purified product was converted to the HCl salt via dissolving in methanolic HCl, and concentration on the Genevac to provide 141 (5 mg, 12% yield) as a dark solid. LC-MS (M+H=414, obsd.=414). $^1$H NMR (400 MHz, d6-DMSO): δ 10.32 (s, 1H), 9.31 (t, 1H), 8.87 (d, 1H), 8.58 (d, 1H), 8.09 (t, 1H), 7.89 (t, 1H), 7.80 (t, 1H), 7.49 (m, 2H), 7.40 (d, 2H), 7.32 (t, 1H), 6.90 (d, 1H), 3.95 (d, 2H), 3.86 (d, 2H), 3.75 (m, 2H), 3.46 (m, 2H), 3.28 (m, 2H), 3.08 (m, 2H), 2.22 (m, 2H).

Example 143

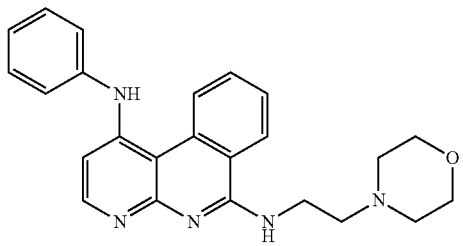 [SMILES: c1ccc(Nc2ccnc3nc(NCCN4CCOCC4)c4ccccc4c23)cc1]

N'6'-(2-Morpholin-4-yl-ethyl)-N'1'-phenyl-benzo[c][1,8]naphthyridine-1,6-diamine (143)

(6-Chloro-benzo[c][1,8]naphthyridin-1-yl)-phenyl-amine (25 mg, 0.08 mmol) and 4-(2-aminoethyl)morpholine (16 mg, 0.12 mmol) were dissolved in iPrOH (2 mL), and stirred overnight at 100° C. The reaction mixture was diluted with MeOH, filtered through a membrane, and purified via prep-LC-MS. The purified product was converted to the HCl salt via dissolving in methanolic HCl, and concentration on the Genevac to provide 142 (4 mg, 10% yield) as a solid. LC-MS (M+H=400, obsd.=400). $^1$H NMR (400 MHz, d6-DMSO): δ 10.37 (s, 1H), 9.45 (t, 1H), 8.88 (d, 1H), 8.66 (d, 1H), 8.14 (t, 1H), 7.90 (t, 1H), 7.81 (t, 1H), 7.50 (m, 2H), 7.42 (d, 2H), 7.32 (t, 1H), 6.93 (d, 1H), 4.06 (m, 4H), 3.86 (m, 2H), 3.66 (m, 2H), 3.55 (m, 2H), 3.42 (m, 2H).

Example 144

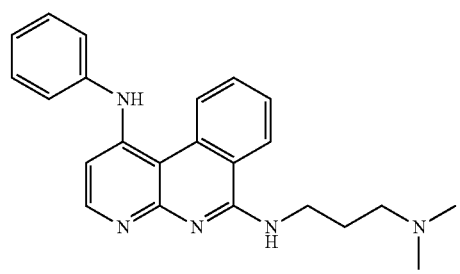 [SMILES: CN(C)CCCNc1nc2nccc(Nc3ccccc3)c2c2ccccc12]

N'6'-(3-Dimethylamino-propyl)-N' t-phenyl-benzo[c][1,8]naphthyridine-1,6-diamine (144)

(6-Chloro-benzo[c][1,8]naphthyridin-1-yl)-phenyl-amine (25 mg, 0.08 mmol) and N,N-dimethyl-1,3-propanediamine (12 mg, 0.12 mmol) were dissolved in iPrOH (2 mL), and stirred overnight at 100° C. The reaction mixture was diluted with MeOH, filtered through a membrane, and purified via prep-LC-MS. The purified product was converted to the HCl salt via dissolving in methanolic HCl, and concentration on the Genevac to provide 143 (6 mg, 15% yield) as a dark solid. LC-MS (M+H=372, obsd.=372). $^1$H NMR (400 MHz, d6-DMSO): δ 10.57 (s, 1H), 10.34 (s, 1H), 9.38 (t, 1H), 8.86 (d, 1H), 8.63 (d, 1H), 8.10 (t, 1H), 7.88 (t, 1H), 7.79 (t, 1H), 7.49 (m, 2H), 7.40 (d, 2H), 7.32 (t, 1H), 6.91 (d, 1H), 3.74 (m, 2H), 3.22 (m, 2H), 2.77 (s, 6H), 2.18 (m, 2H).

Example 145

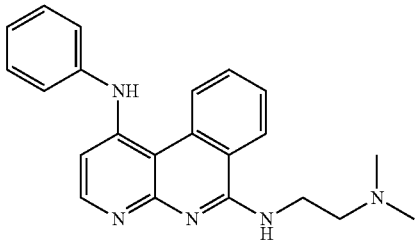 [SMILES: CN(C)CCNc1nc2nccc(Nc3ccccc3)c2c2ccccc12]

N'6'-(2-Dimethylamino-ethyl)-N'1'-phenyl-benzo[c][1,8]naphthyridine-1,6-diamine (145)

(6-Chloro-benzo[c][1,8]naphthyridin-1-yl)-phenyl-amine (25 mg, 0.08 mmol) and N,N-dimethylethylenediamine (11 mg, 0.12 mmol) were dissolved in iPrOH (2 mL), and stirred overnight at 100° C. The reaction mixture was diluted with MeOH, filtered through a membrane, and purified via prep-LC-MS. The purified product was converted to the HCl salt via dissolving in methanolic HCl, and concentration on the Genevac to provide 144 (9 mg, 24% yield) as a solid. LC-MS (M+H=358, obsd.=358). $^1$H NMR (400 MHz, d6-DMSO): δ 10.60 (s, 1H), 10.40 (s, 1H), 9.55 (t, 1H), 8.86 (d, 1H), 8.71 (d, 1H), 8.13 (t, 1H), 7.89 (t, 1H), 7.79 (t, 1H), 7.49 (m, 2H), 7.41 (d, 2H), 7.32 (t, 1H), 6.94 (d, 1H), 4.01 (m, 2H), 3.56 (m, 2H), 2.91 (s, 6H).

Example 146

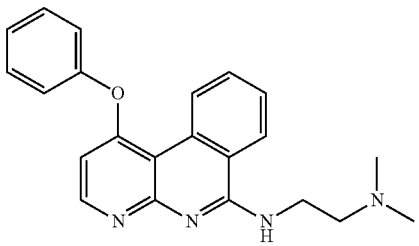 [SMILES: CN(C)CCNc1nc2nccc(Oc3ccccc3)c2c2ccccc12]

N,N-Dimethyl-N'-(1-phenoxy-benzo[c][1,8]naphthyridin-6-yl)-ethane-1,2-diamine (146)

6-Chloro-1-phenoxy-benzo[c][1,8]naphthyridine (15 mg, 0.05 mmol) and N,N-dimethylethylenediamine (6 mg, 0.07 mmol) were dissolved in iPrOH (1.5 mL), and stirred overnight at 100° C. The reaction mixture was diluted with MeOH, filtered through a membrane, and purified via prep-LC-MS. The purified product was converted to the HCl salt via dissolving in methanolic HCl, and concentration on the Genevac to provide 145 (2 mg, 10% yield) as a solid. LC-MS (M+H=359, obsd.=359). $^1$H NMR (400 MHz, d6-DMSO): δ 9.68 (s, 1H), 9.30 (d, 1H), 8.78 (d, 1H), 8.55 (d, 1H), 8.06 (t, 1H), 7.96 (t, 1H), 7.65 (m, 2H), 7.48 (m, 3H), 6.78 (d, 1H), 4.06 (m, 2H), 3.54 (m, 2H), 2.96 (s, 6H).

Example 147

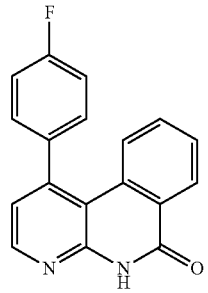 [SMILES: O=c1[nH]c2nccc(-c3ccc(F)cc3)c2c2ccccc12]

1-(4-Fluoro-phenyl)-5H-benzo[c][1,8]naphthyridin-6-one (147)

1-Chloro-5H-benzo[c][1,8]naphthyridin-6-one (100 mg, 0.43 mmol), 4-fluorophenylboronic acid (121 mg, 0.87 mmol), palladium(II) acetate (5 mg, 0.02 mmol), 2-dicyclohexylphosphino-2',6'-dimethoxybiphenyl (18 mg, 0.04 mmol), and potassium carbonate (180 mg, 1.3 mmol) were dissolved in dioxane/H$_2$O (2.2 mL, 10/1, v/v), and stirred overnight at 100° C. The reaction mixture was concentrated, and diluted with H$_2$O/EtOAc. The resulting precipitate was filtered, washed with MeOH, and dried under vacuum to provide 146 (20 mg, 16% yield) as a white solid. LC-MS (M+H=291, obsd.=291). $^1$H NMR (400 MHz, d6-DMSO): δ 12.15 (s, 1H), 8.47 (d, 1H), 8.32 (dd, 1H), 7.56 (dt, 1H), 7.44 (m, 5H), 7.21 (d, 1H), 7.09 (d, 1H).

Example 148

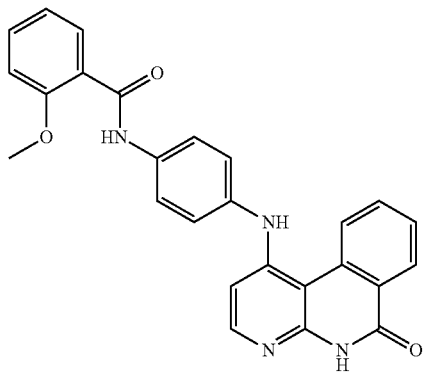 [SMILES: COc1ccccc1C(=O)Nc1ccc(Nc2ccnc3[nH]c(=O)c4ccccc4c23)cc1]

2-Methoxy-N-[4-(6-oxo-5,6-dihydro-benzo[c][1,8]naphthyridin-1-ylamino)-phenyl]-benzamide (148)

1-Chloro-5H-benzo[c][1,8]naphthyridin-6-one (50 mg, 0.22 mmol), N-(4-aminophenyl)-2-methoxybenzamide (105 mg, 0.43 mmol), palladium(II) acetate (2 mg, 0.01 mmol), 2-dicyclohexylphosphino-2',4',6'-triisopropylbiphenyl (10 mg, 0.02 mmol), and sodium tert-butoxide (63 mg, 0.65 mmol) were suspended in dioxane (2 mL), and stirred overnight at 100° C. The reaction mixture was concentrated, and diluted with $H_2O$/EtOAc. The resulting precipitate was filtered, washed with $H_2O$/EtOAc, and dried under vacuum to provide 147 (36 mg, 38% yield) as a solid. LC-MS (M+H=437, obsd.=437). $^1$H NMR (400 MHz, d6-DMSO): δ 11.81 (s, 1H), 10.10 (s, 1H), 8.84 (s, 1H), 8.32 (d, 1H), 8.09 (d, 1H), 7.77 (dt, 1H), 7.70 (d, 2H), 7.65 (dd, 1H), 7.60 (t, 1H), 7.50 (m, 2H), 7.18 (m, 3H), 7.05 (t, 1H), 6.91 (d, 1H), 3.91 (s, 3H).

Example 149

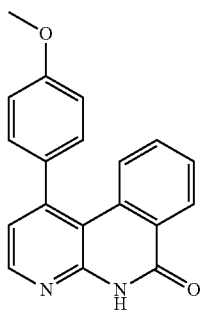 [SMILES: COc1ccc(-c2ccnc3[nH]c(=O)c4ccccc4c23)cc1]

1-(4-Methoxy-phenyl)-5H-benzo[c][1,8]naphthyridin-6-one (149)

1-Chloro-5H-benzo[c][1,8]naphthyridin-6-one (50 mg, 0.22 mmol), 4-methoxyphenylboronic acid (49 mg, 0.33 mmol), palladium(II) acetate (2 mg, 0.01 mmol), 2-dicyclohexylphosphino-2',6'-dimethoxybiphenyl (9 mg, 0.02 mmol), and potassium carbonate (90 mg, 0.65 mmol) were dissolved in dioxane/$H_2O$ (2.2 mL, 10/1, v/v), and stirred overnight at 100° C. The reaction mixture was concentrated, and then diluted with $H_2O$/MeOH. The resulting precipitate was filtered, triturated with MeOH, filtered again, washed with MeOH, and dried under vacuum to provide 148 (20 mg, 31% yield) as a dark solid. LC-MS (M+H=303, obsd.=303). $^1$H NMR (400 MHz, d6-DMSO): δ 12.10 (s, 1H), 8.45 (d, 1H), 8.32 (dd, 1H), 7.54 (t, 1H), 7.42 (t, 1H), 7.33 (m, 3H), 7.11 (d, 2H), 7.06 (d, 1H), 3.86 (s, 3H).

Example 150

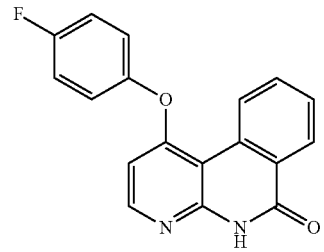 [SMILES: O=c1[nH]c2nccc(Oc3ccc(F)cc3)c2c2ccccc12]

1-(4-Fluoro-phenoxy)-5H-benzo[c][1,8]naphthyridin-6-one (150)

1-Chloro-5H-benzo[c][1,8]naphthyridin-6-one (50 mg, 0.22 mmol), 4-fluorophenol (73 mg, 0.65 mmol), and potassium carbonate (150 mg, 1.08 mmol) were suspended in DMF (2 mL), and stirred overnight at 100° C. The reaction solution was cooled to room temperature, diluted with $H_2O$, and the resulting precipitate was filtered. The precipitate was washed with $H_2O$, and dried under vacuum to provide 149 (14 mg, 21% yield) as a tan solid. LC-MS (M+H=307, obsd.=307). $^1$H NMR (400 MHz, d6-DMSO): δ 12.15 (s, 1H), 9.05 (d, 1H), 8.42 (dd, 1H), 8.29 (d, 1H), 7.88 (dt, 1H), 7.71 (t, 1H), 7.40 (m, 4H), 6.52 (d, 1H).

Example 151

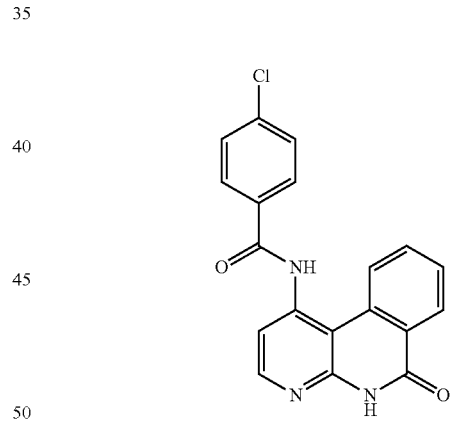

4-Chloro-N-(6-oxo-5,6-dihydro-benzo[c][1,8]naphthyridin-1-yl)-benzamide (151)

1-Amino-5H-benzo[c][1,8]naphthyridin-6-one (25 mg, 0.12 mmol), 4-chlorobenzoic acid (23 mg, 0.15 mmol), DIEA (0.06 mL, 0.36 mmol), and BOP-Cl (60 mg, 0.24 mmol) were suspended in DCM and stirred overnight at room temperature. The reaction solution was acidified with 1M HCl, and filtered through an Extrelut column. The column was washed with DCM, and the filtrate was concentrated. The crude product was purified via prep-LC-MS to provide 150 (3 mg, 7% yield) as a solid. LC-MS (M+H=350, obsd.=350). $^1$H NMR (400 MHz, d6-DMSO): δ 8.45 (d, 1H), 8.35 (m, 2H), 8.02 (d, 1H), 7.93 (m, 3H), 7.69 (t, 1H), 7.57 (d, 2H), 6.81 (d, 1H).

Example 152

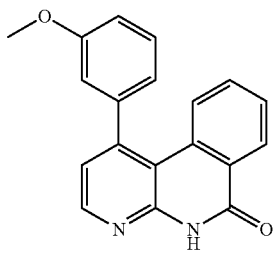 [SMILES: COc1cccc(-c2ccnc3[nH]c(=O)c4ccccc4c23)c1]

1-(3-Methoxy-phenyl)-5H-benzo[c][1,8]naphthyridin-6-one (152)

Compound 83 (50 mg, 0.22 mmol), 3-methoxyphenylboronic acid (49 mg, 0.33 mmol), Pd(OAc)$_2$ (2 mg, 0.01 mmol), S-Phos (9 mg, 0.02 mmol), and K$_2$CO$_3$ (90 mg, 0.65 mmol) were dissolved in dioxane/H$_2$O (2.2 mL, 10/1, v/v), and stirred overnight at 100° C. The reaction mixture was concentrated. The crude product was purified directly via Biotage eluting with a gradient of 25 to 85% EtOAc in hexanes to provide 152 (11 mg, 17% yield) as a white solid. LC-MS (M+H=303, obsd.=303).

Example 153

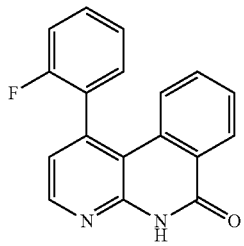

1-(2-Fluoro-phenyl)-5H-benzo[c][1,8]naphthyridin-6-one (153)

Compound 83 (50 mg, 0.22 mmol), 2-fluorophenylboronic acid (46 mg, 0.33 mmol), Pd(OAc)$_2$ (2 mg, 0.01 mmol), S-Phos (9 mg, 0.02 mmol), and K$_2$CO$_3$ (90 mg, 0.65 mmol) were dissolved in dioxane/H$_2$O (2.2 mL, 10/1, v/v), and stirred overnight at 100° C. The reaction mixture was concentrated, diluted with MeOH/DMSO, and filtered. The filtrate was purified via prep-LC-MS. The product was triturated with MeOH, filtered, and dried under vacuum to provide 153 (6 mg, 10% yield) as a white solid. LC-MS (M+H=291, obsd.=291).

Example 154

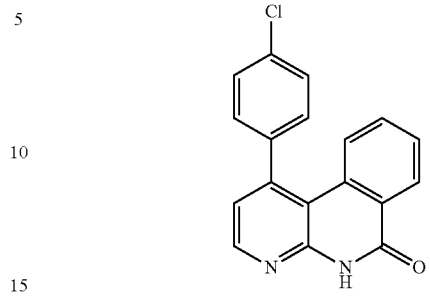

1-(4-Chloro-phenyl)-5H-benzo[c][1,8]naphthyridin-6-one (154)

The title compound was synthesized according to the procedure described for the preparation of Example 153 using Compound 83 (50 mg, 0.22 mmol) and 4-chlorophenylboronic acid (44 mg, 0.33 mmol) to provide 154 (6 mg, 9% yield) as a white solid. LC-MS (M+H=307, obsd.=307).

Example 155

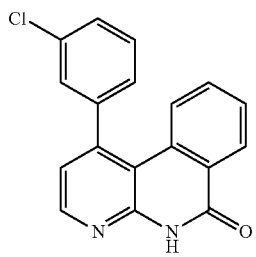 [SMILES: O=c1[nH]c2nccc(-c3cccc(Cl)c3)c2c2ccccc12]

1-(3-Chloro-phenyl)-5H-benzo[c][1,8]naphthyridin-6-one (155)

The title compound was synthesized according to the procedure described for the preparation of Example 153 using Compound 83 (50 mg, 0.22 mmol) and 3-chloro-phenylboronic acid (44 mg, 0.33 mmol) to provide 155 (9 mg, 14% yield) as a white solid. LC-MS (M+H=307, obsd.=307).

Example 156

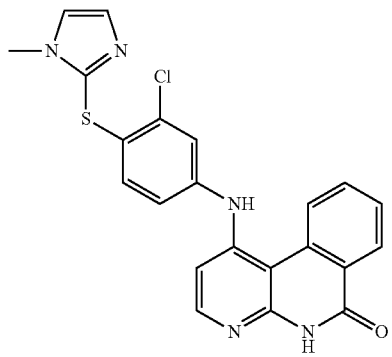 [SMILES: Cn1ccnc1Sc1ccc(Nc2ccnc3[nH]c(=O)c4ccccc4c23)cc1Cl]

1-[3-Chloro-4-(1-methyl-1H-imidazol-2-ylsulfanyl)-phenylamino]-5H-benzo[c][1,8]naphthyridin-6-one (156)

Compound 83 (100 mg, 0.43 mmol), 3-chloro-4-(1-methyl-1H-imidazol-2-ylsulfanyl)-phenylamine (156 mg, 0.65 mmol), Pd(OAc)$_2$ (5 mg, 0.02 mmol), X-Phos (21 mg, 0.04 mmol), and KOH (97 mg, 1.73 mmol) were suspended in tert-amyl alcohol (2 mL), and stirred overnight at 100° C. The reaction mixture was diluted with MeOH, filtered, and purified via prep-LC-MS to provide 156 (4 mg, 2% yield) as a solid. LC-MS (M+H=434, obsd.=434).

Example 157

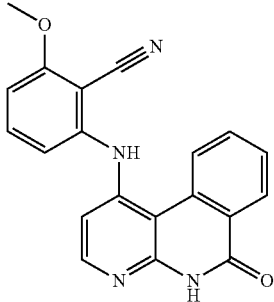 [SMILES: COc1cccc(Nc2ccnc3[nH]c(=O)c4ccccc4c23)c1C#N]

2-Methoxy-6-(6-oxo-5,6-dihydro-benzo[c][1,8]naphthyridin-1-ylamino)-benzonitrile (157)

The title compound was synthesized according to the procedure described for the preparation of Example 113 using Compound 83 (100 mg, 0.43 mmol) and 2-amino-6-methoxy-benzonitrile (77 mg, 0.52 mmol) to provide 157 (128 mg, 86% yield) as a yellow solid. LC-MS (M+H=343, obsd.=343).

Example 158

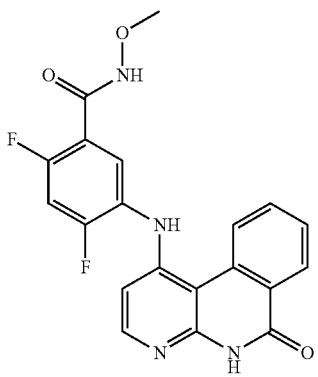 [SMILES: CONC(=O)c1cc(Nc2ccnc3[nH]c(=O)c4ccccc4c23)c(F)cc1F]

2,4-Difluoro-N-methoxy-5-(6-oxo-5,6-dihydro-benzo[c][1,8]naphthyridin-1-ylamino)-benzamide (158)

Compound 83 (100 mg, 0.43 mmol), 5-amino-2,4-difluoro-N-methoxy-benzamide (124 mg, 0.52 mmol), Pd(OAc)$_2$ (5 mg, 0.02 mmol), X-Phos (21 mg, 0.04 mmol), and NaOtBu (125 mg, 1.30 mmol) were suspended in dioxane (2 mL), and stirred overnight at 100° C. The reaction mixture was diluted with EtOAc/H2O, and filtered through an Extrelut column. The column was washed with EtOAc, and the filtrate was concentrated. The crude product was purified via Biotage eluting with a gradient of 0 to 10% MeOH in DCM to provide 158 (5 mg, 3% yield) as a white solid. LC-MS (M+H=397, obsd.=397).

Example 159

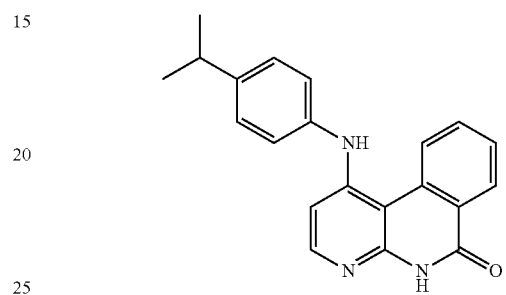

1-(4-Isopropyl-phenylamino)-5H-benzo[c][1,8]naphthyridin-6-one (159)

Compound 83 (100 mg, 0.43 mmol), 1-(4-isopropyl-phenyl)-3-piperidin-4-yl-urea (136 mg, 0.52 mmol), Pd(OAc)$_2$ (5 mg, 0.02 mmol), X-Phos (21 mg, 0.04 mmol), and KOH (73 mg, 1.30 mmol) were suspended in tert-amyl alcohol (2 mL), and stirred overnight at 100° C. The reaction mixture was diluted with EtOAc/H2O. The resulting precipitate was filtered, washed with EtOAc/H2O, and dried under vacuum to provide 159 (40 mg, 28% yield) as a tan solid. LC-MS (M+H=330, obsd.=330).

Example 160

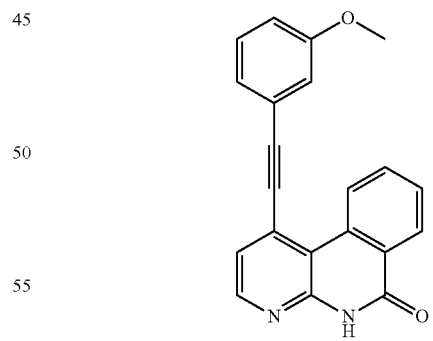

1-(3-Methoxy-phenylethynyl)-5H-benzo[c][1,8]naphthyridin-6-one (160)

Compound 83 (100 mg, 0.43 mmol), Pd(OAc)$_2$ (5 mg, 0.02 mmol), X-Phos (21 mg, 0.04 mmol), and Cs$_2$CO$_3$ (424 mg, 1.30 mmol) were suspended in dioxane (2 mL), and stirred for 20 minutes at room temperature. 1-Ethynyl-3-methoxy-benzene (86 mg, 0.65 mmol) was then added, and the resulting

Example 161

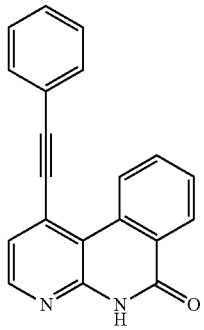 [SMILES: O=c1[nH]c2nccc(C#Cc3ccccc3)c2c2ccccc12]

1-Phenylethynyl-5H-benzo[c][1,8]naphthyridin-6-one (161)

The title compound was synthesized according to the procedure described for the preparation of Example 160 using Compound 83 (100 mg, 0.43 mmol) and ethynyl benzene (66 mg, 0.65 mmol) to provide 161 (87 mg, 67% yield) as a light-yellow solid. LC-MS (M+H=297, obsd.=297).

solution was stirred for 3 h at 100° C. The reaction mixture was diluted with EtOAc/H₂O. The resulting precipitate was filtered, washed with EtOAc/H2O, and dried under vacuum to provide 160 (80 mg, 56% yield) as a light-yellow solid. LC-MS (M+H=327, obsd.=327).

Example 162

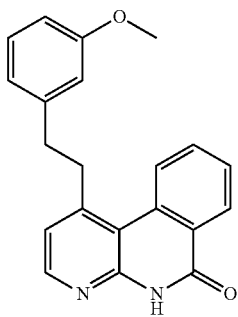 [SMILES: COc1cccc(CCc2ccnc3[nH]c(=O)c4ccccc4c23)c1]

1-[2-(3-Methoxy-phenyl)-ethyl]-5H-benzo[c][1,8]naphthyridin-6-one (162)

Compound 160 (45 mg, 0.14 mmol), ammonium formate (100 mg, 1.60 mmol), and Pd/carbon (100 mg, 10% by weight, wet) were suspended in dioxane (2 mL), and stirred for 4 h at 70° C. The reaction mixture was filtered, and purified via Biotage eluting with a gradient of 25 to 75 EtOAc in hexanes to provide 162 (14 mg, 31% yield) as a white solid. LC-MS (M+H=331, obsd.=331).

Example 163

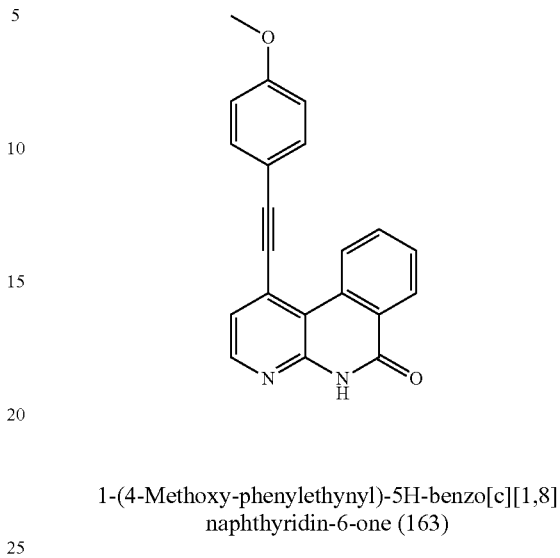

1-(4-Methoxy-phenylethynyl)-5H-benzo[c][1,8]naphthyridin-6-one (163)

The title compound was synthesized according to the procedure described for the preparation of Example 160 using Compound 83 (100 mg, 0.43 mmol) and 1-Ethynyl-4-methoxy-benzene (86 mg, 0.65 mmol) was then added, and the resulting solution was stirred for 3 h at 100° C. The reaction mixture was diluted with EtOAc/H2O. The resulting precipitate was filtered, washed with EtOAc/H2O, and dried under vacuum to provide 163 (101 mg, 71% yield) as a white solid. LC-MS (M+H=327, obsd.=327).

Example 164

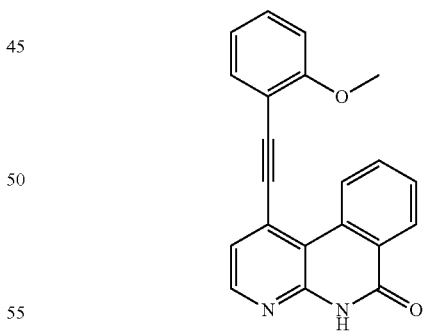

1-(2-Methoxy-phenylethynyl)-5H-benzo[c][1,8]naphthyridin-6-one (164)

The title compound was synthesized according to the procedure described for the preparation of Example 160 using Compound 83 (100 mg, 0.43 mmol) and 1-ethynyl-2-methoxy-benzene (86 mg, 0.65 mmol) to provide 164 (101 mg, 71% yield) as a white solid. LC-MS (M+H=327, obsd.=327).

Example 165

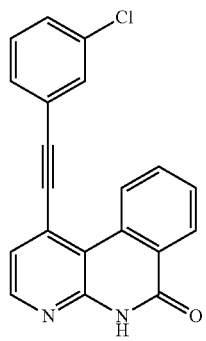 [SMILES: O=c1[nH]c2nccc(C#Cc3cccc(Cl)c3)c2c2ccccc12]

1-(3-Chloro-phenylethynyl)-5H-benzo[c][1,8]naphthyridin-6-one (165)

The title compound was synthesized according to the procedure described for the preparation of Example 160 using Compound 83 (100 mg, 0.43 mmol) and 1-ethynyl-3-chlorobenzene (88 mg, 0.65 mmol) to provide 165 (103 mg, 72% yield) as a white solid. LC-MS (M+H=331, obsd.=331).

Example 166

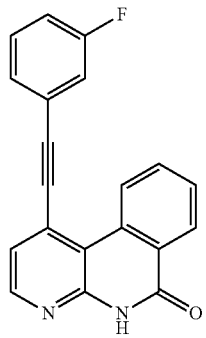 [SMILES: O=c1[nH]c2nccc(C#Cc3cccc(F)c3)c2c2ccccc12]

1-(3-Fluoro-phenylethynyl)-5H-benzo[c][1,8]naphthyridin-6-one (166)

The title compound was synthesized according to the procedure described for the preparation of Example 160 using Compound 83 (100 mg, 0.43 mmol) and 1-ethynyl-3-fluorobenzene (78 mg, 0.65 mmol) to provide 166 (96 mg, 70% yield) as a white solid. LC-MS (M+H=315, obsd.=315).

Example 167

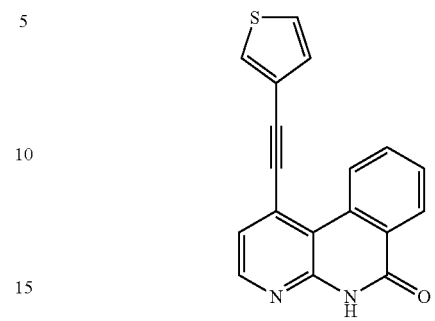

1-Thiophen-3-ylethynyl-5H-benzo[c][1,8]naphthyridin-6-one (167)

The title compound was synthesized according to the procedure described for the preparation of Example 160 using Compound 83 (100 mg, 0.43 mmol) and 3-ethynyl-thiophene (70 mg, 0.65 mmol) to provide 167 (93 mg, 71% yield) as a white solid. LC-MS (M+H=303, obsd.=303).

Example 168

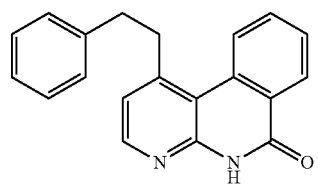 [SMILES: O=c1[nH]c2nccc(CCc3ccccc3)c2c2ccccc12]

1-Phenethyl-5H-benzo[c][1,8]naphthyridin-6-one (168)

The title compound was synthesized according to the procedure described for the preparation of Example 162 using Compound 161 (60 mg, 0.20 mmol) to provide 168 (48 mg, 79% yield) as a light-yellow solid. LC-MS (M+H=301, obsd.=301).

Example 169

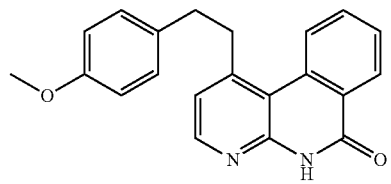 [SMILES: COc1ccc(CCc2ccnc3[nH]c(=O)c4ccccc4c23)cc1]

1-[2-(4-Methoxy-phenyl)-ethyl]-5H-benzo[c][1,8]naphthyridin-6-one (169)

The title compound was synthesized according to the procedure described for the preparation of Example 162 using Compound 163 (70 mg, 0.21 mmol) to provide 169 (40 mg, 56% yield) as a white solid. LC-MS (M+H=331, obsd.=331).

Example 170

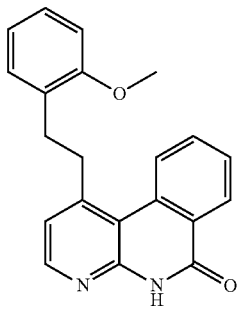 [SMILES: COc1ccccc1CCc1ccnc2[nH]c(=O)c3ccccc3c12]

1-[2-(2-Methoxy-phenyl)-ethyl]-5H-benzo[c][1,8]naphthyridin-6-one (170)

The title compound was synthesized according to the procedure described for the preparation of Example 162 using Compound 164 (70 mg, 0.21 mmol) to provide 170 (27 mg, 38% yield) as a white solid. LC-MS (M+H=331, obsd.=331).

Example 171

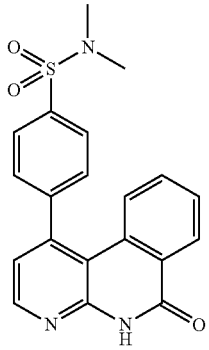 [SMILES: CN(C)S(=O)(=O)c1ccc(-c2ccnc3[nH]c(=O)c4ccccc4c23)cc1]

N,N-Dimethyl-4-(6-oxo-5,6-dihydro-benzo[c][1,8]naphthyridin-1-yl)-benzenesulfonamide (171)

Compound 83 (100 mg, 0.43 mmol), 4-(N,N-dimethylsulfonamidophenyl)boronic acid (198 mg, 0.87 mmol), Pd(OAc)₂ (5 mg, 0.02 mmol), S-Phos (18 mg, 0.04 mmol), and K₂CO₃ (299 mg, 2.17 mmol) were dissolved in dioxane/H₂O (2.2 mL, 10/1, v/v), and stirred overnight at 100° C. The reaction mixture was diluted with H₂O/EtOAc. The resulting precipitate was filtered, washed with H₂O/EtOAc, and dried under vacuum to provide 171 (120 mg, 73% yield) as a grey solid. LC-MS (M+H=380, obsd.=380).

Example 172

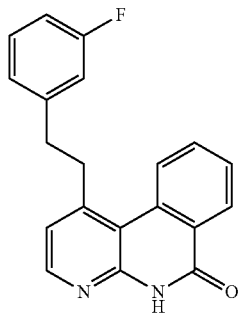 [SMILES: O=c1[nH]c2nccc(CCc3cccc(F)c3)c2c2ccccc12]

1-[2-(3-Fluoro-phenyl)-ethyl]-5H-benzo[c][1,8]naphthyridin-6-one (172)

The title compound was synthesized according to the procedure described for the preparation of Example 162 using Compound 166 (65 mg, 0.21 mmol) to provide 172 (4 mg, 6% yield) as a white solid. LC-MS (M+H=319, obsd.=319).

Example 173

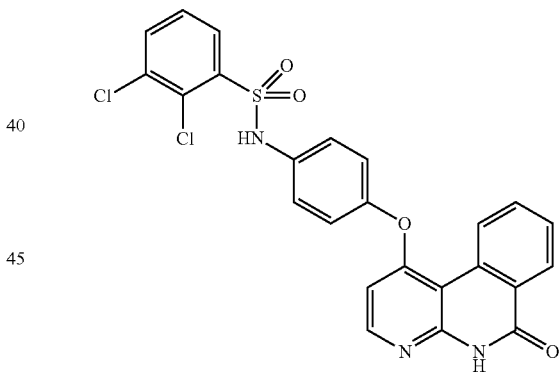

2,3-Dichloro-N-[4-(6-oxo-5,6-dihydro-benzo[c][1,8]naphthyridin-1-yloxy)-phenyl]-benzenesulfonamide (173)

Compound 137 (50 mg, 0.16 mmol), 2,3-dichloro-benzenesulfonyl chloride (45 mg, 0.18 mmol), and Et₃N (0.07 mL, 0.49 mmol) were suspended in dioxane (2 mL), and stirred overnight at 80° C. The reaction mixture was acidified with 1M HCl, and filtered through an Extrelut column. The column was washed with EtOAc, and the filtrate was concentrated. The crude product was purified via Biotage eluting with a gradient of 25 to 100% EtOAc in hexanes to provide 173 (14 mg, 17% yield) as a white solid. LC-MS (M+H=512, obsd.=512).

Example 174

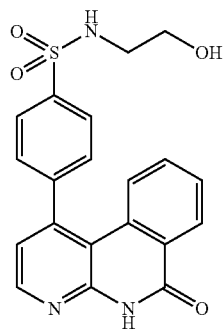 [SMILES: O=c1[nH]c2nccc(-c3ccc(S(=O)(=O)NCCO)cc3)c2c2ccccc12]

N-(2-Hydroxy-ethyl)-4-(6-oxo-5,6-dihydro-benzo[c]
[1,8]naphthyridin-1-yl)-benzenesulfonamide (174)

Compound 83 (100 mg, 0.43 mmol), 4-(2-hydroxyethyl-sulfamoyl)phenylboronic acid (212 mg, 0.87 mmol), Pd(OAc)$_2$ (5 mg, 0.02 mmol), S-Phos (18 mg, 0.04 mmol), and K$_2$CO$_3$ (299 mg, 2.17 mmol) were dissolved in dioxane/H$_2$O (2.2 mL, 10/1, v/v), and stirred overnight at 100° C. The reaction mixture was diluted with H$_2$O/EtOAc, and filtered through an Extrelut column. The column was washed with EtOAc, and the filtrate was concentrated. The crude product was purified via Biotage eluting with a gradient of 0 to 10% MeOH in CH$_2$Cl$_2$. The resulting material was triturated with MeOH, filtered, and dried under vacuum to provide 174 (6 mg, 4% yield) as a light-yellow solid. LC-MS (M+H=396, obsd.=396).

Example 175

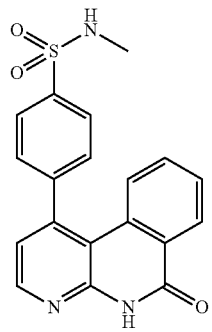 [SMILES: CNS(=O)(=O)c1ccc(-c2ccnc3[nH]c(=O)c4ccccc4c23)cc1]

N-Methyl-4-(6-oxo-5,6-dihydro-benzo[c][1,8]naph-
thyridin-1-yl)-benzenesulfonamide (175)

The title compound was synthesized according to the procedure described for the preparation of Example 171 using Compound 83 (100 mg, 0.43 mmol) and 4-(N-methylsulfonamidophenyl)boronic acid (187 mg, 0.87 mmol) to provide 175 (83 mg, 52% yield) as a grey solid. LC-MS (M+H=366, obsd.=366).

Example 176

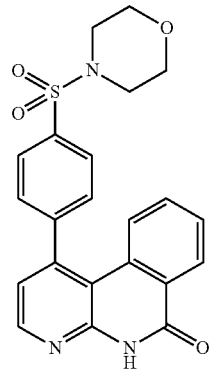 [SMILES: O=c1[nH]c2nccc(-c3ccc(S(=O)(=O)N4CCOCC4)cc3)c2c2ccccc12]

1-[4-(Morpholine-4-sulfonyl)-phenyl]-5H-benzo[c]
[1,8]naphthyridin-6-one (176)

The title compound was synthesized according to the procedure described for the preparation of Example 171 using Compound 83 (100 mg, 0.43 mmol) and 4-(4-boronobenzenesulfonyl)morpholine (235 mg, 0.87 mmol) to provide 176 (145 mg, 79% yield) as a grey solid. LC-MS (M+H=422, obsd.=422).

Example 177

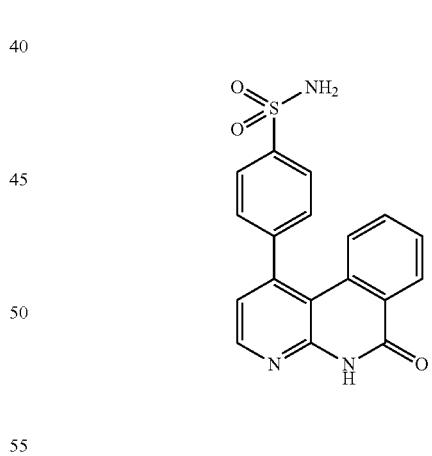

4-(6-Oxo-5,6-dihydro-benzo[c][1,8]naphthyridin-1-
yl)-benzenesulfonamide (177)

The title compound was synthesized according to the procedure described for the preparation of Example 171 using Compound 83 (100 mg, 0.43 mmol) and 4-(aminosulphonyl) benzeneboronic acid (174 mg, 0.87 mmol) to provide 177 (2 mg, 2% yield) as a grey solid. LC-MS (M+H=352, obsd.=352).

Example 178

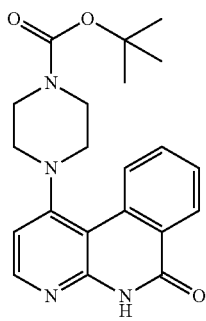 [SMILES: CC(C)(C)OC(=O)N1CCN(c2ccnc3[nH]c(=O)c4ccccc4c23)CC1]

4-(6-Oxo-5,6-dihydro-benzo[c][1,8]naphthyridin-1-yl)-piperazine-1-carboxylic acid tert-butyl ester (178)

Compound 83 (100 mg, 0.43 mmol), 1-Boc-piperazine (161 mg, 0.87 mmol), Pd(OAc)$_2$ (5 mg, 0.02 mmol), X-Phos (21 mg, 0.04 mmol), and NaOtBu (167 mg, 1.73 mmol) were suspended in dioxane (2 mL), and stirred overnight at 100° C. The reaction mixture was diluted with EtOAc/H$_2$O, and filtered through an Extrelut column. The column was washed with EtOAc, and the filtrate was concentrated. The crude product was purified via Biotage eluting with a gradient of 50 to 100% EtOAc in hexanes to provide 178 (70 mg, 42% yield) as a yellow solid. LC-MS (M+H=381, obsd.=381).

Example 179

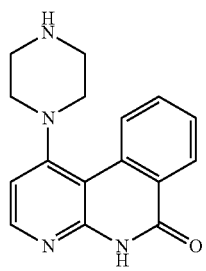 [SMILES: O=c1[nH]c2nccc(N3CCNCC3)c2c2ccccc12]

1-piperazin-1-yl-5H-benzo[c][1,8]naphthyridin-6-one (179)

Compound 178 (70 mg, 0.18 mmol) was dissolved in 1.5 M HCl/MeOH (5 mL), and stirred for 4 h at 60° C. The reaction solution was concentrated, and the resulting precipitate was dried under vacuum to provide 179 (60 mg, 92% yield) as a white solid. LC-MS (M+H=281, obsd.=281).

Example 180

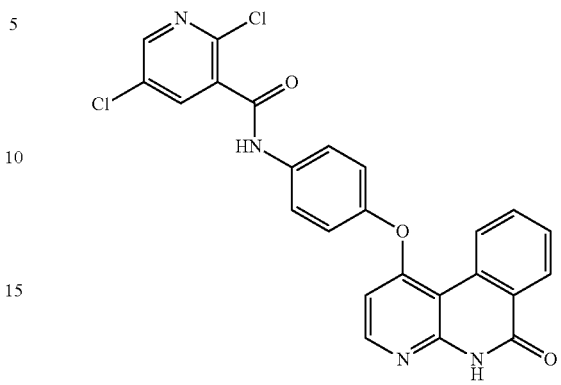

2,5-Dichloro-N-[4-(6-oxo-5,6-dihydro-benzo[c][1,8]naphthyridin-1-yloxy)-phenyl]-nicotinamide (180)

Compound 137 (40 mg, 0.13 mmol), 2,5-dichloro-nicotinoyl chloride (28 mg, 0.13 mmol), and DIEA (0.02 mL, 0.13 mmol) were suspended in dioxane (2 mL), and stirred overnight at room temperature. The reaction mixture was diluted with EtOAc/H$_2$O. The resulting precipitate was filtered, washed with EtOAc/H$_2$O, and dried under vacuum to provide 180 (40 mg, 64% yield) as a white solid. LC-MS (M+H=478, obsd.=478).

Example 181

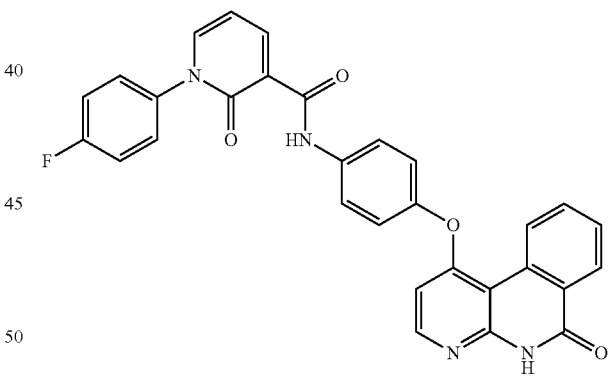

1-(4-Fluoro-phenyl)-2-oxo-1,2-dihydro-pyridine-3-carboxylic acid [4-(6-oxo-5,6-dihydro-benzo[c][1,8]naphthyridin-1-yloxy)-phenyl]-amide (181)

Compound 137 (40 mg, 0.13 mmol), 1-(4-fluoro-phenyl)-2-oxo-1,2-dihydro-pyridine-3-carboxylic acid (37 mg, 0.16 mmol), BOP-Cl (50 mg, 0.20 mmol), and DIEA (0.07 mL, 0.40 mmol) were suspended in dioxane (2 mL), and stirred overnight at room temperature. The reaction mixture was diluted with EtOAc/H$_2$O. The resulting precipitate was filtered, washed with EtOAc/H$_2$O, and dried under vacuum to provide 181 (42 mg, 61% yield) as a white solid. LC-MS (M+H=519, obsd.=519).

Example 182

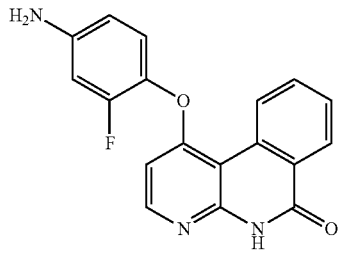 [SMILES: Nc1ccc(Oc2ccnc3[nH]c(=O)c4ccccc4c23)c(F)c1]

1-(4-Amino-2-fluoro-phenoxy)-5H-benzo[c][1,8]naphthyridin-6-one (182)

Compound 83 (250 mg, 1.08 mmol), 4-amino-2-fluoro-phenol (276 mg, 2.17 mmol), and cesium carbonate (1.41 g, 4.34 mmol) were suspended in DMF (5 mL), and stirred for 30 minutes at 120° C. in microwave. The reaction mixture was diluted with H$_2$O. The resulting precipitate was filtered. The precipitate was tritturated with MeOH, filtered, washed with MeOH, and dried under vacuum to provide 182 (312 mg, 90% yield) as a solid. LC-MS (M+H=322, obsd.=322).

Example 183

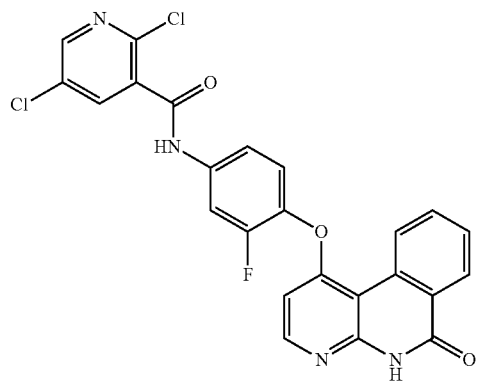 [SMILES: O=C(Nc1ccc(Oc2ccnc3[nH]c(=O)c4ccccc4c23)c(F)c1)c1cc(Cl)cnc1Cl]

2,5-Dichloro-N-[3-fluoro-4-(6-oxo-5,6-dihydro-benzo[c][1,8]naphthyridin-1-yloxy)-phenyl]-nicotinamide (183)

The title compound was synthesized according to the procedure described for the preparation of Example 180 using Compound 182 (50 mg, 0.16 mmol) and 2,5-dichloro-nicotinoyl chloride (36 mg, 0.17 mmol) to provide 183 (35 mg, 45% yield) as a dark solid. LC-MS (M+H=496, obsd.=496).

Example 184

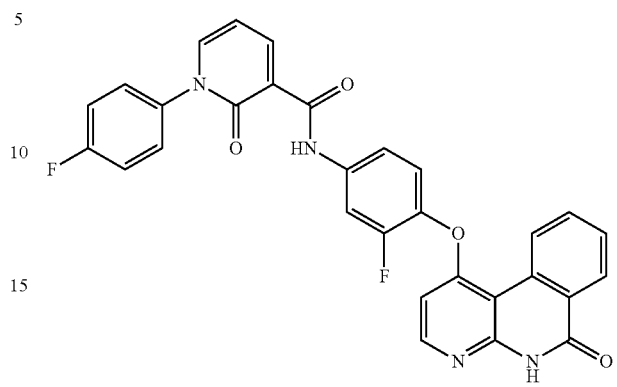

1-(4-Fluoro-phenyl)-2-oxo-1,2-dihydro-pyridine-3-carboxylic acid [3-fluoro-4-(6-oxo-5,6-dihydro-benzo[c][1,8]naphthyridin-1-yloxy)-phenyl]-amide (184)

The title compound was synthesized according to the procedure described for the preparation of Example 181 using Compound 182 (50 mg, 0.16 mmol) and 1-(4-fluoro-phenyl)-2-oxo-1,2-dihydro-pyridine-3-carboxylic acid (44 mg, 0.19 mmol) to provide 184 (75 mg, 90% yield) as a dark solid. LC-MS (M+H=537, obsd.=537).

Example 185

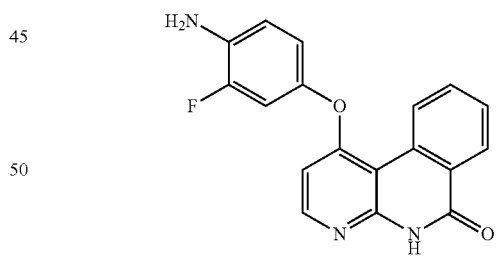

1-(4-Amino-3-fluoro-phenoxy)-5H-benzo[c][1,8]naphthyridin-6-one (185)

The title compound was synthesized according to the procedure described for the preparation of Example 182 using Compound 83 (250 mg, 1.08 mmol) and 4-amino-3-fluoro-phenol (276 mg, 2.17 mmol) to provide 185 (290 mg, 83% yield) as a solid. LC-MS (M+H=322, obsd.=322).

Example 186

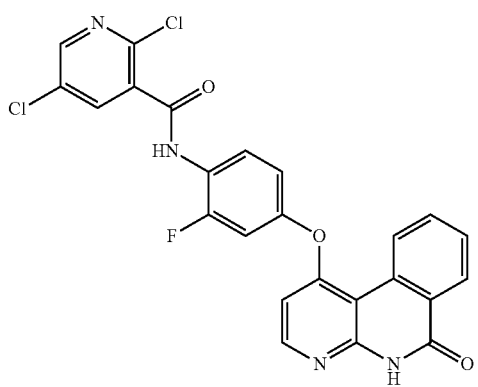 [SMILES: O=C(Nc1ccc(Oc2ccnc3[nH]c(=O)c4ccccc4c23)cc1F)c1cc(Cl)cnc1Cl]

2,5-Dichloro-N-[2-fluoro-4-(6-oxo-5,6-dihydro-benzo[c][1,8]naphthyridin-1-yloxy)-phenyl]-nicotinamide (186)

The title compound was synthesized according to the procedure described for the preparation of Example 180 using Compound 185 (50 mg, 0.16 mmol) and 2,5-dichloro-nicotinoyl chloride (36 mg, 0.17 mmol) to provide 186 (37 mg, 48% yield) as a dark solid. LC-MS (M+H=496, obsd.=496).

Example 187

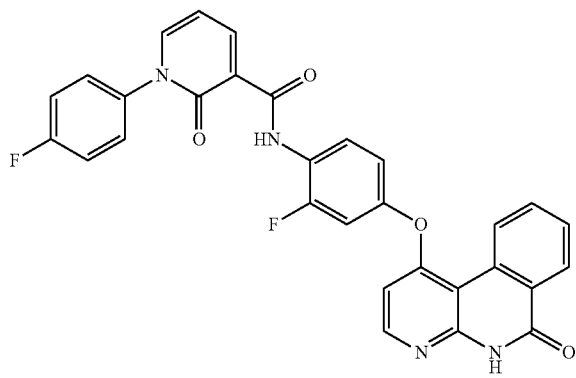 [SMILES: O=C(Nc1ccc(Oc2ccnc3[nH]c(=O)c4ccccc4c23)cc1F)c1cccn(-c2ccc(F)cc2)c1=O]

1-(4-Fluoro-phenyl)-2-oxo-1,2-dihydro-pyridine-3-carboxylic acid [2-fluoro-4-(6-oxo-5,6-dihydro-benzo[c][1,8]naphthyridin-1-yloxy)-phenyl]-amide (187)

The title compound was synthesized according to the procedure described for the preparation of Example 181 using Compound 185 (50 mg, 0.16 mmol) and 1-(4-fluoro-phenyl)-2-oxo-1,2-dihydro-pyridine-3-carboxylic acid (44 mg, 0.19 mmol) to provide 187 (65 mg, 78% yield) as a dark solid. LC-MS (M+H=537, obsd.=537).

Example 188

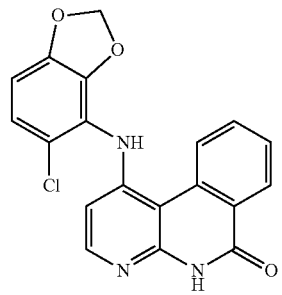 [SMILES: O=c1[nH]c2nccc(Nc3c(Cl)ccc4c3OCO4)c2c2ccccc12]

1-(5-Chloro-benzo[1,3]dioxol-4-ylamino)-5H-benzo[c][1,8]naphthyridin-6-one (188)

Compound 83 (250 mg, 1.08 mmol), 5-chloro-benzo[1,3]dioxol-4-ylamine (279 mg, 1.63 mmol), Pd(OAc)$_2$ (12 mg, 0.05 mmol), X-Phos (52 mg, 0.11 mmol), and NaOtBu (312 mg, 3.25 mmol) were suspended in dioxane (2 mL), and stirred overnight at 100° C. The reaction mixture was diluted with EtOAc/H$_2$O. The resulting precipitate was filtered, washed with EtOAc/H$_2$O, and dried under vacuum to provide 188 (301 mg, 76% yield) as a white solid. LC-MS (M+H=366, obsd.=366).

Example 189

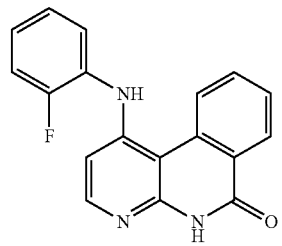 [SMILES: O=c1[nH]c2nccc(Nc3ccccc3F)c2c2ccccc12]

1-(2-Fluoro-phenylamino)-5H-benzo[c][1,8]naphthyridin-6-one (189)

The title compound was synthesized according to the procedure described for the preparation of Example 188 using Compound 83 (100 mg, 0.43 mmol) and 2-fluoroaniline (96 mg, 0.87 mmol) to provide 189 (98 mg, 74% yield) as a white solid. LC-MS (M+H=306, obsd.=306).

Example 190

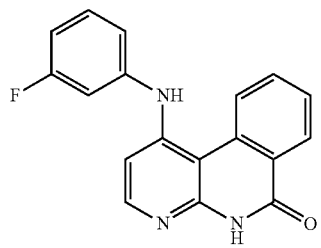 [SMILES: O=c1[nH]c2nccc(Nc3cccc(F)c3)c2c2ccccc12]

1-(3-Fluoro-phenylamino)-5H-benzo[c][1,8]naph-thyridin-6-one (190)

The title compound was synthesized according to the procedure described for the preparation of Example 188 using Compound 83 (100 mg, 0.43 mmol) and 3-fluoroaniline (96 mg, 0.87 mmol) to provide 190 (86 mg, 65% yield) as a white solid. LC-MS (M+H=306, obsd.=306).

Example 191

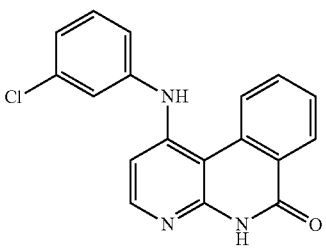 [SMILES: O=c1[nH]c2nccc(Nc3cccc(Cl)c3)c2c2ccccc12]

1-(3-Chloro-phenylamino)-5H-benzo[c][1,8]naph-thyridin-6-one (191)

The title compound was synthesized according to the procedure described for the preparation of Example 188 using Compound 83 (100 mg, 0.43 mmol) and 3-chloroaniline (83 mg, 0.65 mmol) to provide 191 (96 mg, 68% yield) as a white solid. LC-MS (M+H=322, obsd.=322).

Example 192

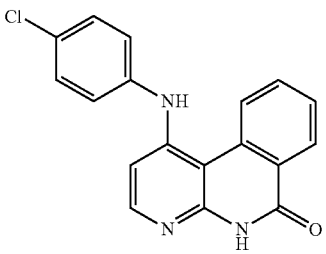 [SMILES: O=c1[nH]c2nccc(Nc3ccc(Cl)cc3)c2c2ccccc12]

1-(4-Chloro-phenylamino)-5H-benzo[c][1,8]naph-thyridin-6-one (192)

The title compound was synthesized according to the procedure described for the preparation of Example 188 using Compound 83 (100 mg, 0.43 mmol) and 4-chloroaniline (83 mg, 0.65 mmol) to provide 192 (136 mg, 97% yield) as a white solid. LC-MS (M+H=322, obsd.=322).

Example 193

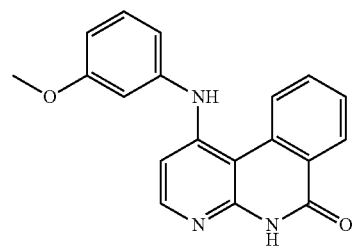 [SMILES: COc1cccc(Nc2ccnc3[nH]c(=O)c4ccccc4c23)c1]

1-(3-Methoxy-phenylamino)-5H-benzo[c][1,8]naph-thyridin-6-one (193)

The title compound was synthesized according to the procedure described for the preparation of Example 188 using Compound 83 (100 mg, 0.43 mmol) and 3-methoxyaniline (107 mg, 0.87 mmol) to provide 193 (107 mg, 78% yield) as a white solid. LC-MS (M+H=318, obsd.=318).

Example 194

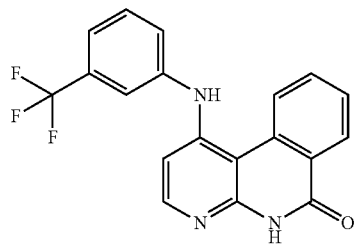 [SMILES: O=c1[nH]c2nccc(Nc3cccc(C(F)(F)F)c3)c2c2ccccc12]

1-(3-Trifluoromethyl-phenylamino)-5H-benzo[c][1,8]naphthyridin-6-one (194)

The title compound was synthesized according to the procedure described for the preparation of Example 188 using Compound 83 (100 mg, 0.43 mmol) and 3-(trifluoromethyl)aniline (140 mg, 0.87 mmol) to provide 194 (52 mg, 34% yield) as a white solid. LC-MS (M+H=356, obsd.=356).

Example 195

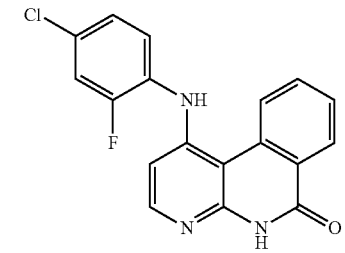 [SMILES: O=c1[nH]c2nccc(Nc3ccc(Cl)cc3F)c2c2ccccc12]

1-(4-Chloro-2-fluoro-phenylamino)-5H-benzo[c][1,8]naphthyridin-6-one (195)

The title compound was synthesized according to the procedure described for the preparation of Example 188 using Compound 83 (100 mg, 0.43 mmol) and 4-chloro-2-fluoroaniline (95 mg, 0.65 mmol) to provide 195 (116 mg, 79% yield) as a white solid. LC-MS (M+H=340, obsd.=340).

Example 196

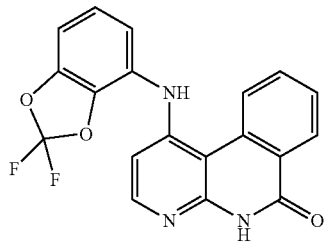 [SMILES: O=c1[nH]c2nccc(Nc3cccc4c3OC(F)(F)O4)c2c2ccccc12]

1-(2,2-Difluoro-benzo[1,3]-dioxol-4-ylamino)-5H-benzo[c][1,8]naphthyridin-6-one (196)

The title compound was synthesized according to the procedure described for the preparation of Example 188 using Compound 83 (100 mg, 0.43 mmol) and 2,2-difluoro-benzo[1,3]dioxol-4-ylamine (150 mg, 0.87 mmol) to provide 196 (122 mg, 77% yield) as a white solid. LC-MS (M+H=368, obsd.=368).

Example 197

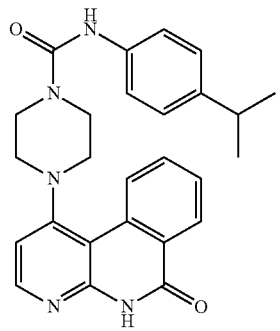 [SMILES: CC(C)c1ccc(NC(=O)N2CCN(c3ccnc4[nH]c(=O)c5ccccc5c34)CC2)cc1]

4-(6-oxo-5,6-dihydro-benzo[c][1,8]naphthyridin-1-yl)-piperazine-1-carboxylic acid (4-isopropyl-phenyl)-amide (197)

Compound 179 (50 mg, 0.14 mmol), 1-isocyanato-4-isopropyl-benzene (34 mg, 0.21 mmol), and DIEA (0.07 mL, 0.42 mmol) were suspended in dioxane (2 mL), and stirred overnight at 80° C. The reaction mixture was quenched with 1M HCl, and diluted with EtOAc. The mixture was filtered through an Extrelut column. The column was washed with EtOAc, and the filtrate was concentrated. The crude product was purified via Biotage eluting with a gradient of 75 to 100 EtOAc in hexane to provide 197 (40 mg, 64% yield) as a yellow solid. LC-MS (M+H=442, obsd.=442).

Example 198

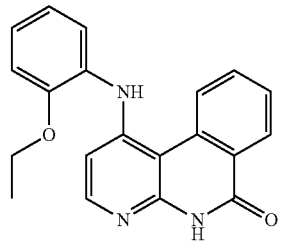 [SMILES: CCOc1ccccc1Nc1ccnc2[nH]c(=O)c3ccccc3c12]

1-(2-Ethoxy-phenylamino)-5H-benzo[c][1,8]naphthyridin-6-one (198)

The title compound was synthesized according to the procedure described for the preparation of Example 188 using Compound 83 (100 mg, 0.43 mmol) and 2-ethoxyaniline (119 mg, 0.87 mmol) to provide 198 (123 mg, 86% yield) as a white solid. LC-MS (M+H=332, obsd.=332).

Example 199

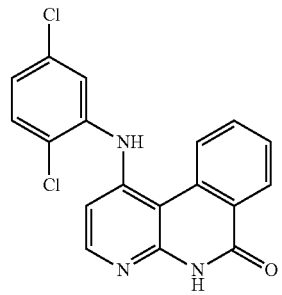 [SMILES: O=c1[nH]c2nccc(Nc3cc(Cl)ccc3Cl)c2c2ccccc12]

1-(2,5-Dichloro-phenylamino)-5H-benzo[c][1,8]naphthyridin-6-one (199)

The title compound was synthesized according to the procedure described for the preparation of Example 188 using Compound 83 (100 mg, 0.43 mmol) and 2,5-di-chloroaniline (105 mg, 0.65 mmol) to provide 199 (50 mg, 32% yield) as a white solid. LC-MS (M+H=356, obsd.=356).

Example 200

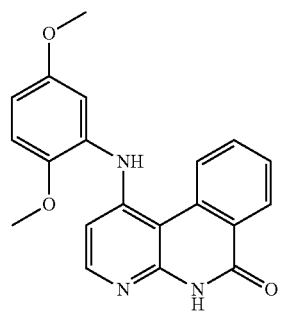 [SMILES: COc1ccc(OC)c(Nc2ccnc3[nH]c(=O)c4ccccc4c23)c1]

1-(2,5-Di-methoxy-phenylamino)-5H-benzo[c][1,8] naphthyridin-6-one (200)

The title compound was synthesized according to the procedure described for the preparation of Example 188 using Compound 83 (100 mg, 0.43 mmol) and 2,5-di-methoxyaniline (133 mg, 0.87 mmol) to provide 200 (114 mg, 76% yield) as a white solid. LC-MS (M+H=348, obsd.=348).

Example 201

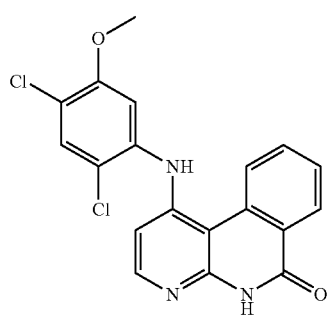 [SMILES: COc1cc(Nc2ccnc3[nH]c(=O)c4ccccc4c23)c(Cl)cc1Cl]

1-(2,4-Dichloro-5-methoxy-phenylamino)-5H-benzo[c][1,8]naphthyridin-6-one (201)

The title compound was synthesized according to the procedure described for the preparation of Example 188 using Compound 83 (100 mg, 0.43 mmol) and 2,4-di-chloro-5-methoxyaniline (125 mg, 0.65 mmol) to provide 201 (77 mg, 56% yield) as a white solid. LC-MS (M+H=386, obsd.=386).

Example 202

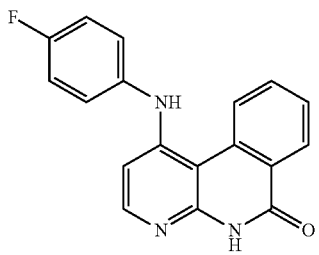

1-(4-Fluoro-phenylamino)-5H-benzo[c][1,8]naphthyridin-6-one (202)

The title compound was synthesized according to the procedure described for the preparation of Example 188 using Compound 83 (100 mg, 0.43 mmol) and 4-fluoroaniline (96 mg, 0.87 mmol) to provide 202 (93 mg, 70% yield) as a white solid. LC-MS (M+H=306, obsd.=306).

Example 203

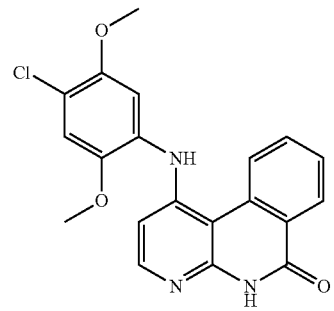 [SMILES: COc1cc(Nc2ccnc3[nH]c(=O)c4ccccc4c23)c(OC)cc1Cl]

1-(4-Chloro-2,5-dimethoxy-phenylamino)-5H-benzo[c][1,8]naphthyridin-6-one (203)

The title compound was synthesized according to the procedure described for the preparation of Example 188 using Compound 83 (100 mg, 0.43 mmol) and 4-chloro-2,5-dimethoxyaniline (122 mg, 0.65 mmol) to provide 203 (80 mg, 48% yield) as a white solid. LC-MS (M+H=382, obsd.=382).

Example 204

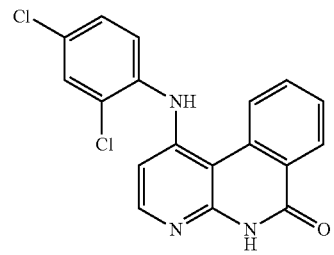 [SMILES: O=c1[nH]c2nccc(Nc3ccc(Cl)cc3Cl)c2c2ccccc12]

1-(2,4-Di-chloro-phenylamino)-5H-benzo[c][1,8] naphthyridin-6-one (204)

The title compound was synthesized according to the procedure described for the preparation of Example 188 using Compound 83 (100 mg, 0.43 mmol) and 2,4-di-chloroaniline (105 mg, 0.65 mmol) to provide 204 (20 mg, 12% yield) as a white solid. LC-MS (M+H=356, obsd.=356).

Example 205

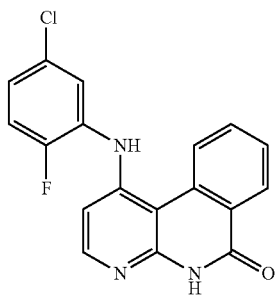 [SMILES: O=c1[nH]c2nccc(Nc3cc(Cl)ccc3F)c2c2ccccc12]

1-(5-Chloro-2-fluoro-phenylamino)-5H-benzo[c][1,8]naphthyridin-6-one (205)

The title compound was synthesized according to the procedure described for the preparation of Example 188 using Compound 83 (100 mg, 0.43 mmol) and 5-chloro-2-fluoroaniline (82 mg, 0.56 mmol) to provide 205 (70 mg, 48% yield) as a white solid. LC-MS (M+H=340, obsd.=340).

Example 206

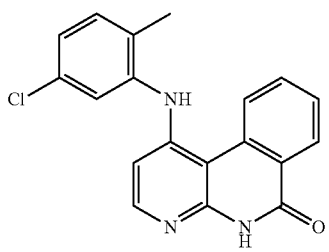 [SMILES: Cc1ccc(Cl)cc1Nc1ccnc2[nH]c(=O)c3ccccc3c12]

1-(5-Chloro-2-methyl-phenylamino)-5H-benzo[c][1,8]naphthyridin-6-one (206)

The title compound was synthesized according to the procedure described for the preparation of Example 188 using Compound 83 (100 mg, 0.43 mmol) and 5-chloro-2-methylaniline (80 mg, 0.56 mmol) to provide 206 (113 mg, 78% yield) as a white solid. LC-MS (M+H=336, obsd.=336).

Example 207

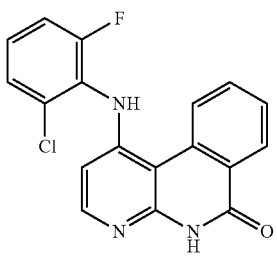 [SMILES: O=c1[nH]c2nccc(Nc3c(F)cccc3Cl)c2c2ccccc12]

1-(2-Chloro-6-fluoro-phenylamino)-5H-benzo[c][1,8]naphthyridin-6-one (207)

The title compound was synthesized according to the procedure described for the preparation of Example 188 using Compound 83 (100 mg, 0.43 mmol) and 2-chloro-6-fluoroaniline (82 mg, 0.56 mmol) to provide 207 (101 mg, 69% yield) as a white solid. LC-MS (M+H=340, obsd.=340).

Example 208

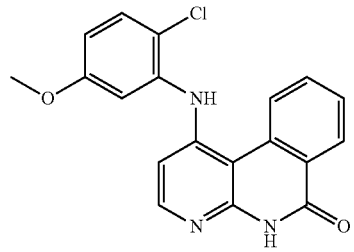 [SMILES: COc1ccc(Cl)c(Nc2ccnc3[nH]c(=O)c4ccccc4c23)c1]

1-(2-Chloro-5-methoxy-phenylamino)-5H-benzo[c][1,8]naphthyridin-6-one (208)

The title compound was synthesized according to the procedure described for the preparation of Example 188 using Compound 83 (100 mg, 0.43 mmol) and 2-chloro-5-methoxyaniline (109 mg, 0.56 mmol) to provide 208 (92 mg, 60% yield) as a white solid. LC-MS (M+H=352, obsd.=352).

Example 209

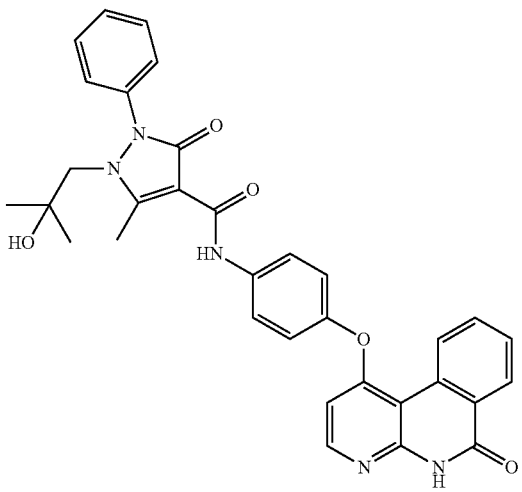 [SMILES: Cc1c(C(=O)Nc2ccc(Oc3ccnc4[nH]c(=O)c5ccccc5c34)cc2)c(=O)n(-c2ccccc2)n1CC(C)(C)O]

1-(2-Hydroxy-2-methyl-propyl)-5-methyl-3-oxo-2-phenyl-2,3-dihydro-1H-pyrazole-4-carboxylic acid [4-(6-oxo-5,6-dihydro-benzo[c][1,8]naphthyridin-1-yloxy)-phenyl]-amide (209)

Compound 137 (50 mg, 0.16 mmol), 1-(2-hydroxy-2-methyl-propyl)-5-methyl-3-oxo-2-phenyl-2,3-dihydro-1H-pyrazole-4-carboxylic acid (57 mg, 0.26 mmol), BOP-Cl (63 mg, 0.25 mmol), and DIEA (0.08 mL, 0.49 mmol) were suspended in dioxane (2 mL), and stirred overnight at room temperature. The reaction mixture was diluted with EtOAc/H$_2$O, and filtered through an Extrelut column. The column was washed with EtOAc and the filtrate was concentrated. The crude material was purified via Biotage eluting with a gradient of 0 to 10% MeOH in CH$_2$Cl$_2$ to provide 209 (28 mg, 30% yield) as a white solid. LC-MS (M+H=576, obsd.=576).

Example 210

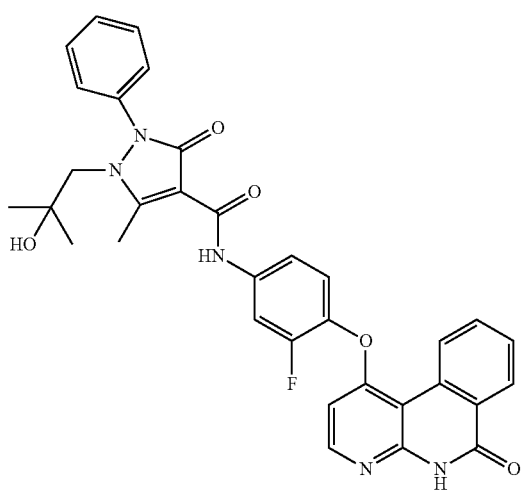 [SMILES: Cc1c(C(=O)Nc2ccc(Oc3ccnc4[nH]c(=O)c5ccccc5c34)c(F)c2)c(=O)n(-c2ccccc2)n1CC(C)(C)O]

1-(2-Hydroxy-2-methyl-propyl)-5-methyl-3-oxo-2-phenyl-2,3-dihydro-1H-pyrazole-4-carboxylic acid [3-fluoro-4-(6-oxo-5,6-dihydro-benzo[c][1,8]naphthyridin-1-yloxy)-phenyl]-amide (210)

The title compound was synthesized according to the procedure described for the preparation of Example 209 using Compound 182 (55 mg, 0.17 mmol) and 1-(2-hydroxy-2-methyl-propyl)-5-methyl-3-oxo-2-phenyl-2,3-dihydro-1H-pyrazole-4-carboxylic acid (60 mg, 0.21 mmol) to provide 210 (34 mg, 33% yield) as a white solid. LC-MS (M+H=594, obsd.=594).

Example 211

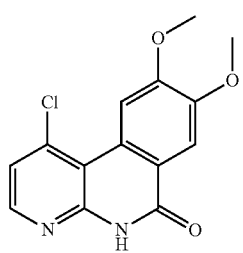 [SMILES: COc1cc2c(=O)[nH]c3nccc(Cl)c3c2cc1OC]

1-Chloro-8,9-dimethoxy-5H-benzo[c][1,8]naphthyridin-6-one (211)

The title compound was synthesized according to the procedure described for the preparation of Example 1 using 2-amino-3-iodo-4-chloropyridine (1.0 g, 3.93 mmol) and 3,4-di-methoxy-2-methoxycarbonylphenylboronic acid (1.41 g, 5.89 mmol) to provide 211 (616 mg, 54% yield) as a white solid. LC-MS (M+H=291, obsd.=291).

Example 212

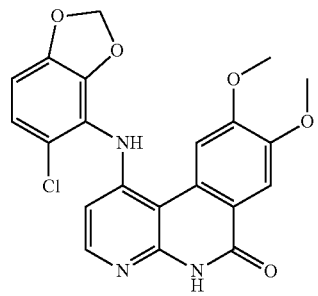 [SMILES: COc1cc2c(=O)[nH]c3nccc(Nc4c(Cl)ccc5c4OCO5)c3c2cc1OC]

1-(5-Chloro-benzo[1,3]dioxol-4-ylamino)-8,9-dimethoxy-5H-benzo[c][1,8]naphthyridin-6-one (212)

Compound 211 (50 mg, 0.17 mmol), 5-chloro-benzo[1,3]dioxol-4-ylamine (38 mg, 0.22 mmol), Pd(OAc)$_2$ (2 mg, 0.01 mmol), X-Phos (8 mg, 0.02 mmol), and NaOtBu (50 mg, 0.52 mmol) were suspended in dioxane (2 mL), and stirred overnight at 100° C. The reaction mixture was diluted with EtOAc/H$_2$O, and filtered. The resulting precipitate was washed with EtOAc/H$_2$O, and then suspended in methanolic HCl. The crude product was purified via prep-LC-MS to provide 212 (2 mg, 3% yield) as a white solid. LC-MS (M+H=426, obsd.=426).

Example 213

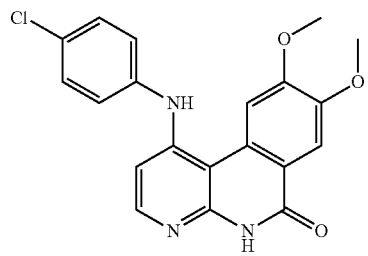 [SMILES: COc1cc2c(=O)[nH]c3nccc(Nc4ccc(Cl)cc4)c3c2cc1OC]

1-(4-Chloro-phenylamino)-8,9-dimethoxy-5H-benzo[c][1,8]naphthyridin-6-one (213)

The title compound was synthesized according to the procedure described for the preparation of Example 212 using Compound 211 (50 mg, 0.17 mmol) and 4-chloroaniline (29 mg, 0.22 mmol) to provide 213 (20 mg, 30% yield) as a white solid. LC-MS (M+H=382, obsd.=382).

Compound 214

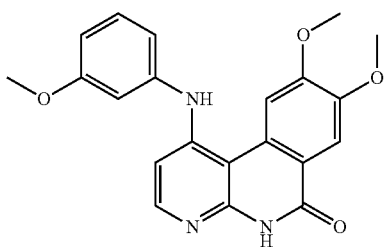

1-(3-Methoxy-phenylamino)-8,9-dimethoxy-5H-benzo[c][1,8]naphthyridin-6-one (214)

The title compound was synthesized according to the procedure described for the preparation of Example 212 using Compound 211 (50 mg, 0.17 mmol) and 3-methoxyaniline (27 mg, 0.22 mmol) to provide 214 (4 mg, 6% yield) as a white solid. LC-MS (M+H=378, obsd.=378).

Example 215

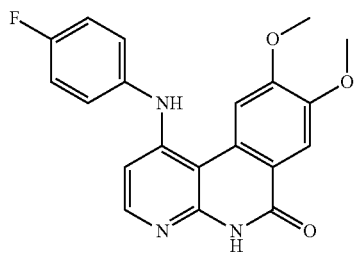 [SMILES: COc1cc2c(=O)[nH]c3nccc(Nc4ccc(F)cc4)c3c2cc1OC]

1-(4-Fluoro-phenylamino)-8,9-dimethoxy-5H-benzo[c][1,8]naphthyridin-6-one (215)

The title compound was synthesized according to the procedure described for the preparation of Example 212 using Compound 211 (50 mg, 0.17 mmol) and 4-fluoroaniline (25 mg, 0.22 mmol) to provide 215 (2 mg, 2% yield) as a white solid. LC-MS (M+H=366, obsd.=366).

Example 216

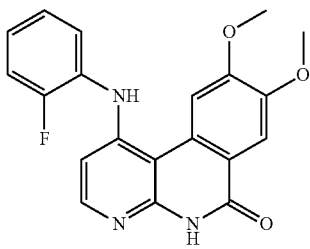 [SMILES: COc1cc2c(=O)[nH]c3nccc(Nc4ccccc4F)c3c2cc1OC]

1-(2-Fluoro-phenylamino)-8,9-dimethoxy-5H-benzo[c][1,8]naphthyridin-6-one (216)

The title compound was synthesized according to the procedure described for the preparation of Example 212 using Compound 211 (50 mg, 0.17 mmol) and 2-fluoroaniline (25 mg, 0.22 mmol) to provide 216 (2 mg, 3% yield) as a white solid. LC-MS (M+H=366, obsd.=366).

Compound 217

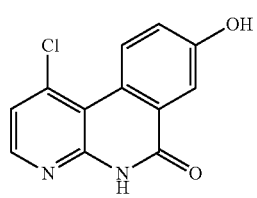 [SMILES: O=c1[nH]c2nccc(Cl)c2c2ccc(O)cc12]

1-Chloro-8-hydroxy-5H-benzo[c][1,8]naphthyridin-6-one (217)

The title compound was synthesized according to the procedure described for the preparation of Example 1 using 4-chloro-3-iodopyridin-2-amine (500 mg, 1.96 mmol) and 2-methoxycarbonyl-4-hydroxy-phenylboronic acid (765 mg, 2.75 mmol) to provide 217 (83 mg, 17% yield) as a white solid. LC-MS (M+H=247, obsd.=247).

Compound 218

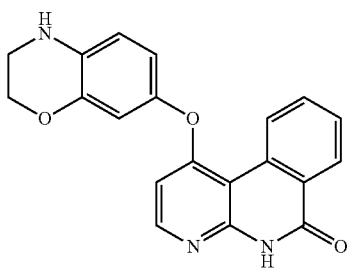 [SMILES: O=c1[nH]c2nccc(Oc3ccc4c(c3)OCCN4)c2c2ccccc12]

1-(3,4-Dihydro-2H-benzo[1,4]oxazin-7-yloxy)-5H-benzo[c][1,8]naphthyridin-6-one (218)

The title compound was synthesized according to the procedure described for the preparation of Example 182 using Compound 83 (250 mg, 1.08 mmol) and 3,4-dihydro-2H-benzo[1,4]oxazin-7-ol (328 mg, 2.17 mmol) to provide 218 (276 mg, 74% yield) as a tan solid. LC-MS (M+H=346, obsd.=346).

Example 219

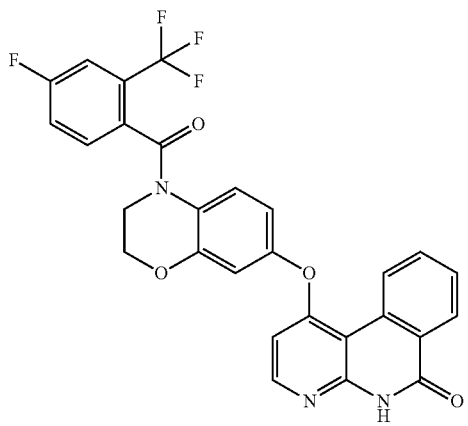 [SMILES: O=C(c1ccc(F)cc1C(F)(F)F)N1CCOc2cc(Oc3ccnc4[nH]c(=O)c5ccccc5c34)ccc21]

1-[4-(4-Fluoro-2-trifluoromethyl-benzoyl)-3,4-dihydro-2H-benzo[1,4]oxazin-7-yloxy]-5H-benzo[c][1,8]naphthyridin-6-one (219)

Compound 218 (50 mg, 0.14 mmol), 4-fluoro-2-trifluoromethyl-benzoyl chloride (49 mg, 0.22 mmol), and DIEA (0.07 mL, 0.43 mmol) were dissolved in dioxane (2 mL) and stirred for 1 h at room temperature. The reaction was quenched with $H_2O$, diluted with EtOAc, and filtered through an Extrelut column. The column was washed with EtOAc, and the filtrate was concentrated. The crude product was purified via Biotage eluting with a gradient of 0 to 100% EtOAc in hexanes to provide 219 (28 mg, 36% yield) as a tan solid. LC-MS (M+H=536, obsd.=536).

Compound 220

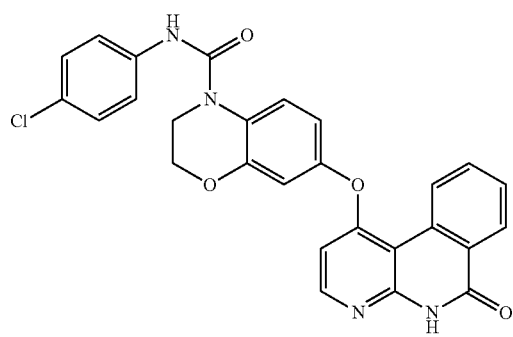 [SMILES: O=C(Nc1ccc(Cl)cc1)N1CCOc2cc(Oc3ccnc4[nH]c(=O)c5ccccc5c34)ccc21]

7-(6-Oxo-5,6-dihydro-benzo[c][1,8]naphthyridin-1-yloxy)-2,3-dihydro-benzo[1,4]oxazine-4-carboxylic acid (4-chloro-phenyl)-amide (220)

Compound 218 (50 mg, 0.14 mmol), 1-chloro-4-isocyanato-benzene (33 mg, 0.22 mmol), and DIEA (0.07 mL, 0.43 mmol) were dissolved in dioxane (2 mL) and stirred and stirred for 30 minutes at 100° C. in microwave. The reaction mixture was diluted with $H_2O$/EtOAc. The resulting precipitate was filtered, washed with EtOAc, and dried under vacuum to provide 220 (51 mg, 71% yield) as a tan solid. LC-MS (M+H=499, obsd.=499).

Example 221

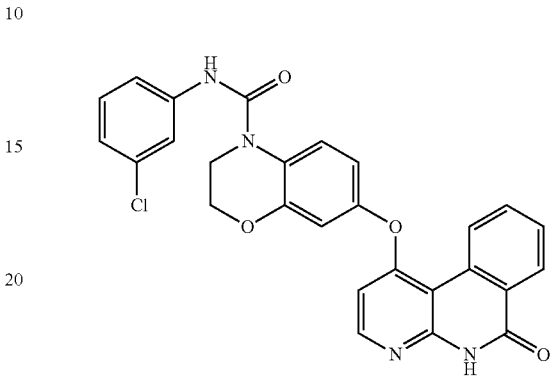

7-(6-Oxo-5,6-dihydro-benzo[c][1,8]naphthyridin-1-yloxy)-2,3-dihydro-benzo[1,4]oxazine-4-carboxylic acid (3-chloro-phenyl)-amide (221)

Compound 218 (25 mg, 0.07 mmol), 1-chloro-3-isocyanato-benzene (17 mg, 0.11 mmol), and DIEA (0.04 mL, 0.22 mmol) were dissolved in dioxane (2 mL) and stirred and stirred for 30 minutes at 100° C. in microwave. The reaction mixture was diluted with $H_2O$/EtOAc, and filtered through an Extrelut column. The column was washed with EtOAc, and the filtrate was concentrated. The crude product was purified via Biotage eluting with a gradient of 50 to 100% EtOAc in hexanes to provide 221 (8 mg, 22% yield) as a tan solid. LC-MS (M+H=499, obsd.=499).

Example 222

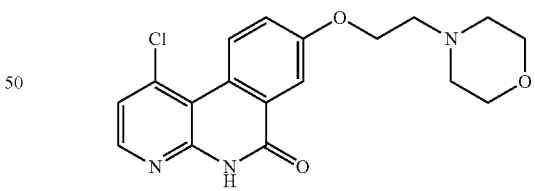

1-Chloro-8-(2-morpholin-4-yl-ethoxy)-5H-benzo[c][1,8]naphthyridin-6-one (222)

The title compound was synthesized according to the procedure described for the preparation of Example 1 using 4-chloro-3-iodopyridin-2-amine (65 mg, 0.26 mmol) and 5-(2-morpholin-4-yl-ethoxy)-2-(4,4,5,5-tetramethyl[1,3,2]-dioxaborolan-2-yl)-benzoic acid methyl ester (110 mg, 0.28 mmol) to provide 222 (6 mg, 6% yield) as a white solid. LC-MS (M+H=360, obsd.=360).

Example 223

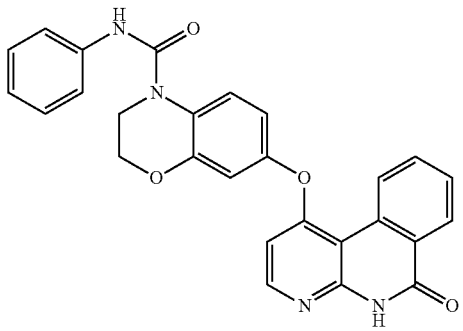 [SMILES: O=C(Nc1ccccc1)N1CCOc2cc(Oc3ccnc4[nH]c(=O)c5ccccc5c34)ccc21]

7-(6-Oxo-5,6-dihydro-benzo[c][1,8]naphthyridin-1-yloxy)-2,3-dihydro-benzo[1,4]oxazine-4-carboxylic acid phenylamide (223)

The title compound was synthesized according to the procedure described for the preparation of Example 221 using 218 (50 mg, 0.14 mmol) and isocyanato benzene (26 mg, 0.22 mmol) to provide 223 (5 mg, 7% yield) as a tan solid. LC-MS (M+H=465, obsd.=465).

Example 224

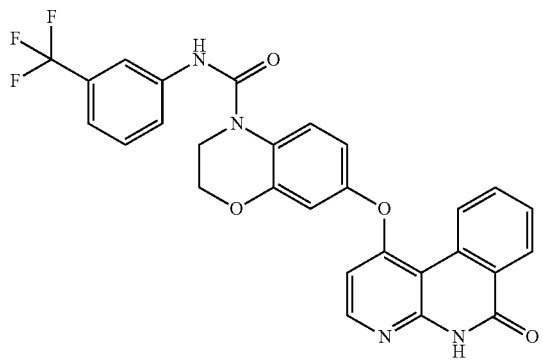 [SMILES: O=C(Nc1cccc(C(F)(F)F)c1)N1CCOc2cc(Oc3ccnc4[nH]c(=O)c5ccccc5c34)ccc21]

7-(6-Oxo-5,6-dihydro-benzo[c][1,8]naphthyridin-1-yloxy)-2,3-dihydro-benzo[1,4]oxazine-4-carboxylic acid (3-trifluoromethyl-phenyl)-amide (224)

The title compound was synthesized according to the procedure described for the preparation of Example 221 using 218 (50 mg, 0.14 mmol) and 1-isocyanato-3-trifluoromethyl-benzene (41 mg, 0.22 mmol) to provide 224 (17 mg, 22% yield) as a tan solid. LC-MS (M+H=533, obsd.=533).

Example 225

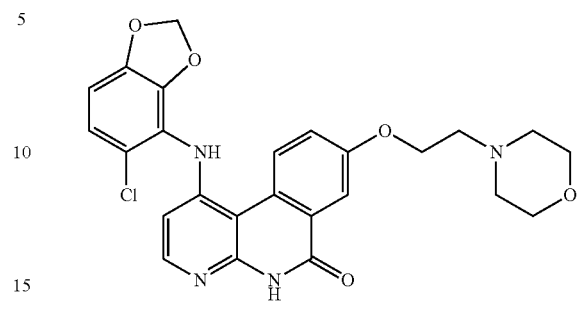

1-(5-Chloro-benzo[1,3]dioxol-4-ylamino)-8-(2-morpholin-4-yl-ethoxy)-5H-benzo[c][1,8]naphthyridin-6-one (225)

The title compound was synthesized according to the procedure described for the preparation of Example 212 using 222 (90 mg, 0.25 mmol) and 5-chloro-benzo[1,3]dioxol-4-ylamine (56 mg, 0.33 mmol) to provide 225 (8 mg, 6% yield) as a white solid. LC-MS (M+H=568, obsd.=568).

Example 226

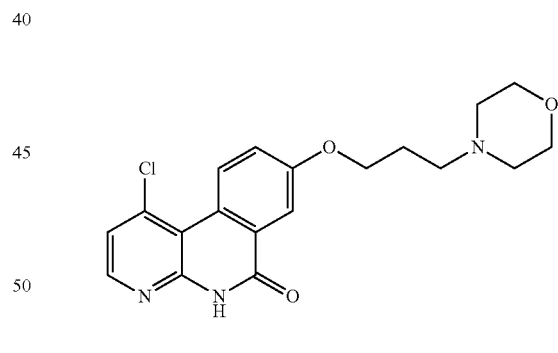

1-Chloro-8-(3-morpholin-4-yl-propoxy)-5H-benzo[c][1,8]naphthyridin-6-one (226)

The title compound was synthesized according to the procedure described for the preparation of Example 1 using 4-chloro-3-iodopyridin-2-amine (350 mg, 1.38 mmol) and 5-(3-morpholin-4-yl-propoxy)-2-(4,4,5,5-tetramethyl[1,3,2]-dioxaborolan-2-yl)-benzoic acid methyl ester (697 mg, 1.72 mmol) to provide 226 (120 mg, 23% yield) as a white solid. LC-MS (M+H=374, obsd.=374).

Example 227

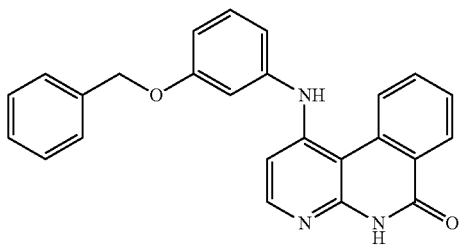 [SMILES: O=c1[nH]c2nccc(Nc3cccc(OCc4ccccc4)c3)c2c2ccccc12]

1-(3-Benzyloxy-phenylamino)-5H-benzo[c][1,8]naphthyridin-6-one (227)

The title compound was synthesized according to the procedure described for the preparation of Example 188 using 83 (100 mg, 0.43 mmol) and 3-benzyloxy-phenylamine (130 mg, 0.65 mmol) to provide 227 (121 mg, 71% yield) as a tan solid. LC-MS (M+H=394, obsd.=394).

Example 228

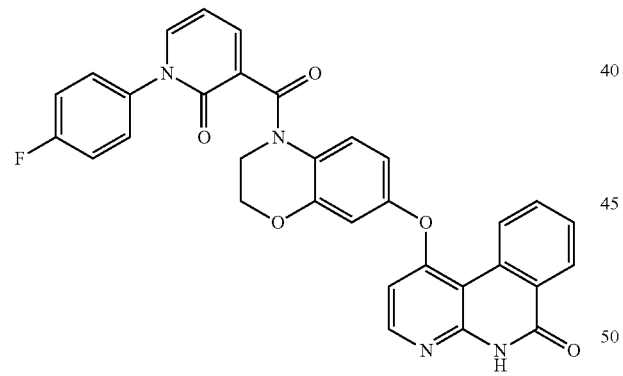

1-{4-[1-(4-Fluoro-phenyl)-2-oxo-1,2-dihydro-pyridine-3-carbonyl]-3,4-dihydro-2H-benzo[1,4]oxazin-7-yloxy}-5H-benzo[c][1,8]naphthyridin-6-one (228)

The title compound was synthesized according to the procedure described for the preparation of Example 181 using 218 (40 mg, 0.12 mmol) and 1-(4-fluoro-phenyl)-2-oxo-1,2-dihydro-pyridine-3-carboxylic acid (41 mg, 0.17 mmol) to provide 228 (54 mg, 83% yield) as a tan solid. LC-MS (M+H=561, obsd.=561).

Example 229

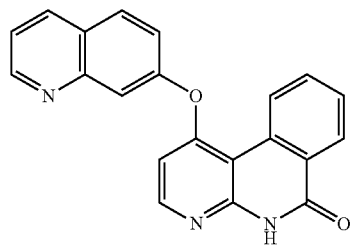 [SMILES: O=c1[nH]c2nccc(Oc3ccc4cccnc4c3)c2c2ccccc12]

1-(Quinolin-7-yloxy)-5H-benzo[c][1,8]naphthyridin-6-one (229)

The title compound was synthesized according to the procedure described for the preparation of Example 182 using 83 (50 mg, 0.22 mmol) and quinolin-7-ol (63 mg, 0.43 mmol) to provide 229 (51 mg, 69% yield) as a tan solid. LC-MS (M+H=340, obsd.=340).

Example 230

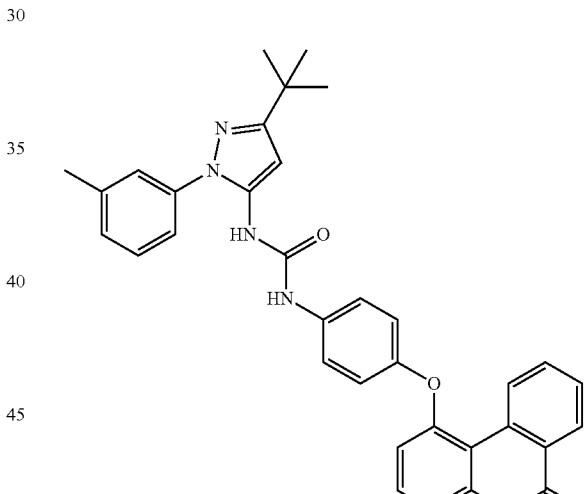

1-(5-tert-Butyl-2-m-tolyl-2H-pyrazol-3-yl)-3-[4-(6-oxo-5,6-dihydro-benzo[c][1,8]naphthyridin-1-yloxy)-phenyl]-urea (230)

Compound 137 (50 mg, 0.16 mmol), (5-tert-butyl-2-m-tolyl-2H-pyrazol-3-yl)-carbamic acid 2,2,2-trichloro-ethyl ester (80 mg, 0.20 mmol), and DIEA (0.08 mL, 0.49 mmol) were suspended in DMSO (2 mL), and stirred overnight at 60° C. The reaction solution was diluted with $H_2O$/EtOAc, and filtered through an Extrelut column. The column was washed with EtOAc, and the filtrate was concentrated. The crude product was purified via Biotage eluting with a gradient of 25 to 100% EtOAc in hexanes to provide 230 (22 mg, 24% yield) as a tan solid. LC-MS (M+H=559, obsd.=559).

Example 231

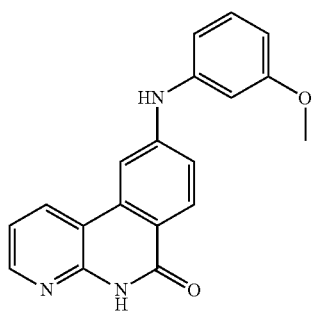 [SMILES: COc1cccc(Nc2ccc3c(=O)[nH]c4ncccc4c3c2)c1]

9-(3-Methoxy-phenylamino)-5H-benzo[c][1,8]naph-thyridin-6-one (231)

Compound 6 (50 mg, 0.22 mmol), Pd(OAc)$_2$ (4 mg, 0.02 mmol), X-Phos (17 mg, 0.03 mmol), NaOtBu (125 mg, 1.30 mmol), and m-anisidine (0.04 mL, 0.33 mmol) were dissolved in dioxane (2 ml) and stirred for 72 hrs at 100° C. The crude material was purified directly via Biotage eluting with a gradient of 0 to 10% MeOH in CH$_2$Cl$_2$ to provide 231 (14 mg, 19% yield) as a white solid. LC-MS (M+H=318, obsd.=318).

Example 232

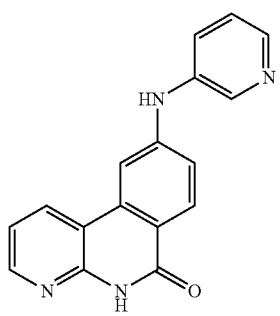 [SMILES: O=c1[nH]c2ncccc2c2cc(Nc3cccnc3)ccc12]

9-(Pyridin-3-ylamino)-5H-benzo[c][1,8]naphthyri-din-6-one (232)

The title compound was synthesized according to the procedure described for the preparation of Example 231 using 6 (50 mg, 0.22 mmol) and 3-aminopyridine (61 mg, 0.65 mmol) to provide 232 (31 mg, 54% yield) as a white solid. LC-MS (M+H=289, obsd.=289). $^1$H NMR (400 MHz, d$_6$-DMSO): δ 11.74 (s, 1H), 9.10 (s, 1H), 8.54 (m, 2H), 8.47 (dd 1H), 8.23 (dd, 1H), 8.19 (d, 1H), 7.91 (d, 1H), 7.75 (m, 1H), 7.39 (m, 1H), 7.30 (m, 2H).

Example 233

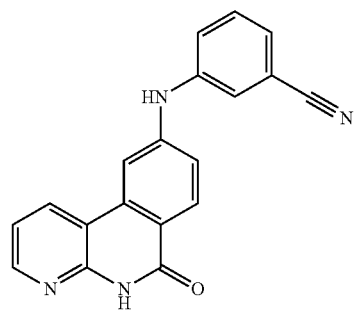 [SMILES: N#Cc1cccc(Nc2ccc3c(=O)[nH]c4ncccc4c3c2)c1]

3-(6-oxo-5,6-dihydro-benzo[c][1,8]naphthyridin-9-ylamino)-benzonitrile (233)

The title compound was synthesized according to the procedure described for the preparation of Example 231 using 6 (50 mg, 0.22 mmol) and 3-aminobenzonitrile (38 mg, 0.33 mmol) to provide 233 (11 mg, 16% yield) as a white solid. LC-MS (M+H=313, obsd.=313).

Example 234

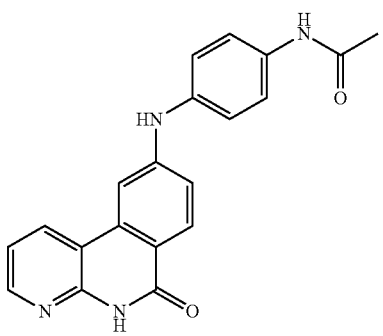 [SMILES: CC(=O)Nc1ccc(Nc2ccc3c(=O)[nH]c4ncccc4c3c2)cc1]

N-[4-(6-Oxo-5,6-dihydro-benzo[c][1,8]naphthyridin-9-ylamino)-phenyl]-acetamide (234)

The title compound was synthesized according to the procedure described for the preparation of Example 231 using 6 (50 mg, 0.22 mmol) and N-(4-Amino-phenyl)-acetamide (38 mg, 0.33 mmol) to provide 234 (10 mg, 17% yield) as a brown solid. LC-MS (M+H=345, obsd.=345).

Example 235

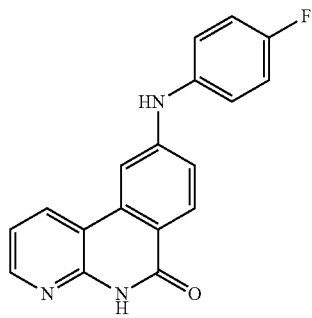 [SMILES: O=c1[nH]c2ncccc2c2cc(Nc3ccc(F)cc3)ccc12]

9-(4-Fluoro-phenylamino)-5H-benzo[c][1,8]naph-
thyridin-6-one (235)

The title compound was synthesized according to the procedure described for the preparation of Example 231 using 6 (50 mg, 0.22 mmol) and 4-fluoroaniline (0.03 mL, 0.33 mmol) to provide 235 (17 mg, 23% yield) as a green/brown solid. LC-MS (M+H=306, obsd.=306).

Example 236

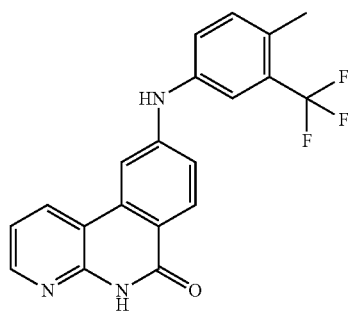 [SMILES: Cc1ccc(Nc2ccc3c(=O)[nH]c4ncccc4c3c2)cc1C(F)(F)F]

9-(4-Methyl-3-trifluoromethyl-phenylamino)-5H-
benzo[c][1,8]naphthyridin-6-one (236)

The title compound was synthesized according to the procedure described for the preparation of Example 231 using 6 (50 mg, 0.22 mmol) and 4-methyl-3-trifluoromethyl-phenylamine (0.03 mL, 0.33 mmol) to provide 236 (14 mg, 17% yield) as a brown solid. LC-MS (M+H=370, obsd.=370). $^1$H NMR (400 MHz, $d_6$-DMSO): δ 11.73 (s, 1H), 9.11 (s, 1H), 8.52 (dd, 1H), 8.47 (dd, 1H), 8.18 (d, 1H), 7.90 (d, 1H), 7.54 (dd, 1H), 7.43 (m, 2H), 7.28 (m, 2H), 2.41 (s, 3).

Example 237

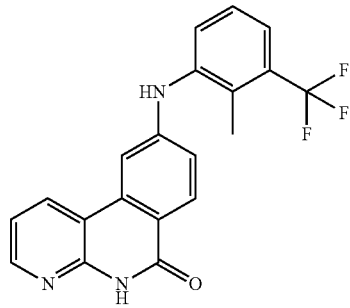 [SMILES: Cc1c(Nc2ccc3c(=O)[nH]c4ncccc4c3c2)cccc1C(F)(F)F]

9-(2-Methyl-3-trifluoromethyl-phenylamino)-5H-
benzo[c][1,8]naphthyridin-6-one (237)

The title compound was synthesized according to the procedure described for the preparation of Example 231 using 6 (50 mg, 0.22 mmol) and 2-methyl-3-trifluoromethyl-phenylamine (0.03 mL, 0.33 mmol) to provide 237 (23 mg, 28% yield) as a brown solid. LC-MS (M+H=370, obsd.=370).

Example 238

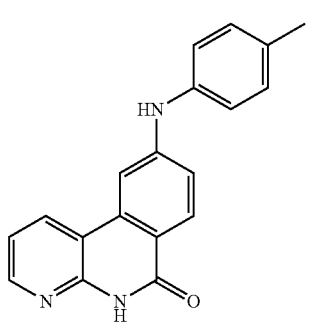 [SMILES: Cc1ccc(Nc2ccc3c(=O)[nH]c4ncccc4c3c2)cc1]

9-p-Tolylamino-5H-benzo[c][1,8]naphthyridin-6-one
(238)

The title compound was synthesized according to the procedure described for the preparation of Example 231 using 6 (50 mg, 0.22 mmol) and p-toluidine (35 mg, 0.33 mmol) to provide 238 (14 mg, 21% yield) as a black solid. LC-MS (M+H=302, obsd.=302). $^1$H NMR (400 MHz, $d_6$-DMSO): δ 11.64 (s, 1H), 8.82 (s, 1H), 8.44 (m, 2H), 8.12 (d, 1H), 7.78 (d, 1H), 7.27 (m, 1H), 7.22 (dd, 1H), 7.19 (s, 3H), 2.30 (s, 4H).

Example 239

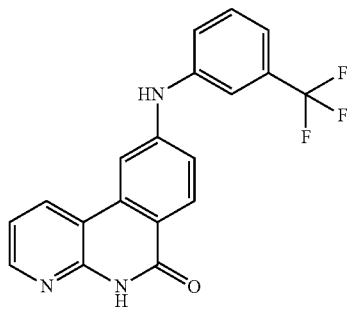 [SMILES: O=c1[nH]c2ncccc2c2cc(Nc3cccc(C(F)(F)F)c3)ccc12]

9-(3-Trifluoromethyl-phenylamino)-5-H-benzo[c][1,8]naphthyridin-6-one (239)

The title compound was synthesized according to the procedure described for the preparation of Example 231 using 6 (50 mg, 0.22 mmol) and 3-(trifluoromethyl)aniline (0.04 mL, 0.33 mmol) to provide 239 (2 mg, 3% yield) as a brown solid. LC-MS (M+H=356, obsd.=356).

Example 240

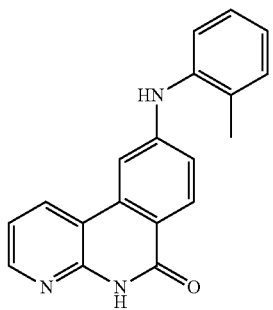 [SMILES: Cc1ccccc1Nc1ccc2c(=O)[nH]c3ncccc3c2c1]

9-o-Tolylamino-5H-benzo[c][1,8]naphthyridin-6-one (240)

The title compound was synthesized according to the procedure described for the preparation of Example 231 using 6 (100 mg, 0.43 mmol) and o-toluidine (0.07 mL, 0.65 mmol) to provide 240 (31 mg, 21% yield) as a yellow/green powder. LC-MS (M+H (parent)=302, obsd.=302). $^1$H NMR (400 MHz, $d_6$-DMSO): δ 11.63 (s, 1H), 8.44 (dd, 1H), 8.37 (s, 1H), 8.33 (dd, 1H), 8.10 (d, 1H), 7.55 (d, 1H), 7.33 (m, 2H), 7.25 (m, 2H), 7.11 (m, 1H), 7.07 (dd, 1H), 2.24 (s, 3H).

Example 241

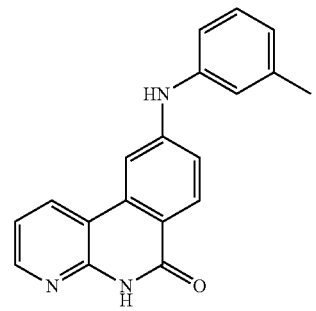 [SMILES: Cc1cccc(Nc2ccc3c(=O)[nH]c4ncccc4c3c2)c1]

9-m-Tolylamino-5H-benzo[c][1,8]naphthyridin-6-one (241)

The title compound was synthesized according to the procedure described for the preparation of Example 231 using 6 (100 mg, 0.43 mmol) and m-toluidine (0.07 mL, 0.65 mmol) to provide 241 (29 mg, 20% yield) as a black powder. LC-MS (M+H (parent)=302, obsd.=302).

Example 242

9-(4-Isopropyl-phenylamino)-5H-benzo[c][1,8]naphthyridin-6-one (242)

The title compound was synthesized according to the procedure described for the preparation of Example 231 using 6 (100 mg, 0.43 mmol) and 4-isopropylaniline (0.09 mL, 0.65 mmol) to provide 242 (24 mg, 15% yield) as a brown solid. LC-MS (M+H (parent)=330, obsd.=330).

Example 243

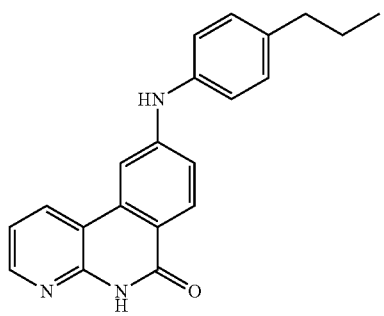 [SMILES: CCCc1ccc(Nc2ccc3c(=O)[nH]c4ncccc4c3c2)cc1]

9-(4-Propyl-phenylamino)-5H-benzo[c][1,8]naph-thyridin-6-one (243)

The title compound was synthesized according to the procedure described for the preparation of Example 231 using 6 (100 mg, 0.43 mmol) and 4-propylaniline (0.10 mL; 0.65 mmol) to provide 243 (23 mg, 15% yield) as a brown solid. LC-MS (M+H (parent)=330, obsd.=330).

Example 244

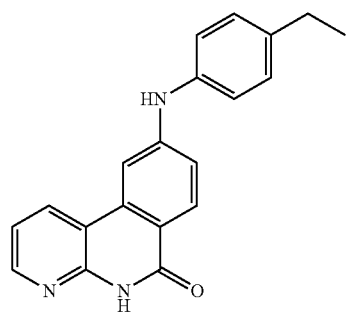 [SMILES: CCc1ccc(Nc2ccc3c(=O)[nH]c4ncccc4c3c2)cc1]

9-(4-Ethyl-phenylamino)-5H-benzo[c][1,8]naphthy-ridin-6-one (244)

The title compound was synthesized according to the procedure described for the preparation of Example 231 using 6 (100 mg, 0.43 mmol) and 4-ethylaniline (0.08 mL, 0.65 mmol) to provide 244 (4 mg, 15% yield) as a dark brown solid. LC-MS (M+H (parent)=316, obsd.=316).

Example 245

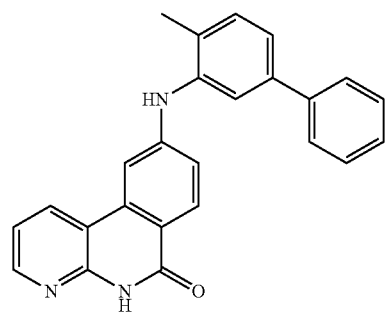 [SMILES: Cc1ccc(-c2ccccc2)cc1Nc1ccc2c(=O)[nH]c3ncccc3c2c1]

9-(4-Methyl-biphenyl-3-ylamino)-5H-benzo[c][1,8] naphthyridin-6-one (245)

The title compound was synthesized according to the procedure described for the preparation of Example 231 using 6 (100 mg, 0.43 mmol) and 5-phenyl-o-toluidine (119 mg, 0.65 mmol) to provide 245 (25 mg, 14% yield) as a brown solid. LC-MS (M+H (parent)=378, obsd.=378). $^1$H NMR (400 MHz, $d_6$-DMSO): δ 11.63 (s, 1H), 8.45 (m, 2H), 8.37 (d, 1H), 8.13 (d, 1H), 7.63 (m, 3H), 7.58 (s, 1H), 7.44 (m, 4H), 7.34 (m, 1H), 7.26 (m, 1H), 7.14 (dd, 1H). 2.28 (s, 3H).

Example 246

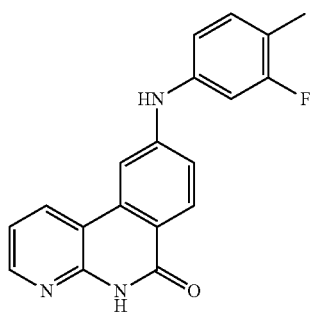 [SMILES: Cc1ccc(Nc2ccc3c(=O)[nH]c4ncccc4c3c2)cc1F]

9-(3-Fluoro-4-methyl-phenylamino)-5-H-benzo[c][1, 8]naphthyridin-6-one (246)

The title compound was synthesized according to the procedure described for the preparation of Example 231 using 6 (100 mg, 0.43 mmol) and 3-fluoro-4-methylaniline (0.07 mL, 0.65 mmol) to provide 246 (31 mg, 20% yield) as a brown solid. LC-MS (M+H (parent)=321, obsd.=321).

Example 247

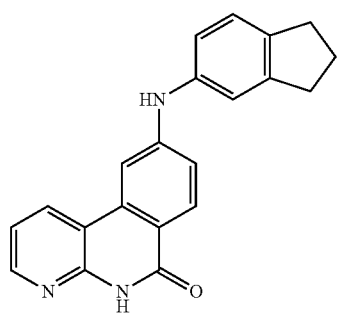 [SMILES: O=c1[nH]c2ncccc2c2cc(Nc3ccc4c(c3)CCC4)ccc12]

9-(Indan-5-ylamino)-5H-benzo[c][1,8]naphthyridin-6-one (247)

The title compound was synthesized according to the procedure described for the preparation of Example 231 using 6 (1000 mg, 0.43 mmol) and 5-aminoindan (87 mg; 0.65 mmol) to provide 247 (41 mg, 26% yield) as a brown solid. LC-MS (M+H (parent)=328, obsd.=328).

Example 248

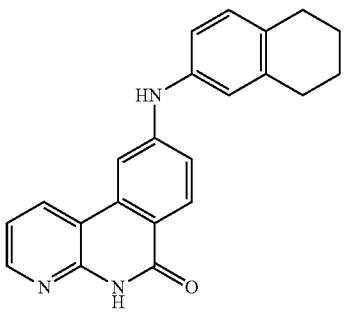 [SMILES: O=c1[nH]c2ncccc2c2cc(Nc3ccc4c(c3)CCCC4)ccc12]

9-(5,6,7,8-Tetrahydro-naphthalen-2-ylamino)-5H-benzo[c][1,8]naphthyridin-6-one (248)

The title compound was synthesized according to the procedure described for the preparation of Example 231 using 6 (50 mg, 0.22 mmol) and 5,6,7,8-tetrahydro-2-naphthylamine (96 mg; 0.65 mmol) to provide 248 (49 mg, 27% yield) as a brown solid. LC-MS (M+H (parent)=343, obsd.=343).

Example 249

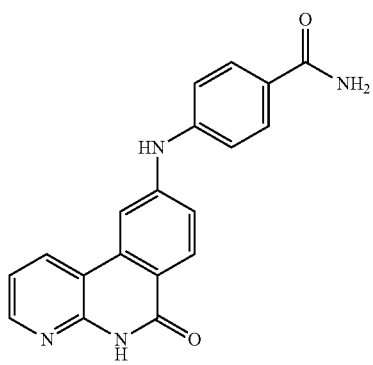 [SMILES: NC(=O)c1ccc(Nc2ccc3c(=O)[nH]c4ncccc4c3c2)cc1]

4-(6-Oxo-5,6-dihydro-benzo[c][1,8]naphthyridin-9-ylamino)-benzamide (249)

4-[(6-Oxo-5,6-dihydrobenzo[c]-1,8-naphthyridin-9-yl) amino]benzonitrile (40 mg, 0.13 mmol) and NaOH (1.3 mL, 1.00 M; 1.28 mmol) were suspended in dioxane (2 mL), and stirred for 120 min at 120° C. in the microwave. The crude material was purified directly via prep-LC-MS to provide 249 (2 mg, 6% yield) as a brown solid. LC-MS (M+H=331 obsd.=331).

Example 250

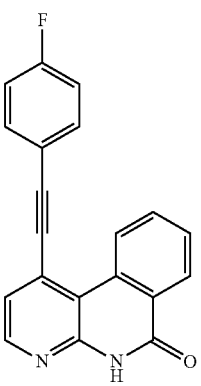 [SMILES: O=c1[nH]c2nccc(C#Cc3ccc(F)cc3)c2c2ccccc12]

1-[(4-fluorophenyl)ethynyl]benzo[c]-1,8-naphthyridin-6(5H)-one (250)

The title compound was synthesized according to the procedure described for the preparation of Example 160 using 83 (100 mg, 0.43 mmol) and 1-ethynyl-4-fluorobenzene (0.07 mL, 0.65 mmol) to provide 250 (74 mg, 54% yield) as a tan solid. LC-MS (M+H=315 obsd.=315).

Example 251

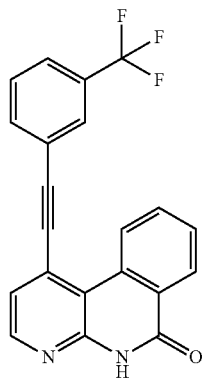 [SMILES: O=c1[nH]c2nccc(C#Cc3cccc(C(F)(F)F)c3)c2c2ccccc12]

1-{[3-(trifluoromethyl)phenyl]ethynyl}benzo[c]-1,8-naphthyridin-6(5H)-one (251)

The title compound was synthesized according to the procedure described for the preparation of Example 160 using 83 (100 mg, 0.43 mmol) and 1,3-ethynyl-αα,α,-trifluorotoluene (0.09 mL, 0.65 mmol) to provide 251 (109 mg, 69% yield) as a tan solid. LC-MS (M+H=365 obsd.=365).

Example 252

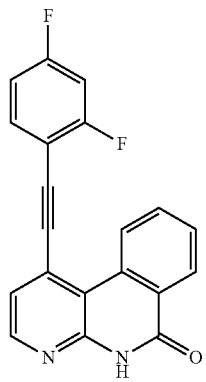 [SMILES: O=c1[nH]c2nccc(C#Cc3ccc(F)cc3F)c2c2ccccc12]

1-[(2,4-difluorophenyl)ethynyl]benzo[c]-1,8-naphthyridin-6(5H)-one (252)

The title compound was synthesized according to the procedure described for the preparation of Example 160 using 83 (100 mg, 0.43 mmol) and 1-ethynyl-2,4-difluorobenzene (90 mg, 0.65 mmol) to provide 252 (91 mg, 63% yield) as a tan solid. LC-MS (M+H=333 obsd.=333).

Example 253

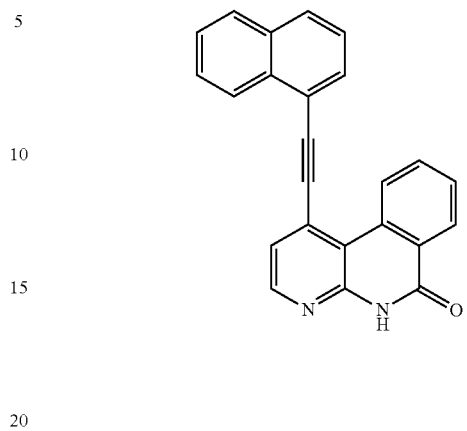

1-(1-Naphthylethynyl)benzo[c]-1,8-naphthyridin-6(5H)-one (253)

The title compound was synthesized according to the procedure described for the preparation of Example 160 using 83 (100 mg, 0.43 mmol) and 1-ethynylnaphthalene (0.09 mL, 0.65 mmol) to provide 253 (99 mg, 66% yield) as a tan solid. LC-MS (M+H=347 obsd.=347). $^1$H NMR (400 MHz, d$_6$-DMSO): δ 12.25 (s, 1H), 9.89 (d, 1H), 8.55 (d, 1H), 8.46 (d, 2H), 8.16 (d, 1H), 8.10 (m, 2H), 8.01 (m, 1H), 7.75 (m, 5H).

Example 254

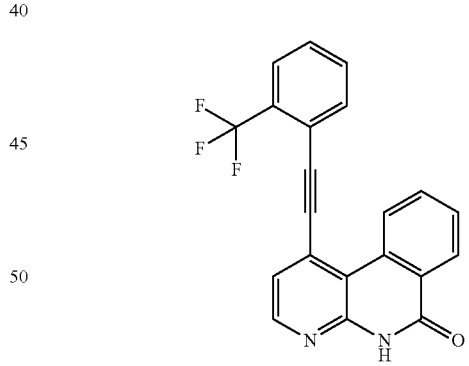

1-{[2-(trifluoromethyl)phenyl]ethynyl}benzo[c]-1,8-naphthyridin-6(5H)-one (254)

The title compound was synthesized according to the procedure described for the preparation of Example 160 using 83 (100 mg, 0.43 mmol) and 2-ethynyl-α,α,α-trifluorotoluene (0.09 mL, 0.65 mmol) to provide 254 (18 mg, 12% yield) as a tan solid. LC-MS (M+H=365 obsd.=365). $^1$H NMR (400 MHz, d$_6$-DMSO): δ 9.62 (d, 1H), 8.50 (d, 1H), 8.41 (dd, 1H), 8.08 (d, 1H), 7.95 (d, 1H), 7.86 (m, 2H), 7.74 (m, 2H), 7.39 (d, 1H).

Example 255

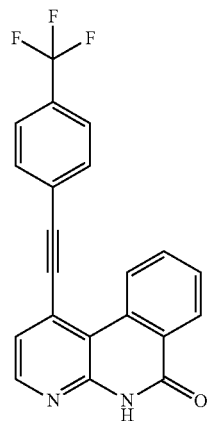

1-{[4-(trifluoromethyl)phenyl]ethynyl}benzo[c]-1,8-naphthyridin-6(5H)-one (255)

The title compound was synthesized according to the procedure described for the preparation of Example 160 using 83 (100 mg, 0.43 mmol) and 4-ethynyl-α,α,α-trifluorotoluene (0.11 mL, 0.65 mmol) to provide 255 (75 mg, 48% yield) as a tan solid. LC-MS (M+H=365 obsd.=365).

Example 256

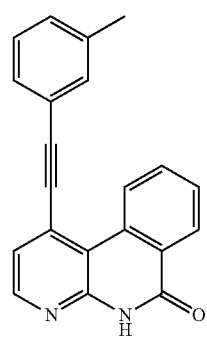 [SMILES: Cc1cccc(C#Cc2ccnc3[nH]c(=O)c4ccccc4c23)c1]

1-[(3-methylphenyl)ethynyl]benzo[c]-1,8-naphthyridin-6(5H)-one (256)

The title compound was synthesized according to the procedure described for the preparation of Example 160 using 83 (100 mg, 0.43 mmol) and 3-ethynyltoluene (0.08 mL, 0.65 mmol) to provide 256 (80 mg, 60% yield) as a tan solid. LC-MS (M+H=311 obsd.=311).

Example 257

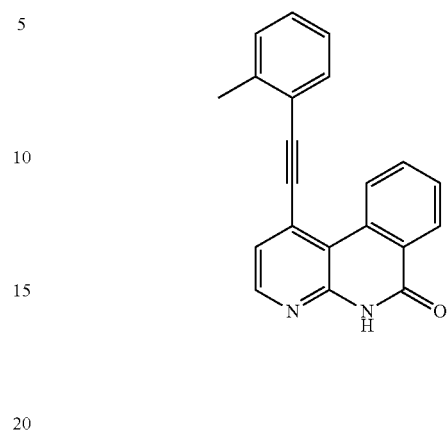

1-[(2-methylphenyl)ethynyl]benzo[c]-1,8-naphthyridin-6(5H)-one (257)

The title compound was synthesized according to the procedure described for the preparation of Example 160 using 83 (100 mg, 0.43 mmol) and 2-ethynyltoluene (0.08 mL, 0.65 mmol) to provide 257 (88 mg, 65% yield) as a tan solid. LC-MS (M+H=311 obsd.=311). $^1$H NMR (400 MHz, d$_6$-DMSO): δ 9.79 (d, 1H), 8.48 (d, 1H), 8.42 (dd, 1H), 7.95 (m, 1H), 7.75 (m, 2H), 7.46 (m, 3H), 7.36 (m, 1H), 2.61 (s, 3H).

Example 258

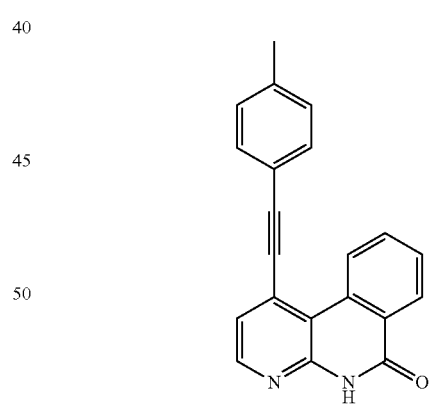

1-[(4-methylphenyl)ethynyl]benzo[c]-1,8-naphthyridin-6(5H)-one (258)

The title compound was synthesized according to the procedure described for the preparation of Example 160 using 83 (100 mg, 0.43 mmol) and 4-ethynyltoluene (0.08 mL, 0.65 mmol) to provide 258 (85 mg, 64% yield) as a brown solid. LC-MS (M+H=311 obsd.=311).

Example 259

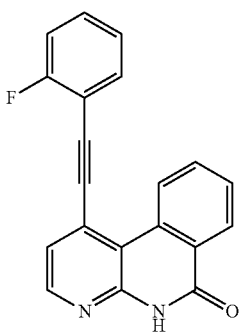

1-[(2-fluorophenyl)ethynyl]benzo[c]-1,8-naphthyridin-6(5H)-one (259)

The title compound was synthesized according to the procedure described for the preparation of Example 160 using 83 (100 mg, 0.43 mmol) and 1-ethynyl-2-fluorobenzene (0.07 mL, 0.65 mmol) to provide 259 (101 mg, 75% yield) as a tan solid. LC-MS (M+H=315 obsd.=315).

Example 260

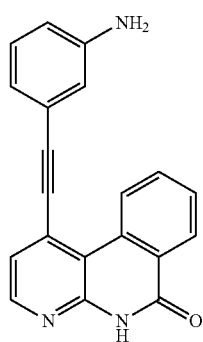 [SMILES: Nc1cccc(C#Cc2ccnc3[nH]c(=O)c4ccccc4c23)c1]

1-[(3-aminophenyl)ethynyl]benzo[c]-1,8-naphthyridin-6(5H)-one (260)

The title compound was synthesized according to the procedure described for the preparation of Example 160 using 83 (100 mg, 0.43 mmol) and 3-ethynylaniline (0.07 mL, 0.65 mmol) to provide 260 (100 mg, 74% yield) as a brown solid. LC-MS (M+H=312 obsd.=312).

Example 261

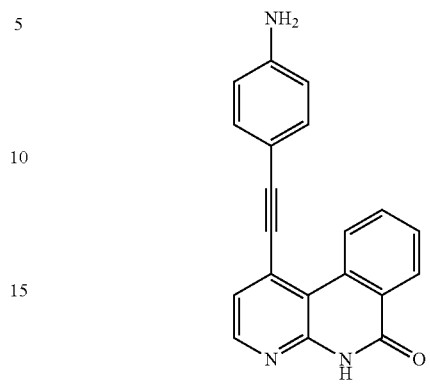

1-[(4-aminophenyl)ethynyl]benzo[c]-1,8-naphthyridin-6(5H)-one (261)

The title compound was synthesized according to the procedure described for the preparation of Example 160 using 83 (100 mg, 0.43 mmol) and 4-ethynylaniline (76 mg, 0.65 mmol) to provide 261 (115 mg, 85% yield) as a brown solid. LC-MS (M+H=312 obsd.=312).

Example 262

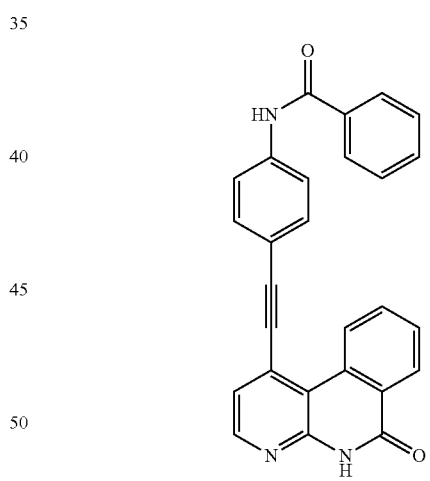

N-{4-[6-oxo-5,6-dihydrobenzo[c]-1,8-naphthyridin-1yl)ethynyl]phenyl}benzamide (262)

261 (30 mg, 0.10 mmol) and TEA (0.04 mL, 0.29 mmol) were dissolved in CH$_2$Cl$_2$ (2 mL), and stirred for 20 min. at room temperature. Benzoyl chloride (0.01 mL, 0.11 mmol) was added, and the reaction mixture was stirred overnight at 40° C. overnight. The reaction mixture concentrated, and then suspended between diethyl ether and H$_2$O. The resulting precipitate was filtered and dried under vacuum to provide 262 (21 mg, 52% yield) as a brown solid. LC-MS (M+H=416 obsd.=416).

Example 263

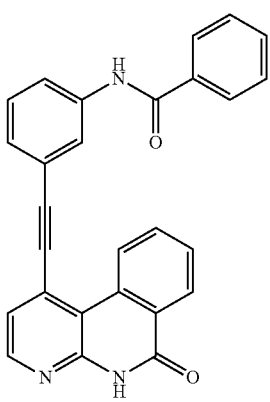 [SMILES: O=C(Nc1cccc(C#Cc2ccnc3[nH]c(=O)c4ccccc4c23)c1)c1ccccc1]

N-{3-[6-oxo-5,6-dihydrobenzo[c]-1,8-naphthyridin-1-yl)ethynyl]phenyl}benzamide (263)

The title compound was synthesized according to the procedure described for the preparation of Example 262 using 260 (35 mg, 0.11 mmol) and benzoyl chloride (0.01 mL, 0.12 mmol) to afford 263 (42 mg, 90% yield) as a brown solid. LC-MS (M+H=416 obsd.=416). $^1$H NMR (400 MHz, $d_6$-DMSO): δ 12.23 (s, 1H), 10.51 (s, 1H), 9.78 (d, 1H), 8.51 (d, 1H), 8.45 (d, 1H), 8.31 (s, 1H), 8.06 (m, 1H), 8.01 (d, 2H), 7.93 (d, 1H), 7.81 (m, 1H), 7.58 (m, 6H).

Example 264

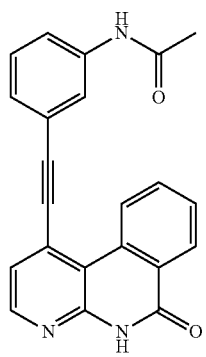 [SMILES: CC(=O)Nc1cccc(C#Cc2ccnc3[nH]c(=O)c4ccccc4c23)c1]

N-{3-[(6-oxo-5,6-dihydrobenzo[c]-1,8-naphthyridin-1-yl)ethynyl]phenyl}acetimide (264)

The title compound was synthesized according to the procedure described for the preparation of Example 262 using 260 (30 mg, 0.10 mmol) and acetic anhydride (0.01 mL, 0.11 mmol) to provide 264 (7 mg, 21% yield) as a brown solid. LC-MS (M+H=354 obsd.=354).

Example 265

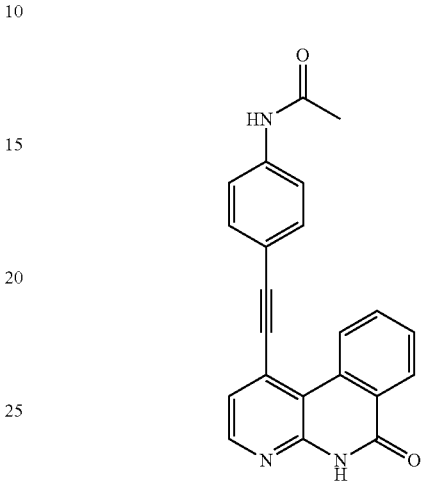

N-{4-[6-oxo-5,6-dihydrobenzo[c]-1,8-naphthyridin-1-yl)ethynyl]phenyl}acetamide (265)

The title compound was synthesized according to the procedure described for the preparation of Example 262 using 261 (30 mg, 0.10 mmol) and acetic anhydride (0.01 mL, 0.11 mmol) to provide 265 (5 mg, 14% yield) as a brown solid. LC-MS (M+H=354 obsd.=354).

Example 266

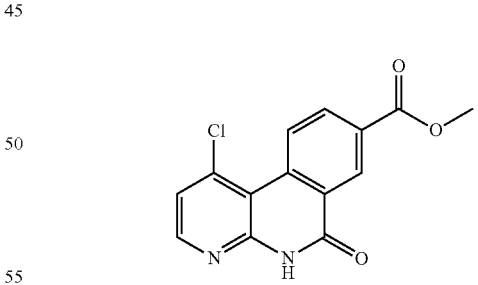

Methyl 1-chloro-6-oxo-5,6-dihydrobenzo[c][1,8]naphthyridine-8-carboxylate (266)

The title compound was synthesized according to the procedure described for the preparation of Example 1 using 4-chloro-3-iodopyridin-2-amine (510 mg, 2.0 mmol) and dimethyl 4-(4,4,5,5-tetramethyl-1,3,2-dioxaborolan-2-yl)isophthalate (705 mg, 2.2 mmol) to provide 266 (280 mg, 48% yield) as a white solid. LC-MS (M+H=289, obsd.=289).

Example 267

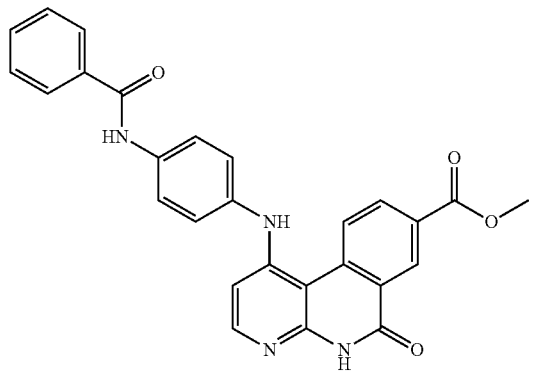 [SMILES: COC(=O)c1ccc2c(c1)c(=O)[nH]c1nccc(Nc3ccc(NC(=O)c4ccccc4)cc3)c12]

Methyl 1-(4-benzamidophenylamino)-6-oxo-5,6-dihydrobenzo[c][1,8]naphthyridine-8-carboxylate (267)

266 (250 mg, 0.77 mol), N-(4-aminophenyl)benzamide (179 mg, 0.85 mmol), and HCl (19 μm, 0.77 mmol, 4.0 M in dioxane) were suspended in NMP (5 mL) and stirred for 30 h at 115° C. The reaction mixture was diluted with H₂O. The resulting precipitate was filtered, washed with H₂O and MeOH, and dried under vacuum to provide 267 (341 mg, 96% yield) as a white solid. LC-MS (M+H=465, obsd.=465).

Example 268

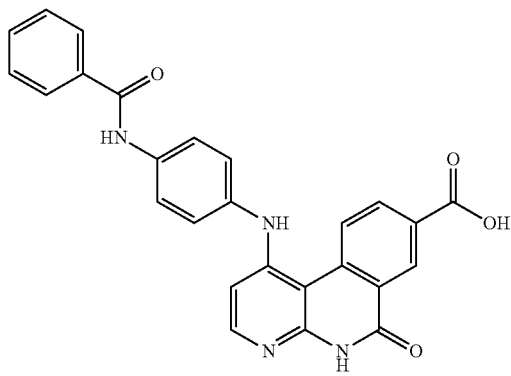 [SMILES: O=C(O)c1ccc2c(c1)c(=O)[nH]c1nccc(Nc3ccc(NC(=O)c4ccccc4)cc3)c12]

1-(4-Benzamidophenylamino)-6-oxo-5,6-dihydrobenzo[c][1,8]naphthyridine-8-carboxylic acid (268)

267 (220 mg, 0.47 mmol) and LiOH (56 mg, 2.37 mmol) were suspended in THF (2 mL) and H₂O (2 mL) and stirred overnight at room temperature. The THF was removed, the mixture was diluted with H₂O, and acidified to pH=5 with 1M HCl. The crude product was purified via HP-LC to provide 268 (120 mg, 56% yield) as a white solid. LC-MS (M+H=451, obsd.=451).

Example 269

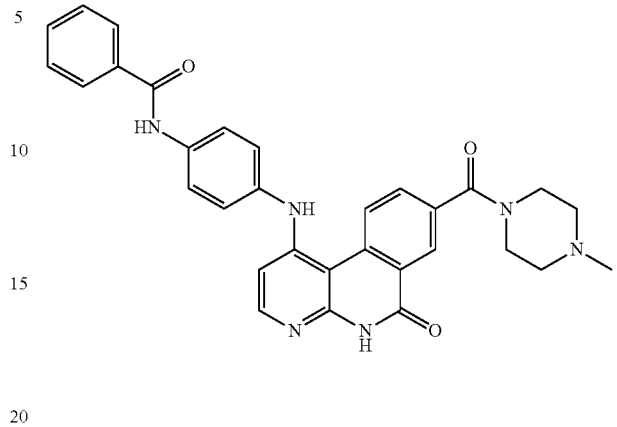

N-(4-(8-(4-Methylpiperazine-1-carbonyl)-6-oxo-5,6-dihydrobenzo[c][1,8]naphthyridin-1-ylamino)phenyl)benzamide (269)

268 (30 mg, 0.07 mmol), DIEA (25 mg, 0.2 mmol), HATU (31 mg, 0.08 mmol), and 1-methylpiperazine (20 mg, 0.2 mmol) were dissolved in DMF (1 mL), and stirred for 3 h at room temperature. The crude product was purified directlyl via HPLC to provide 269 (27 mg, 63% yield) as a solid. LC-MS (M+H=533, obsd.=533).

Example 270

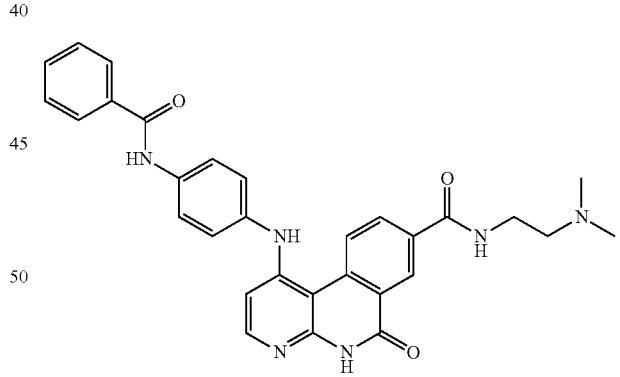

1-(4-Benzamidophenylamino)-N-(2-(dimethylamino)ethyl)-6-oxo-5,6-dihydrobenzo[c][1,8]naphthyridine-8-carboxamide (270)

The title compound was synthesized according to the procedure described for the preparation of Example 269 using 268 (30 mg, 0.07 mmol) and N*1*,N*1*-dimethyl-ethane-1,2-diamine to provide 270. LC-MS (M+H=521, obsd.=521).

Example 271

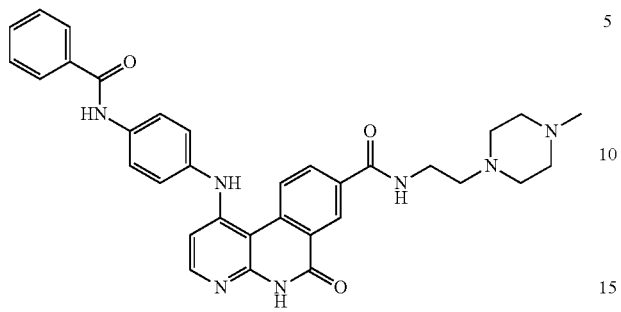

1-(4-Benzamidophenylamino)-N-(2-(4-methylpiperazin-1-yl)ethyl)-6-oxo-5,6-dihydrobenzo[c][1,8]naphthyridine-8-carboxamide (271)

The title compound was synthesized according to the procedure described for the preparation of Example 269 using 268 (30 mg, 0.07 mmol) and 2-(4-methyl-piperazin-1-yl)-ethylamine to provide 271. LC-MS (M+H=576, obsd.=576).

Example 272

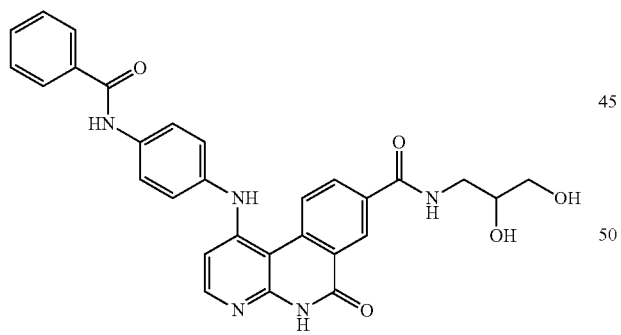

1-(4-Benzamidophenylamino)-N-(2,3-dihydroxypropyl)-6-oxo-5,6-dihydrobenzo[c][1,8]naphthyridine-8-carboxamide (272)

The title compound was synthesized according to the procedure described for the preparation of Example 269 using 268 (30 mg, 0.07 mmol) and 3-amino-propane-1,2-diol to provide 272. LC-MS (M+H=524, obsd.=524).

Example 273

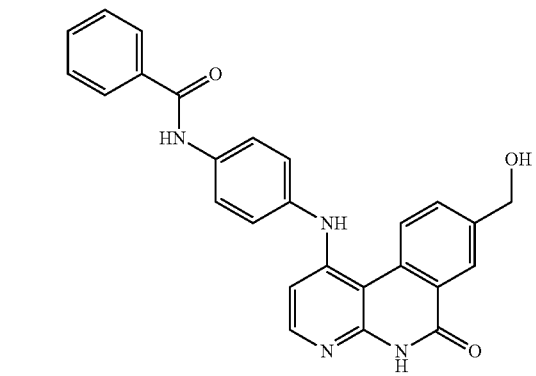 [SMILES: O=C(Nc1ccc(Nc2ccnc3[nH]c(=O)c4cc(CO)ccc4c23)cc1)c1ccccc1]

N-(4-(8-(Hydroxymethyl)-6-oxo-5,6-dihydrobenzo[c][1,8]naphthyridin-1-ylamino)phenyl)benzamide (273)

Lithium borohydride (33 mg, 1.51 mmol) was added to a stirred solution of 267 (100 mg, 0.22 mmol) in THF (10 mL) at 0° C., and stirred for 20 min. at room temperature, then overnight at 45° C. The reaction solution was quenched with MeOH and H$_2$O, acidified with HCl (1 mL, conc.), and stirred for 20 min. The crude product was purified via HP-LC to provide 273 (29 mg, 31% yield) as a solid. LC-MS (M+H=437, obsd.=437).

Example 274

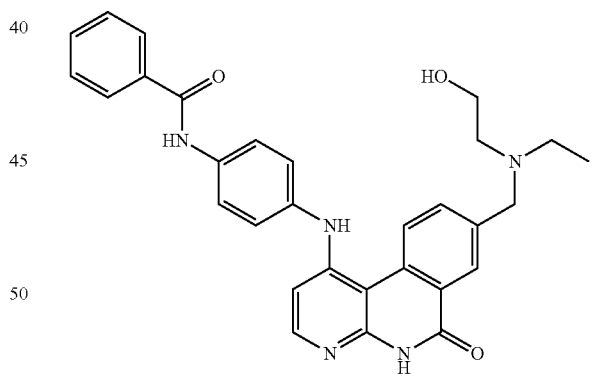

N-(4-(8-((Ethyl(2-hydroxyethyl)amino)methyl)-6-oxo-5,6-dihydrobenzo[c][1,8]naphthyridin-1-ylamino)phenyl)benzamide (274)

DIEA (0.03 mL, 0.19 mmol) and methanesulfonyl chloride (0.01 mL, 0.09 mmol) were added to a solution of 273 (27 mg, 0.06 mmol) in CH$_2$Cl$_2$ and stirred for 2 h at room temperature. 2-(Ethylamino)ethanol (17 mg, 0.19 mmol) was added, and the reaction mixture was stirred for 1 h. The crude product was purified directly via HP-LC to provide 274 (6 mg, 16% yield) as a solid. LC-MS (M+H=508, obsd.=508).

Example 275

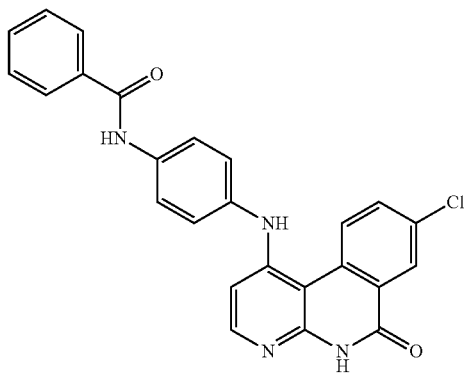 [SMILES: O=C(Nc1ccc(Nc2ccnc3[nH]c(=O)c4cc(Cl)ccc4c23)cc1)c1ccccc1]

N-(4-(8-Chloro-6-oxo-5,6-dihydrobenzo[c][1,8]naphthyridin-1-ylamino)phenyl)benzamide (275)

The title compound was synthesized according to the procedure described for the preparation of Example 267 using 1,8-dichloro-5H-benzo[c][1,8]naphthyridin-6-one and N-(4-aminophenyl)benzamide to provide 275. LC-MS (M+H=442, obsd.=442).

Example 276

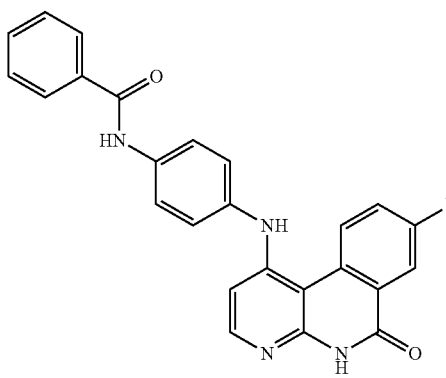

N-(4-(8-(4-Methylpiperazin-1-yl)-6-oxo-5,6-dihydrobenzo[c][1,8]naphthyridin-1-ylamino)phenyl)benzamide (276)

275 (44 mg, 0.10 mmol), Pd(OAc)$_2$ (6 mg 0.02 mmol), X-Phos (19 mg, 0.04 mmol), and 1-methylpiperazine (0.02 mL, 0.20 mmol) were suspended in dioxane (3 mL), and stirred overnight at 100° C. for overnight. The crude reaction mixture purified via HP-LC to provide 276. LC-MS (M+H=505, obsd.=505).

Example 277

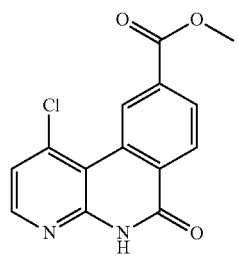 [SMILES: COC(=O)c1ccc2c(=O)[nH]c3nccc(Cl)c3c2c1]

Methyl 1-chloro-6-oxo-5,6-dihydrobenzo[c][1,8]naphthyridine-9-carboxylate (277)

The title compound was synthesized according to the procedure described for the preparation of Example 1 using 4-chloro-3-iodopyridin-2-amine and 2-(4,4,5,5-tetramethyl-[1,3,2]dioxaborolan-2-yl)-terephthalic acid dimethyl ester to provide 277. LC-MS (M+H=289, obsd.=289).

Example 278

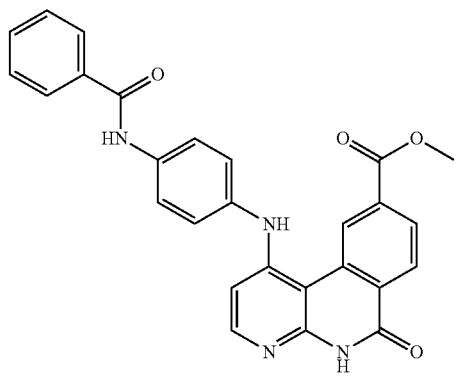 [SMILES: COC(=O)c1ccc2c(=O)[nH]c3nccc(Nc4ccc(NC(=O)c5ccccc5)cc4)c3c2c1]

Methyl 1-(4-benzamidophenylamino)-6-oxo-5,6-dihydrobenzo[c][1,8]naphthyridine-9-carboxylate (278)

The title compound was synthesized according to the procedure described for the preparation of Example 267 using 277 and N-(4-aminophenyl)benzamide to provide 278. LC-MS (M+H=465, obsd.=465).

Example 279

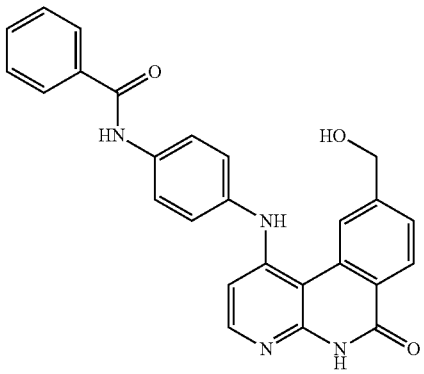 [SMILES: O=C(Nc1ccc(Nc2ccnc3[nH]c(=O)c4ccc(CO)cc4c23)cc1)c1ccccc1]

N-(4-(9-(Hydroxymethyl)-6-oxo-5,6-dihydrobenzo[c][1,8]naphthyridin-1-ylamino)phenyl)benzamide (279)

The title compound was synthesized according to the procedure described for the preparation of Example 273 using 278 to provide 279. LC-MS (M+H=437, obsd.=437).

Example 280

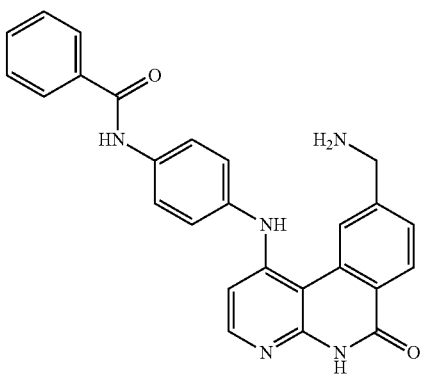 [SMILES: NCc1ccc2c(=O)[nH]c3nccc(Nc4ccc(NC(=O)c5ccccc5)cc4)c3c2c1]

N-(4-(9-(Aminomethyl)-6-oxo-5,6-dihydrobenzo[c][1,8]naphthyridin-1-ylamino)phenyl)benzamide (280)

The title compound was synthesized according to the procedure described for the preparation of Example 274 using 279 to provide 280. LC-MS (M+H=436, obsd.=436).

Example 281

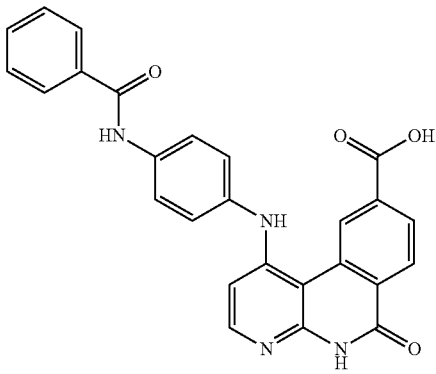 [SMILES: O=C(O)c1ccc2c(=O)[nH]c3nccc(Nc4ccc(NC(=O)c5ccccc5)cc4)c3c2c1]

1-(4-Benzamidophenylamino)-6-oxo-5,6-dihydrobenzo[c][1,8]naphthyridine-9-carboxylic acid (281)

The title compound was synthesized according to the procedure described for the preparation of Example 268 using 278 to provide 281. LC-MS (M+H=451, obsd.=451).

Example 282

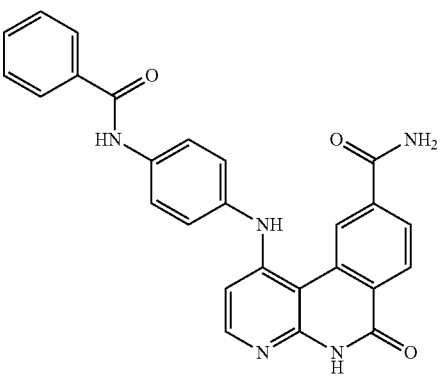 [SMILES: NC(=O)c1ccc2c(=O)[nH]c3nccc(Nc4ccc(NC(=O)c5ccccc5)cc4)c3c2c1]

1-(4-benzamidophenylamino)-6-oxo-5,6-dihydrobenzo[c][1,8]naphthyridine-9-carboxamide (282)

The title compound was synthesized according to the procedure described for the preparation of Example 269 using 281 and ammonia to provide 282. LC-MS (M+H=450, obsd.=450).

Example 283

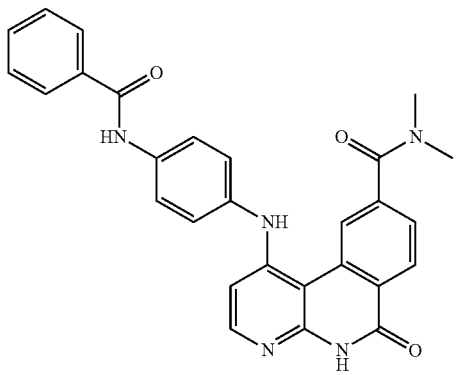 [SMILES: CN(C)C(=O)c1ccc2c(=O)[nH]c3nccc(Nc4ccc(NC(=O)c5ccccc5)cc4)c3c2c1]

1-(4-Benzamidophenylamino)-N,N-dimethyl-6-oxo-5,6-dihydrobenzo[c][1,8]naphthyridine-9-carboxamide (283)

The title compound was synthesized according to the procedure described for the preparation of Example 269 using 281 and dimethylamine to provide 283. LC-MS (M+H=478, obsd.=478).

Example 284

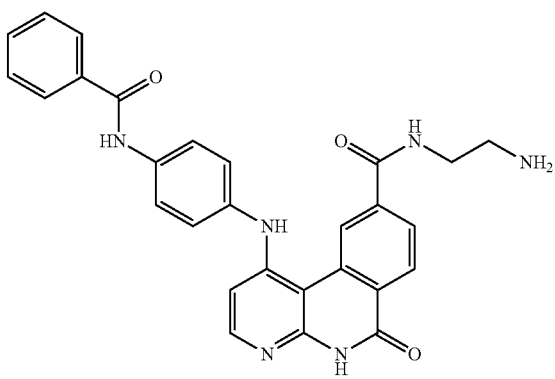 [SMILES: NCCNC(=O)c1ccc2c(=O)[nH]c3nccc(Nc4ccc(NC(=O)c5ccccc5)cc4)c3c2c1]

N-(2-Aminoethyl)-1-(4-benzamidophenylamino)-6-oxo-5,6-dihydrobenzo[c][1,8]naphthyridine-9-carboxamide (284)

The title compound was synthesized according to the procedure described for the preparation of Example 269 using 281 and ethane-1,2-diamine to provide 284. LC-MS (M+H=493, obsd.=493).

Example 285

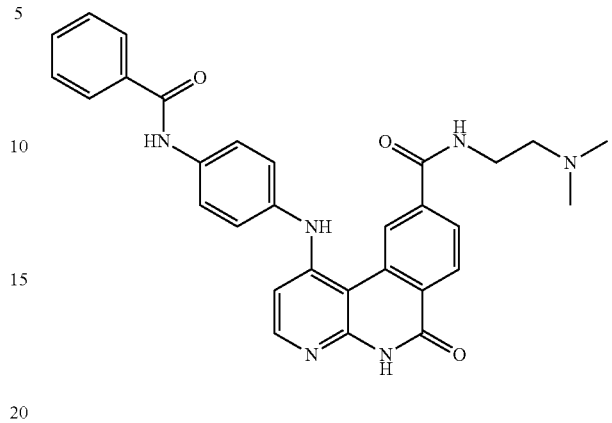

1-(4-benzamidophenylamino)-N-(2-(dimethylamino)ethyl)-6-oxo-5,6-dihydrobenzo[c][1,8]naphthyridine-9-carboxamide (285)

The title compound was synthesized according to the procedure described for the preparation of Example 269 using 281 and N*1*,N*1*-dimethyl-ethane-1,2-diamine to provide 285. LC-MS (M+H=521, obsd.=521).

Example 286

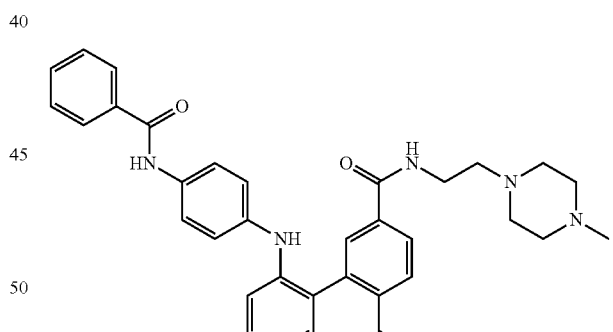

1-(4-benzamidophenylamino)-N-(2-(4-methylpiperazin-1-yl)ethyl)-6-oxo-5,6-dihydrobenzo[c][1,8]naphthyridine-9-carboxamide (286)

The title compound was synthesized according to the procedure described for the preparation of Example 269 using 281 and 2-(4-methyl-piperazin-1-yl)-ethylamine to provide 288. LC-MS (M+H=576, obsd.=576).

Example 287

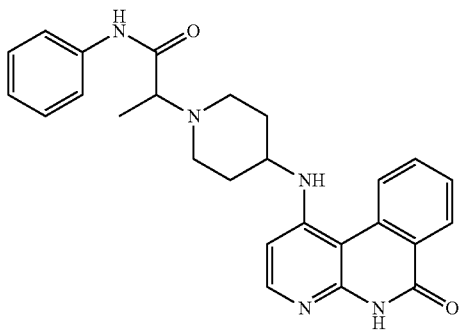 [SMILES: CC(C(=O)Nc1ccccc1)N1CCC(Nc2ccnc3[nH]c(=O)c4ccccc4c23)CC1]

2-(4-(6-oxo-5,6-dihydrobenzo[c][1,8]naphthyridin-1-ylamino)piperidin-1-yl)-N-phenylpropanamide (287)

358 (40 mg, 0.14 mmol), DIEA (0.07 mL, 0.41 mmol), and 2-chloro-N-phenylpropanamide (30 mg, 0.16 mmol) were suspended in DMSO (1 mL), and stirred overnight at room temperature. The crude reaction mixture was purified directly via HPLC to provide 287 (8 mg, 13% yield). LC-MS (M+H=442, obsd.=442).

Example 288

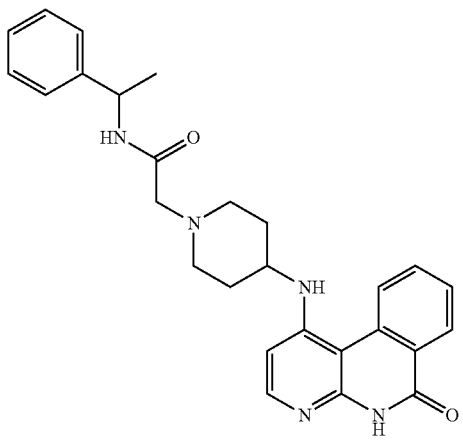 [SMILES: CC(NC(=O)CN1CCC(Nc2ccnc3[nH]c(=O)c4ccccc4c23)CC1)c1ccccc1]

2-(4-(6-Oxo-5,6-dihydrobenzo[c][1,8]naphthyridin-1-ylamino)piperidin-1-yl)-N-(1-phenylethyl)acetamide (288)

The title compound was synthesized according to the procedure described for the preparation of Example 287 using 358 and 2-chloro-N-(1-phenyl-ethyl)-acetamide to provide 288. LC-MS (M+H=456, obsd.=456).

Example 289

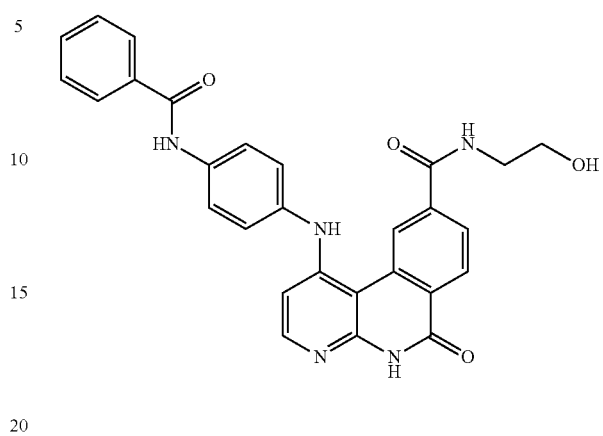

1-(4-Benzamidophenylamino)-N-(2-hydroxyethyl)-6-oxo-5,6-dihydrobenzo[c][1,8]naphthyridine-9-carboxamide (289)

The title compound was synthesized according to the procedure described for the preparation of Example 269 using 281 and 2-amino-ethanol to provide 289. LC-MS (M+H=494, obsd.=494).

Example 290

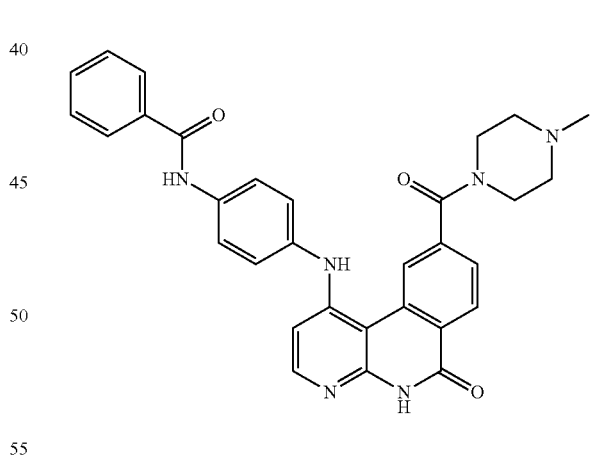

N-(4-(9-(4-Methylpiperazine-1-carbonyl)-6-oxo-5,6-dihydrobenzo[c][1,8]naphthyridin-1-ylamino)phenyl)benzamide (290)

The title compound was synthesized according to the procedure described for the preparation of Example 269 using 281 and 1-methyl-piperazine to provide 290. LC-MS (M+H=533, obsd.=533).

Example 291

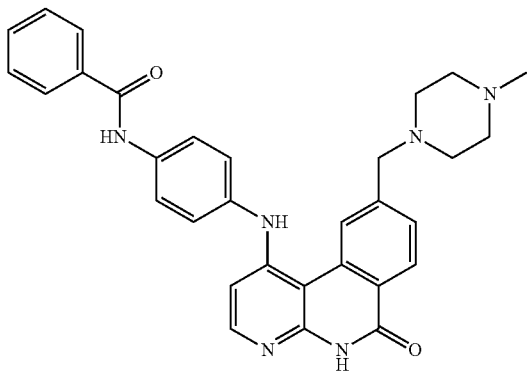 [SMILES: CN1CCN(Cc2ccc3c(=O)[nH]c4nccc(Nc5ccc(NC(=O)c6ccccc6)cc5)c4c3c2)CC1]

N-(4-(9-((4-methylpiperazin-1-yl)methyl)-6-oxo-5,6-dihydrobenzo[c][1,8]naphthyridin-1-ylamino)phenyl)benzamide (291)

The title compound was synthesized according to the procedure described for the preparation of Example 274 using 279 and 1-methyl-piperazine to provide 291. LC-MS (M+H=519, obsd.=519).

Example 292

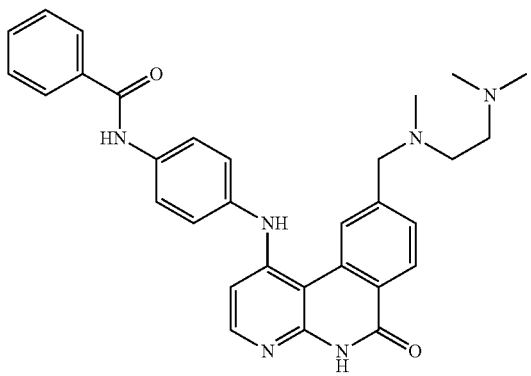 [SMILES: CN(C)CCN(C)Cc1ccc2c(=O)[nH]c3nccc(Nc4ccc(NC(=O)c5ccccc5)cc4)c3c2c1]

N-(4-(9-(((2-(Dimethylamino)ethyl)(methyl)amino)methyl)-6-oxo-5,6-dihydro benzo[c][1,8]naphthyridin-1-ylamino)phenyl)benzamide (292)

The title compound was synthesized according to the procedure described for the preparation of Example 274 using 279 and N,N,N'-trimethyl-ethane-1,2-diamine to provide 292. LC-MS (M+H=521, obsd.=521).

Example 293

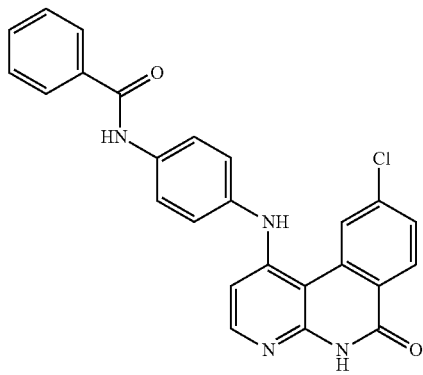

N-(4-(9-Chloro-6-oxo-5,6-dihydrobenzo[c][1,8]naphthyridin-1-ylamino)phenyl)benzamide (293)

The title compound was synthesized according to the procedure described for the preparation of Example 267 using 1,9-dichloro-5H-benzo[c][1,8]naphthyridin-6-one and N-(4-aminophenyl)benzamide to provide 293. LC-MS (M+H=442, obsd.=442).

Example 294

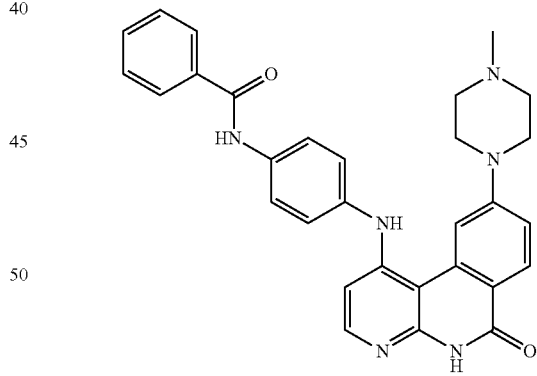

N-(4-(9-(4-methylpiperazin-1-yl)-6-oxo-5,6-dihydrobenzo[c][1,8]naphthyridin-1-ylamino)phenyl)benzamide (294)

The title compound was synthesized according to the procedure described for the preparation of Example 276 using 293 and 1-methyl-piperazine to provide 294. LC-MS (M+H=505, obsd.=505).

Example 295

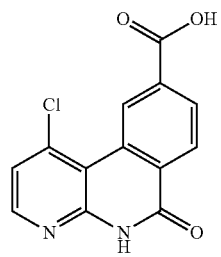 [SMILES: O=C(O)c1ccc2c(=O)[nH]c3nccc(Cl)c3c2c1]

1-Chloro-6-oxo-5,6-dihydrobenzo[c][1,8]naphthyridine-9-carboxylic acid (295)

The title compound was synthesized according to the procedure described for the preparation of Example 268 using methyl 1-chloro-6-oxo-5,6-dihydrobenzo[c][1,8]naphthyridine-9-carboxylate to provide 295 (87 mg, 71% yield) as a solid. LC-MS (M+H=276, obsd.=276).

Example 296

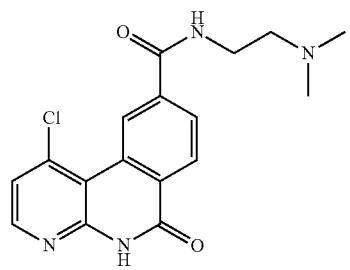 [SMILES: CN(C)CCNC(=O)c1ccc2c(=O)[nH]c3nccc(Cl)c3c2c1]

1-Chloro-N-(2-(dimethylamino)ethyl)-6-oxo-5,6-dihydrobenzo[c][1,8]naphthyridine-9-carboxamide (296)

295 (60 mg, 0.22 mol), DIEA (0.08 mL, 0.44 mmol), and CDI (71 mg, 0.44 mmol) were suspended in DMF (2 mL) and stirred for 4 h at room temperature. N1,N1-Dimethylethane-1,2-diamine (77 mg, 0.87 mmol) was added, and the reaction mixture was stirred for another 3 h. The reaction mixture was quenched with water. The resulting precipitate was filtered, washed with MeOH and H2O, and dried under vacuum to produce provide 296 (61 mg, 81% yield) as a solid. LC-MS (M+H=345, obsd.=345).

Example 297

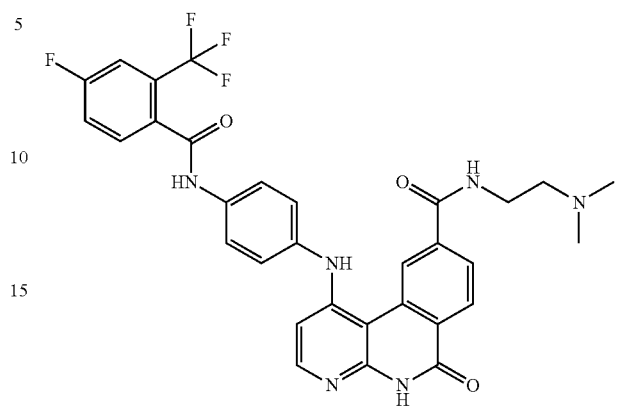

N-(2-(Dimethylamino)ethyl)-1-(4-(4-fluoro-2-(trifluoromethyl)benzamido)phenyl amino)-6-oxo-5,6-dihydrobenzo[c][1,8]naphthyridine-9-carboxamide (297)

The title compound was synthesized according to the procedure described for the preparation of Example 267 using 296 (40 mg, 0.12 mmol), and N-(4-aminophenyl)-4-fluoro-2-(trifluoromethyl)benzamide (36 mg, 0.12 mmol) to provide 297 (35 mg, 50% yield) as a solid. LC-MS (M+H=607, obsd.=607).

Example 298

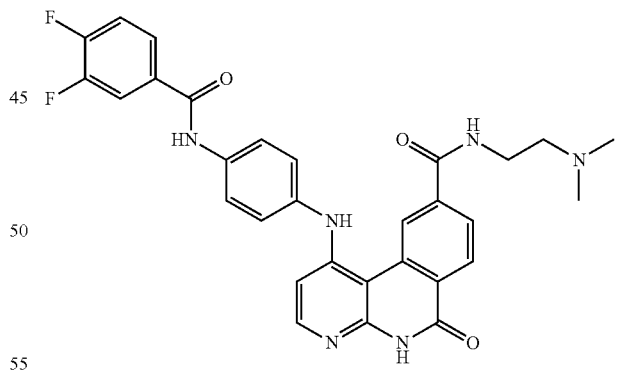

1-(4-(3,4-Difluorobenzamido)phenylamino)-N-(2-(dimethylamino)ethyl)-6-oxo-5,6-dihydrobenzo[c][1,8]naphthyridine-9-carboxamide (298)

The title compound was synthesized according to the procedure described for the preparation of Example 267 using 296 (40 mg, 0.12 mmol), and N-(4-amino-phenyl)-3,4-difluoro-benzamide (36 mg, 0.12 mmol) to provide 298. LC-MS (M+H=557, obsd.=557).

Example 299

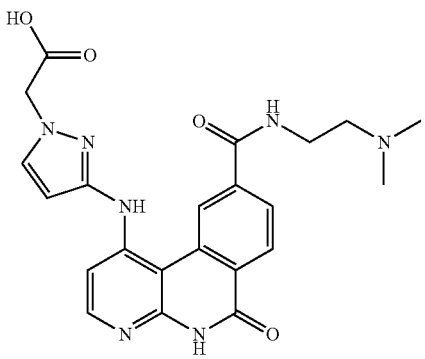 [SMILES: CN(C)CCNC(=O)c1ccc2c(=O)[nH]c3nccc(Nc4ccn(CC(=O)O)n4)c3c2c1]

2-(3-(9-(2-(dimethylamino)ethylcarbamoyl)-6-oxo-5,6-dihydrobenzo[c][1,8]naphthyridin-1-ylamino)-1H-pyrazol-1-yl)acetic acid (299)

296 (100 mg, 0.26 mmol), and methyl 2-(3-amino-1H-pyrazol-1-yl)acetate (43 mg, 0.28 mmol) were suspended in NMP (1 mL), and stirred at 115° C. for 2 h. The crude product mixture was purified directly via HP-LC.

The methyl ester intermediate (90 mg, 0.19 mmol), and LiOH (14 mg, 0.57 mmol) were suspended in THF (2 mL) and H$_2$O (2 mL), and stirred overnight and room temperature. The THF was removed, the mixture was diluted with H$_2$O, and acidified to pH=5 with 1M HCl. The resulting precipitate was filtered, washed with H$_2$O, and dried under vacuum to provide 299 (50 mg, 59% yield) as a solid. LC-MS (M+H=450, obsd.=450).

Example 300

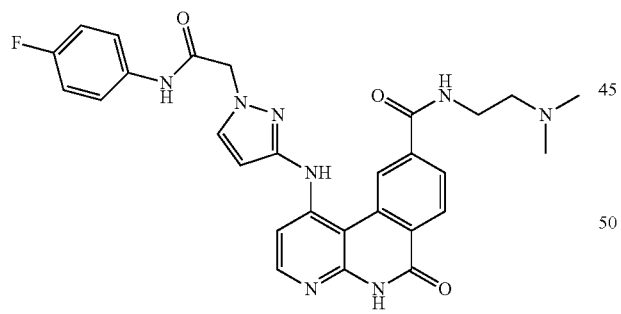

N-(2-(Dimethylamino)ethyl)-1-(1-(2-(3-fluorophenylamino)-2-oxoethyl)-1H-pyrazol-3-ylamino)-6-oxo-5,6-dihydrobenzo[c][1,8]naphthyridine-9-carboxamide (300)

299 (18 mg, 0.04 mmol), DIEA (16 mg, 0.12 mmol), BOP-Cl (13 mg, 0.05 mmol), and 3-fluoroaniline (13 mg, 0.12 mmol) were suspended in CH$_2$Cl$_2$ (1 mL), and stirred overnight at room temperature. The crude reaction mixture was purified directly via HP-LC to provide 300 (10 mg, 37% yield) as a solid. LC-MS (M+H=543, obsd.=543).

Example 301

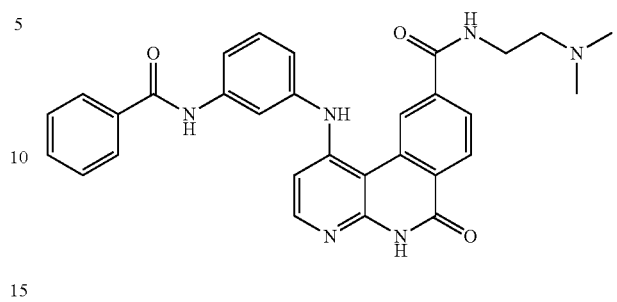

1-(3-Benzamidophenylamino)-N-(2-(dimethylamino)ethyl)-6-oxo-5,6-dihydrobenzo[c][1,8]naphthyridine-9-carboxamide (301)

The title compound was synthesized according to the procedure described for the preparation of Example 267 using 296 (40 mg, 0.12 mmol) and N-(3-amino-phenyl)-benzamide to provide 301. LC-MS (M+H=521, obsd.=521).

Example 302

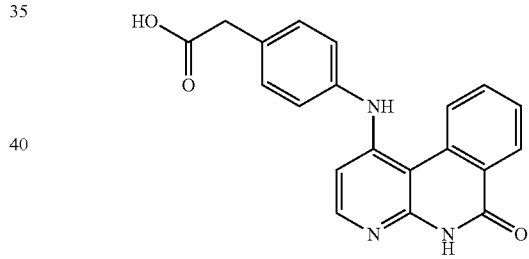

2-(4-(6-Oxo-5,6-dihydrobenzo[c][1,8]naphthyridin-1-ylamino)phenyl)acetic acid (302)

83 (550 mg, 2.17 mmol), methyl 2-(4-aminophenyl)acetate (376 mg, 2.28 mmol), and HCl (0.65 mL, 2.17 mmol, 4.0 M in dioxane) were suspended in NMP (5 mL), and stirred for 3 h at 140° C. The reaction mixture was quenched with saturated aqueous NaHCO$_3$ (100 mL), and stirred for 30 min. The resulting precipitate was filtered, washed with H$_2$O, and dried under vacuum. The methyl ester intermediate (750 mg, 2.09 mmol) and LiOH (150 mg, 6.26 mmol) were dissolved in THF (4 mL) and H$_2$O (4 mL), and stirred for 48 h at room temperature. The THF was removed, the mixture was diluted with H$_2$O, and acidified to pH=5 with 1M HCl. The resulting precipitate was filtered, washed with H$_2$O, and dried under vacuum to provide 302 (550 mg, 76% yield) as a white solid. 1HNMR(DMSO-D6): 3.52(s, 2H), 6.97 (d, 1H), 7.13 (m, 2H), 7.21 (m, 2H), 7.58 (m, 1H), 7.61 (m, 1H)m 8.10 (d, 1H), 8.34(d, 1H), 8.84-8.90 (m, 2H). LC-MS (M+H=346, obsd.=346).

Example 303

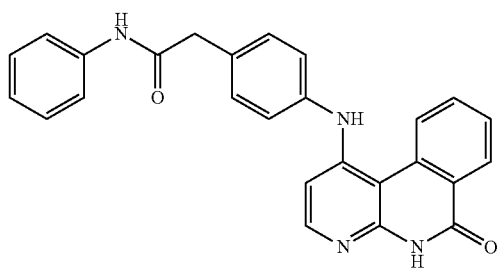 [SMILES: O=C(Cc1ccc(Nc2ccnc3[nH]c(=O)c4ccccc4c23)cc1)Nc1ccccc1]

2-(4-(6-Oxo-5,6-dihydrobenzo[c][1,8]naphthyridin-1-ylamino)phenyl)-N phenylacetamide (303)

The title compound was synthesized according to the procedure described for the preparation of Example 300 using 302 (50 mg, 0.14 mmol), and aniline to provide 303. LC-MS (M+H=421, obsd.=421).

Example 304

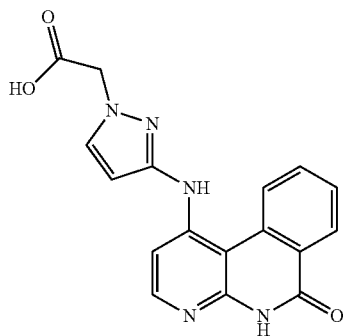 [SMILES: O=C(O)Cn1ccc(Nc2ccnc3[nH]c(=O)c4ccccc4c23)n1]

2-(3-(6-Oxo-5,6-dihydrobenzo[c][1,8]naphthyridin-1-ylamino)-1H-pyrazol-1-yl)acetic acid (304)

The title compound was synthesized according to the procedure described for the preparation of Example 299 using 83 and methyl 2-(3-amino-1H-pyrazol-1-yl)acetate to provide 304. LC-MS (M+H=336, obsd.=336).

Example 305

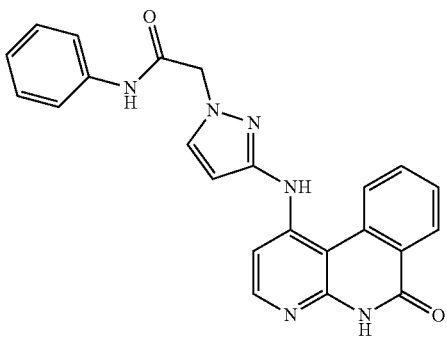 [SMILES: O=C(Cn1ccc(Nc2ccnc3[nH]c(=O)c4ccccc4c23)n1)Nc1ccccc1]

2-(3-(6-Oxo-5,6-dihydrobenzo[c][1,8]naphthyridin-1-ylamino)-1H-pyrazol-1-yl)-N-phenylacetamide (305)

The title compound was synthesized according to the procedure described for the preparation of Example 300 using 304 and aniline to provide 305. LC-MS (M+H=411, obsd.=411).

Example 306

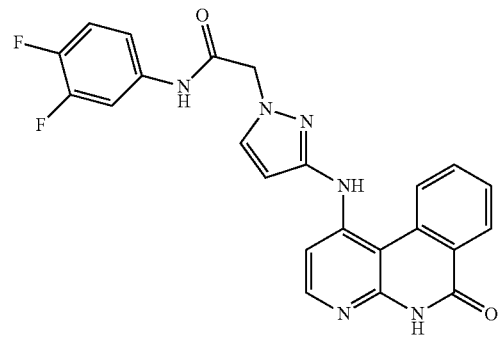 [SMILES: O=C(Cn1ccc(Nc2ccnc3[nH]c(=O)c4ccccc4c23)n1)Nc1ccc(F)c(F)c1]

N-(3,4-Difluorophenyl)-2-(3-(6-oxo-5,6-dihydrobenzo[c][1,8]naphthyridin-1-ylamino)-1H-pyrazol-1-yl)acetamide (306)

The title compound was synthesized according to the procedure described for the preparation of Example 300 using 304 and 3,4-di-fluoroaniline to provide 306. LC-MS (M+H=447, obsd.=447).

Example 307

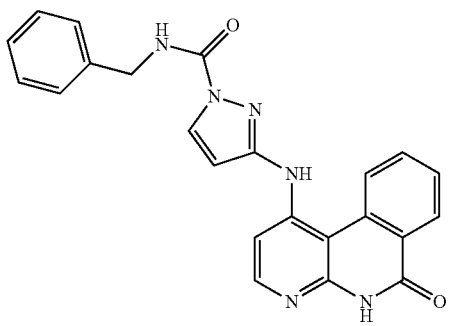 [SMILES: O=C(NCc1ccccc1)n1ccc(Nc2ccnc3[nH]c(=O)c4ccccc4c23)n1]

N-Benzyl-3-(6-oxo-5,6-dihydrobenzo[c][1,8]naphthyridin-1-ylamino)-1H-pyrazole-5-carboxamide (307)

The intermediate carboxylic acid was synthesized according to the procedure described for the preparation of Example 299 using 83 and 3-amino-pyrazole-1-carboxylic acid methyl ester.

The title compound was synthesized according to the procedure described for the preparation of Example 300 using the carboxylic acid intermediate and benzylamine to provide 307. LC-MS (M+H=411, obsd.=411).

Example 308

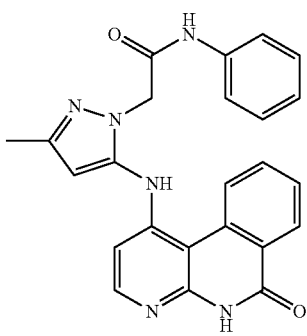 [SMILES: Cc1cc(Nc2ccnc3[nH]c(=O)c4ccccc4c23)n(CC(=O)Nc2ccccc2)n1]

2-(3-Methyl-5-(6-oxo-5,6-dihydrobenzo[c][1,8]
naphthyridin-1-ylamino)-1H-pyrazol-1-yl)-N-phenylacetamide (308)

The intermediate carboxylic acid was synthesized according to the procedure described for the preparation of Example 299 using 83 and (5-amino-3-methyl-pyrazol-1-yl)-acetic acid methyl ester.

The title compound was synthesized according to the procedure described for the preparation of Example 300 using the carboxylic acid intermediate and aniline to provide 308. LC-MS (M+H=425, obsd.=425).

Example 309

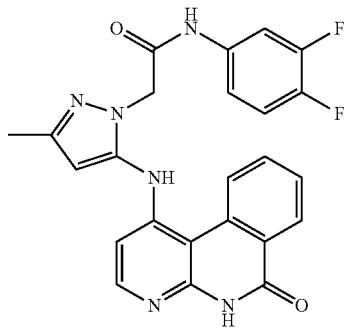 [SMILES: Cc1cc(Nc2ccnc3[nH]c(=O)c4ccccc4c23)n(CC(=O)Nc2ccc(F)c(F)c2)n1]

N-(3,4-difluorophenyl)-2-(3-methyl-5-(6-oxo-5,6-dihydrobenzo[c][1,8]naphthyridin-1-ylamino)-1H-pyrazol-1-yl)acetamide (309)

The title compound was synthesized according to the procedure described for the preparation of Example 300 using the carboxylic acid intermediate from example 308 and 3,4-di-fluoroaniline to provide 309. LC-MS (M+H=461, obsd.=461).

Example 310

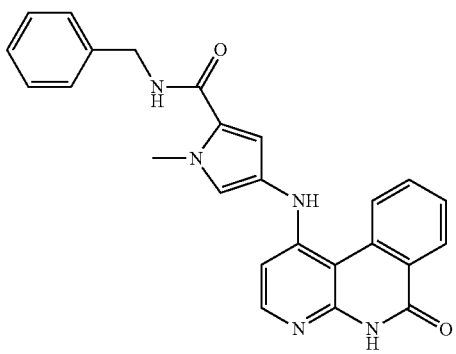 [SMILES: Cn1cc(Nc2ccnc3[nH]c(=O)c4ccccc4c23)cc1C(=O)NCc1ccccc1]

N-Benzyl-1-methyl-4-(6-oxo-5,6-dihydrobenzo[c][1,8]naphthyridin-1-ylamino)-1H-pyrrole-2-carboxamide (310)

The intermediate carboxylic acid was synthesized according to the procedure described for the preparation of Example 299 using 83 and 4-amino-1-methyl-1H-pyrrole-2-carboxylic acid methyl ester.

The title compound was synthesized according to the procedure described for the preparation of Example 300 using the carboxylic acid intermediate and benzylamine to provide 310. LC-MS (M+H=425, obsd.=425).

Example 311

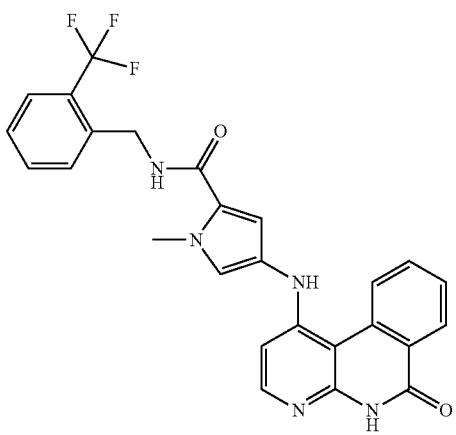 [SMILES: Cn1cc(Nc2ccnc3[nH]c(=O)c4ccccc4c23)cc1C(=O)NCc1ccccc1C(F)(F)F]

1-Methyl-4-(6-oxo-5,6-dihydrobenzo[c][1,8]naphthyridin-1-ylamino)-N-(2-(trifluoromethyl)benzyl)-1H-pyrrole-2-carboxamide (311)

The title compound was synthesized according to the procedure described for the preparation of Example 300 using the carboxylic acid intermediate from example 310 and 2-trifluoromethyl-benzylamine to provide 311. LC-MS (M+H=492, obsd.=492).

Example 312

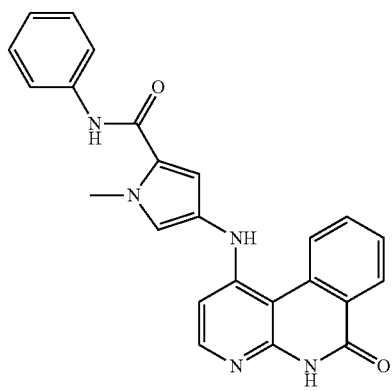 [SMILES: Cn1cc(Nc2ccnc3[nH]c(=O)c4ccccc4c23)cc1C(=O)Nc1ccccc1]

1-Methyl-4-(6-oxo-5,6-dihydrobenzo[c][1,8]naph-thyridin-1-ylamino)-N-phenyl-1H-pyrrole-2-carboxamide (312)

The title compound was synthesized according to the procedure described for the preparation of Example 300 using the carboxylic acid intermediate from example 310 and aniline to provide 312. LC-MS (M+H=410, obsd.=410).

Example 313

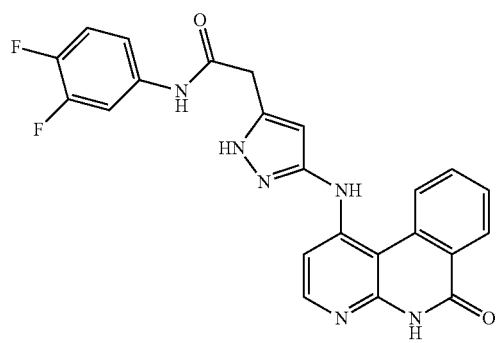 [SMILES: O=C(Cc1cc(Nc2ccnc3[nH]c(=O)c4ccccc4c23)n[nH]1)Nc1ccc(F)c(F)c1]

N-(3,4-Difluorophenyl)-2-(3-(6-oxo-5,6-dihydrobenzo[c][1,8]naphthyridin-1-ylamino)-1H-pyrazol-5-yl)acetamide (313)

The intermediate carboxylic acid was synthesized according to the procedure described for the preparation of Example 299 using 83 and (5-amino-2H-pyrazol-3-yl)-acetic acid methyl ester.
The title compound was synthesized according to the procedure described for the preparation of Example 300 using the carboxylic acid intermediate and 3,4-di-fluoroaniline to provide 313. LC-MS (M+H=447, obsd.=447).

Example 314

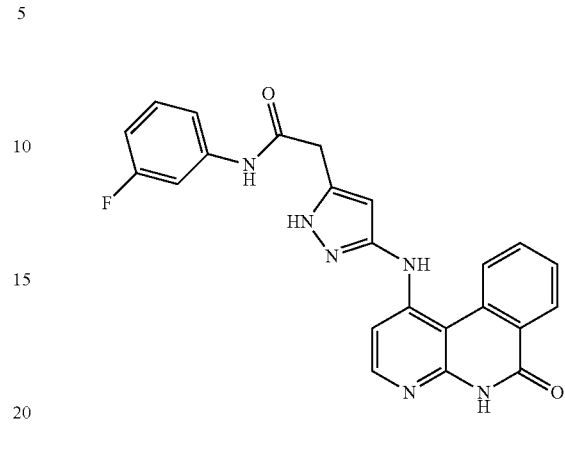

N-(3-Fluorophenyl)-2-(3-(6-oxo-5,6-dihydrobenzo[c][1,8]naphthyridin-1-ylamino)-1H-pyrazol-5-yl)acetamide (314)

The title compound was synthesized according to the procedure described for the preparation of Example 300 using the carboxylic acid intermediate from example 313 and 3-fluoroaniline to provide 314. LC-MS (M+H=429, obsd.=429).

Example 315

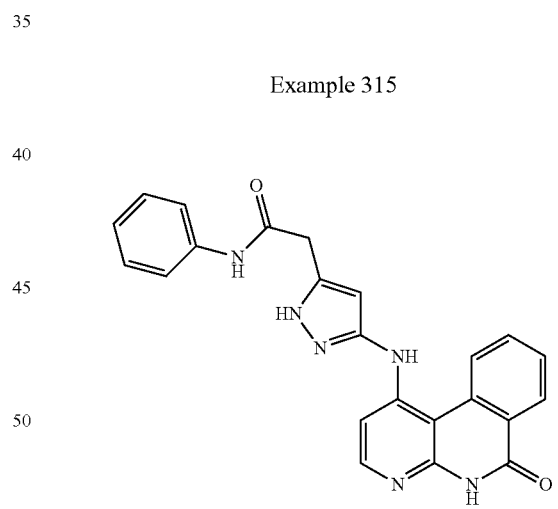

2-(3-(6-Oxo-5,6-dihydrobenzo[c][1,8]naphthyridin-1-ylamino)-1H-pyrazol-5-yl)-N-phenylacetamide (315)

The title compound was synthesized according to the procedure described for the preparation of Example 300 using the carboxylic acid intermediate from example 313 and aniline to provide 315. LC-MS (M+H=411, obsd.=411).

Example 316

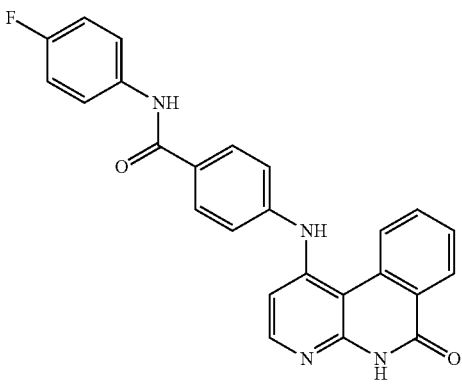 [SMILES: O=C(Nc1ccc(F)cc1)c1ccc(Nc2ccnc3[nH]c(=O)c4ccccc4c23)cc1]

N-(4-Fluorophenyl)-4-(6-oxo-5,6-dihydrobenzo[c][1,8]naphthyridin-1-ylamino)benzamide (316)

The intermediate carboxylic acid was synthesized according to the procedure described for the preparation of Example 299 using 83 and 4-amino-benzoic acid methyl ester.

The title compound was synthesized according to the procedure described for the preparation of Example 300 using the carboxylic acid intermediate and 4-fluoroaniline to provide 316. LC-MS (M+H=425, obsd.=425).

Example 317

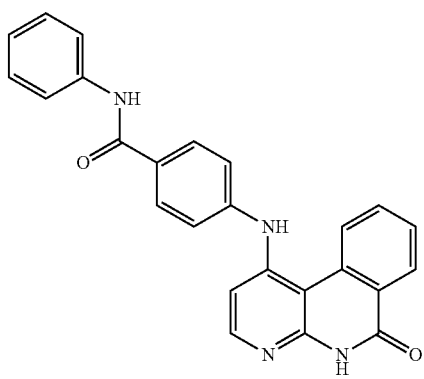 [SMILES: O=C(Nc1ccccc1)c1ccc(Nc2ccnc3[nH]c(=O)c4ccccc4c23)cc1]

4-(6-Oxo-5,6-dihydrobenzo[c][1,8]naphthyridin-1-ylamino)-N-phenylbenzamide (317)

The title compound was synthesized according to the procedure described for the preparation of Example 300 using the carboxylic acid intermediate from example 316 and aniline to provide 317. LC-MS (M+H=407, obsd.=407).

Example 318

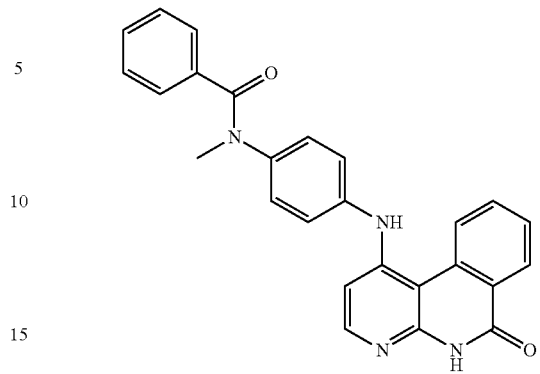

N-Methyl-N-(4-(6-oxo-5,6-dihydrobenzo[c][1,8]naphthyridin-1-ylamino) phenyl)benzamide (318)

The title compound was synthesized according to the procedure described for the preparation of Example 267 using 83 and N-(4-Amino-phenyl)-N-methyl-benzamide to provide 318. LC-MS (M+H=421, obsd.=421).

Example 319

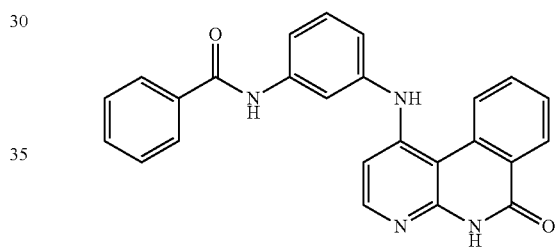

N-(3-(6-oxo-5,6-dihydrobenzo[c][1,8]naphthyridin-1-ylamino)phenyl)benzamide (319)

The title compound was synthesized according to the procedure described for the preparation of Example 267 using 83 and N-(3-Amino-phenyl)-benzamide to provide 319. LC-MS (M+H=407, obsd.=407).

Example 320

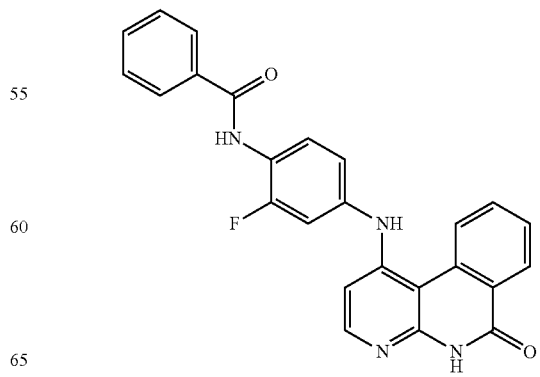

N-(2-Fluoro-4-(6-oxo-5,6-dihydrobenzo[c][1,8]naphthyridin-1-ylamino)phenyl) benzamide (320)

The reaction mixture of 83 (80 mg, 0.35 mmol), N-(4-(4-amino-2-fluorophenyl amino)phenyl)benzamide (96 mg, 0.42 mmol), Pd(OAc)$_2$ (12 mg, 0.05 mmol), X-Phos (50 mg, 0.10 mmol), and NaOtBu (67 mg, 0.69 mmol) in dioxane (2 mL) was stirred at 100° C. for 2 days. The reaction mixture was diluted with EtOAc/H$_2$O. The resulting precipitate was filtered, washed with H$_2$O, and dried under vacuum to provide 320 (23 mg, 16% yield) as a solid. LC-MS (M+H=425, obsd.=425).

Example 321

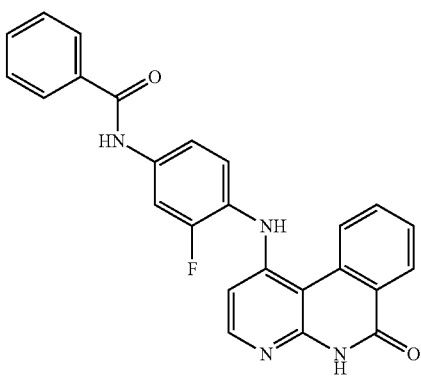 [SMILES: O=C(Nc1ccc(Nc2ccnc3[nH]c(=O)c4ccccc4c23)c(F)c1)c1ccccc1]

N-(3-Fluoro-4-(6-oxo-5,6-dihydrobenzo[c][1,8]naphthyridin-1-ylamino)phenyl)benzamide (321)

The title compound was synthesized according to the procedure described for the preparation of Example 320 using 83 (80 mg, 0.35 mmol) and N-(4-(4-amino-3-fluorophenyl amino)phenyl)benzamide (96 mg, 0.42 mmol) to provide 321. LC-MS (M+H=425, obsd.=425).

Example 322

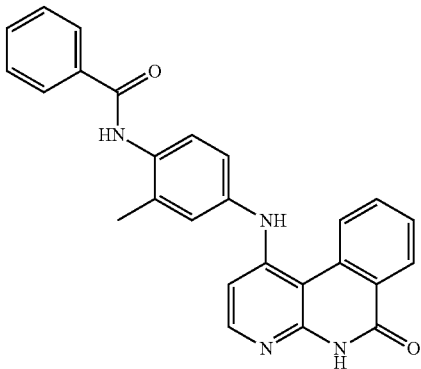 [SMILES: Cc1cc(Nc2ccnc3[nH]c(=O)c4ccccc4c23)ccc1NC(=O)c1ccccc1]

N-(2-Methyl-4-(6-oxo-5,6-dihydrobenzo[c][1,8]naphthyridin-1-ylamino)phenyl)benzamide (322)

The title compound was synthesized according to the procedure described for the preparation of Example 267 using 83 and N-(4-amino-2-methyl-phenyl)-benzamide to provide 322. LC-MS (M+H=421, obsd.=421).

Example 323

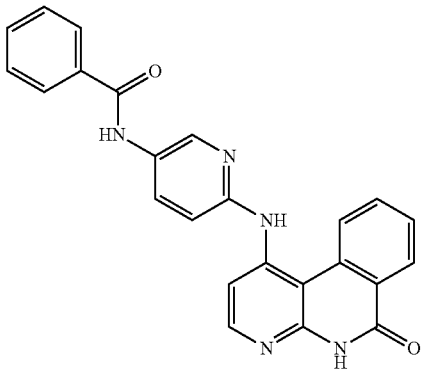 [SMILES: O=C(Nc1ccc(Nc2ccnc3[nH]c(=O)c4ccccc4c23)nc1)c1ccccc1]

N-(6-(6-Oxo-5,6-dihydrobenzo[c][1,8]naphthyridin-1-ylamino)pyridin-3-yl)benzamide (323)

The title compound was synthesized according to the procedure described for the preparation of Example 320 using 83 and N-(6-amino-pyridin-3-yl)-benzamide to provide 323. LC-MS (M+H=408, obsd.=408).

Example 324

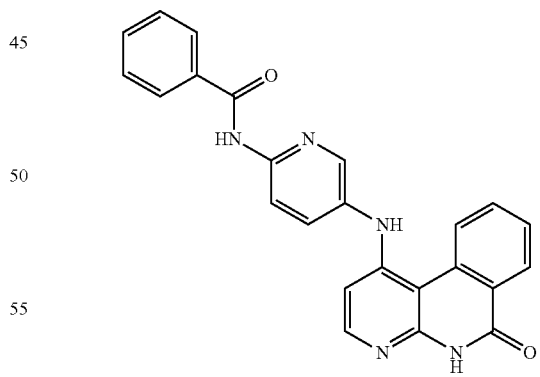

N-(5-(6-Oxo-5,6-dihydrobenzo[c][1,8]naphthyridin-1-ylamino)pyridin-2-yl)benzamide (324)

The title compound was synthesized according to the procedure described for the preparation of Example 320 using 83 and N-(6-amino-pyridin-2-yl)-benzamide to provide 324. LC-MS (M+H=408, obsd.=408).

Example 325

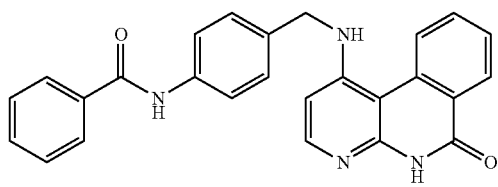 [SMILES: O=C(Nc1ccc(CNc2ccnc3[nH]c(=O)c4ccccc4c23)cc1)c1ccccc1]

N-(4-((6-Oxo-5,6-dihydrobenzo[c][1,8]naphthyridin-1-ylamino)methyl)phenyl)benzamide (325)

83 (200 mg, 0.87 mmol), 4-(aminomethyl)aniline (169 mg, 1.39 mmol), and $K_2CO_3$ (240 mg; 1.73 mmol) were suspended in iPrOH (5 mL), and stirred overnight at 100° C. The crude reaction mixture was filtered to provide desired intermediate.

The intermediate aniline, benzoic acid (23 mg, 0.19 mmol), HATU (75 mg, 0.20 mmol), and TEA (0.04 mL, 0.32 mmol; 2.00 eq.) were suspended in DMF (1 mL), and stirred at room temperature for 2 h. The reaction mixture was diluted with $H_2O$. The resulting precipitate was filtered, washed with MeOH, and dried under vacuum to provide 326 (49 mg, 74% yield). LC-MS (M+H=421, obsd.=421).

Example 326

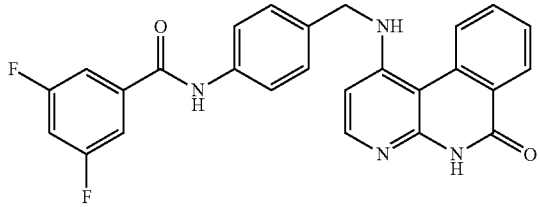 [SMILES: O=C(Nc1ccc(CNc2ccnc3[nH]c(=O)c4ccccc4c23)cc1)c1cc(F)cc(F)c1]

3,5-Difluoro-N-(4-((6-oxo-5,6-dihydrobenzo[c][1,8]naphthyridin-1-ylamino) methyl)phenyl)benzamide (326)

The title compound was synthesized according to the procedure described for the preparation of Example 325 using the aniline intermediate and 3,5-di-fluorobenzoic acid to provide 326. LC-MS (M+H=457, obsd.=457).

Example 327

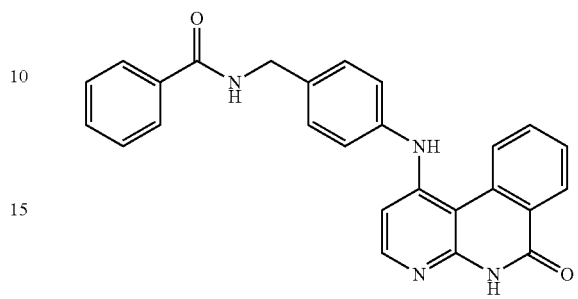

N-(4-(6-oxo-5,6-dihydrobenzo[c][1,8]naphthyridin-1-ylamino)benzyl)benzamide (327)

The title compound was synthesized according to the procedure described for the preparation of Example 320 using 83 and N-(4-amino-benzyl)-benzamide to provide 327. LC-MS (M+H=421, obsd.=421).

Example 328

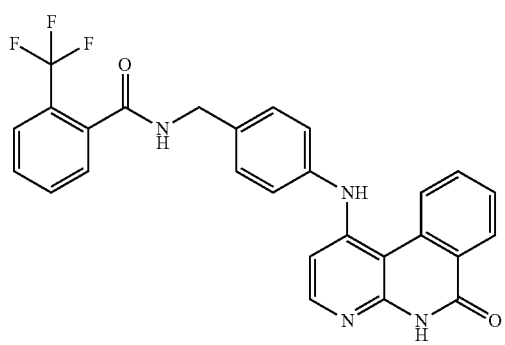 [SMILES: O=C(NCc1ccc(Nc2ccnc3[nH]c(=O)c4ccccc4c23)cc1)c1ccccc1C(F)(F)F]

N-(4-(6-Oxo-5,6-dihydrobenzo[c][1,8]naphthyridin-1-ylamino)benzyl)-2-(trifluoromethyl)benzamide (328)

The title compound was synthesized according to the procedure described for the preparation of Example 320 using 83 and N-(4-amino-benzyl)-2-trifluoro-methyl-benzamide to provide 328. LC-MS (M+H=489, obsd.=489).

Example 329

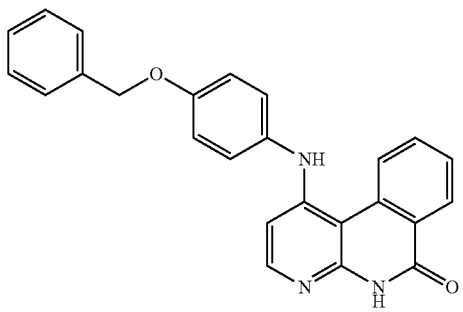 [SMILES: O=c1[nH]c2nccc(Nc3ccc(OCc4ccccc4)cc3)c2c2ccccc12]

1-(4-(Benzyloxy)phenylamino)benzo[c][1,8]naph-
thyridin-6(5H)-one (329)

The title compound was synthesized according to the procedure described for the preparation of Example 267 using 83 and 4-benzyloxy-phenylamine to provide 329. LC-MS (M+H=394, obsd.=394).

Example 330

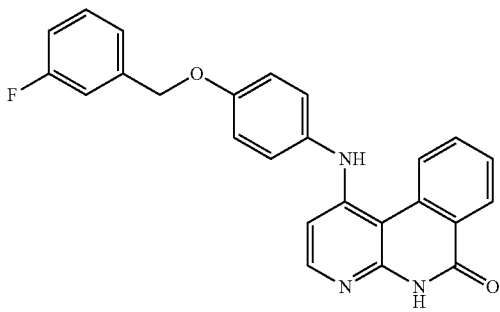 [SMILES: O=c1[nH]c2nccc(Nc3ccc(OCc4cccc(F)c4)cc3)c2c2ccccc12]

1-(4-(3-Fluorobenzyloxy)phenylamino)benzo[c][1,8]
naphthyridin-6(5H)-one (330)

The title compound was synthesized according to the procedure described for the preparation of Example 267 using 83 and 4-(3-fluoro-benzyloxy)-phenylamine to provide 330. LC-MS (M+H=412, obsd.=412).

Example 331

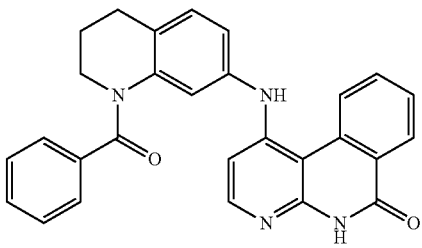 [SMILES: O=C(c1ccccc1)N1CCCc2ccc(Nc3ccnc4[nH]c(=O)c5ccccc5c34)cc21]

1-(1-Benzoyl-1,2,3,4-tetrahydroquinolin-6-ylamino)
benzo[c][1,8]naphthyridin-6(5H)-one (331)

The title compound was synthesized according to the procedure described for the preparation of Example 267 using 83 and (7-amino-3,4-dihydro-2H-quinolin-1-yl)-phenyl-methanone to provide 331. LC-MS (M+H=447, obsd.=447).

Example 332

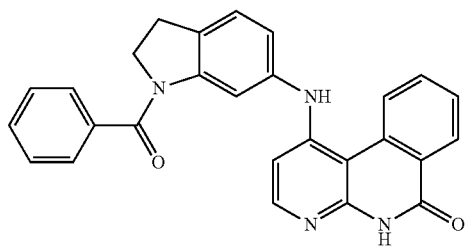 [SMILES: O=C(c1ccccc1)N1CCc2ccc(Nc3ccnc4[nH]c(=O)c5ccccc5c34)cc21]

1-(1-Benzoylindolin-5-ylamino)benzo[c][1,8]naph-
thyridin-6(5H)-one (332)

The title compound was synthesized according to the procedure described for the preparation of Example 267 using 83 and (6-amino-2,3-dihydro-indol-1-yl)-phenyl-methanone to provide 332. LC-MS (M+H=433, obsd.=433).

Example 333

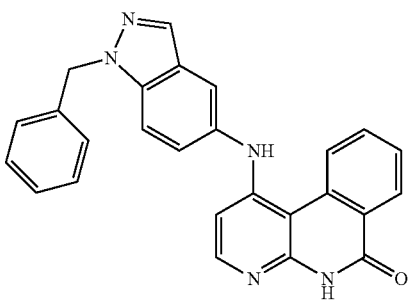 [SMILES: O=c1[nH]c2nccc(Nc3ccc4c(cnn4Cc4ccccc4)c3)c2c2ccccc12]

1-(1-Benzyl-1H-indazol-5-ylamino)benzo[c][1,8]
naphthyridin-6(5H)-one (333)

The title compound was synthesized according to the procedure described for the preparation of Example 267 using 83 and 1-benzyl-1H-indazol-5-ylamine to provide 333. LC-MS (M+H=418, obsd.=418).

Example 334

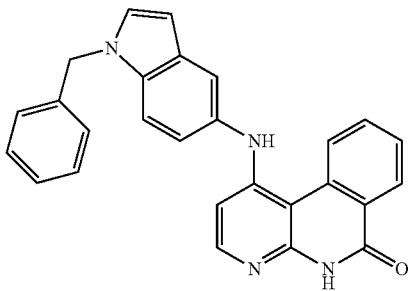 [SMILES: O=c1[nH]c2nccc(Nc3ccc4c(ccn4Cc4ccccc4)c3)c2c2ccccc12]

1-(1-Benzyl-1H-indol-5-ylamino)benzo[c][1,8]naph-thyridin-6(5H)-one (334)

The title compound was synthesized according to the procedure described for the preparation of Example 267 using 83 and 1-benzyl-1H-indol-5-ylamine to provide 334. LC-MS (M+H=417, obsd.=417).

Example 335

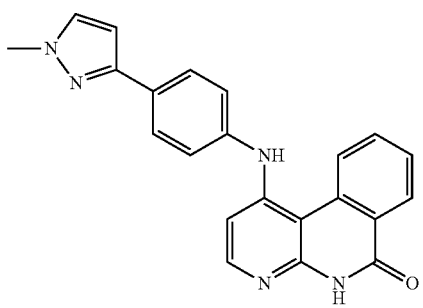 [SMILES: Cn1ccc(-c2ccc(Nc3ccnc4[nH]c(=O)c5ccccc5c34)cc2)n1]

1-(4-(1-Methyl-1H-pyrazol-3-yl)phenylamino)benzo [c][1,8]naphthyridin-6(5H)-one (335)

The title compound was synthesized according to the procedure described for the preparation of Example 267 using 83 and 4-(1-methyl-1H-pyrazol-3-yl)-phenylamine to provide 335. LC-MS (M+H=368, obsd.=368).

Example 336

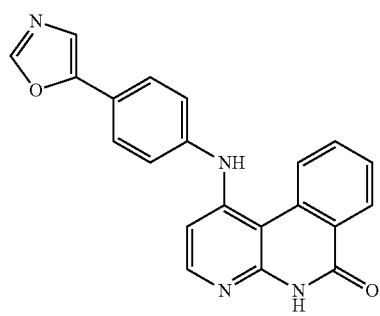 [SMILES: O=c1[nH]c2nccc(Nc3ccc(-c4cnco4)cc3)c2c2ccccc12]

1-(4-(Oxazol-5-yl)phenylamino)benzo[c][1,8]naph-thyridin-6(5H)-one (336)

The title compound was synthesized according to the procedure described for the preparation of Example 267 using 83 and 4-oxazol-5-yl-phenylamine to provide 336. LC-MS (M+H=355, obsd.=355).

Example 337

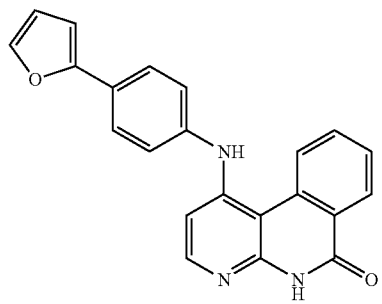 [SMILES: O=c1[nH]c2nccc(Nc3ccc(-c4ccco4)cc3)c2c2ccccc12]

1-(4-(Furan-2-yl)phenylamino)benzo[c][1,8]naph-thyridin-6(5H)-one (337)

The title compound was synthesized according to the procedure described for the preparation of Example 267 using 83 and 4-furan-2-yl-phenylamine to provide 337. LC-MS (M+H=354, obsd.=354).

Example 338

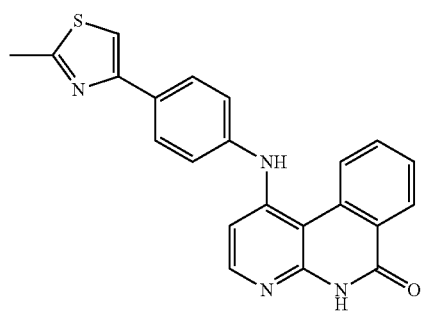 [SMILES: Cc1nc(-c2ccc(Nc3ccnc4[nH]c(=O)c5ccccc5c34)cc2)cs1]

1-(4-(2-Methylthiazol-4-yl)phenylamino)benzo[c][1, 8]naphthyridin-6(5H)-one (338)

The title compound was synthesized according to the procedure described for the preparation of Example 267 using 83 and 4-(2-methyl-thiazol-4-yl)-phenylamine to provide 338. LC-MS (M+H=385, obsd.=385).

Example 339

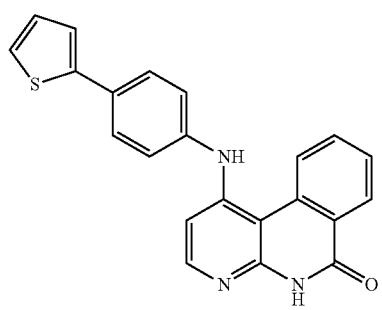 [SMILES: O=c1[nH]c2nccc(Nc3ccc(-c4cccs4)cc3)c2c2ccccc12]

1-(4-(Thiophen-2-yl)phenylamino)benzo[c][1,8] naphthyridin-6(5H)-one (339)

The title compound was synthesized according to the procedure described for the preparation of Example 267 using 83 and 4-thiophen-2-yl-phenylamine to provide 339. LC-MS (M+H=370, obsd.=370).

Example 340

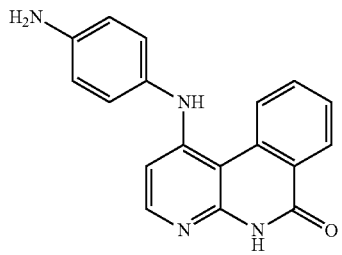 [SMILES: Nc1ccc(Nc2ccnc3[nH]c(=O)c4ccccc4c23)cc1]

1-(4-Aminophenylamino)benzo[c][1,8]naphthyridin-6(5H)-one (340)

83 (500 mg, 1.87 mmol), and tert-butyl 4-aminophenylcarbamate (428 mg, 2.06 mmol) were suspended in NMP (4 mL), was stirred overnight at 125° C. The reaction mixture was quenched with $H_2O$, filtered, and washed with $H_2O$.

The Boc-protected intermediate and TFA (2 mL) were suspended in $CH_2Cl_2$ (10 mL), and stirred overnight at room temperature. The solvent was removed, and aqueous 5% $NaHCO_3$ was added. The resulting precipitate was filtered, washed with H2O, and dried under vacuum to provide 340 (410 mg, 72% yield) as a solid. LC-MS (M+H=303, obsd.=303).

Example 341

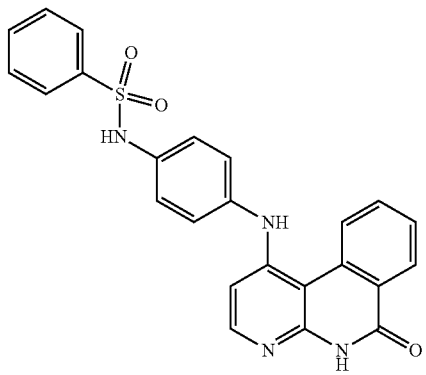 [SMILES: O=c1[nH]c2nccc(Nc3ccc(NS(=O)(=O)c4ccccc4)cc3)c2c2ccccc12]

N-(4-(6-Oxo-5,6-dihydrobenzo[c][1,8]naphthyridin-1-ylamino)phenyl)benzenesulfonamide (341)

340 (40 mg, 0.13 mmol), DIEA (34 mg, 0.26 mmol), and benzenesulfonyl chloride (47 mg, 0.26 mmol) were suspended in DME (2 mL), and stirred for 4 h at room temperature. The precipitate formed during the reaction was filtered, washed with EtOAc, and dried under vacuum to provide 341 (20 mg, 34% yield) as a solid. LC-MS (M+H=443, obsd.=443).

Example 342

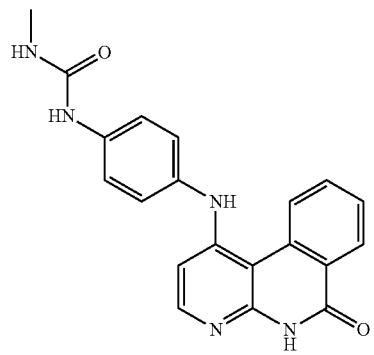 [SMILES: CNC(=O)Nc1ccc(Nc2ccnc3[nH]c(=O)c4ccccc4c23)cc1]

1-Methyl-3-(4-(6-oxo-5,6-dihydrobenzo[c][1,8]naphthyridin-1-ylamino)phenyl)urea (342)

340 (40 mg, 0.13 mmol), DIEA (34 mg, 0.26 mmol), and isocyanatomethane (11 mg, 0.18 mmol) were suspended in DMSO (1 mL), and stirred for 4 h at room temperature. The reaction mixture was quenched with $H_2O$, filtered, washed with $H_2O$ and MeOH, and dried under vacuum to provide 342 (23 mg, 46% yield) as a solid. LC-MS (M+H=361, obsd.=361).

Example 343

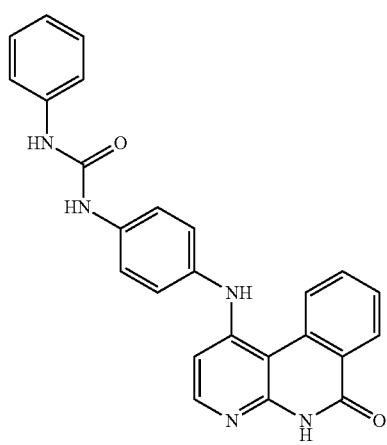 [SMILES: O=C(Nc1ccccc1)Nc1ccc(Nc2ccnc3[nH]c(=O)c4ccccc4c23)cc1]

1-(4-(6-Oxo-5,6-dihydrobenzo[c][1,8]naphthyridin-1-ylamino)phenyl)-3-phenylurea (343)

The title compound was synthesized according to the procedure described for the preparation of Example 342 using 340 and isocyanato-benzene to provide 343. LC-MS (M+H=422, obsd.=422).

Example 344

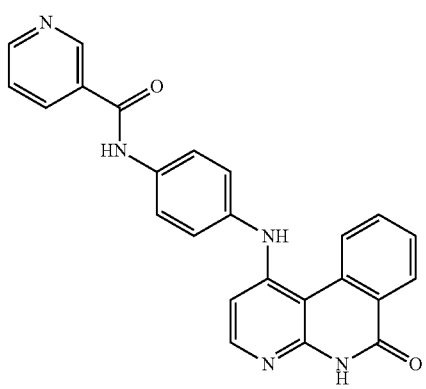 [SMILES: O=C(Nc1ccc(Nc2ccnc3[nH]c(=O)c4ccccc4c23)cc1)c1cccnc1]

N-(4-(6-Oxo-5,6-dihydrobenzo[c][(1,8]naphthyridin-1-ylamino)phenyl)nicotinamide (344)

340 (35 mg, 0.12 mmol), DIEA (0.04 mL, 0.23 mmol), nicotinic acid (17 mg, 0.14 mmol), and Bop-Cl (44 mg; 0.17 mmol) were suspended in DMF (1 mL), and stirred overnight at room temperature. The crude product mixture was purified directly via HP-LC to provide 344 (35 mg, 58% yield). LC-MS (M+H=408, obsd.=408).

Example 345

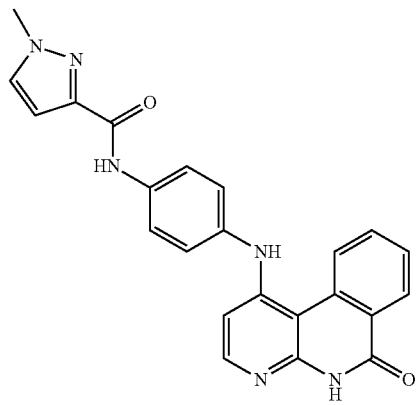 [SMILES: Cn1ccc(C(=O)Nc2ccc(Nc3ccnc4[nH]c(=O)c5ccccc5c34)cc2)n1]

1-methyl-N-(4-(6-oxo-5,6-dihydrobenzo[c][1,8]naphthyridin-1-ylamino)phenyl)-1H-pyrazole-3-carboxamide (345)

The title compound was synthesized according to the procedure described for the preparation of Example 344 using 340 and 1-methyl-1H-pyrazole-3-carboxylic acid to provide 345. LC-MS (M+H=411, obsd.=411).

Example 346

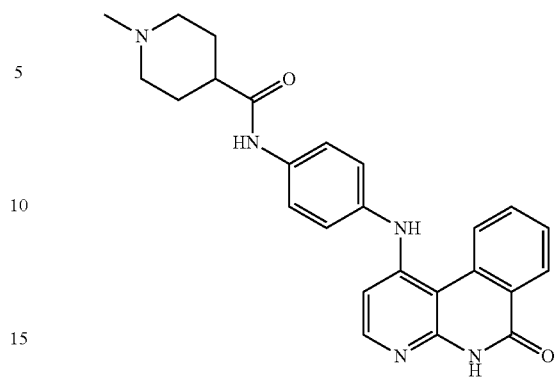

1-Methyl-N-(4-(6-oxo-5,6-dihydrobenzo[c][1,8]naphthyridin-1-ylamino)phenyl)piperidine-4-carboxamide (346)

The title compound was synthesized according to the procedure described for the preparation of Example 344 using 340 and 1-methyl-piperidine-4-carboxylic acid to provide 346. LC-MS (M+H=428, obsd.=428).

Example 347

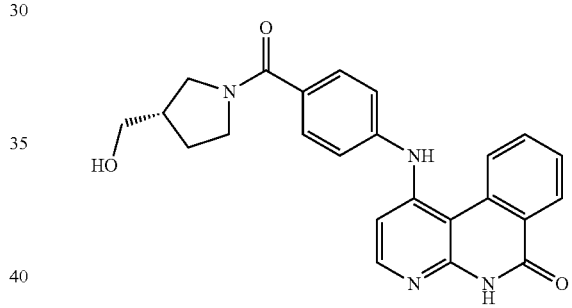

1-[4-((S)-3-Hydroxymethyl-pyrrolidine-1-carbonyl)-phenylamino]-5H-benzo[c][1,8]naphthyridin-6-one (347)

The title compound was synthesized according to the procedure described for the preparation of Example 300 using the carboxylic acid intermediate from example 316 and (S)-1-pyrrolidin-3-yl-methanol to provide 317. LC-MS (M+H=407, obsd.=407).

Example 348

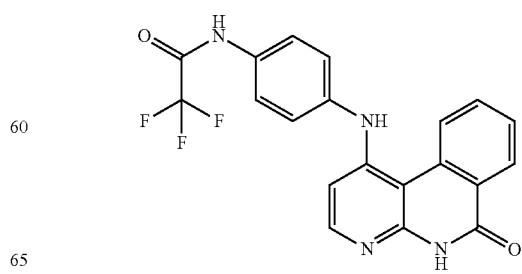

2,2,2-Trifluoro-N-(4-(6-oxo-5,6-dihydrobenzo[c][1,8]naphthyridin-1-ylamino) phenyl)acetamide (348)

The title compound was synthesized according to the procedure described for the preparation of Example 267 using 83 and N-(4-amino-phenyl)-2,2,2-trifluoro-acetamide to provide 348. LC-MS (M+H=399, obsd.=399).

Example 349

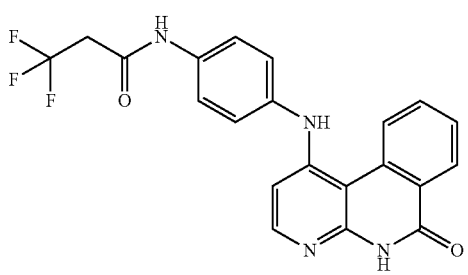 [SMILES: O=C(CC(F)(F)F)Nc1ccc(Nc2ccnc3[nH]c(=O)c4ccccc4c23)cc1]

3,3,3-Trifluoro-N-(4-(6-oxo-5,6-dihydrobenzo[c][1,8]naphthyridin-1-ylamino)phenyl)propanamide (349)

The title compound was synthesized according to the procedure described for the preparation of Example 267 using 83 and N-(4-amino-phenyl)-3,3,3-trifluoro-propionamide to provide 349. LC-MS (M+H=413, obsd.=413).

Example 350

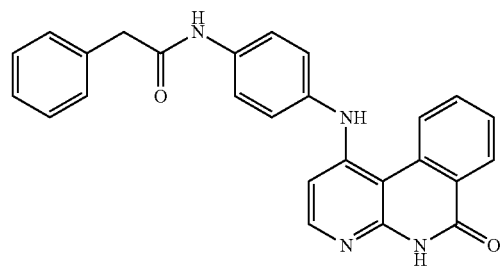 [SMILES: O=C(Cc1ccccc1)Nc1ccc(Nc2ccnc3[nH]c(=O)c4ccccc4c23)cc1]

N-(4-(6-Oxo-5,6-dihydrobenzo[c][1,8]naphthyridin-1-ylamino)phenyl)-2-phenylacetamide (350)

The title compound was synthesized according to the procedure described for the preparation of Example 267 using 83 and N-(4-amino-phenyl)-2-phenyl-acetamide to provide 350. LC-MS (M+H=421, obsd.=421).

Example 351

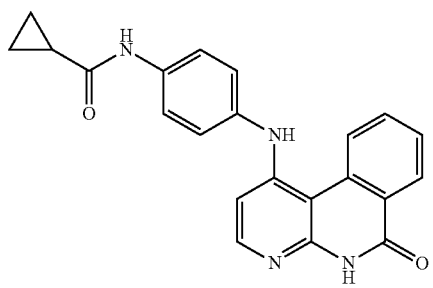 [SMILES: O=C(Nc1ccc(Nc2ccnc3[nH]c(=O)c4ccccc4c23)cc1)C1CC1]

N-(4-(6-Oxo-5,6-dihydrobenzo[c][1,8]naphthyridin-1-ylamino)phenyl)cyclopropanecarboxamide (351)

The title compound was synthesized according to the procedure described for the preparation of Example 267 using 83 and cyclopropanecarboxylic acid (4-amino-phenyl)-amide to provide 351. LC-MS (M+H=371, obsd.=371).

Example 352

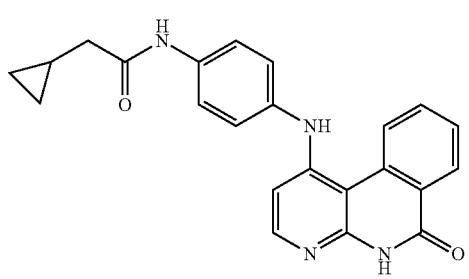 [SMILES: O=C(CC1CC1)Nc1ccc(Nc2ccnc3[nH]c(=O)c4ccccc4c23)cc1]

2-Cyclopropyl-N-(4-(6-oxo-5,6-dihydrobenzo[c][1,8]naphthyridin-1-ylamino)phenyl)acetamide (352)

The title compound was synthesized according to the procedure described for the preparation of Example 267 using 83 and N-(4-amino-phenyl)-2-cyclopropyl-acetamide to provide 352. LC-MS (M+H=385, obsd.=385).

Example 353

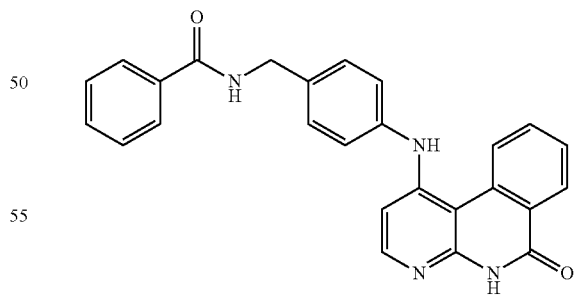

N-(4-(6-Oxo-5,6-dihydrobenzo[c][1,8]naphthyridin-1-ylamino)benzyl)benzamide (353)

The title compound was synthesized according to the procedure described for the preparation of Example 327 using the benzylamine intermediate and benzoic acid to provide 353. LC-MS (M+H=421, obsd.=421).

Example 354

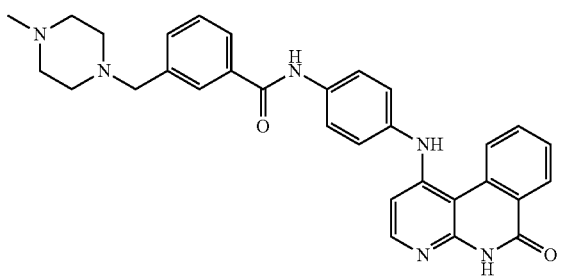 [SMILES: CN1CCN(Cc2cccc(C(=O)Nc3ccc(Nc4ccnc5[nH]c(=O)c6ccccc6c45)cc3)c2)CC1]

3-((4-Methylpiperazin-1-yl)methyl)-N-(4-(6-oxo-5,6-dihydrobenzo[c][1,8]naphthyridin-1-ylamino)phenyl)benzamide (354)

The title compound was synthesized according to the procedure described for the preparation of Example 344 using 340 and 3-(4-methyl-piperazin-1-ylmethyl)-benzoic acid to provide 354. LC-MS (M+H=519, obsd.=519).

Example 355

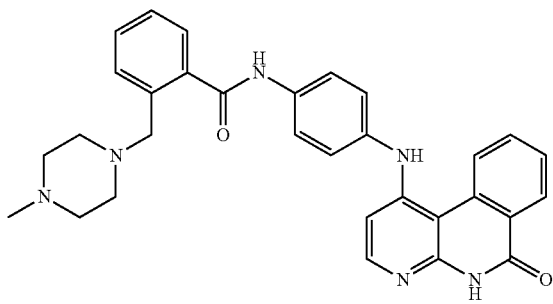 [SMILES: CN1CCN(Cc2ccccc2C(=O)Nc2ccc(Nc3ccnc4[nH]c(=O)c5ccccc5c34)cc2)CC1]

2-((4-Methylpiperazin-1-yl)methyl)-N-(4-(6-oxo-5,6-dihydrobenzo[c][1,8]naphthyridin-1-ylamino)phenyl)benzamide (355)

The title compound was synthesized according to the procedure described for the preparation of Example 344 using 340 and 2-(4-methyl-piperazin-1-ylmethyl)-benzoic acid to provide 355. LC-MS (M+H=519, obsd.=519).

Example 356

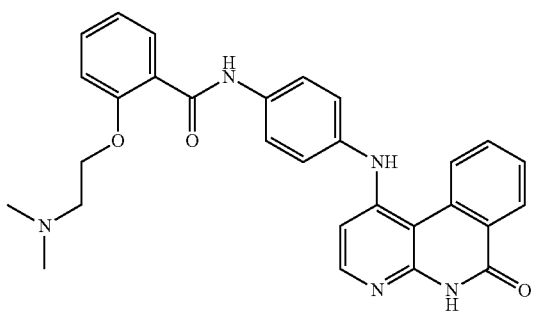 [SMILES: CN(C)CCOc1ccccc1C(=O)Nc1ccc(Nc2ccnc3[nH]c(=O)c4ccccc4c23)cc1]

2-(2-(Dimethylamino)ethoxy)-N-(4-(6-oxo-5,6-dihydrobenzo[c][1,8]naphthyridin-1-ylamino)phenyl)benzamide (356)

The title compound was synthesized according to the procedure described for the preparation of Example 344 using 340 and 2-(2-dimethylamino-ethoxy)-benzoic acid to provide 356. LC-MS (M+H=494, obsd.=494).

Example 357

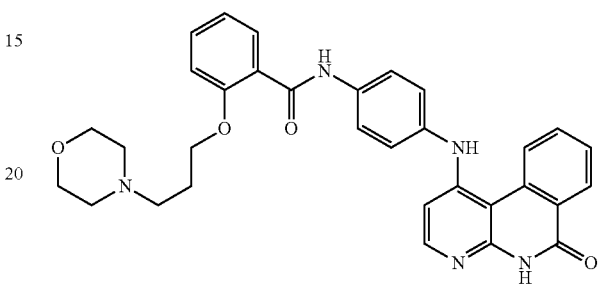

2-(3-morpholinopropoxy)-N-(4-(6-oxo-5,6-dihydrobenzo[c][1,8]naphthyridin-1-ylamino)phenyl)benzamide (357)

The title compound was synthesized according to the procedure described for the preparation of Example 344 using 340 and 2-(3-morpholin-4-yl-propoxy)-benzoic acid to provide 357. LC-MS (M+H=550, obsd.=550).

Example 358

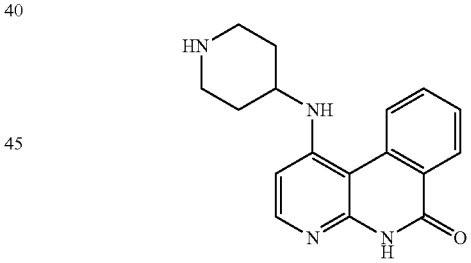

1-(Piperidin-4-ylamino)benzo[c][1,8]naphthyridin-6(5H)-one (358)

83 (2.0 g, 8.67 mmol), tert-butyl 4-aminophenylcarbamate (2.6 g, 13.01 mmol), and $K_2CO_3$ (1.8 g, 13.01 mmol) were suspended in NMP (15 mL), and stirred for 40 h at 120° C. The reaction mixture was quenched with $H_2O$, filtered, and washed with $H_2O$.

The Boc-protected intermediate and HCl (15 mL, 4 M in dioxane) were suspended in MeOH (30 mL), and stirred for 3 h at room temperature. The solvent was removed, and aqueous 5% $NaHCO_3$ was added. The resulting precipitate was filtered, washed with $H_2O$, and dried under vacuum to provide 358 (2.45 g, 96% yield) as a solid. LC-MS (M+H=295, obsd.=295).

Example 359

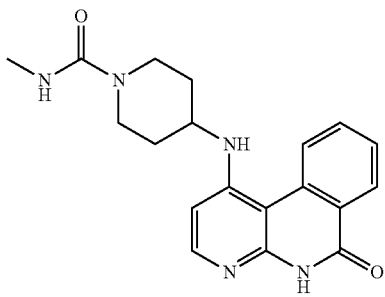 [SMILES: CNC(=O)N1CCC(Nc2ccnc3[nH]c(=O)c4ccccc4c23)CC1]

N-Methyl-4-(6-oxo-5,6-dihydrobenzo[c][1,8]naph-thyridin-1-ylamino)piperidine-1-carboxamide (359)

358 (50 mg, 0.17 mmol) and isocyanatomethane (15 mg, 0.25 mmol) were suspended in DCE (2 mL), and stirred overnight at room temperature. The crude material was purified directly via HPLC to provide 359 (26 mg, 44% yield) as a solid. LC-MS (M+H=351, obsd.=351).

Example 360

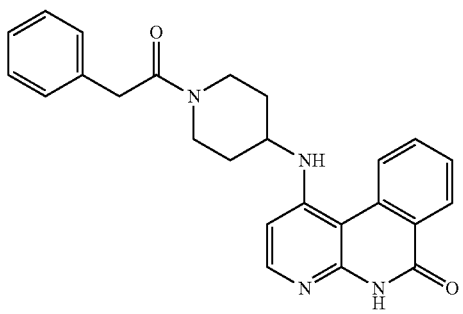 [SMILES: O=C(Cc1ccccc1)N1CCC(Nc2ccnc3[nH]c(=O)c4ccccc4c23)CC1]

1-(1-(2-Phenylacetyl)piperidin-4-ylamino)benzo[c][1,8]naphthyridin-6(5H)-one (360)

Phenylacetic acid (10 mg, 0.07 mmol), DIEA (28 mg, 0.22 mmol), and HATU (28 mg, 0.07 mmol) were dissolved in DMF (1 mL), and stirred for 30 min at room temperature. 358 (17 mg, 0.06 mmol) was added, and the reaction mixture was stirred for another 1 h at room temperature. The crude material was purified directly via HPLC to provide 360 (10 mg, 30% yield) as a solid. LC-MS (M+H=413, obsd.=413).

Example 361

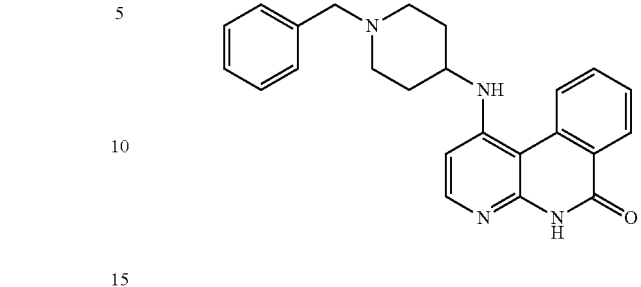

1-(1-Benzylpiperidin-4-ylamino)benzo[c][1,8]naph-thyridin-6(5H)-one (361)

358 (60 mg, 0.20 mmol) and benzaldehyde (0.03 mL, 0.26 mmol) were suspended in DCE (4 mL), and stirred for 2 h at room temperature. NaBH(OAc)$_3$ (130 mg, 0.61 mmol) was added, and the reaction mixture was stirred overnight at room temperature. The reaction mixture was quenched with 1NHCl and the crude material was purified directly via HPLC to provide 361 (22 mg, 28% yield) as a solid. LC-MS (M+H=385, obsd.=385).

Example 362

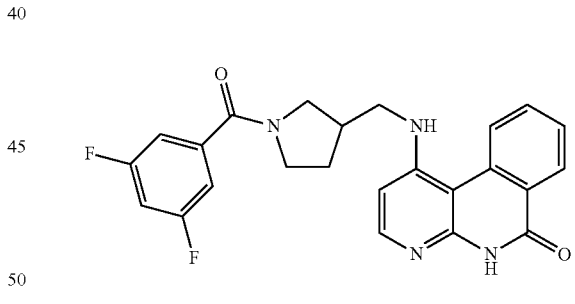

1-((1-(3,5-Difluorobenzoyl)pyrrolidin-3-yl)methy-lamino)benzo[c][1,8]naphthyridin-6(5H)-one (362)

The intermediate amine was synthesized according to the procedure described for the preparation of Example 358 using 83 and 3-aminomethyl-pyrrolidine-1-carboxylic acid tert-butyl ester.

The title compound was synthesized according to the procedure described for the preparation of Example 360 using the amine intermediate and 3,5-di-fluorobenzoic acid to provide 362. LC-MS (M+H=435, obsd.=435).

Example 363

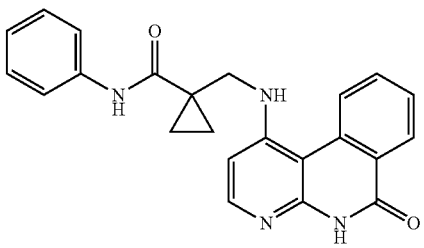 [SMILES: O=C(Nc1ccccc1)C1(CNc2ccnc3[nH]c(=O)c4ccccc4c23)CC1]

1-((6-Oxo-5,6-dihydrobenzo[c][1,8]naphthyridin-1-ylamino)methyl)-N-phenylcyclopropanecarboxamide (363)

The intermediate carboxylic acid was synthesized according to the procedure described for the preparation of Example 299 using 83 and 1-aminomethyl-cyclopropanecarboxylic acid methyl ester.

The title compound was synthesized according to the procedure described for the preparation of Example 300 using the carboxylic acid intermediate and aniline to provide 363. LC-MS (M+H=385, obsd.=385).

Example 364

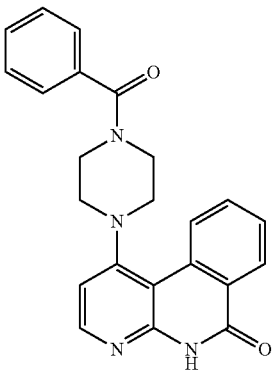 [SMILES: O=C(c1ccccc1)N1CCN(c2ccnc3[nH]c(=O)c4ccccc4c23)CC1]

1-(4-Benzoylpiperazin-1-yl)benzo[c][1,8]naphthyridin-6(5H)-one (364)

The intermediate amine was synthesized according to the procedure described for the preparation of Example 358 using 83 and piperazine-1-carboxylic acid tert-butyl ester.

The title compound was synthesized according to the procedure described for the preparation of Example 360 using the amine intermediate and benzoic acid to provide 364. LC-MS (M+H=385, obsd.=385).

Example 365

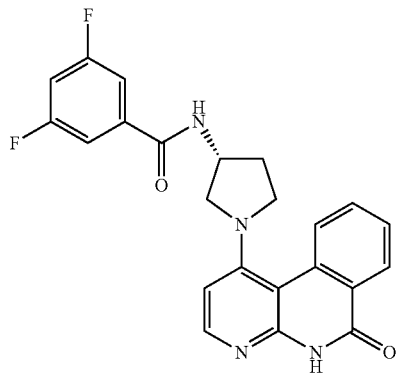 [SMILES: O=C(N[C@@H]1CCN(c2ccnc3[nH]c(=O)c4ccccc4c23)C1)c1cc(F)cc(F)c1]

(R)-3,5-Difluoro-N-(1-(6-oxo-5,6-dihydrobenzo[c][1,8]naphthyridin-1-yl)pyrrolidin-3-yl)benzamide (365)

The intermediate amine was synthesized according to the procedure described for the preparation of Example 358 using 83 and (R)-pyrrolidin-3-yl-carbamic acid tert-butyl ester.

The title compound was synthesized according to the procedure described for the preparation of Example 360 using the amine intermediate and 3,5-di-fluorobenzoic acid to provide 365. LC-MS (M+H=421, obsd.=421).

Example 366

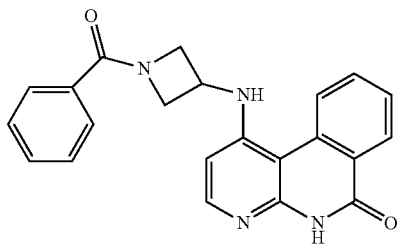 [SMILES: O=C(c1ccccc1)N1CC(Nc2ccnc3[nH]c(=O)c4ccccc4c23)C1]

1-(1-Benzoylazetidin-3-ylamino)benzo[c][1,8]naphthyridin-6(5H)-one (366)

The intermediate amine was synthesized according to the procedure described for the preparation of Example 358 using 83 and 3-amino-azetidine-1-carboxylic acid tert-butyl ester.

The title compound was synthesized according to the procedure described for the preparation of Example 360 using the amine intermediate and benzoic acid to provide 366. LC-MS (M+H=371, obsd.=371).

Example 367

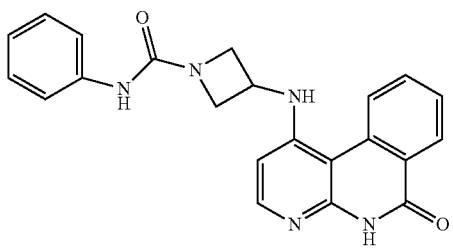 [SMILES: O=C(Nc1ccccc1)N1CC(Nc2ccnc3[nH]c(=O)c4ccccc4c23)C1]

3-(6-Oxo-5,6-dihydrobenzo[c][1,8]naphthyridin-1-ylamino)-N-phenylazetidine-1-carboxamide (367)

The title compound was synthesized according to the procedure described for the preparation of Example 359 using the amine intermediate from example 366 and isocyanato benzene to provide 367. LC-MS (M+H=386, obsd.=386).

Example 368

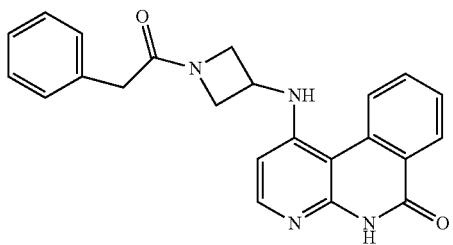 [SMILES: O=C(Cc1ccccc1)N1CC(Nc2ccnc3[nH]c(=O)c4ccccc4c23)C1]

1-(1-(2-Phenylacetyl)azetidin-3-ylamino)benzo[c][1,8]naphthyridin-6(5H)-one (368)

The title compound was synthesized according to the procedure described for the preparation of Example 360 using the amine intermediate from example 366 and phenylacetic acid to provide 368. LC-MS (M+H=385, obsd.=385).

Example 369

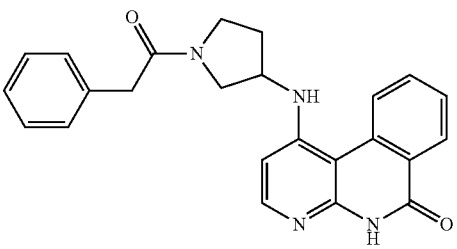 [SMILES: O=C(Cc1ccccc1)N1CCC(Nc2ccnc3[nH]c(=O)c4ccccc4c23)C1]

1-(1-(2-Phenylacetyl)pyrrolidin-3-ylamino)benzo[c][1,8]naphthyridin-6(5H)-one (369)

The intermediate amine was synthesized according to the procedure described for the preparation of Example 358 using 83 and 3-Amino-pyrrolidine-1-carboxylic acid tert-butyl ester.

The title compound was synthesized according to the procedure described for the preparation of Example 360 using the amine intermediate and phenylacetic acid to provide 369. LC-MS (M+H=399, obsd.=399).

Example 370

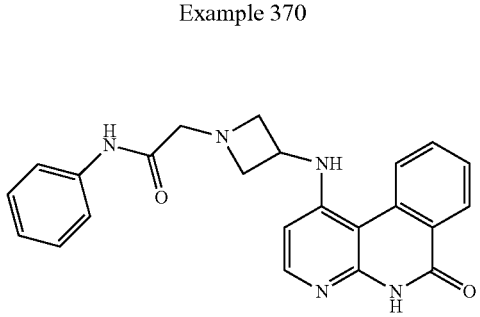

2-(3-(6-Oxo-5,6-dihydrobenzo[c][1,8]naphthyridin-1-ylamino)azetidin-1-yl)-N-phenylacetamide (370)

The amine intermediate from Example 366 (60 mg, 0.16 mmol), K$_2$CO$_3$ (33 mg, 0.24 mmol), and 2-chloro-N-phenylacetamide (26 mg, 0.16 mmol) were suspended in MeOH (2 mL), and stirred for 40 h at room temperature. The crude reaction mixture was purified directly via HP-LC to provide 370 (5 mg, 6% yield) as a solid. LC-MS (M+H=400, obsd.=400).

Example 371

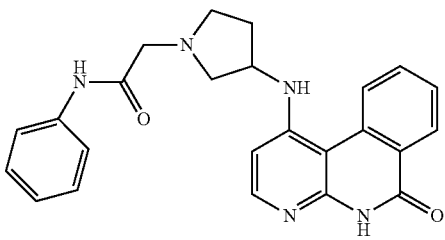 [SMILES: O=C(CN1CCC(Nc2ccnc3[nH]c(=O)c4ccccc4c23)C1)Nc1ccccc1]

2-(3-(6-Oxo-5,6-dihydrobenzo[c][1,8]naphthyridin-1-ylamino)pyrrolidin-1-yl)-N-phenylacetamide (371)

The title compound was synthesized according to the procedure described for the preparation of Example 370 using the amine intermediate from example 369 and 2-chloro-N-phenylacetamide to provide 371. LC-MS (M+H=414, obsd.=414).

Example 372

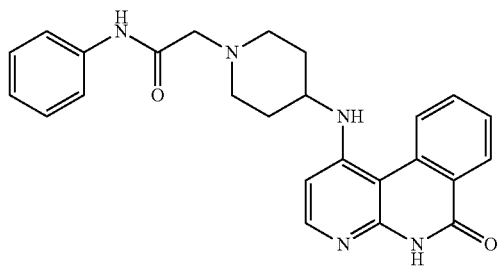 [SMILES: O=C(CN1CCC(Nc2ccnc3[nH]c(=O)c4ccccc4c23)CC1)Nc1ccccc1]

2-(4-(6-Oxo-5,6-dihydrobenzo[c][1,8]naphthyridin-1-ylamino)piperidin-1-yl)-N-phenylacetamide (372)

83 (200 mg, 0.87 mmol), 2-(4-aminocyclohexyl)-N-phenylacetamide *2HCl (278 mg, 0.91 mmol), and $K_2CO_3$ (360 mg, 2.6 mmol) were suspended in NMP (2 mL), and stirred for 90 min. at 130° C. in microwave. The crude reaction mixture was purified directly via HP-LC to provide 372 (60 mg, 16% yield) as a solid. LC-MS (M+H=428, obsd.=428).

Example 373

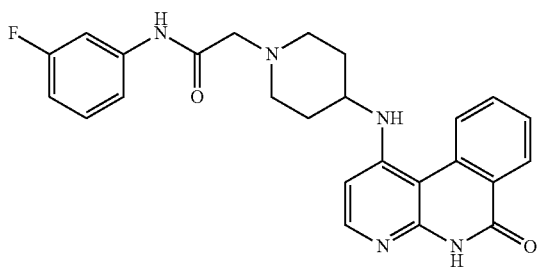 [SMILES: O=C(CN1CCC(Nc2ccnc3[nH]c(=O)c4ccccc4c23)CC1)Nc1cccc(F)c1]

N-(3-Fluorophenyl)-2-(4-(6-oxo-5,6-dihydrobenzo[c][1,8]naphthyridin-1-ylamino)piperidin-1-yl)acetamide (373)

The title compound was synthesized according to the procedure described for the preparation of Example 372 using 83 and 2-(4-amino-piperidin-1-yl)-N-(3-fluoro-phenyl)-acetamide to provide 373. LC-MS (M+H=446, obsd.=446).

Example 374

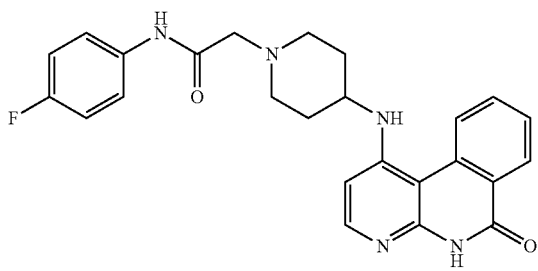 [SMILES: O=C(CN1CCC(Nc2ccnc3[nH]c(=O)c4ccccc4c23)CC1)Nc1ccc(F)cc1]

N-(4-Fluorophenyl)-2-(4-(6-oxo-5,6-dihydrobenzo[c][1,8]naphthyridin-1-ylamino)piperidin-1-yl)acetamide (374)

The title compound was synthesized according to the procedure described for the preparation of Example 372 using 83 and 2-(4-amino-piperidin-1-yl)-N-(4-fluoro-phenyl)-acetamide to provide 374. LC-MS (M+H=446, obsd.=446).

Example 375

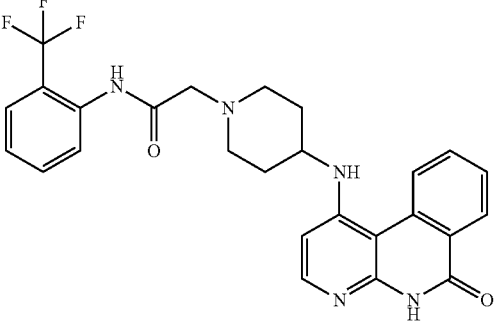

2-(4-(6-Oxo-5,6-dihydrobenzo[c][1,8]naphthyridin-1-ylamino)piperidin-1-yl)-N-(2-(trifluoromethyl)phenyl)acetamide (375)

The title compound was synthesized according to the procedure described for the preparation of Example 372 using 83 and 2-(4-amino-piperidin-1-yl)-N-(2-trifluoromethyl-phenyl)-acetamide to provide 375. LC-MS (M+H=496, obsd.=496).

Example 376

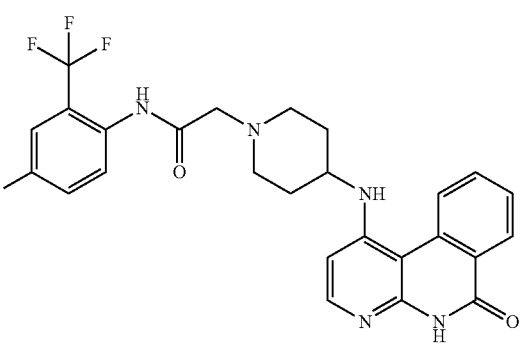

N-(4-Fluoro-2-(trifluoromethyl)phenyl)-2-(4-(6-oxo-5,6-dihydrobenzo[c][1,8]naphthyridin-1-ylamino)piperidin-1-yl)acetamide (376)

The title compound was synthesized according to the procedure described for the preparation of Example 372 using 83 and 2-(4-amino-piperidin-1-yl)-N-(4-fluoro-2-trifluoromethyl-phenyl)-acetamide to provide 376. LC-MS (M+H=514, obsd.=514).

Example 377

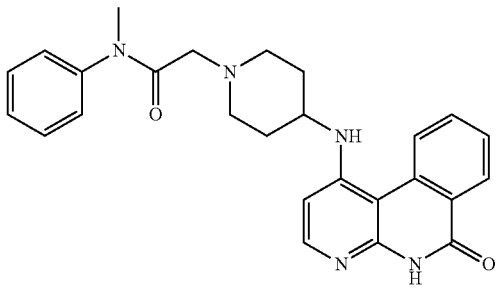 [SMILES: CN(C(=O)CN1CCC(Nc2ccnc3[nH]c(=O)c4ccccc4c23)CC1)c1ccccc1]

N-Methyl-2-(4-(6-oxo-5,6-dihydrobenzo[c][1,8]
naphthyridin-1-ylamino) piperidin-1-yl)-N-phenylac-
etamide (377)

The title compound was synthesized according to the procedure described for the preparation of Example 372 using 83 and 2-(4-amino-piperidin-1-yl)-N-methyl-N-phenyl-acetamide to provide 377. LC-MS (M+H=442, obsd.=442).

Example 378

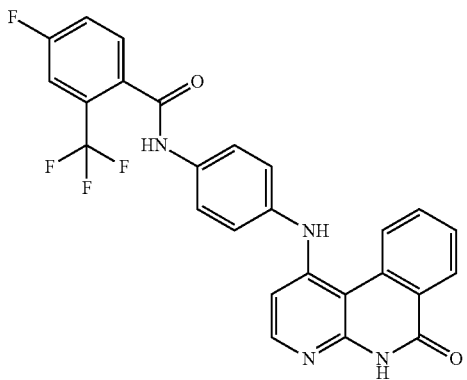 [SMILES: O=C(Nc1ccc(Nc2ccnc3[nH]c(=O)c4ccccc4c23)cc1)c1ccc(F)cc1C(F)(F)F]

4-Fluoro-N-[4-(6-oxo-5,6-dihydro-benzo[c][1,8]
naphthyridin-1-ylamino)-phenyl]-2-trifluoromethyl-
benzamide (378)

Method 1: 83 (60 mg, 0.26 mmol), N-(4-aminophenyl)-4-fluoro-2-(trifluoromethyl)benzamide (116 mg, 0.39 mmol), Pd(OAc)$_2$ (6 mg, 0.01 mmol), X-Phos (10 mg, 0.02 mmol), and NaOtBu (100 mg, 1.04 mmol) were suspended in dioxane (2 mL), in sealed vial was stirred overnight at 100° C. The reaction mixture was diluted with EtOAc/H$_2$O. The resulting precipitate was filtered, washed with EtOAc, and dried under vacuum to provide 378 (10 mg, 14% yield) as pale solid. LC-MS (M+H=493, obsd.=493). $^1$H NMR (400 MHz, DMSO-d6): δ 7.21 (d, 2H), 7.67 (m, 4H), 7.79 (m, 4H), 8.08 (d, 1H), 8.30 (d, 1H), 8.81 (d, 1H), 9.07 (s, 1H), 10.56 (s, 1H).

Method 2: To a suspension of 83 (135 mg, 0.59 mmol) in ether (10 mL) was added HCl (1.17 mL, 1.00 M, 1.17 mmol) in ether. The mixture was stirred for 3 h and the solvent was removed under vacuo. A suspension of this HCl salt in NMP (3 mL) was added N-(4-aminophenyl)-4-fluoro-2-(trifluoromethyl)benzamide (209 mg, 0.70 mmol). The mixture was stirred at 150° C. for 3 h. After cooling to room temperature, H$_2$O was added. The resulting product precipitate and the solid was filtered, washed with H$_2$O and MeOH, and dried under vacuum to provide 378 (210 mg, 73% yield) as pale solid.

Example 379

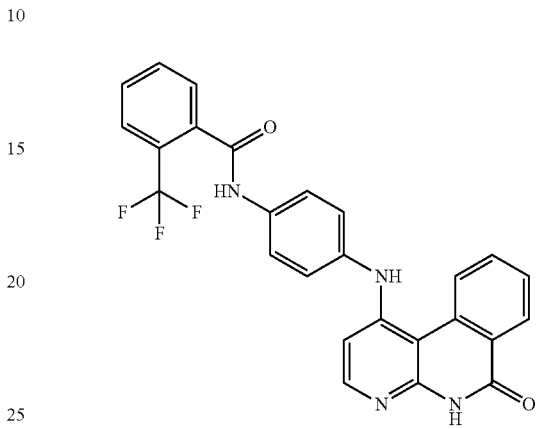

N-[4-(6-Oxo-5,6-dihydro-benzo[c][1,8]naphthyridin-
1-ylamino)-phenyl]-2-trifluoromethyl-benzamide
(379)

The title compound was synthesized according to the procedure described for the preparation of Example 378, method 1 using 83 and N-(4-aminophenyl)-2-(trifluoromethyl)benzamide to provide 379. LC-MS (M+H=475, obsd.=475). $^1$H NMR (400 MHz, DMSO-d6): δ 6.92 (d, 1H), 7.22 (d, 2H), 7.67 (m, 4H), 7.79 (m, 4H), 8.08 (d, 1H), 8.30 (d, 1H), 8.84 (d, 1H), 9.11 (s, 1H), 10.56 (s, 1H).

Example 380

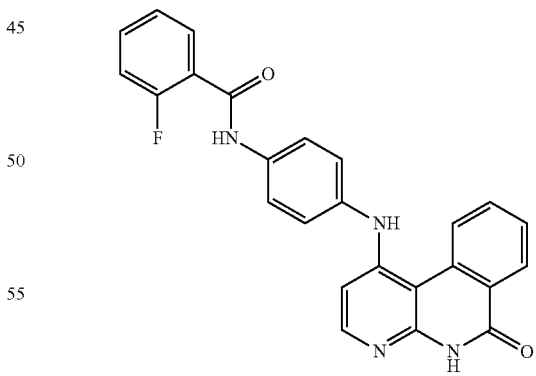

2-Fluoro-N-[4-(6-oxo-5,6-dihydro-benzo[c][1,8]
naphthyridin-1-ylamino)-phenyl]-benzamide (380)

The title compound was synthesized according to the procedure described for the preparation of Example 378, method 1 using 83 and N-(4-aminophenyl)-2-fluoro benzamide to provide 380. LC-MS (M+H=425, obsd.=425). $^1$H NMR (400

MHz, DMSO-d6): δ 6.92(d, 1H), 7.18 (d, 2H), 7.35 (m, 3H), 7.69 (m, 6H), 8.09 (d, 1H), 8.34 (d, 1H), 8.81 (d, 1H), 9.00 (s, 1H), 10.41 (s, 1H).

Example 381

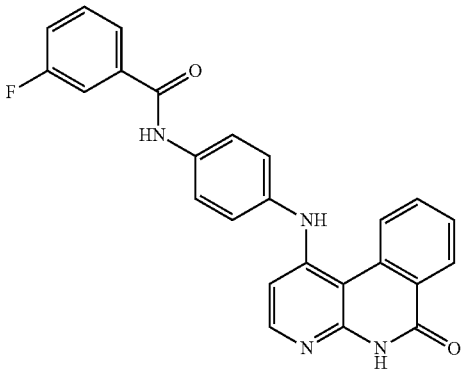 [SMILES: O=C(Nc1ccc(Nc2ccnc3[nH]c(=O)c4ccccc4c23)cc1)c1cccc(F)c1]

3-Fluoro-N-[4-(6-oxo-5,6-dihydro-benzo[c][1,8]naphthyridin-1-ylamino)-phenyl]-benzamide (381)

The title compound was synthesized according to the procedure described for the preparation of Example 378, method 1 using 83 and N-(4-aminophenyl)-3-fluoro benzamide to provide 381. LC-MS (M+H=425, obsd.=425). $^1$H NMR (400 MHz, DMSO-d6): δ 6.93 (d, 1H), 7.27 (d, 2H), 7.43 (m, 1H), 7.58 (m, 2H), 7.78 (m, 5H), 8.09 (d, 1H), 8.34 (d, 1H), 8.82 (d, 1H), 9.20 (s, 1H), 10.42 (s, 1H).

Example 382

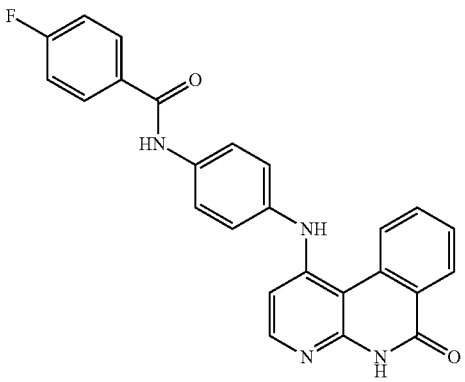 [SMILES: O=C(Nc1ccc(Nc2ccnc3[nH]c(=O)c4ccccc4c23)cc1)c1ccc(F)cc1]

4-Fluoro-N-[4-(6-oxo-5,6-dihydro-benzo[c][1,8]naphthyridin-1-ylamino)-phenyl]-benzamide (382)

The title compound was synthesized according to the procedure described for the preparation of Example 378, method 1 using 83 and N-(4-aminophenyl)-4-fluoro benzamide to provide 382. LC-MS (M+H=425, obsd.=425). $^1$H NMR (400 MHz, DMSO-d6): δ 6.93(d, 1H), 7.23 (d, 2H), 7.38 (m, 2H), 7.58 (m, 1H), 7.78 (m, 3H), 8.09 (m, 3H), 8.30 (d, 1H), 8.82 (d, 1H), 9.23 (s, 1H), 10.30 (s, 1H).

Example 383

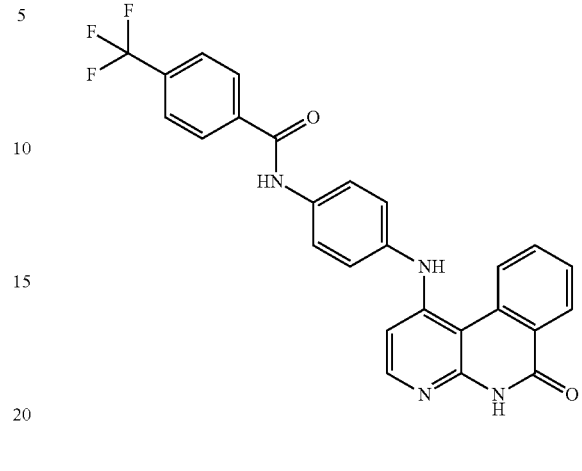

N-[4-(6-Oxo-5,6-dihydro-benzo[c][1,8]naphthyridin-1-ylamino)-phenyl]-2-trifluoromethyl-benzamide (383)

The title compound was synthesized according to the procedure described for the preparation of Example 378, method 1 using 83 and N-(4-amino-phenyl)-4-trifluoromethyl-benzamide to provide 383. LC-MS (M+H=475, obsd.=475). $^1$H NMR (400 MHz, DMSO-d6): δ 6.94(d, 1H), 7.22 (d, 2H), 7.60 (t, 1H), 7.77 (m, 3H), 8.10 (m, 3H), 8.30 (d, 1H), 8.83 (d, 1H), 9.09 (s, 1H), 10.48 (s, 1H).

Example 384

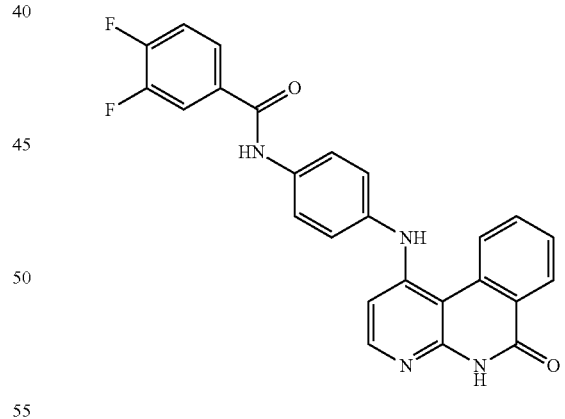

3,4-Difluoro-N-[4-(6-oxo-5,6-dihydro-benzo[c][1,8]naphthyridin-1-ylamino)-phenyl]-benzamide (384)

The title compound was synthesized according to the procedure described for the preparation of Example 378, method 1 using 83 and N-(4-amino-phenyl)-3,4-difluoro-benzamide to provide 384. LC-MS (M+H=443, obsd.=443). $^1$H NMR (400 MHz, DMSO-d6): δ, 6.94 (d, 1H), 7.192 (m, 2H), 7.59 (t, 1H), 7.70 (m, 2H), 8.10 (m, 2H), 8.31 (d, 1H), 8.88 (d, 1H), 8.99 (s, 1H), 10.30 (s, 1H).

Example 385

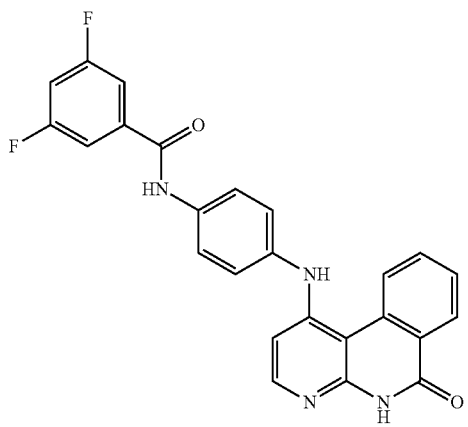 [SMILES: O=C(Nc1ccc(Nc2ccnc3[nH]c(=O)c4ccccc4c23)cc1)c1cc(F)cc(F)c1]

3,5-Difluoro-N-[4-(6-oxo-5,6-dihydro-benzo[c][1,8]
naphthyridin-1-ylamino)-phenyl]-benzamide (385)

The title compound was synthesized according to the procedure described for the preparation of Example 378, method 1 using 83 and N-(4-amino-phenyl)-3,5-difluoro-benzamide to provide 385. LC-MS (M+H=443, obsd.=443). $^1$H NMR (400 MHz, DMSO-d6): δ, 6.96 (d, 1H), 7.17 (m, 2H), 7.70 (m, 2H), 7.73 (m, 4H), 8.12 (m, 1H), 8.30 (d, 1H), 8.84 (d, 1H), 8.96 (s, 1H), 10.35 (s, 1H).

Example 386

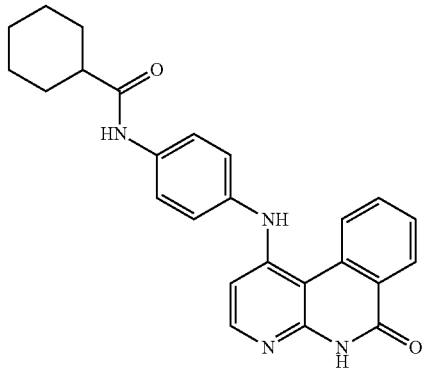 [SMILES: O=C(Nc1ccc(Nc2ccnc3[nH]c(=O)c4ccccc4c23)cc1)C1CCCCC1]

Cyclohexanecarboxylic acid-[4-(6-oxo-5,6-dihydro-benzo[c][1,8]naphthyridin-1-ylamino)-phenyl]-amide (386)

The title compound was synthesized according to the procedure described for the preparation of Example 378, method 1 using 83 and cyclohexane carboxylic acid (4-amino-phenyl)-amide to provide 386. LC-MS (M+H=413, obsd.=413). $^1$H NMR (400 MHz, DMSO-d6): δ, 1.22 (m, 3H), 1.39 (m, 2H), 1.65 (m, 1H), 1.77 (m, 3H), 2.34 (m, 1H), 6.84 (d, 1H), 7.15 (d, 2H), 7.61 (m, 3H), 7.79 (m, 1H), 8.04 (d, 1H), 8.33 (d, 1H), 8.79 (d, 1H), 7.93 (s, 1H), 9.82 (s, 1H).

Example 387

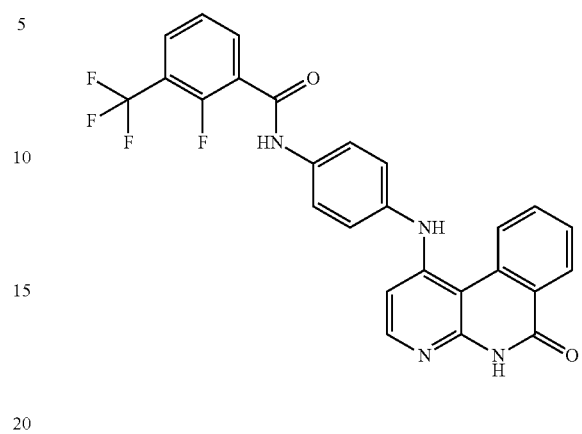

2-Fluoro-N-[4-(6-oxo-5,6-dihydro-benzo[c][1,8]
naphthyridin-1-ylamino)-phenyl]-3-trifluoromethyl-
benzamide (387)

The title compound was synthesized according to the procedure described for the preparation of Example 378, method 1 using 83 and N-(4-amino-phenyl)-2-fluoro-3-trifluoromethyl-benzamide to provide 387. LC-MS (M+H=493, obsd.=493). $^1$H NMR (400 MHz, DMSO-d6): δ 6.95 (d, 1H), 7.17 (m, 2H), 7.60 (m, 2H), 7.66 (m, 3H), 8.02 (m, 2H), 8.11 (s, 1H), 8.30 (d, 1H), 8.84 (d, 1H), 8.97 (s, 1H), 10.61 (s, 1H).

Example 388

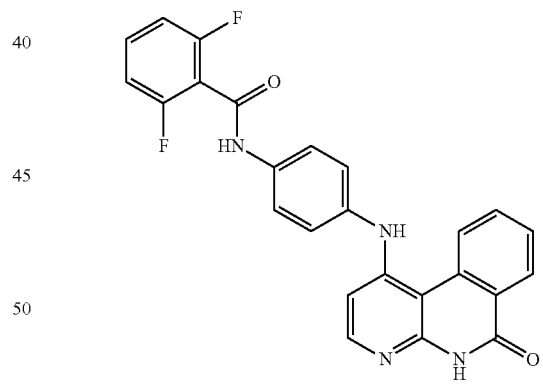

2,6-Difluoro-N-[4-(6-oxo-5,6-dihydro-benzo[c][1,8]
naphthyridin-1-ylamino)-phenyl]-benzamide (388)

The title compound was synthesized according to the procedure described for the preparation of Example 378, method 1 using 83 and N-(4-amino-phenyl)-2,6-difluoro-benzamide to provide 388. LC-MS (M+H=443, obsd.=443). $^1$H NMR (400 MHz, DMSO-d6): δ 6.93 (d, 1H), 7.17 (m, 2H), 7.26 (t, 1H), 7.60 (m, 2H), 7.66 (m, 2H), 7.78 (m, 1H), 8.02 (m, 1H), 8.11 (s, 1H), 8.30 (d, 1H), 8.88 (d, 1H), 9.02 (s, 1H), 10.77 (s, 1H).

Example 389

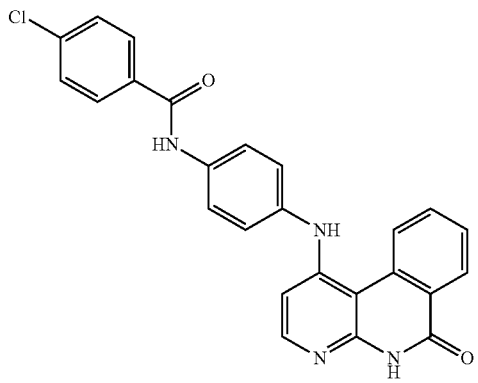 [SMILES: O=C(Nc1ccc(Nc2ccnc3[nH]c(=O)c4ccccc4c23)cc1)c1ccc(Cl)cc1]

4-Chloro-N-[4-(6-oxo-5,6-dihydro-benzo[c][1,8]
naphthyridin-1-ylamino)-phenyl]-benzamide (389)

The title compound was synthesized according to the procedure described for the preparation of Example 378, method 1 using 83 and N-(4-amino-phenyl)-4-chloro-benzamide to provide 389. LC-MS (M+H=441, obsd.=441). $^1$H NMR (400 MHz, DMSO-d6): δ 6.93 (d, 1H), 7.18 (m, 2H), 7.62 (m, 3H), 7.73 (m, 2H), 7.98 (m, 1H), 8.10 (m, 1H), 8.30 (m, 1H), 8.85 (d, 1H), 8.89 (s, 1H), 10.31 (s, 1H).

Example 390

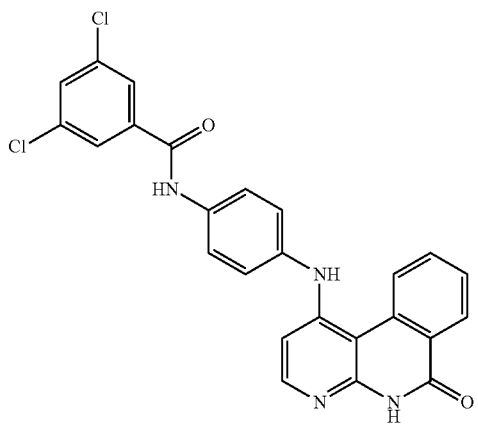 [SMILES: O=C(Nc1ccc(Nc2ccnc3[nH]c(=O)c4ccccc4c23)cc1)c1cc(Cl)cc(Cl)c1]

3,5-Dichloro-N-[4-(6-oxo-5,6-dihydro-benzo[c][1,8]
naphthyridin-1-ylamino)-phenyl]-benzamide (390)

The title compound was synthesized according to the procedure described for the preparation of Example 378, method 1 using 83 and N-(4-amino-phenyl)-3,5-dichloro-benzamide to provide 390. LC-MS (M+H=476, obsd.=476). $^1$H NMR (400 MHz, DMSO-d6): δ 6.95 (d, 1H), 7.24 (m, 2H), 7.62 (m, 1H), 7.74 (m, 2H), 7.88 (s, 1H), 7.99 (m, 2H), 8.11 (s, 1H), 8.36 (m, 1H), 8.88 (d, 1H), 9.23 (s, 1H), 10.46 (s, 1H).

Example 391

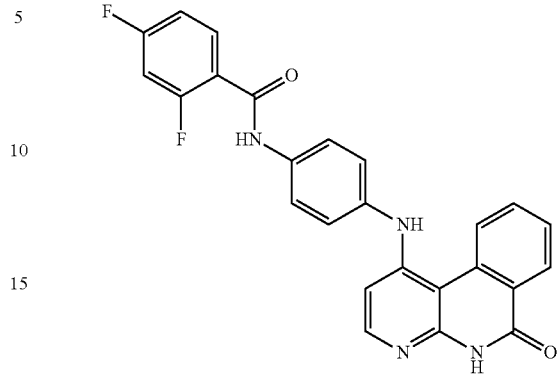

2,4-Difluoro-N-[4-(6-oxo-5,6-dihydro-benzo[c][1,8]
naphthyridin-1-ylamino)-phenyl]-benzamide (391)

The title compound was synthesized according to the procedure described for the preparation of Example 378, method 1 using 83 and N-(4-amino-phenyl)-2,4-fluoro-benzamide to provide 391. LC-MS (M+H=443, obsd.=443). $^1$H NMR (400 MHz, DMSO-d6): δ 6.94 (d, 1H), 7.18 (m, 3H), 7.42 (m, 1H), 7.59 (m, 1H), 7.66 (m, 2H), 7.75 (m, 2H), 8.11 (s, 1H), 8.35 (m, 1H), 8.84 (d, 1H), 8.88 (s, 1H), 10.39 (s, 1H).

Example 392

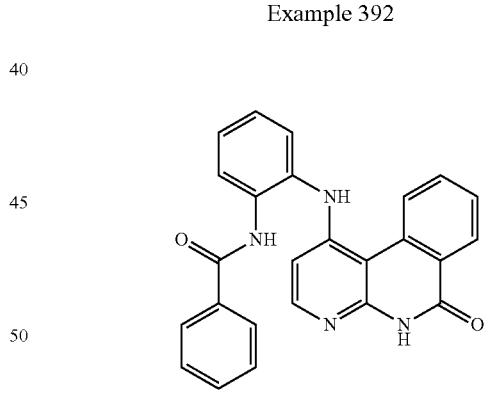

N-[2-(6-Oxo-5,6-dihydro-benzo[c][1,8]naphthyridin-
1-ylamino)-phenyl]-benzamide (392)

The title compound was synthesized according to the procedure described for the preparation of Example 378, method 1 using 83 and N-(2-amino-phenyl)-benzamide to provide 392. LC-MS (M+H=407, obsd.=407). $^1$H NMR (400 MHz, DMSO-d6): δ, 7.03 (d, 1H), 7.23 (m, 2H), 7.57 (m, 4H), 7.82 (m, 2H), 8.11 (s, 1H), 8.35 (m, 1H), 9.00 (d, 1H), 9.84 (s, 1H), 10.51 (s, 1H).

Example 393

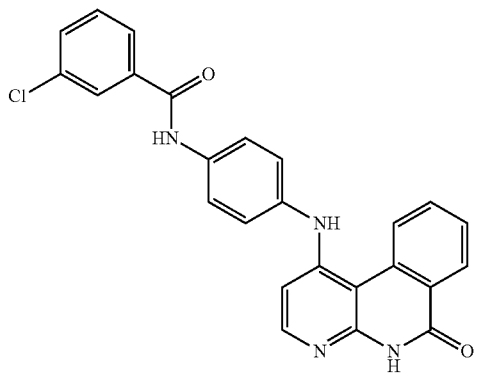 [SMILES: O=C(Nc1ccc(Nc2ccnc3[nH]c(=O)c4ccccc4c23)cc1)c1cccc(Cl)c1]

3-Chloro-N-[4-(6-oxo-5,6-dihydro-benzo[c][1,8]
naphthyridin-1-ylamino)-phenyl]-benzamide (393)

The title compound was synthesized according to the procedure described for the preparation of Example 378, method 1 using 83 and N-(4-Amino-phenyl)-3-chloro-benzamide to provide 393. LC-MS (M+H=441, obsd.=441). $^1$H NMR (400 MHz, DMSO-d6): δ, 6.94 (d, 1H), 7.18 (m, 3H), 7.42 (m, 1H), 7.59 (m, 1H), 7.66 (m, 2H), 7.75 (m, 2H), 8.11 (s, 1H), 8.35 (m, 1H), 8.84 (d, 1H), 8.88 (s, 1H), 10.39 (s, 1H).

Example 394

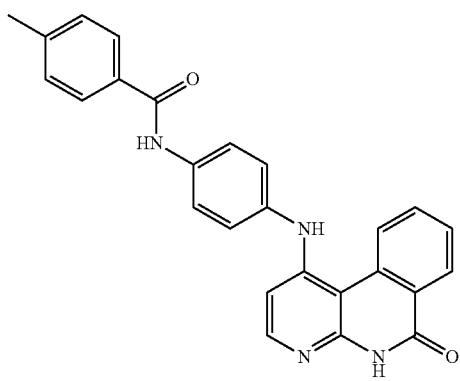 [SMILES: Cc1ccc(C(=O)Nc2ccc(Nc3ccnc4[nH]c(=O)c5ccccc5c34)cc2)cc1]

4-Methyl-N-[4-(6-oxo-5,6-dihydro-benzo[c][1,8]
naphthyridin-1-ylamino)-phenyl]-benzamide (394)

The title compound was synthesized according to the procedure described for the preparation of Example 378, method 1 using 83 and N-(4-Amino-phenyl)-4-methyl-benzamide to provide 394. LC-MS (M+H=421, obsd.=421). $^1$H NMR (400 MHz, DMSO-d6): δ, 2.39 (s, 2H), 6.92 (d, 1H), 7.17 (m, 2H), 7.32 (m, 2H), 7.59 (m, 1H), 7.74 (m, 2H), 7.86 (m, 2H), 8.09 (s, 1H), 8.32 (d, 1H), 8.85 (d, 1H), 10.15 (s, 1H).

Example 395

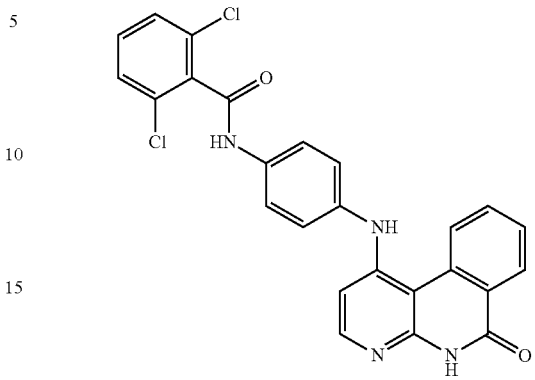

2,6-Dichloro-N-[4-(6-oxo-5,6-dihydro-benzo[c][1,8]
naphthyridin-1-ylamino)-phenyl]-benzamide (395)

The title compound was synthesized according to the procedure described for the preparation of Example 378, method 1 using 83 and N-(4-Amino-phenyl)-2,6-di-chloro-benzamide to provide 395. LC-MS (M+H=476, obsd.=476). $^1$H NMR (400 MHz, DMSO-d6): δ, 6.94 (d, 1H), 7.18 (m, 3H), 7.42 (m, 1H), 7.59 (m, 1H), 7.66 (m, 2H), 7.75 (m, 2H), 8.11 (s, 1H), 8.35 (m, 1H), 8.8630 (d, 1H), 8.89 (s, 1H), 10.71 (s, 1H).

Example 396

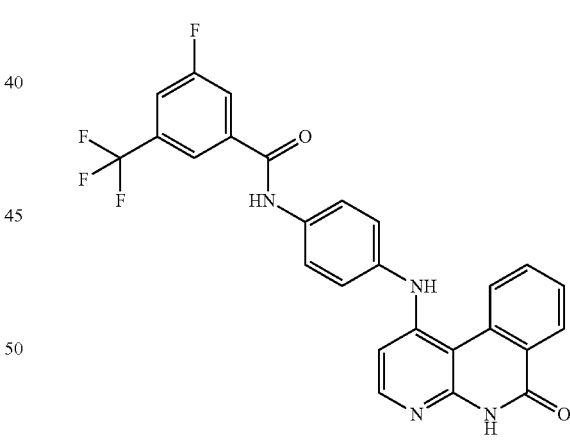

3-Fluoro-N-[4-(6-oxo-5,6-dihydro-benzo[c][1,8]
naphthyridin-1-ylamino)-phenyl]-5-trifluoromethyl-
benzamide (396)

The title compound was synthesized according to the procedure described for the preparation of Example 378, method 1 using 83 and N-(4-amino-phenyl)-3-fluoro-5-trifluoromethyl-benzamide to provide 396. LC-MS (M+H=493, obsd.=493). $^1$H NMR (400 MHz, DMSO-d6): δ, 6.97 (d, 1H), 7.20 (m, 2H), 7.592 (m, 1H), 7.72 (m, 3H), 7.97 (d, 1H), 8.16 (d, 1H), 8.84 (m, 1H), 8.92 (d, 1H), 10.50 (s, 1H).

Example 397

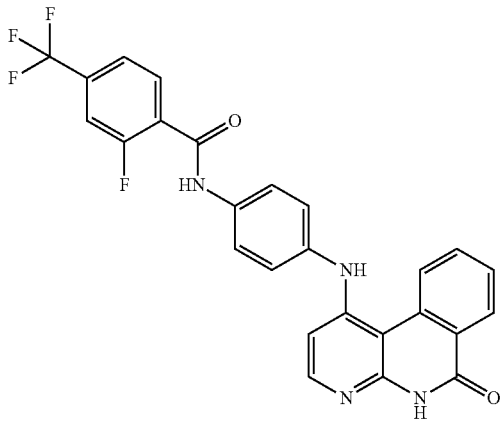 [SMILES: O=C(Nc1ccc(Nc2ccnc3[nH]c(=O)c4ccccc4c23)cc1)c1ccc(C(F)(F)F)cc1F]

2-Fluoro-N-[4-(6-oxo-5,6-dihydro-benzo[c][1,8]
naphthyridin-1-ylamino)-phenyl]-4-trifluoromethyl-
benzamide (397)

The title compound was synthesized according to the procedure described for the preparation of Example 378, method 1 using 83 and N-(4-amino-phenyl)-2-fluoro-4-trifluoromethyl-benzamide to provide 397. LC-MS (M+H=493, obsd.=493). $^1$H NMR (400 MHz, DMSO-d6): δ 6.97 (d, 1H), 7.20 (m, 2H), 7.59 (m, 1H), 7.72 (m, 3H), 7.97 (d, 1H), 8.16 (d, 1H), 8.84 (m, 1H), 8.92 (d, 1H), 10.50 (s, 1H).

Example 398

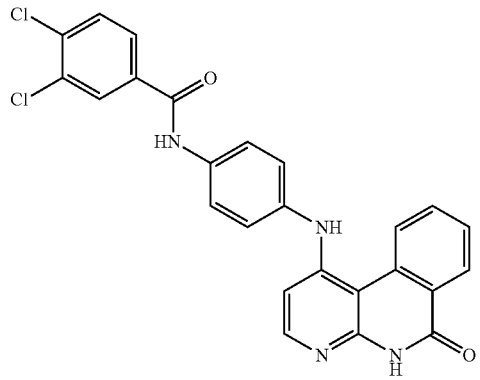 [SMILES: O=C(Nc1ccc(Nc2ccnc3[nH]c(=O)c4ccccc4c23)cc1)c1ccc(Cl)c(Cl)c1]

3,4-Dichloro-N-[4-(6-oxo-5,6-dihydro-benzo[c][1,8]
naphthyridin-1-ylamino)-phenyl]-benzamide (398)

The title compound was synthesized according to the procedure described for the preparation of Example 378, method 1 using 83 and N-(4-amino-phenyl)-3,4-di-chloro-benzamide to provide 398. LC-MS (M+H=476, obsd.=476). $^1$H NMR (400 MHz, DMSO-d6): δ 6.94 (d, 1H), 7.18 (m, 3H), 7.42 (m, 1H), 7.59 (m, 1H), 7.66 (m, 2H), 7.75 (m, 2H), 8.11 (s, 1H), 8.3543 (m, 1H), 8.86 (d, 1H), 8.89 (s, 1H), 10.71 (s, 1H).

Example 399

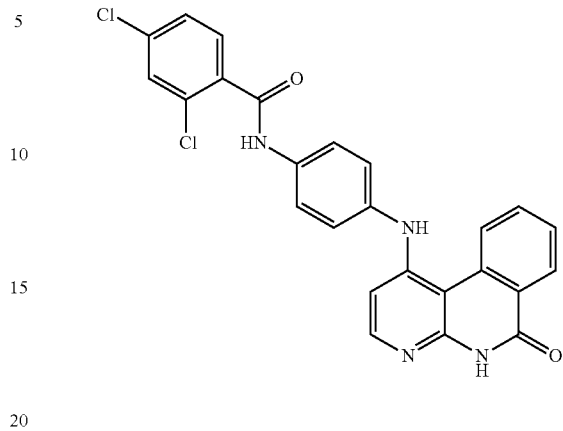

2,4-Dichloro-N-[4-(6-oxo-5,6-dihydro-benzo[c][1,8]
naphthyridin-1-ylamino)-phenyl]-benzamide (399)

The title compound was synthesized according to the procedure described for the preparation of Example 378, method 1 using 83 and N-(4-amino-phenyl)-2,4-di-chloro-benzamide to provide 399. LC-MS (M+H=476, obsd.=476). $^1$H NMR (400 MHz, DMSO-d6): δ 6.94 (d, 1H), 7.18 (m, 3H), 7.42 (m, 1H), 7.59 (m, 1H), 7.66 (m, 2H), 7.75 (m, 2H), 8.11 (s, 1H), 8.35 (m, 1H), 8.86 (d, 1H), 8.89 (s, 1H), 10.71 (s, 1H).

Example 400

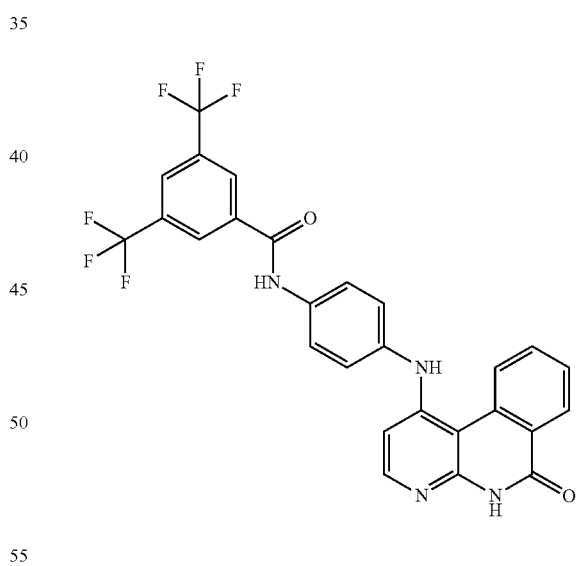

N-[4-(6-Oxo-5,6-dihydro-benzo[c][1,8]naphthyridin-
1-ylamino)-phenyl]-3,5-bis-trifluoromethyl-benza-
mide (400)

The title compound was synthesized according to the procedure described for the preparation of Example 378, method 1 using 83 and N-(4-amino-phenyl)-3,5-trifluoromethyl-benzamide to provide 400. LC-MS (M+H=543, obsd.=543). $^1$H NMR (400 MHz, DMSO-d6): δ 6.98 (d, 1H), 7.20 (m, 3H), 7.42 (m, 1H), 7.73 (m, 2H), 8.13 (d, 1H), 8.18 (m, 1H), 8.38 (s, 1H), 8.61 (s, 1H), 8.82 (d, 1H), 8.92 (s, 1H), 10.64 (s, 1H).

Example 401

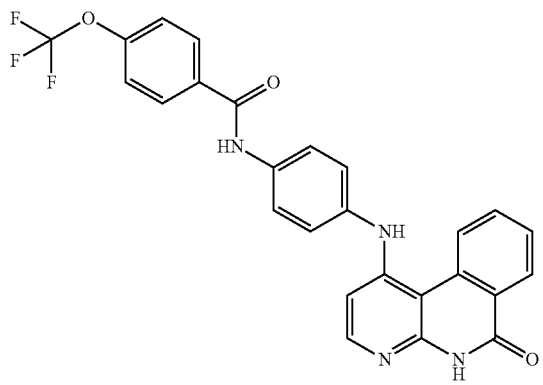 [SMILES: O=C(Nc1ccc(Nc2ccnc3[nH]c(=O)c4ccccc4c23)cc1)c1ccc(OC(F)(F)F)cc1]

N-[4-(6-Oxo-5,6-dihydro-benzo[c][1,8]naphthyridin-1-ylamino)-phenyl]-4-trifluoromethoxy-benzamide (401)

The title compound was synthesized according to the procedure described for the preparation of Example 378, method 1 using 83 and N-(4-amino-phenyl)-4-trifluoromethoxy-benzamide to provide 401. LC-MS (M+H=491, obsd.=491). $^1$H NMR (400 MHz, DMSO-d6): δ, 6.98 (d, 1H), 7.20 (m, 3H), 7.42 (m, 1H), 7.73 (m, 2H), 8.13 (d, 1H), 8.18 (m, 1H), 8.38 (s, 1H), 8.61 (s, 1H), 8.82 (d, 1H), 8.92 (s, 1H), 10.64 (s, 1H).

Example 402

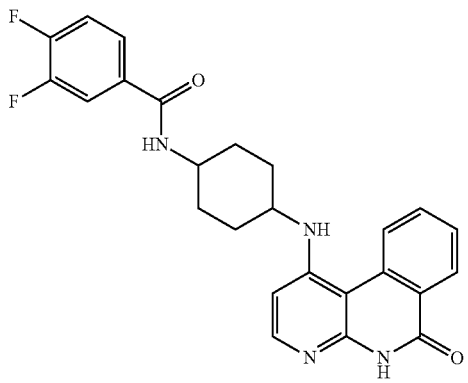 [SMILES: O=C(NC1CCC(Nc2ccnc3[nH]c(=O)c4ccccc4c23)CC1)c1ccc(F)c(F)c1]

3,4-Difluoro-N-[4-(6-oxo-5,6-dihydro-benzo[c][1,8]naphthyridin-1-ylamino)-cyclohexy]-benzamide (402)

The title compound was synthesized according to the procedure described for the preparation of Example 378, method 1 using 83 and N-(4-amino-cyclohexyl)-3,4-difluoro-benzamide to provide 402. LC-MS (M+H=449, obsd.=449). $^1$H NMR (400 MHz, DMSO-d6): δ, 1.54 (m, 4H), 1.93 (m, 2H), 2.12 (m, 2H), 6.98 (d, 1H), 7.73 (m, 2H), 8.13 (d, 1H), 8.18 (m, 1H), 8.38 (s, 1H), 8.61 (s, 1H), 8.82 (d, 1H), 8.92 (s, 1H), 10.64 (s, 1H).

Example 403

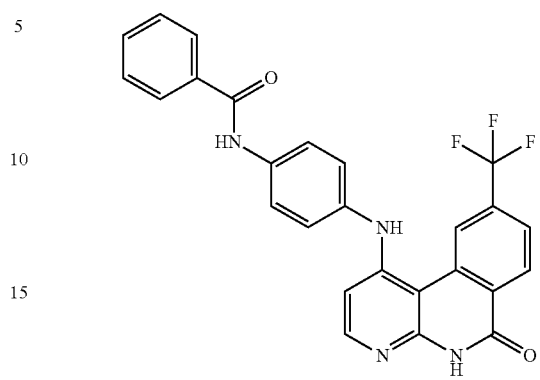

N-[4-(9-Trifluoromethyl-6-oxo-5,6-dihydro-benzo[c][1,8]naphthyridin-1-ylamino)-phenyl]-benzamide (403)

The title compound was synthesized according to the procedure described for the preparation of Example 378, method 2 using 1-chloro-9-trifluoromethyl-5H-benzo[c][1,8]naphthyridin-6-one and N-(4-amino-phenyl)-benzamide to provide 403. LC-MS (M+H=475, obsd.=475). $^1$H NMR (400 MHz, DMSO-d6): δ 6.96 (d, 1H), 7.18 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 8.99 (s, 1H), 10.25 (s, 1H).

Example 404

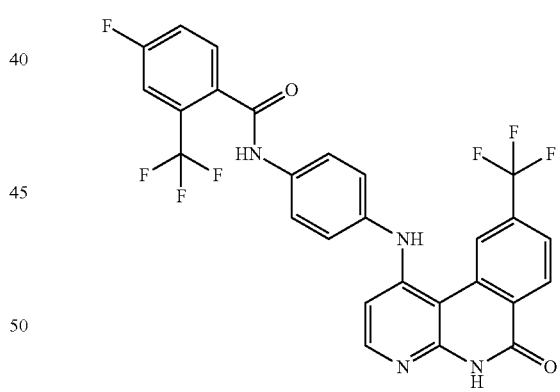

4-Fluoro-N-[4-(9-trifluoromethyl-6-oxo-5,6-dihydro-benzo[c][1,8]naphthyridin-1-ylamino)-phenyl]-2-trifluoromethyl-benzamide (404)

The title compound was synthesized according to the procedure described for the preparation of Example 378, method 2 using 1-chloro-9-trifluoromethyl-5H-benzo[c][1,8]naphthyridin-6-one and N-(4-amino-phenyl)-4-fluoro-2-trifluoromethyl-benzamide to provide 404. LC-MS (M+H=561, obsd.=561). $^1$H NMR (400 MHz, DMSO-d6): δ, 6.96 (d, 1H), 7.18 (d, 2H), 7.54 (m, 2H), 7.76 (m, 2H), 7.78 (d, 1H), 7.97 (d, 1H), 8.10 (d, 1H), 8.27 (s, 1H), 8.99 (s, 1H), 10.25 (s, 1H).

Example 405

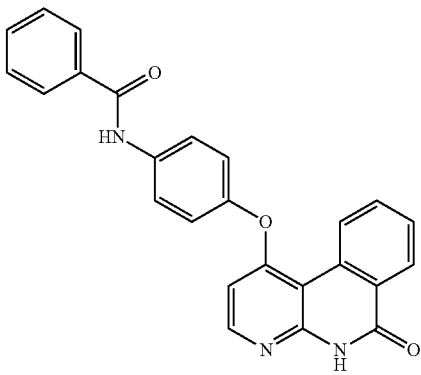 [SMILES: O=C(Nc1ccc(Oc2ccnc3[nH]c(=O)c4ccccc4c23)cc1)c1ccccc1]

N-[4-(6-Oxo-5,6-dihydro-benzo[c][1,8]naphthyridin-1-yloxy)-phenyl]-benzamide (405)

The title compound was synthesized according to the procedure described for the preparation of Example 378, method 1 using 83 and N-(4-hydroxy-phenyl)-benzamide to provide 405. LC-MS (M+H=408, obsd.=408). $^1$H NMR (400 MHz, DMSO-d6): δ, 6.94 (d, 1H), 7.19 (m, 2H), 7.59 (m, 2H), 7.70 (m, 2H), 8.10 (m, 2H), 8.31 (d, 1H), 8.88 (d, 1H), 8.99 (s, 1H), 10.30 (s, 1H).

Example 406

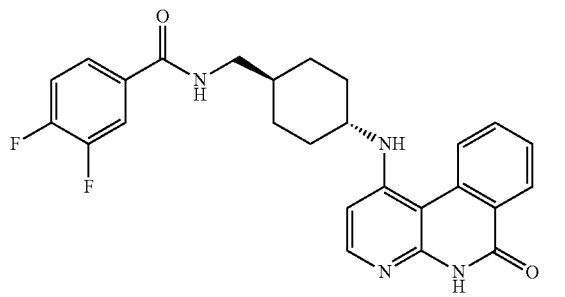 [SMILES: O=C(NC[C@H]1CC[C@H](Nc2ccnc3[nH]c(=O)c4ccccc4c23)CC1)c1ccc(F)c(F)c1]

3,4-Difluoro-N-[4-(6-oxo-5,6-dihydro-benzo[c][1,8]naphthyridin-1-ylamino)-cyclohexylmethyl]-benzamide (406)

The title compound was synthesized according to the procedure described for the preparation of Example 378, method 2 using 83 and N-(4-amino-cyclohexylmethyl)-3,4-difluoro-benzamide to provide 406. LC-MS (M+H=463, obsd.=463). $^1$H NMR (400 MHz, DMSO-d6): δ, 2.31 (m, 4H), 2.50 (m, 4H), 2.74 (m, 2H), 7.59 (m, 2H), 7.70 (m, 2H), 8.10 (m, 2H), 8.33 (d, 1H), 8.88 (d, 1H), 8.99 (s, 1H), 10.30 (s, 1H).

Example 407

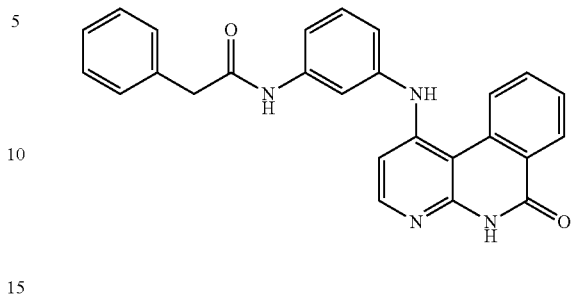

N-[3-(6-Oxo-5,6-dihydro-benzo[c][1,8]naphthyridin-1-ylamino)-phenyl]-2-phenyl-acetamide (407)

The title compound was synthesized according to the procedure described for the preparation of Example 378, method 2 using 83 and N-(3-amino-phenyl)-2-phenyl-acetamide to provide 407. LC-MS (M+H=421, obsd.=421). $^1$H NMR (400 MHz, DMSO-d6): δ 3.54 (s, 2H), 6.94 (d, 1H), 7.19 (m, 2H), 7.59 (m, 2H), 7.70 (m, 2H), 8.10 (m, 2H), 8.31 (d, 1H), 8.88 (d, 1H), 8.99 (s, 1H), 10.30 (s, 1H).

Example 408

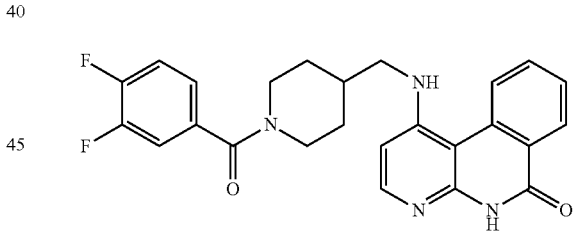

1-{[1-(3,4-Difluoro-benzoyl)-piperidin-4-ylmethyl]-amino}-5H-benzo[c][1,8]naphthyridin-6-one (408)

The title compound was synthesized according to the procedure described for the preparation of Example 378, method 2 using 83 and (4-aminomethyl-piperidin-1-yl)-(3,4-difluoro-phenyl)-methanone to provide 408. LC-MS (M+H=449, obsd.=449). $^1$H NMR (400 MHz, DMSO-d6): 1.58 (m, 5H), 1.85 (m, 4H), 2.65 (m, 2H), 6.94 (d, 1H), 7.19 (m, 2H), 7.59 (m, 2H), 7.70 (m, 2H), 8.10 (m, 2H), 8.31 (d, 1H), 8.88 (d, 1H), 8.99 (s, 1H), 10.30 (s, 1H).

Example 409

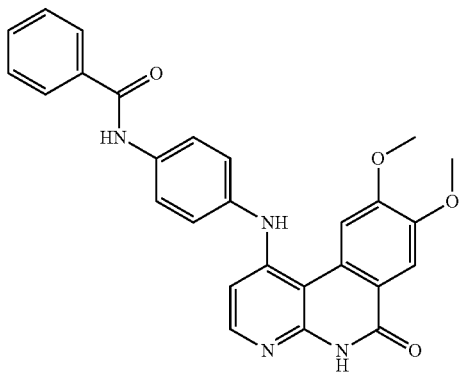 [SMILES: COc1cc2c(=O)[nH]c3nccc(Nc4ccc(NC(=O)c5ccccc5)cc4)c3c2cc1OC]

N-[4-(8,9-Dimethoxy-6-oxo-5,6-dihydro-benzo[c][1, 8]naphthyridin-1-ylamino)-phenyl]-benzamide (409)

The title compound was synthesized according to the procedure described for the preparation of Example 378, method 2 using 211 and N-(4-amino-phenyl)-benzamide to provide 404. LC-MS (M+H=467, obsd.=467). $^1$H NMR (400 MHz, DMSO-d6): δ 3.70 (s, 3H), 3.90 (s, 3H), 7.02 (m, 4H), 7.59 (m, 2H), 7.70 (m, 2H), 8.10 (m, 2H), 8.31 (d, 1H), 8.88 (d, 1H), 8.93 (s, 1H), 10.19 (s, 1H).

Example 410

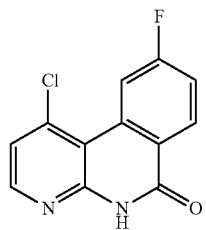 [SMILES: O=c1[nH]c2nccc(Cl)c2c2cc(F)ccc12]

1-Chloro-9-fluoro-5H-benzo[c][1,8]naphthyridin-6-one (410)

The title compound was synthesized according to the procedure described for the preparation of Example 1 using 4-chloro-3-iodopyridin-2-amine (1.20 g, 4.72 mmol) and 5-fluoro-2-methoxycarbonylphenylboronic acid (1.03 g, 5.19 mmol) to provide 410 (250 mg, 21% yield) as a solid. LC-MS (M+H=249, obsd.=249).

Example 411

1-Chloro-8-fluoro-5H-benzo[c][1,8]naphthyridin-6-one (411)

The title compound was synthesized according to the procedure described for the preparation of Example 1 using 4-chloro-3-iodopyridin-2-amine (1.20 g, 4.72 mmol) and 4-fluoro-2-methoxycarbonylphenylboronic acid (1.03 g, 5.19 mmol) to provide 411 (250 mg, 21% yield) as a solid. LC-MS (M+H=249, obsd.=249).

Example 412

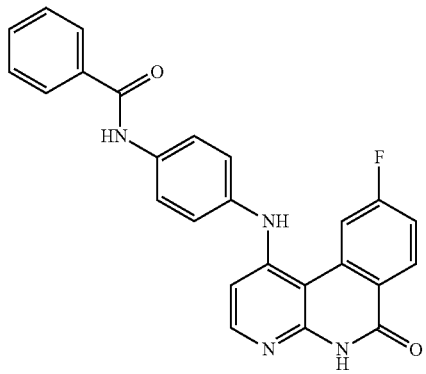 [SMILES: O=C(Nc1ccc(Nc2ccnc3[nH]c(=O)c4ccc(F)cc4c23)cc1)c1ccccc1]

N-[4-(9-Fluoro-6-oxo-5,6-dihydro-benzo[c][1,8] naphthyridin-1-ylamino)-phenyl]-benzamide (412)

The title compound was synthesized according to the procedure described for the preparation of Example 378, method 2 using 410 and N-(4-amino-phenyl)-benzamide to provide 412. LC-MS (M+H=425, obsd.=425). $^1$H NMR (400 MHz, DMSO-d6): δ 6.96 (d, 1H), 7.18 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 8.99 (s, 1H), 10.25 (s, 1H).

Example 413

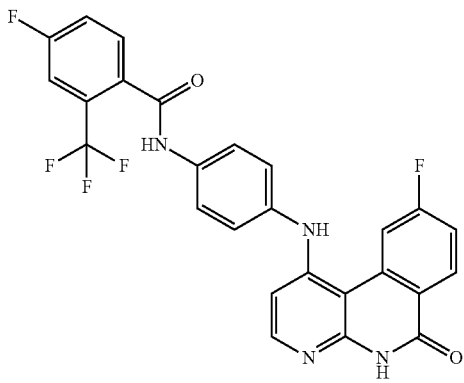 [SMILES: O=C(Nc1ccc(Nc2ccnc3[nH]c(=O)c4ccc(F)cc4c23)cc1)c1ccc(F)cc1C(F)(F)F]

4-Fluoro-N-[4-(9-fluoro-6-oxo-5,6-dihydro-benzo[c]
[1,8]naphthyridin-1-ylamino)-phenyl]-2-trifluorom-
ethyl-benzamide (413)

The title compound was synthesized according to the procedure described for the preparation of Example 378, method 2 using 410 and N-(4-amino-phenyl)-4-fluoro-2-trifluoro-methyl-benzamide to provide 413. LC-MS (M+H=511, obsd.=511). $^1$H NMR (400 MHz, DMSO-d6): δ, 6.96 (d, 1H), 7.18 (d, 2H), 7.54 (m, 2H), 7.76 (m, 2H), 7.78 (d, 1H), 7.97 (d, 1H), 8.10 (d, 1H), 8.27 (s, 1H), 8.99 (s, 1H), 10.25 (s, 1H).

Example 414

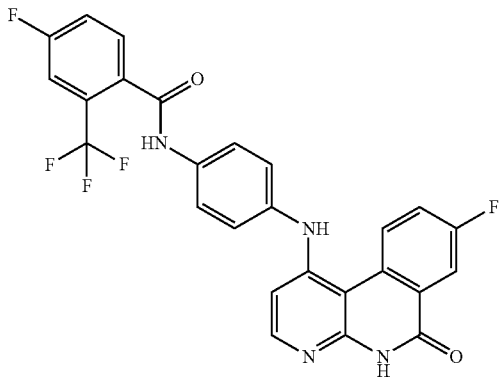 [SMILES: O=C(Nc1ccc(Nc2ccnc3[nH]c(=O)c4cc(F)ccc4c23)cc1)c1ccc(F)cc1C(F)(F)F]

4-Fluoro-N-[4-(8-fluoro-6-oxo-5,6-dihydro-benzo[c]
[1,8]naphthyridin-1-ylamino)-phenyl]-2-trifluorom-
ethyl-benzamide (414)

The title compound was synthesized according to the procedure described for the preparation of Example 378, method 2 using 411 and N-(4-amino-phenyl)-4-fluoro-2-trifluoro-methyl-benzamide to provide 414. LC-MS (M+H=511, obsd.=511). $^1$H NMR (400 MHz, DMSO-d6): δ, 6.96 (d, 1H), 7.18 (d, 2H), 7.54 (m, 2H), 7.76 (m, 2H), 7.78 (d, 1H), 7.97 (d, 1H), 8.10 (d, 1H), 8.27 (s, 1H), 8.99 (s, 1H), 10.25 (s, 1H).

Example 415

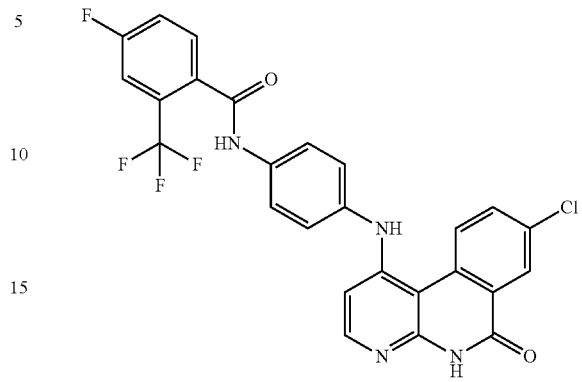

4-Fluoro-N-[4-(8-chloro-6-oxo-5,6-dihydro-benzo[c]
[1,8]naphthyridin-1-ylamino)-phenyl]-2-trifluorom-
ethyl-benzamide (415)

The title compound was synthesized according to the procedure described for the preparation of Example 378, method 2 using 1,8-di-chloro-5H-benzo[c][1,8]naphthyridin-6-one and N-(4-amino-phenyl)-4-fluoro-2-trifluoro-methyl-benzamide to provide 415. LC-MS (M+H=527, obsd.=527). $^1$H NMR (400 MHz, DMSO-d6): δ, 6.96 (d, 1H), 7.18 (d, 2H), 7.66 (m, 3H), 7.78 (m, 3H), 8.10 (d, 1H), 8.27 (s, 1H), 8.87 (d, 1H), 8.93 (s, 1H), 10.56 (s, 1H).

Example 416

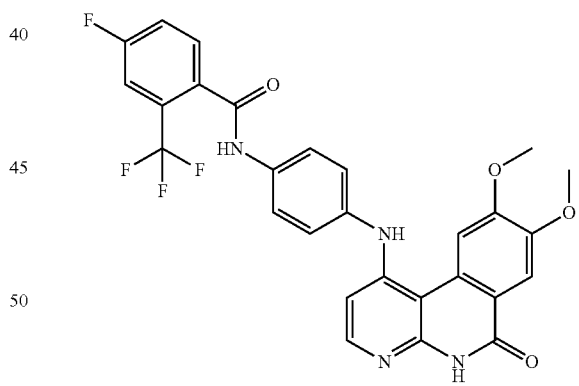

4-Fluoro-N-[4-(8,9-dimethoxy-6-oxo-5,6-dihydro-
benzo[c][1,8]naphthyridin-1-ylamino)-phenyl]-2-
trifluoromethyl-benzamide (416)

The title compound was synthesized according to the procedure described for the preparation of Example 378, method 2 using 211 and N-(4-Amino-phenyl)-4-fluoro-2-trifluoromethyl-benzamide to provide 416. LC-MS (M+H=553, obsd.=553). $^1$H NMR (400 MHz, DMSO-d6): δ, 3.71 (s, 3H), 3.90 (s, 3H), 6.96 (d, 1H), 7.18 (d, 2H), 7.66 (m, 2H), 7.78 (m, 3H), 8.10 (d, 1H), 8.27 (s, 1H), 8.97 (s, 1H), 10.56 (s, 1H).

Example 417

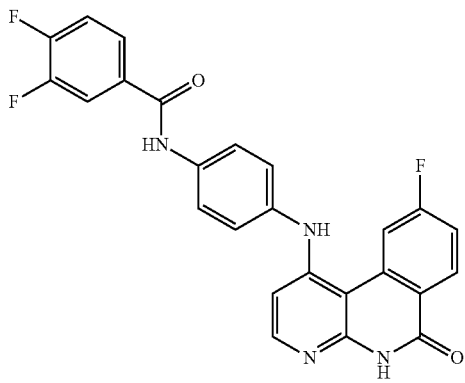 [SMILES: O=C(Nc1ccc(Nc2ccnc3[nH]c(=O)c4ccc(F)cc4c23)cc1)c1ccc(F)c(F)c1]

3,4-Difluoro-N-[4-(9-fluoro-6-oxo-5,6-dihydro-benzo[c][1,8]naphthyridin-1-ylamino)-phenyl]-benzamide (417)

The title compound was synthesized according to the procedure described for the preparation of Example 378, method 2 using 410 and N-(4-amino-phenyl)-3,4-difluoro-benzamide to provide 417. LC-MS (M+H=461, obsd.=461). $^1$H NMR (400 MHz, DMSO-d6): δ, 6.92 (d, 1H), 7.16 (d, 2H), 7.46 (m, 1H), 7.63 (m, 1H), 7.71 (m, 2H), 7.85 (m, 1H), 8.04 (m, 1H), 8.14 (d, 1H), 8.37 (s, 1H), 8.56 (d, 1H), 8.95 (s, 1H), 10.31 (s, 1H).

Example 418

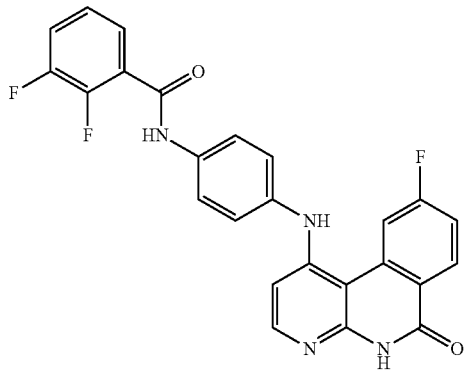 [SMILES: O=C(Nc1ccc(Nc2ccnc3[nH]c(=O)c4ccc(F)cc4c23)cc1)c1cccc(F)c1F]

2,3-Difluoro-N-[4-(9-fluoro-6-oxo-5,6-dihydro-benzo[c][1,8]naphthyridin-1-ylamino)-phenyl]-benzamide (418)

The title compound was synthesized according to the procedure described for the preparation of Example 378, method 2 using 410 and N-(4-amino-phenyl)-2,3-difluoro-benzamide to provide 418. LC-MS (M+H=461, obsd.=461). $^1$H NMR (400 MHz, DMSO-d6): δ 6.91 (d, 1H), 7.16 (d, 2H), 7.32 (m, 1H), 7.46 (m, 2H), 7.67 (m, 3H), 8.14 (d, 1H), 8.39 (m, 1H), 8.52 (d, 1H), 8.96 (s, 1H), 10.54 (s, 1H).

Example 419

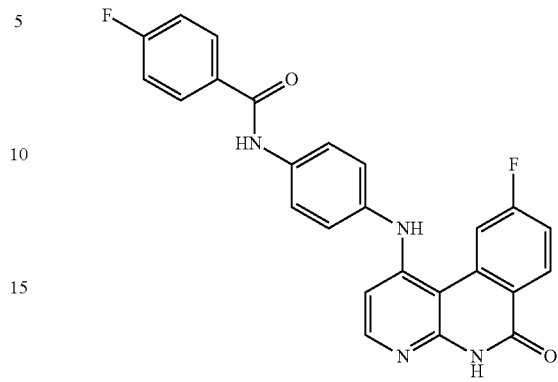

4-Fluoro-N-[4-(9-fluoro-6-oxo-5,6-dihydro-benzo[c][1,8]naphthyridin-1-ylamino)-phenyl]-benzamide (419)

The title compound was synthesized according to the procedure described for the preparation of Example 378, method 2 using 410 and N-(4-amino-phenyl)-4-fluoro-benzamide to provide 419. LC-MS (M+H=443, obsd.=443). $^1$H NMR (400 MHz, DMSO-d6): δ, 6.90 (d, 1H), 7.15 (d, 2H), 7.35 (m, 2H), 7.44 (m, 1H), 7.72 (d, 2H), 8.04 (m, 2H), 8.14 (d, 1H), 8.34 (m, 1H), 8.51 (d, 1H), 8.93 (s, 1H), 10.27 (s, 1H).

Example 420

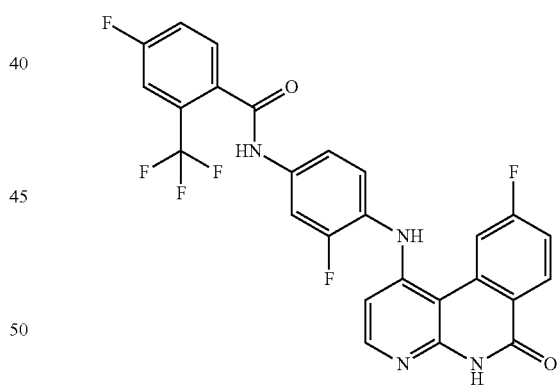

4-Fluoro-N-[3-fluoro-4-(9-fluoro-6-oxo-5,6-dihydro-benzo[c][1,8]naphthyridin-1-ylamino)-phenyl]-2-trifluoromethyl-benzamide (420)

The title compound was synthesized according to the procedure described for the preparation of Example 378, method 2 using 410 and N-(4-amino-3-fluoro-phenyl)-4-fluoro-2-trifluoromethyl-benzamide to provide 420. LC-MS (M+H=529, obsd.=529). $^1$H NMR (400 MHz, DMSO-d6): δ, 6.53 (d, 1H), 7.23 (m, 1H), 7.39 (m, 1H), 7.49 (m, 1H), 7.68 (m, 1H), 7.85 (m, 1H), 8.11 (d, 1H), 8.42 (m, 1H), 8.53 (m, 1H), 8.88 (s, 1H), 10.82 (s, 1H).

Example 421

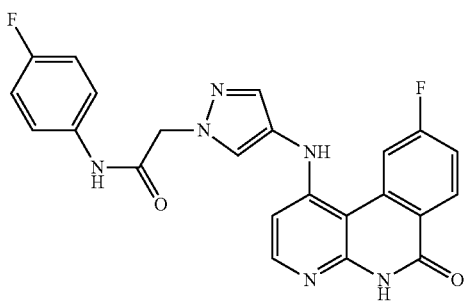 [SMILES: O=C(Cn1cc(Nc2ccnc3[nH]c(=O)c4ccc(F)cc4c23)cn1)Nc1ccc(F)cc1]

9-Fluoro-1-{1-[(2-(4-fluoro-phenyl)-2-oxo-ethyl]-1H-pyrazol-4-ylamino}-5H-benzo[c][1,8]naphthyridin-6-one (421)

The title compound was synthesized according to the procedure described for the preparation of Example 378, method 2 using 410 and 2-(4-amino-pyrazol-1-yl)-N-(4-fluoro-phenyl)-acetamide to provide 421. LC-MS (M+H=447, obsd.=447). ¹H NMR (400 MHz, DMSO-d6): δ, 5.03 (s, 2H), 6.70 (m, 1H), 7.18 (m, 3H), 7.48 (m, 4H), 7.83 (s, 1H), 8.04 (m, 1H), 8.39 (m, 1H), 8.42 (d, 1H), 8.61 (s, 1H), 10.41 (s, 1H)

Example 422

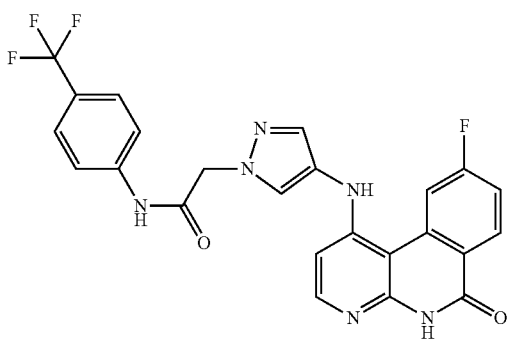 [SMILES: O=C(Cn1cc(Nc2ccnc3[nH]c(=O)c4ccc(F)cc4c23)cn1)Nc1ccc(C(F)(F)F)cc1]

9-Fluoro-1-{1-[(2-(4-trifluoromethyl-phenyl)-2-oxo-ethyl]-1H-pyrazol-4-ylamino}-5H-benzo[c][1,8]naphthyridin-6-one (422)

The title compound was synthesized according to the procedure described for the preparation of Example 378, method 2 using 410 and 2-(4-amino-pyrazol-1-yl)-N-(4-trifluoromethyl-phenyl)-acetamide to provide 422. LC-MS (M+H=497, obsd.=497). ¹H NMR (400 MHz, DMSO-d6): 5.09 (s, 2H), 6.70 (m, 1H), 7.19 (m, 3H), 7.52 (m, 1H), 7.59 (m, 4H), 7.84 (m, 1H), 8.04 (m, 1H), 8.38 (m, 1H), 8.61 (s, 1H), 8.59 (s, 1H), 10.72 (s, 1H), 11.80 (s, 1H)

Example 423

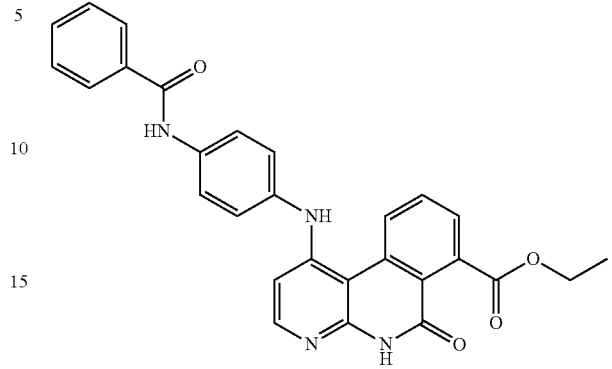

1-[4-Benzoylamino-phenylamino)-6-oxo-5,6-dihydro-benzo[c][1,8]naphthyridin-7-carboxylic acid ethyl ester (423)

The title compound was synthesized according to the procedure described for the preparation of Example 378, method 2 using 1-chloro-6-oxo-5,6-dihydro-benzo[c][1,8]naphthyridine-7-carboxylic acid methyl ester and N-(4-amino-phenyl)-benzamide to provide 423. LC-MS (M+H=479, obsd.=479). ¹H NMR (400 MHz, DMSO-d6): δ, 1.31 (t, 3H), 4.32 (q, 2H), 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 424

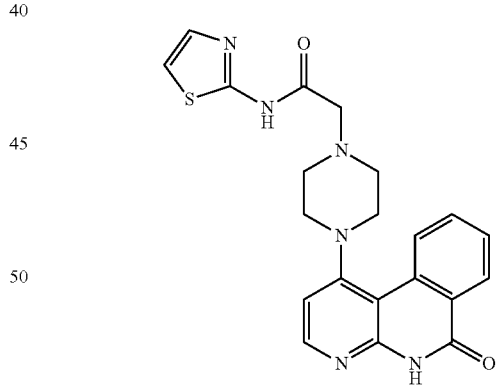

2-[4-(6-Oxo-5,6-dihydro-benzo[c][1,8]naphthyridin-1-yl)-piperazin-1-yl]-n-thiazol-2-yl-acetamide (424)

The title compound was synthesized according to the procedure described for the preparation of Example 378, method 2 using 83 and 2-piperazin-1-yl-N-thiazol-2-yl-acetamide to provide 424. LC-MS (M+H=421, obsd.=421). ¹H NMR (400 MHz, DMSO-d6): δ, 2.65 (m, 4H), 2.98 (m, 4H), 3.21 (s, 2H), 7.05 (d, 2H), 7.34 (m, 1H), 7.55 (m, 3H), 7.89 (m, 2H), 8.35 (m, 3H), 9.17 (s, 1H)

Example 425

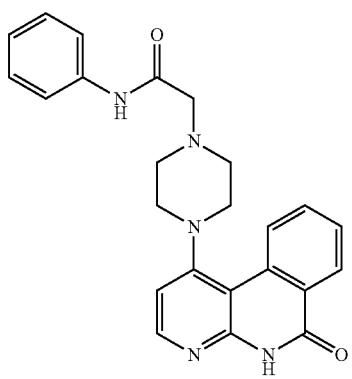 [SMILES: O=C(CN1CCN(c2ccnc3[nH]c(=O)c4ccccc4c23)CC1)Nc1ccccc1]

2-[4-(6-Oxo-5,6-dihydro-benzo[c][1,8]naphthyridin-1-yl)-piperazin-1-yl]-n-phenyl-acetamide (425)

The title compound was synthesized according to the procedure described for the preparation of Example 378, method 2 using 83 and N-phenyl-2-piperazin-1-yl-acetamide to provide 425. LC-MS (M+H=414, obsd.=414). $^1$H NMR (400 MHz, DMSO-d6): δ, 2.65 (m, 4H), 2.98 (m, 4H), 3.21 (s, 2H), 7.06 (d, 2H), 7.34 (m, 2H), 7.55 (m, 4H), 7.86 (m, 1H), 8.35 (m, 3H), 9.17 (s, 1H)

Example 426

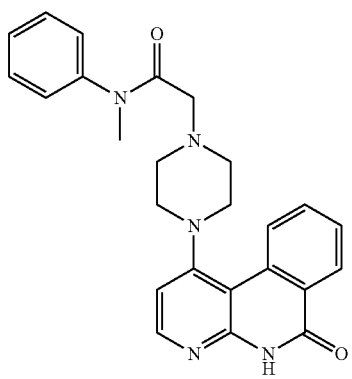 [SMILES: CN(C(=O)CN1CCN(c2ccnc3[nH]c(=O)c4ccccc4c23)CC1)c1ccccc1]

N-Methyl-2-[4-(6-oxo-5,6-dihydro-benzo[c][1,8]naphthyridin-1-yl)-piperazin-1-yl]-n-phenyl-acetamide (426)

The title compound was synthesized according to the procedure described for the preparation of Example 378, method 2 using 83 and N-methyl-N-phenyl-2-piperazin-1-yl-acetamide to provide 426. LC-MS (M+H=428, obsd.=428). $^1$H NMR (400 MHz, DMSO-d6): δ, 2.68 (m, 4H), 2.98 (m, 4H), 3.21 (s, 2H), 4.08 (s, 3H), 7.06 (d, 2H), 7.34 (m, 2H), 7.55 (m, 4H), 7.86 (m, 1H), 8.35 (m, 3H), 9.17 (s, 1H)

Example 427

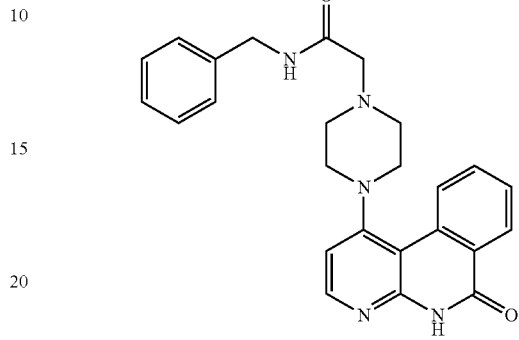

N-Benzyl-2-[4-(6-oxo-5,6-dihydro-benzo[c][1,8]naphthyridin-1-yl)-piperazin-1-yl]-acetamide (427)

The title compound was synthesized according to the procedure described for the preparation of Example 378, method 2 using 83 and N-benzyl-2-piperazin-1-yl-acetamide to provide 427. LC-MS (M+H=427, obsd.=427). $^1$H NMR (400 MHz, DMSO-d6): δ, 2.65 (m, 4H), 2.98 (m, 4H), 3.43 (s, 2H), 7.06 (d, 2H), 7.34 (m, 2H), 7.55 (m, 4H), 7.86 (m, 1H), 8.35 (m, 3H), 9.17 (s, 1H)

Example 428

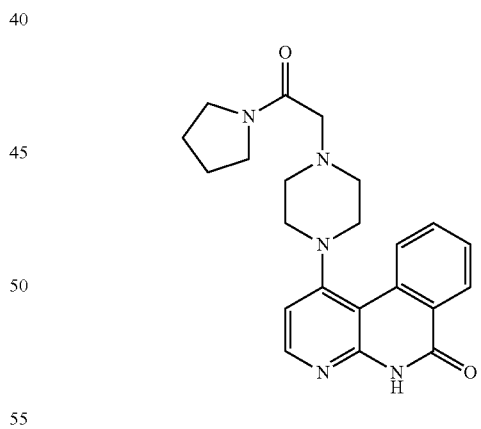

1-[4-(2-oxo-2-pyrrolidin-1-yl-ethyl)-piperazin-1-yl]-5H-benzo[c][1,8]naphthyridin-6-one (428)

The title compound was synthesized according to the procedure described for the preparation of Example 378, method 2 using 83 and 2-piperazin-1-yl-1-pyrrolidin-1-yl-ethanone to provide 428. LC-MS (M+H=392, obsd.=392). $^1$H NMR (400 MHz, DMSO-d6): δ 1.81 (m, 4H), 1.83 (m, 4H), 2.65 (m, 4H), 2.98 (m, 4H), 4.34 (s, 2H), 7.06 (d, 1H), 7.68 (m, 1H), 7.86 (m, 1H), 8.35 (m, 2H), 9.17 (s, 1H)

Example 429

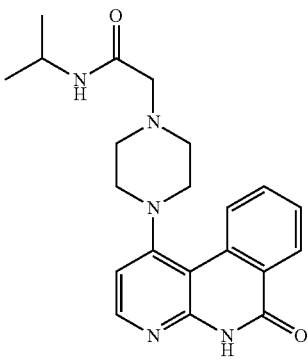 [SMILES: CC(C)NC(=O)CN1CCN(c2ccnc3[nH]c(=O)c4ccccc4c23)CC1]

N-Isopropyl-2-[4-(6-oxo-5,6-dihydro-benzo[c][1,8]
naphthyridin-1-yl)-piperazin-1-yl]-acetamide (429)

The title compound was synthesized according to the procedure described for the preparation of Example 378, method 2 using 83 and N-isopropyl-2-piperazin-1-yl-acetamide to provide 429. LC-MS (M+H=380, obsd.=380). $^1$H NMR (400 MHz, DMSO-d6): δ 1.11 (s, 6H), 3.15 (m, 1H), 3.47 (m, 3H), 3.60 (m, 3H), 3.92 (m, 1H), 4.04 (s, 2H), 7.06 (d, 1H), 7.68 (m, 2H), 8.38 (m, 2H), 8.54 (s, 1H), 9.17 (s, 1H)

Example 430

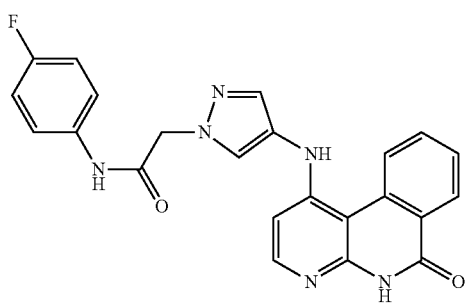 [SMILES: O=C(Cn1cc(Nc2ccnc3[nH]c(=O)c4ccccc4c23)cn1)Nc1ccc(F)cc1]

1-{1-[2-(4-Fluorophenyl)-2-oxo-ethyl]-1H-pyrazol-
4-ylamino}-5H-benzo[c][1,8]naphthyridin-6-one
(430)

The title compound was synthesized according to the procedure described for the preparation of Example 378, method 2 using 83 and 2-(4-amino-pyrazol-1-yl)-N-(4-fluoro-phenyl)-acetamide to provide 430. LC-MS (M+H=429, obsd.=429). $^1$H NMR (400 MHz, DMSO-d6): δ, 5.03 (s, 2H), 6.72 (m, 1H), 7.19 (m, 3H), 7.52 (m, 1H), 7.59 (m, 4H), 7.84 (m, 1H), 8.01 (m, 1H), 8.38 (m, 1H), 8.61 (s, 1H), 8.79 (s, 1H)

Example 431

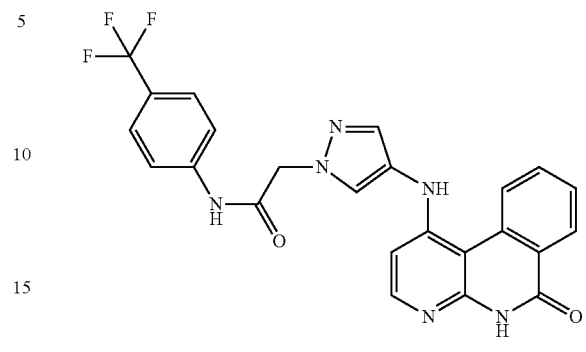

1-{1-[2-(4-Trifluoromethyl-phenyl)-2-oxo-ethyl]-
1H-pyrazol-4-ylamino}-5H-benzo[c][1,8]naphthyri-
din-6-one (431)

The title compound was synthesized according to the procedure described for the preparation of Example 378, method 2 using 83 and 2-(4-amino-pyrazol-1-yl)-N-(4-trifluoromethyl-phenyl)-acetamide to provide 431. LC-MS (M+H=479, obsd.=479). $^1$H NMR (400 MHz, DMSO-d6): δ 5.03 (s, 2H), 6.72 (m, 1H), 7.19 (m, 3H), 7.52 (m, 1H), 7.59 (m, 4H), 7.84 (m, 1H), 8.01 (m, 1H), 8.38 (m, 1H), 8.61 (s, 1H), 8.79 (s, 1H)

Example 432

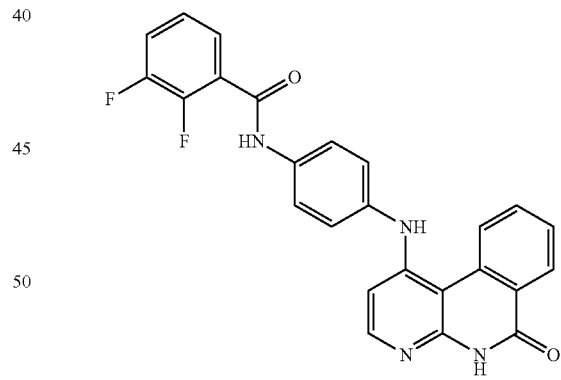

2,3-Difluoro-N-[4-(6-oxo-5,6-dihydro-benzo[c][1,8]
naphthyridin-1-ylamino)-phenyl]-benzamide (432)

The title compound was synthesized according to the procedure described for the preparation of Example 378, method 1 using 83 and N-(4-amino-phenyl)-2,3-difluoro-benzamide to provide 432. LC-MS (M+H=443, obsd.=443). $^1$H NMR (400 MHz, DMSO-d6): δ 6.94 (d, 1H), 7.192 (m, 2H), 7.59 (t, 1H), 7.70 (m, 2H), 8.10 (m, 2H), 8.31 (d, 1H), 8.88 (d, 1H), 8.99 (s, 1H), 10.30 (s, 1H).

Example 433

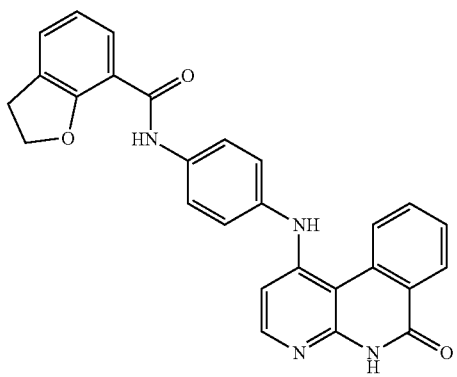 [SMILES: O=C(Nc1ccc(Nc2ccnc3[nH]c(=O)c4ccccc4c23)cc1)c1cccc2c1OCC2]

2,3-Dihydro-benzofuran-7-carboxylic acid [4-(6-oxo-5,6-dihydro-benzo[c][1,8]naphthyridin-1-ylamino)-phenyl]-amide (433)

The title compound was synthesized according to the procedure described for the preparation of Example 378, method 1 using 83 and 2,3-dihydro-benzofuran-7-carboxylicacid (4-amino-phenyl)-amide to provide 433. LC-MS (M+H=449, obsd.=449). $^1$H NMR (400 MHz, DMSO-d6): 3.30 (2H), 4.76 (2H), 6.94 (d, 1H), 7.19 (m, 2H), 7.59 (t, 1H), 7.70 (m, 2H), 8.10 (m, 2H), 8.31 (d, 1H), 8.88 (d, 1H), 8.99 (s, 1H), 10.30 (s, 1H).

Example 434

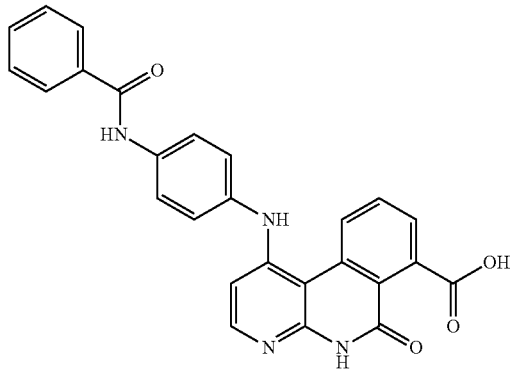 [SMILES: O=C(Nc1ccc(Nc2ccnc3[nH]c(=O)c4c(C(=O)O)cccc4c23)cc1)c1ccccc1]

1-[4-Benzoylamino-phenylamino)-6-oxo-5,6-dihydro-benzo[c][1,8]naphthyridin-7-carboxylic acid (434)

NaOH (4.2 mL, 1.00 M, 4.18 mmol) was added to a suspension of 423 (200 mg, 0.42 mmol) in THF (5 mL), and stirred overnight at room temperature. The crude reaction mixture was purified directly via HP-LC to provide 434 (17 mg) as a solid. LC-MS (M+H=451, obsd.=451). $^1$H NMR (400 MHz, DMSO-d6): δ 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 435

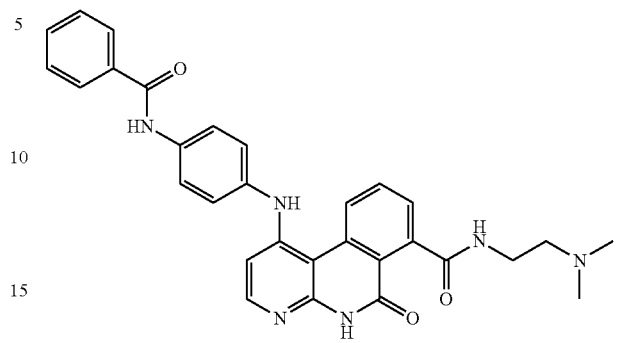

1-[4-Benzoylamino-phenylamino)-6-oxo-5,6-dihydro-benzo[c][1,8]naphthyridin-7-carboxylic acid 2-dimethylamino-ethyl amide (435)

434 (20 mg, 0.04 mmol), and CDI (14 mg, 0.09 mmol) were suspended in DMF (1 mL), and stirred for 2 h. N,N-dimethylethane-1,2-diamine (8 mg, 0.09 mmol) was added, and the mixture was stirred overnight at room temperature. The reaction mixture was diluted with $H_2O$. The resulting precipitate was filtered, washed with MeOH, and dried under vacuum to provide 435. LC-MS (M+H=521, obsd.=521). $^1$H NMR (400 MHz, DMSO-d6): δ 2.19 (s, 6H), 2.49 (4H), 6.93 (d, 1H), 7.20 (d, 2H), 7.54 (m, 3H), 7.76 (m, 3H), 7.97 (d, 1H), 8.10 (d, 1H), 8.27 (s, 1H), 8.85 (d, 1H), 9.18 (s, 1H), 10.27 (s, 1H).

Example 436

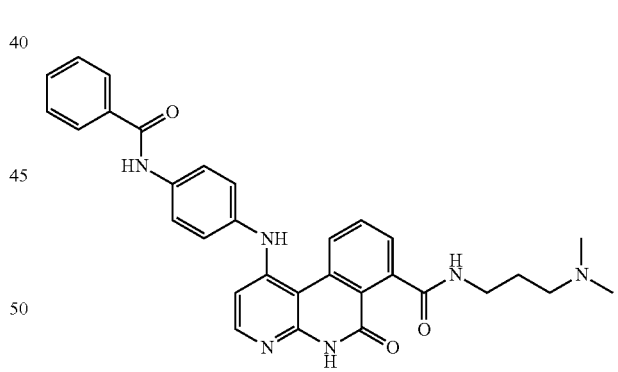

1-(4-Benzoylamino-phenylamino)-6-oxo-5,6-dihydro-benzo[c][1,8]naphthyridine-7-carboxylic acid (3-dimethylamino-propyl)-amide (436)

The title compound was synthesized according to the procedure described for the preparation of Example 435 using 434 and N*1*,N*1*-Dimethyl-propane-1,3-diamine to provide 436. LC-MS (M+H=535, obsd.=535). $^1$H NMR (400 MHz, DMSO-d6): δ 1.96 (s, 2H), 2.86 (10H), 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 437

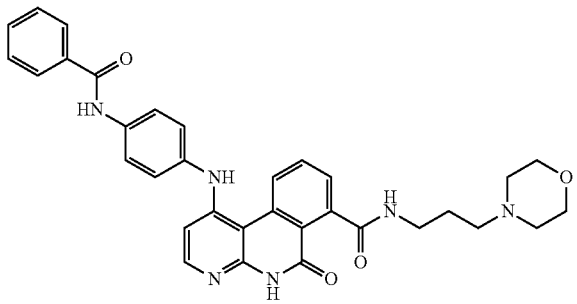 [SMILES: O=C(Nc1ccc(Nc2ccnc3[nH]c(=O)c4c(C(=O)NCCCN5CCOCC5)cccc4c23)cc1)c1ccccc1]

1-[4-Benzoylamino-phenylamino)-6-oxo-5,6-dihydro-benzo[c][1,8]naphthyridin-7-carboxylic acid 3-morpholin-4-yl-propyl amide (437)

The title compound was synthesized according to the procedure described for the preparation of Example 435 using 434 and 3-morpholin-4-yl-propylamine to provide 437. LC-MS (M+H=577, obsd.=577). $^1$H NMR (400 MHz, DMSO-d6): δ, 2.00 (m, 2H), 3.11 (m, 4H), 3.61 (m, 4H), 4.05 (m, 2H), 4.83 (m, 2H), 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 438

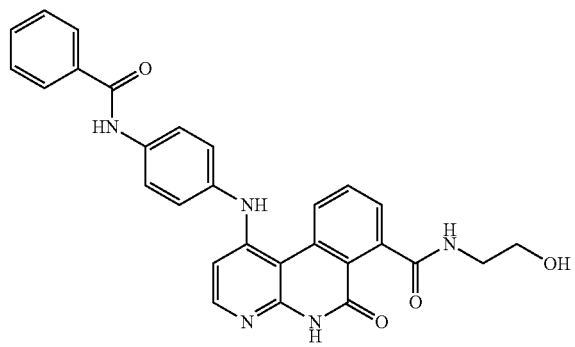 [SMILES: O=C(Nc1ccc(Nc2ccnc3[nH]c(=O)c4c(C(=O)NCCO)cccc4c23)cc1)c1ccccc1]

1-[4-Benzoylamino-phenylamino)-6-oxo-5,6-dihydro-benzo[c][1,8]naphthyridin-7-carboxylic acid 2-hydroxy ethyl amide (438)

The title compound was synthesized according to the procedure described for the preparation of Example 435 using 434 and 2-amino-ethanol to provide 438. LC-MS (M+H=494, obsd.=494). $^1$H NMR (400 MHz, DMSO-d6): δ, 3.31 (t, 2H), 3.59 (t, 2H), 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 439

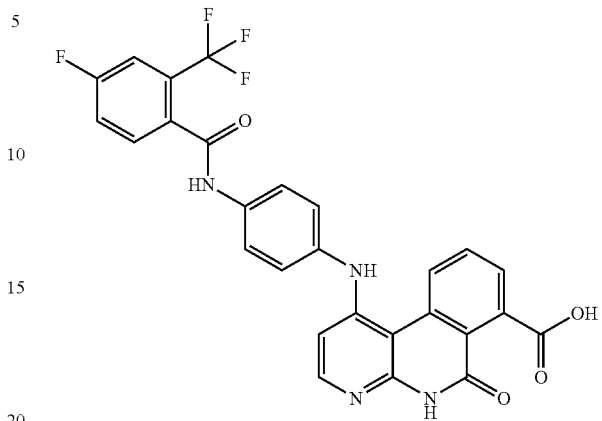

1-[4-(4-Fluoro-2-trifluoromethyl-benzoylamino)-phenylamino)-6-oxo-5,6-dihydro-benzo[c][1,8]naphthyridin-7-carboxylic acid (439)

The intermediate ethyl ester was synthesized according to the procedure described for the preparation of Example 378, method 2 using 1-chloro-6-oxo-5,6-dihydro-benzo[c][1,8]naphthyridine-7-carboxylic acid methyl ester and N-(4-amino-phenyl)-4-fluoro-2-trifluoromethyl-benzamide.

The title compound was synthesized according to the procedure described for the preparation of Example 434 using the ethyl ester intermediate to provide 439. LC-MS (M+H=537, obsd.=537). $^1$H NMR (400 MHz, DMSO-d6): δ, 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 440

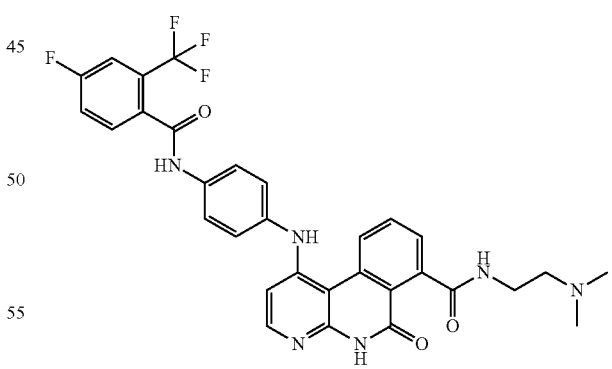

1-[4-(4-Fluoro-2-trifluoromethyl-benzoylamino)-phenylamino)-6-oxo-5,6-dihydro-benzo[c][1,8]naphthyridin-7-carboxylic acid 2-dimethylamino-ethyl amide (440)

The title compound was synthesized according to the procedure described for the preparation of Example 435 using 439 and N,N-dimethylethane-1,2-diamine to provide 440.

LC-MS (M+H=606, obsd.=606). ¹H NMR (400 MHz, DMSO-d6): δ, 2.97 (s, 6H), 3.37 (m, 2H), 3.64 (m, 2H), 6.93 (d, 1H), 7.20 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 441

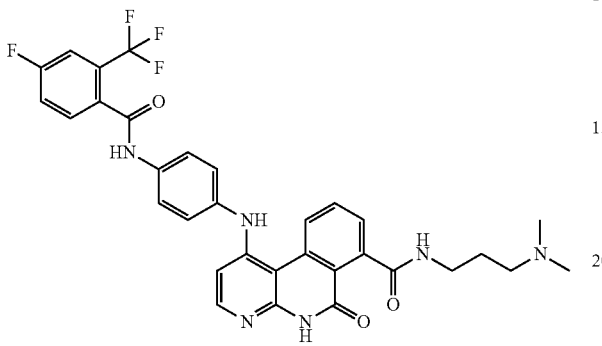

1-[4-(4-Fluoro-2-trifluoromethyl-benzoylamino)-phenylamino)-6-oxo-5,6-dihydro-benzo[c]1,8]naphthyridin-7-carboxylic acid 2-dimethylamino-propyl amide (441)

The title compound was synthesized according to the procedure described for the preparation of Example 435 using 439 and N*1*,N*1*-Dimethyl-propane-1,3-diamine to provide 441. LC-MS (M+H=621, obsd.=621). ¹H NMR (400 MHz, DMSO-d6): δ 1.94 (s, 2H), 2.86 (s, 6H), 3.32 (m, 4H), 6.93 (d, 1H), 7.17 (d, 2H), 7.40 (m, 1H), 7.66 (m, 2H), 7.78 (d, 1H), 7.97 (d, 1H), 8.1221 (d, 1H), 8.26 (s, 1H), 8.85 (d, 1H), 9.06 (s, 1H), 9.31 (s, 1H), 10.57 (s, 1H), 11.95 (s, 1H).

Example 442

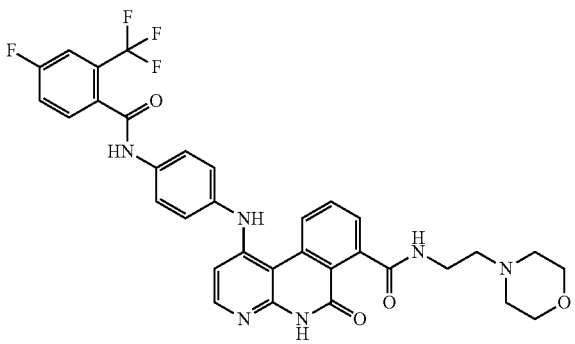 [SMILES: O=C(Nc1ccc(Nc2ccnc3[nH]c(=O)c4c(C(=O)NCCN5CCOCC5)cccc4c23)cc1)c1ccc(F)cc1C(F)(F)F]

1-[4-(4-Fluoro-2-trifluoromethyl-benzoylamino)-phenylamino]-6-oxo-5,6-dihydro-benzo[c][1,8]naphthyridine-7-carboxylic acid (2-morpholin-4-yl-ethyl)-amide (442)

The title compound was synthesized according to the procedure described for the preparation of Example 435 using 439 and 2-morpholin-4-yl-ethylamine to provide 442. LC-MS (M+H=649, obsd.=649). ¹H NMR (400 MHz, DMSO-d6): δ, 3.3 (m, 2H), 3.47 (m, 2H), 3.65 (m, 4H), 3.90 (m, 2H), 4.03 (m, 2H), 6.93 (d, 1H), 7.40 (d, 2H), 7.54 (m, 3H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 443

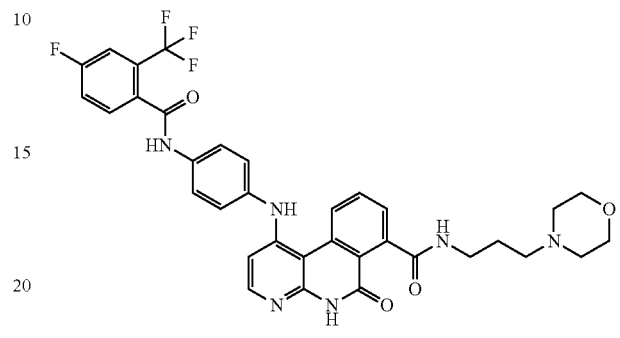

1-[4-(4-Fluoro-2-trifluoromethyl-benzoylamino)-phenylamino)-6-oxo-5,6-dihydro-benzo[c][1,8]naphthyridin-7-carboxylic acid 3-morpholin-4-yl-propyl amide (443)

The title compound was synthesized according to the procedure described for the preparation of Example 435 using 439 and 3-morpholin-4-yl-propylamine to provide 443. LC-MS (M+H=663, obsd.=663). ¹H NMR (400 MHz, DMSO-d6): δ, 2.00 (m, 2H), 3.11 (m, 2H), 3.35 (m, 4H), 3.53 (m, 2H), 3.72 (m, 2H), 4.01 (m, 2H), 6.93 (d, 1H), 7.20 (d, 2H), 7.54 (m, 1H), 7.76 (m, 2H), 7.78 (d, 1H), 7.97 (d, 1H), 8.10 (d, 1H), 8.27 (s, 1H), 8.85 (d, 1H), 9.18 (s, 1H), 10.27 (s, 1H).

Example 444

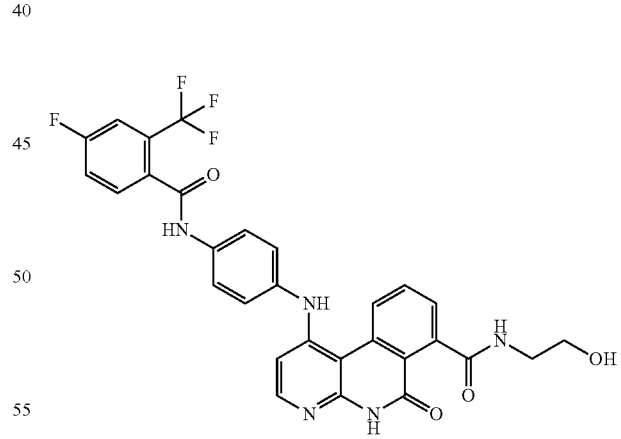

1-[4-(4-Fluoro-2-trifluoromethyl-benzoylamino)-phenylamino)-6-oxo-5,6-dihydro-benzo[c][1,8]naphthyridin-7-carboxylic acid 2-hydroxy ethyl amide (444)

The title compound was synthesized according to the procedure described for the preparation of Example 435 using 439 and 2-amino-ethanol to provide 444. LC-MS (M+H=580, obsd.=580). ¹H NMR (400 MHz, DMSO-d6): δ, 3.33 (t, 2H), 3.59 (t, 2H), 6.9 (d, 1H), 7.16 (d, 2H), 7.34 (m, 1H), 7.76 (m, 4H), 7.78 (d, 1H), 7.97 (d, 1H), 8.11 (d, 1H), 8.84 (s, 1H), 9.08 (d, 1H), 10.56 (s, 1H), 11.90 (s, 1H).

Example 445

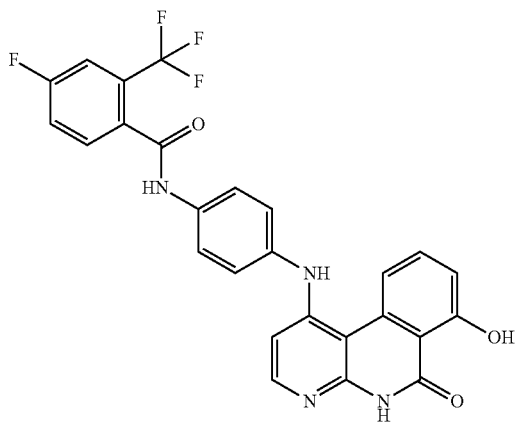 [SMILES: O=C(Nc1ccc(Nc2ccnc3[nH]c(=O)c4c(O)cccc4c23)cc1)c1ccc(F)cc1C(F)(F)F]

4-Fluoro-N-[4-(7-hydroxy-6-oxo-5,6-dihydro-benzo[c][1,8]naphthyridin-1-ylamino)-phenyl]-2-trifluoromethyl-benzamide (445)

The intermediate ethyl ester was synthesized according to the procedure described for the preparation of Example 378, method 2 using 1-chloro-7-hydroxy-5H-benzo[c][1,8]naphthyridin-6-one and N-(4-amino-phenyl)-4-fluoro-2-trifluoromethyl-benzamide to provide 445. LC-MS (M+H=509, obsd.=509). $^1$H NMR (400 MHz, DMSO-d6): δ, 6.95 (m, 2H), 7.18 (m, 2H), 7.67 (m, 4H), 7.81 (m, 3H), 8.11 (d, 1H), 8.24 (s, 1H), 8.79 (d, 1H), 10.53 (s, 1H).

Example 446

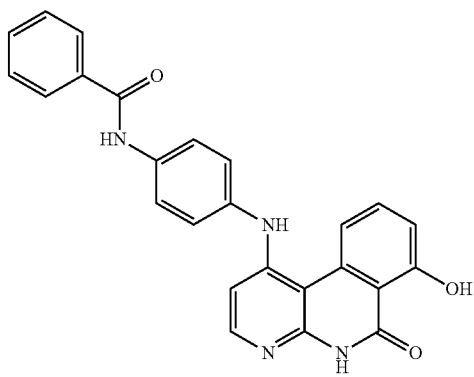 [SMILES: O=C(Nc1ccc(Nc2ccnc3[nH]c(=O)c4c(O)cccc4c23)cc1)c1ccccc1]

N-[4-(7-Hydroxy-6-oxo-5,6-dihydro-benzo[c][1,8]naphthyridin-1-ylamino)-phenyl]-benzamide (446)

The intermediate ethyl ester was synthesized according to the procedure described for the preparation of Example 378, method 2 using 1-chloro-7-hydroxy-5H-benzo[c][1,8]naphthyridin-6-one and N-(4-amino-phenyl)-benzamide to provide 446. LC-MS (M+H=423, obsd.=423). $^1$H NMR (400 MHz, DMSO-d6): δ, 6.95 (d, 2H), 7.21 (d, 2H), 7.55 (m, 2H), 7.76 (d, 2H), 7.95 (d, 2H), 8.09 (d, 1H), 8.21 (d, 1H), 8.88 (s, 1H), 10.23 (s, 1H).

Example 447

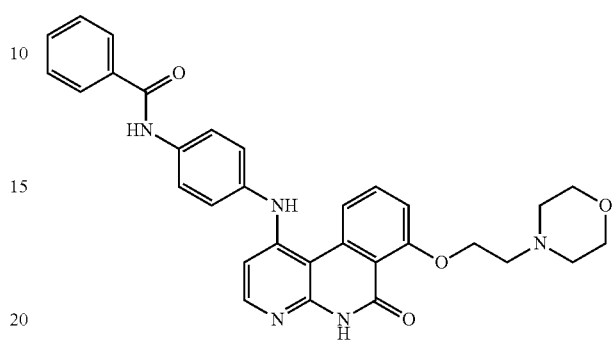

N-{4-[(7-(2-Morpholin-4-yl-ethoxy)-6-oxo-5,6-dihydro-benzo[c][1,8]naphthyridin-1-ylamino]-phenyl}-benzamide (447)

446 (50 mg, 0.12 mmol), 2-morpholine ethyl alcohol (17 mg, 0.13 mmol), and triphenylphosphine (37 mg, 0.14 mmol) were suspended in CH$_2$Cl$_2$ (1 mL), and cooled to 0° C. DIAD (289 mg, 0.14 mmol) was added dropwise, and the reaction mixture was stirred for overnight at room temperature. The crude product was purified directly via HP-LC to provide 447 (8 mg). LC-MS (M+H=536, obsd.=536).

Example 448

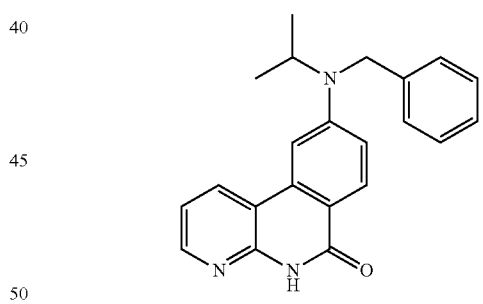

9-(Benzyl(isopropyl)amino)benzo[c][1,8]naphthyridin-6(5H)-one (448)

6 (200 mg, 0.87 mmol), N-benzylpropan-2-amine (0.58 mL, 3.47 mmol), Pd(OAc)$_2$ (8 mg, 0.03 mmol), X-Phos (33 mg, 0.07 mmol), and NaOtBu (250 mg, 2.6 mmol) were suspended in dioxane (3 mL), and stirred for 5 minutes at 150° C. via microwave. The reaction solution was diluted with DMSO and filtered. The crude product was purified directly via prep-LC-MS to provide 448 (21 mg, 7% yield) as a white powder. LC-MS (M+H=344, obsd.=344). $^1$H NMR (400 MHz, DMSO-D6) δ 11.45 (m, 1H), 8.53 (m, 1H), 8.38 (m, 1H), 8.00 (s, 1H), 7.49 (m, 1H), 7.32 (m, 5H), 7.18 (m, 1H), 7.00 (m, 1H), 4.66 (s, 2H), 1.25 (d, J=6.6, 6H), 0.84 (m, 1H).

Example 449

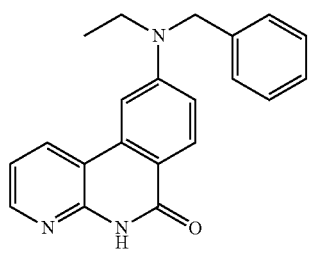 [SMILES: CCN(Cc1ccccc1)c1ccc2c(=O)[nH]c3ncccc3c2c1]

9-(Benzyl(ethyl)amino)benzo[c][1,8]naphthyridin-6(5H)-one (449)

The title compound was synthesized according to the procedure described for the preparation of Example 448 using 6 (200 mg, 0.87 mmol) and N-benzylethylamine (0.51 ml, 3.47 mmol) to provide 449 (55 mg, 19% yield) as a white powder. LC-MS (M+H=330, obsd.=330). $^1$H NMR (400 MHz, DMSO-D6) δ 11.50 (s, 1H), 8.66 (d, J=8.0, 1H), 8.42 (dd, J=1.5, 4.7, 1H), 8.05 (d, J=9.0, 1H), 7.49 (d, J=2.4, 1H), 7.17 (m, 5H), 7.02 (dd, J=2.4, 9.1, 1H), 4.79 (s, 2H), 3.69 (q, J=6.9, 2H), 1.11 (m, 3H).

Example 450

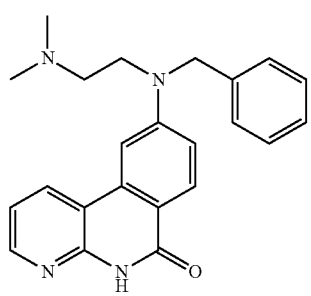 [SMILES: CN(C)CCN(Cc1ccccc1)c1ccc2c(=O)[nH]c3ncccc3c2c1]

9-(Benzyl(2-(dimethylamino)ethyl)amino)benzo[c][1,8]naphthyridin-6(5H)-one (450)

The title compound was synthesized according to the procedure described for the preparation of Example 448 using 6 (200 mg, 0.87 mmol) and N'-benzyl-N,N-dimethylethane-1,2-diamine (0.67 ml, 3.47 mmol) to provide 450 (11 mg, 3% yield) as a white powder. LC-MS (M+H=373, obsd.=373). $^1$H NMR (400 MHz, DMSO-D6) δ 11.61 (s, 1H), 9.88 (m, 1H), 8.76 (d, J=7.5, 1H), 8.45 (d, J=3.4, 1H), 8.08 (d, J=9.0, 1H), 7.57 (s, 1H), 7.20 (m, 6H), 7.10 (d, J=7.0, 1H), 4.86 (s, 2H), 4.02 (m, 4H), 2.89 (d, J=4.7, 6H).

Example 451

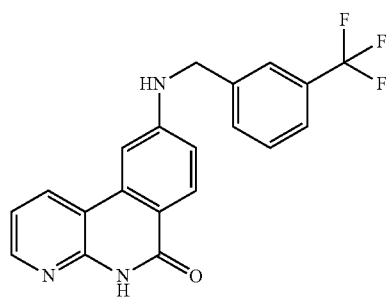 [SMILES: O=c1[nH]c2ncccc2c2cc(NCc3cccc(C(F)(F)F)c3)ccc12]

9-(3-(Trifluoromethyl)benzylamino)benzo[c][1,8]naphthyridin-6(5H)-one (451)

The title compound was synthesized according to the procedure described for the preparation of Example 448 using 6 (230 mg, 1.0 mmol) and (3-(trifluoro-methyl)phenyl)methanamine (350 mg, 1.00 mmol) to provide 451 (76 mg, 20% yield) as a white powder. LC-MS (M+H=370, obsd.=370). $^1$H NMR (400 MHz, DMSO-D6) δ 11.51 (s, 1H), 8.59 (d, J=8.1, 1H), 8.42 (dd, J=1.6, 4.7, 1H), 8.00 (d, J=8.8, 1H), 7.70 (m, 2H), 7.60 (d, J=6.9, 2H), 7.41 (d, J=2.1, 1H), 7.25 (dd, J=4.7, 8.0, 1H), 6.97 (dd, J=2.2, 8.8, 1H), 4.63 (s, 2H).

Example 452

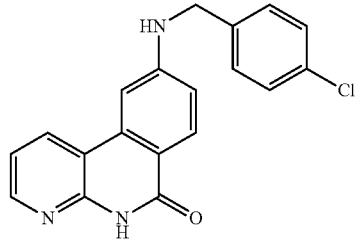 [SMILES: O=c1[nH]c2ncccc2c2cc(NCc3ccc(Cl)cc3)ccc12]

9-(4-Chlorobenzylamino)benzo[c][1,8]naphthyridin-6(5H)-one (452)

The title compound was synthesized according to the procedure described for the preparation of Example 448 using 6 (100 mg, 0.43 mmol) and (4-chloro-phenyl)methanamine (245 mg, 1.73 mmol) to provide 452 (20 mg, 14% yield) as a white powder. LC-MS (M+H=337, obsd.=337). $^1$H NMR (400 MHz, DMSO-D6) δ 11.49 (s, 1H), 8.56 (d, J=8.3, 1H), 8.41 (s, 1H), 7.99 (d, J=8.8, 1H), 7.44 (dd, J=8.5, 22.3, 2H), 7.37 (s, 2H), 7.25 (d, J=12.5, 2H), 6.95 (s, 1H), 4.51 (s, 2H).

Example 453

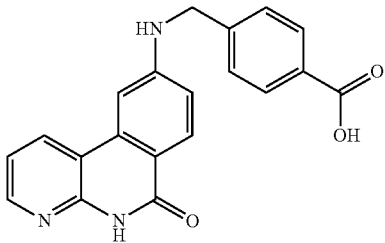 [SMILES: O=C(O)c1ccc(CNc2ccc3c(=O)[nH]c4ncccc4c3c2)cc1]

4-((6-oxo-5,6-dihydrobenzo[c][1,8]naphthyridin-9-ylamino)methyl)benzoic acid (453)

6 (100 mg, 0.43 mmol), 4-(aminomethyl)benzoic acid (0.19 mL, 1.30 mmol), $Pd_2(dba)_3$ (16 mg, 0.02 mmol), X-Phos (24 mg, 0.05 mmol), and KOH (73 mg, 1.30 mmol) were suspended in tert-butanol (3 mL), and stirred for 10 minutes at 125° C. via microwave. The reaction mixture was diluted with DMF and filtered. The crude product was purified directly via prep-LC-MS to provide 453 (11 mg, 7% yield) as a white powder. LC-MS (M+H=346, obsd.=346). $^1$H NMR (400 MHz, DMSO-D6) δ 11.49 (s, 0H), 8.55 (s, 2H), 8.41 (s, 1H), 7.95 (d, J=29.0, 3H), 7.56 (s, 2H), 7.38 (s, 2H), 7.25 (s, 1H), 6.97 (s, 1H), 4.60 (s, 2H).

Example 454

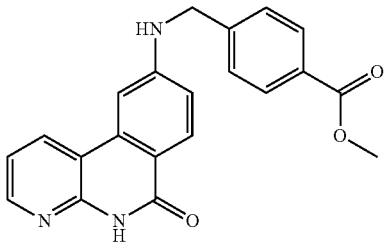 [SMILES: COC(=O)c1ccc(CNc2ccc3c(=O)[nH]c4ncccc4c3c2)cc1]

Methyl 4-((6-oxo-5,6-dihydrobenzo[c][1,8]naphthyridin-9-ylamino)methyl)-benzoate (454)

70 (172 mg, 0.81 mmol), methyl 4-(bromomethyl)benzoate (205 mg, 0.89 mmol), and $K_2CO_3$ (225 mg, 1.63 mmol) were suspended in DMF (3.00 mL), and stirred overnight at room temperature. The reaction mixture was purified directly via flash chromatography on silica gel to provide 454 (34 mg, 11% yield) as a white powder. LC-MS (M+H=360, obsd.=360). $^1$H NMR (400 MHz, DMSO-D6) δ 11.49 (s, 1H), 8.51 (m, 1H), 8.41 (d, J=3.0, 1H), 7.97 (dd, J=8.6, 19.3, 2H), 7.58 (d, J=8.2, 2H), 7.38 (m, 1H), 7.37 (s, 1H), 7.24 (dd, J=4.7, 7.9, 1H), 6.95 (d, J=11.0, 1H), 4.62 (s, 2H), 3.83 (s, 3H).

Example 455

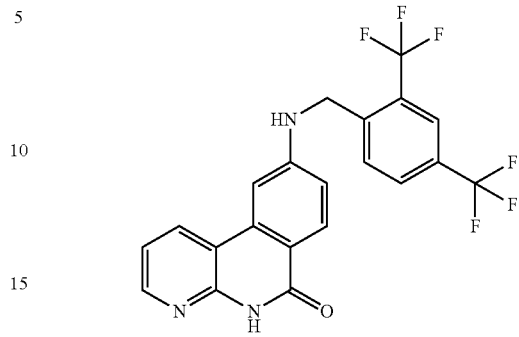

9-(2,4-Bis(trifluoromethyl)benzylamino)benzo[c][1,8]naphthyridin-6(5H)-one (455)

The title compound was synthesized according to the procedure described for the preparation of Example 454 using 70 (121 mg, 0.57 mmol) and 1-(bromo-methyl)-2,4-bis(trifluoromethyl)benzene (176 mg, 0.57 mmol) to provide 455 (55 mg, 22% yield) as a white powder. LC-MS (M+H=438, obsd.=438). $^1$H NMR (400 MHz, DMSO-D6) δ 11.55 (s, 1H), 8.37 (m, 2H), 8.06 (dd, J=7.9, 13.0, 2H), 7.84 (d, J=8.5, 1H), 7.31 (m, 2H), 7.24 (dd, J=4.7, 7.9, 1H), 6.94 (dd, J=2.1, 8.8, 1H), 4.77 (d, J=5.7, 2H).

Example 456

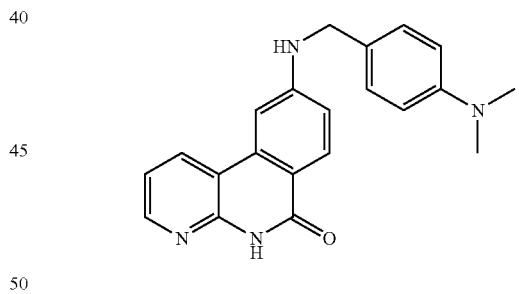

9-(4-(Dimethylamino)benzylamino)benzo[c][1,8]naphthyridin-6(5H)-one (456)

6 (200 mg, 0.87 mmol), 4-(aminomethyl)-N,N-dimethylaniline dihydrochloride (774 mg, 3.47 mmol), Pd(OAc)$_2$ (8 mg, 0.03 mmol), X-Phos (33 mg, 0.07 mmol), and KOH (438 mg, 8 mmol) were suspended in tert-butanol (3 mL), and stirred for 5 minutes at 170° C. via microwave. The reaction mixture was diluted with DMF and filtered. The crude product was purified directly via prep-LC-MS to provide 456 (6 mg, 2% yield) as a white powder. LC-MS (M+H=345, obsd.=345). $^1$H NMR (400 MHz, DMSO-D6) δ 11.46 (s, 1H), 8.58 (d, J=8.0, 1H), 8.42 (d, J=3.3, 1H), 7.97 (d, J=8.8, 2H), 7.38 (s, 1H), 7.26 (t, J=7.7, 2H), 7.08 (s, 1H), 6.71 (d, J=8.6, 2H), 4.35 (d, J=5.6, 2H), 2.85 (s, 6H).

Example 457

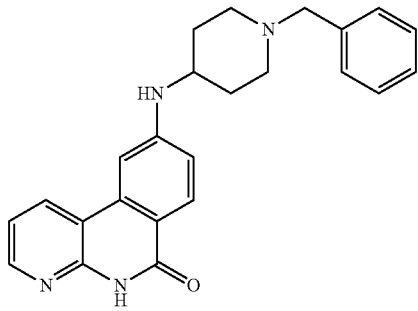 [SMILES: O=c1[nH]c2ncccc2c2cc(NC3CCN(Cc4ccccc4)CC3)ccc12]

9-(1-Benzylpiperidin-4-ylamino)benzo[c][1,8]naph-thyridin-6(5H)-one (457)

The title compound was synthesized according to the procedure described for the preparation of Example 456 using 6 (400 mg, 1.73 mmol) and 1-benzyl-piperidin-4-amine (1.31 mL, 6.94 mmol) to provide 457 (337 mg, 50% yield) as a white powder. LC-MS (M+H=385, obsd.=385).

Example 458

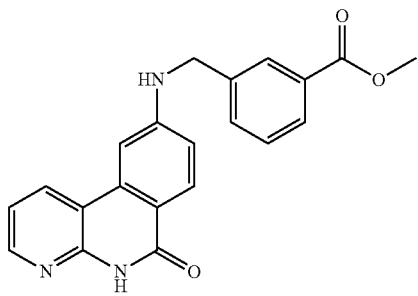 [SMILES: COC(=O)c1cccc(CNc2ccc3c(=O)[nH]c4ncccc4c3c2)c1]

Methyl 3-((6-oxo-5,6-dihydrobenzo[c][1,8]naphthy-ridin-9-ylamino)methyl)-benzoate (458)

70 (171 mg, 0.81 mmol), methyl 3-(bromomethyl)benzoate (0.01 mL, 0.97 mmol), and $Cs_2CO_3$ (791 mg, 2.43 mmol) were suspended in DMF (3 mL), and stirred overnight at ambient temperature. The reaction solution was purified directly via flash chromatography on silica gel to provide 458 (130 mg, 44% yield) as a white powder. LC-MS (M+H=360, obsd.=360). $^1$H NMR (400 MHz, DMSO-D6) δ 8.53 (dd, J=6.3, 11.9, 2H), 8.06 (d, J=8.7, 1H), 7.86 (s, 1H), 7.80 (d, J=8.0, 1H), 7.56 (d, J=7.6, 1H), 7.44 (d, J=8.5, 2H), 7.31 (m, 1H), 6.91 (d, J=9.0, 1H), 6.22 (s, 1H), 5.71 (s, 2H), 3.80 (s, 3H).

Example 459

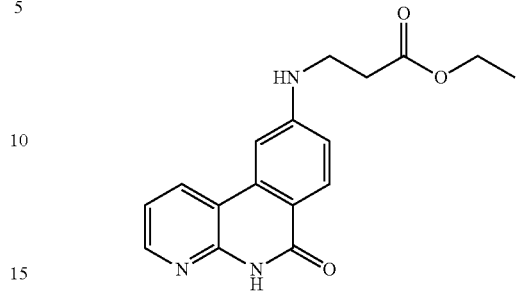

Ethyl 3-(6-oxo-5,6-dihydrobenzo[c][1,8]naphthyri-din-9-ylamino)propanoate (459)

The title compound was synthesized according to the procedure described for the preparation of Example 458 using 70 (100 mg, 0.47 mmol) and ethyl 3-bromopropanoate (0.01 mL, 0.57 mmol) to provide 459 (97 mg, 66% yield) as a white powder. LC-MS (M+H=312, obsd.=312). $^1$H NMR (400 MHz, DMSO-D6) δ 8.54 (dd, J=6.3, 14.0, 1H), 8.03 (d, J=8.7, 1H), 7.29 (m, 2H), 6.88 (d, J=6.8, 1H), 6.17 (s, 1H), 4.68 (t, J=7.5, 2H), 4.01 (q, J=7.1, 2H), 2.63 (dd, J=21.6, 29.0, 4H), 1.10 (t, J=7.1, 3H).

Example 460

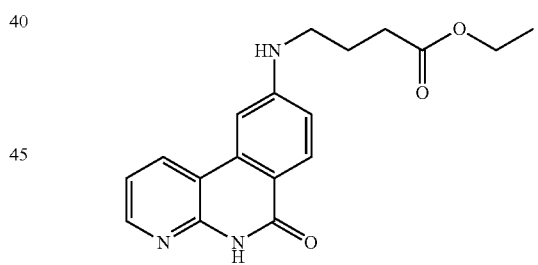

Ethyl 4-(6-oxo-5,6-dihydrobenzo[c][1,8]naphthyri-din-9-ylamino)butanoate (460)

The title compound was synthesized according to the procedure described for the preparation of Example 458 using 70 (160 mg, 0.76 mmol) and ethyl 3-bromobutanoate (0.01 mL, 0.91 mmol) to provide 460 (32 mg, 13% yield) as a white powder. LC-MS (M+H=326, obsd.=326). $^1$H NMR (400 MHz, DMSO-D6) δ 8.53 (ddd, J=1.7, 6.4, 9.7, 2H), 8.03 (d, J=8.6, 1H), 7.27 (m, 2H), 6.88 (dd, J=2.1, 8.7, 1H), 6.14 (s, 2H), 4.47 (t, J=6.9, 2H), 3.97 (q, J=7.1, 2H), 2.33 (t, J=7.4, 2H), 1.95 (p, J=7.3, 2H), 1.12 (t, J=7.1, 3H).

Example 461

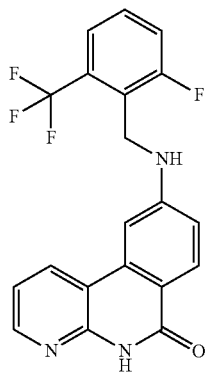

9-(2-Fluoro-6-(trifluoromethyl)benzylamino)benzo[c][1,8]naphthyridin-6(5H)-one (461)

The title compound was synthesized according to the procedure described for the preparation of Example 458 using 70 (122 mg, 0.58 mmol) and 2-(bromomethyl)-1-fluoro-3-(trifluoromethyl)benzene (179 mg, 0.70 mmol) to provide 461 (12 mg, 5% yield) as a white powder. LC-MS (M+H=388, obsd.=388). $^1$H NMR (400 MHz, DMSO-D6) δ 8.53 (dd, J=1.7, 8.0, 1H), 8.43 (dd, J=1.6, 4.7, 1H), 8.00 (d, J=8.7, 1H), 7.95 (s, 1H), 7.63 (d, J=7.8, 1H), 7.46 (dd, J=8.1, 13.2, 1H), 7.40 (d, J=2.1, 1H), 7.32 (dd, J=4.7, 7.9, 2H), 6.88 (dd, J=2.0, 8.7, 1H), 6.20 (s, 2H), 5.90 (s, 1H).

Example 462

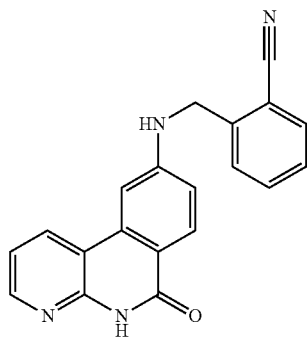 [SMILES: N#Cc1ccccc1CNc1ccc2c(=O)[nH]c3ncccc3c2c1]

2-((6-oxo-5,6-dihydrobenzo[c][1,8]naphthyridin-9-ylamino)methyl)benzonitrile (462)

The title compound was synthesized according to the procedure described for the preparation of Example 458 using 70 (140 mg, 0.66 mmol) and 2-(bromomethyl)benzonitrile (156 mg, 0.80 mmol) to provide 462 (45 mg, 21% yield) as a white powder. LC-MS (M+H=327, obsd.=327). $^1$H NMR (400 MHz, DMSO-D6) δ 8.56 (dd, J=1.6, 8.0, 1H), 8.47 (dd, J=1.6, 4.7, 1H), 8.06 (d, J=8.7, 1H), 7.87 (dd, J=1.2, 7.7, 1H), 7.47 (m, 1H), 7.41 (m, 1H), 7.40 (d, J=7.7, 1H), 7.36 (dd, J=4.7, 7.9, 1H), 6.98 (d, J=7.9, 1H), 6.91 (dd, J=2.0, 8.7, 1H), 6.25 (s, 1H), 5.81 (s, 2H).

Example 463

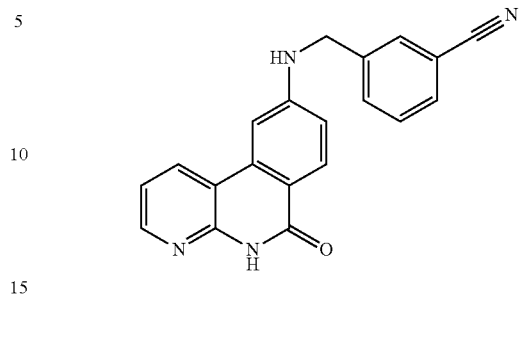

3-((6-Oxo-5,6-dihydrobenzo[c][1,8]naphthyridin-9-ylamino)methyl)benzonitrile (463)

The title compound was synthesized according to the procedure described for the preparation of Example 458 using 70 (141 mg, 0.67 mmol) and 3-(bromo methyl)benzonitrile (157 mg, 0.80 mmol) to provide 463 (35 mg, 16% yield) as a white powder. LC-MS (M+H=327, obsd.=327). $^1$H NMR (400 MHz, DMSO-D6) δ 8.46 (m, 2H), 8.06 (d, J=8.6, 1H), 7.73 (s, 1H), 7.69 (d, J=7.6, 1H), 7.57 (d, J=8.0, 1H), 7.48 (t, J=7.8, 1H), 7.42 (d, J=2.0, 1H), 7.36 (dd, J=4.7, 7.8, 1H), 6.90 (dd, J=2.1, 8.7, 1H), 6.22 (s, 2H), 5.69 (s, 2H).

Example 464

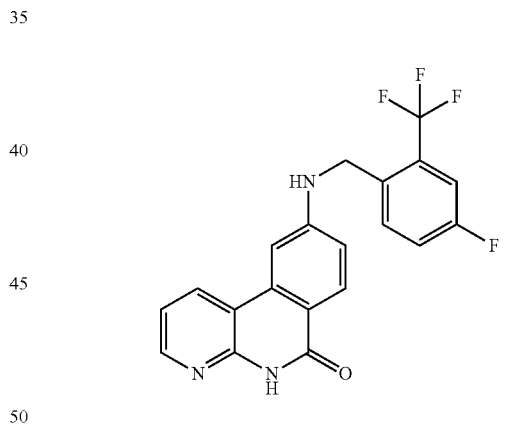

9-(4-Fluoro-2-(trifluoromethyl)benzylamino)benzo[c][1,8]naphthyridin-6(5H)-one (464)

The title compound was synthesized according to the procedure described for the preparation of Example 458 using 70 (97 mg, 0.45 mmol) and 2-(bromo methyl)-4-fluoro-3-(trifluoromethyl)benzene (142 mg, 0.55 mmol) to provide 464 (30 mg, 17% yield) as a white powder. LC-MS (M+H=388, obsd.=388). $^1$H NMR (400 MHz, DMSO-D6) δ 8.52 (m, 1H), 8.45 (dd, J=1.4, 4.7, 1H), 8.04 (d, J=8.7, 1H), 7.95 (s, 1H), 7.69 (dd, J=2.6, 9.1, 1H), 7.45 (d, J=1.9, 1H), 7.36 (dd, J=4.7, 7.8, 1H), 7.30 (dd, J=7.2, 9.9, 1H), 6.92 (dd, J=1.9, 8.7, 1H), 6.78 (dd, J=5.4, 8.6, 1H), 6.26 (s, 1H), 5.78 (d, J=8.8, 2H).

Example 465

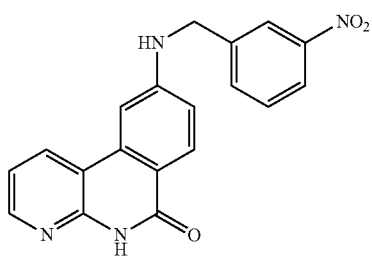 [SMILES: O=c1[nH]c2ncccc2c2cc(NCc3cccc([N+](=O)[O-])c3)ccc12]

9-(3-Nitrobenzylamino)benzo[c][1,8]naphthyridin-6(5H)-one (465)

The title compound was synthesized according to the procedure described for the preparation of Example 458 using 70 (115 mg, 0.55 mmol) and 3-nitro-benzyl bromide (113 mg, 0.66 mmol) to provide 465 (22 mg, 11% yield) as a white powder. LC-MS (M+H=347, obsd.=347). $^1$H NMR (400 MHz, DMSO-D6) δ 8.47 (m, 2H), 8.13 (s, 1H), 8.05 (m, 2H), 7.74 (d, J=7.7, 1H), 7.58 (t, J=7.9, 1H), 7.42 (d, J=2.0, 1H), 7.37 (dd, J=4.7, 7.8, 1H), 6.91 (dd, J=2.0, 8.7, 1H), 6.24 (s, 2H), 5.76 (s, 2H).

Example 466

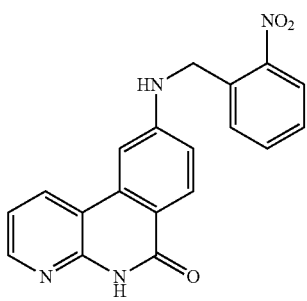

9-(2-Nitrobenzylamino)benzo[c][1,8]naphthyridin-6(5H)-one (466)

The title compound was synthesized according to the procedure described for the preparation of Example 458 using 70 (121 mg, 0.57 mmol) and 2-nitro-benzyl bromide (118 mg, 0.69 mmol) to provide 466 (24 mg, 12% yield) as a white powder. LC-MS (M+H=347, obsd.=347). $^1$H NMR (400 MHz, DMSO-D6) δ 8.56 (d, J=6.6, 1H), 8.41 (d, J=3.1, 1H), 8.07 (dd, J=8.3, 15.1, 2H), 7.51 (dt, J=6.5, 14.0, 2H), 7.43 (d, J=1.9, 1H), 7.35 (dd, J=4.7, 7.9, 1H), 7.03 (d, J=7.6, 1H), 6.91 (dd, J=2.0, 8.7, 1H), 6.25 (s, 2H), 5.89 (s, 2H).

Example 467

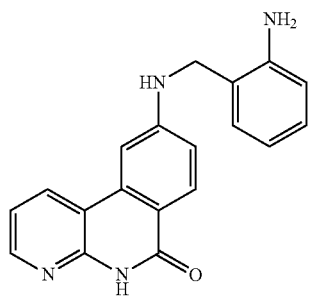

9-(2-Aminobenzylamino)benzo[c][1,8]naphthyridin-6(5H)-one (467)

466 (21 mg, 0.6 mmol) was dissolved in MeOH (130 mL) then reduced by flow chemistry on an H-Cube instrument (Pd/C cartridge, flow rate of 1.9 mL/min, 10 bar). The reaction solution was concentrated and purified via prep-LC-MS to provide 467 (5 mg, 24% yield) as a white powder. LC-MS (M+H=317, obsd.=317). $^1$H NMR (400 MHz, DMSO-D6) δ 8.53 (d, J=9.0, 2H), 8.22 (s, 1H), 8.07 (d, J=8.6, 1H), 7.42 (s, 1H), 7.34 (d, J=5.0, 1H), 6.84 (m, 2H), 6.66 (dd, J=7.5, 20.2, 2H), 6.34 (s, 1H), 6.20 (s, 2H), 5.46 (s, 2H), 5.32 (s, 1H).

Example 468

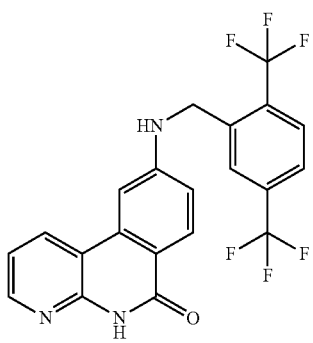 [SMILES: O=c1[nH]c2ncccc2c2cc(NCc3cc(C(F)(F)F)ccc3C(F)(F)F)ccc12]

9-(2,5-Bis(trifluoromethyl)benzylamino)benzo[c][1,8]naphthyridin-6(5H)-one (468)

The title compound was synthesized according to the procedure described for the preparation of Example 458 using 70 (88 mg, 0.42 mmol) and 2-(bromo-methyl)-1,4-bis(trifluoromethyl)benzene (154 mg, 0.50 mmol) to provide 466

(28 mg, 15% yield) as a white powder. LC-MS (M+H=438, obsd.=438). $^1$H NMR (400 MHz, DMSO-D6) δ 8.60 (d, J=8.0, 1H), 8.45 (d, J=3.3, 1H), 8.00 (m, 2H), 7.86 (d, J=7.7, 1H), 7.32 (m, 2H), 6.87 (m, 2H), 6.30 (s, 2H), 5.87 (s, 2H).

Example 469

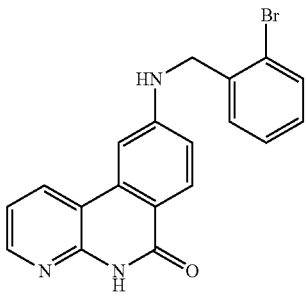

9-(2-Bromobenzylamino)benzo[c][1,8]naphthyridin-6(5H)-one (469)

The title compound was synthesized according to the procedure described for the preparation of Example 458 using 70 (151 mg, 0.71 mmol) and 1-(bromo-methyl)-2-bromobenzene (214 mg, 0.86 mmol) to provide 469 (11 mg, 4% yield) as a white powder. LC-MS (M+H=381, obsd.=381). $^1$H NMR (400 MHz, DMSO-D6) δ 11.50 (m, 1H), 8.53 (m, 1H), 8.39 (m, 1H), 8.01 (d, J=8.9, 1H), 7.68 (s, 1H), 7.43 (m, 2H), 7.37 (s, 1H), 7.23 (s, 2H), 6.92 (m, 2H), 4.55 (s, 2H).

Example 470

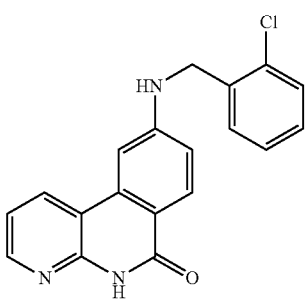

9-(2-Chlorobenzylamino)benzo[c][1,8]naphthyridin-6(5H)-one (470)

The title compound was synthesized according to the procedure described for the preparation of Example 458 using 70 (139 mg, 0.66 mmol) and 1-(bromo-methyl)-2-chlorobenzene (162 mg, 0.79 mmol) to provide 470 (14 mg, 6% yield) as a white powder. LC-MS (M+H=337, obsd.=337). $^1$H NMR (400 MHz, DMSO-D6) δ 11.51 (s, 1H), 8.56 (d, J=6.8, 1H), 8.42 (dd, J=1.6, 4.7, 1H), 8.01 (d, J=8.8, 1H), 7.44 (m, 2H), 7.39 (d, J=2.1, 1H), 7.29 (m, 2H), 7.18 (m, 2H), 6.95 (dd, J=2.1, 8.8, 1H), 4.58 (d, J=5.9, 2H).

Example 471

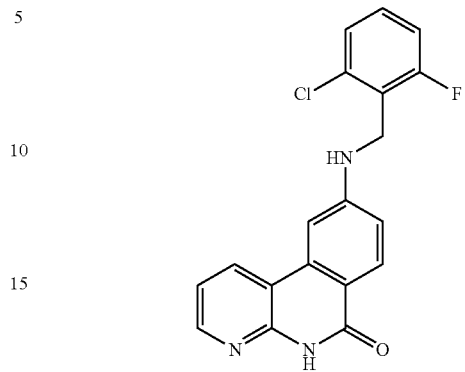

9-(2-Chloro-6-fluorobenzylamino)benzo[c][1,8]naphthyridin-6(5H)-one (471)

The title compound was synthesized according to the procedure described for the preparation of Example 458 using 70 (149 mg, 0.70 mmol) and 2-(bromo-methyl)-1-chloro-3-fluorobenzene (189 mg, 0.85 mmol) to provide 471 (14 mg, 6% yield) as a white powder. LC-MS (M+H=355, obsd.=355). $^1$H NMR (400 MHz, DMSO-D6) δ 11.53 (s, 1H), 8.64 (m, 1H), 8.45 (s, 1H), 8.01 (s, 1H), 7.99 (s, 1H), 7.50 (s, 2H), 7.43 (s, 2H), 7.30 (s, 1H), 6.97 (s, 1H), 4.55 (s, 2H).

Example 472

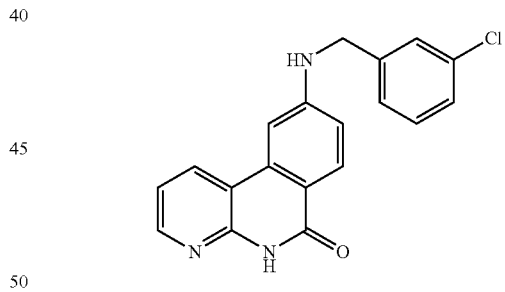

9-(3-Chlorobenzylamino)benzo[c][1,8]naphthyridin-6(5H)-one (472)

The title compound was synthesized according to the procedure described for the preparation of Example 458 using 70 (162 mg, 0.77 mmol) and 1-(bromo-methyl)-3-chlorobenzene (189 mg, 0.92 mmol) to provide 472 (20 mg, 8% yield) as a white powder. LC-MS (M+H=337, obsd.=337). $^1$H NMR (400 MHz, DMSO-D6) δ 8.46 (m, 1H), 8.06 (d, J=8.7, 1H), 7.42 (d, J=1.7, 1H), 7.36 (dd, J=4.7, 7.8, 1H), 7.26 (m, 3H), 7.21 (d, J=6.8, 1H), 6.90 (dd, J=2.0, 8.7, 1H), 6.23 (s, 2H), 5.65 (s, 2H).

Example 473

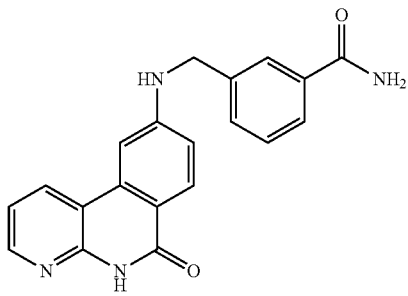 [SMILES: NC(=O)c1cccc(CNc2ccc3c(=O)[nH]c4ncccc4c3c2)c1]

3-((6-Oxo-5,6-dihydrobenzo[c][1,8]naphthyridin-9-ylamino)methyl)benzamide (473)

463 (48 mg, 0.15 mmol) and NaOH (1M, aqueous, 0.73 mL) were suspended in N,N-dimethylacetamide (2 mL), and stirred for 16 h at 100° C. The reaction mixture was purified directly via prep-LC-MS to provide 473 (24 mg, 47% yield) as a white powder. LC-MS (M+H=345, obsd.=345). $^1$H NMR (400 MHz, DMSO-D6) δ 8.55 (d, J=7.8, 1H), 8.50 (d, J=4.3, 1H), 8.06 (d, J=8.5, 1H), 7.94 (s, 1H), 7.74 (s, 1H), 7.69 (d, J=7.5, 1H), 7.43 (s, 1H), 7.35 (dd, J=7.2, 14.4, 2H), 6.91 (d, J=8.8, 1H), 5.70 (s, 2H).

Example 474

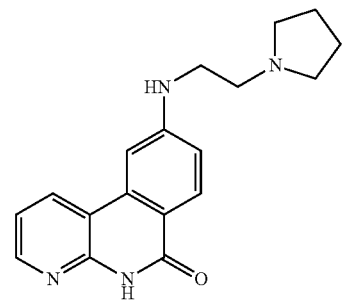 [SMILES: O=c1[nH]c2ncccc2c2cc(NCCN3CCCC3)ccc12]

9-(2-(Pyrrolidin-1-yl)ethylamino)benzo[c][1,8]naphthyridin-6(5H)-one (474)

The title compound was synthesized according to the procedure described for the preparation of Example 456 using 6 (100 mg, 0.43 mmol) and 2-pyrrolidin-1-ylethanamine (0.22 mL, 1.73 mmol) to provide 474 (24 mg, 18% yield) as a white powder. LC-MS (M+H=309, obsd.=309). $^1$H NMR (400 MHz, DMSO-D6) δ 11.59 (s, 1H), 9.65 (s, 1H), 8.75 (d, J=8.0, 1H), 8.39 (m, 1H), 8.05 (d, J=8.7, 1H), 7.42 (s, 1H), 7.28 (dd, J=4.6, 7.9, 1H), 6.95 (d, J=8.7, 1H), 3.65 (s, 4H), 3.41 (s, 2H), 3.10 (s, 2H), 1.96 (d, J=59.8, 4H).

Example 475

9-(2-(1-Methylpyrrolidin-2-yl)ethylamino)benzo[c][1,8]naphthyridin-6(5H)-one (475)

The title compound was synthesized according to the procedure described for the preparation of Example 456 using 6 (100 mg, 0.43 mmol) and 2-(1-methyl-pyrrolidin-2-yl)ethanamine (0.25 mL, 1.73 mmol) to provide 475 (35 mg, 25% yield) as a white powder. LC-MS (M+H=322, obsd.=322). $^1$H NMR (400 MHz, DMSO-D6) δ 11.47 (s, 1H), 8.65 (d, J=8.1, 1H), 8.43 (d, J=4.7, 1H), 7.99 (d, J=8.8, 1H), 7.18 (m, 2H), 6.89 (d, J=8.8, 1H), 6.65 (s, 1H), 3.24 (s, 2H), 2.98 (m, 1H), 2.25 (d, J=1.4, 3H), 2.02 (m, 2H), 1.97 (s, 2H), 1.66 (s, 2H), 1.52 (s, 2H).

Example 476

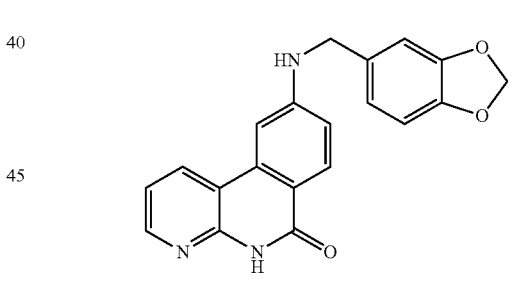

9-(Benzo[d][1,3]dioxol-5-ylmethylamino)benzo[c][1,8]naphthyridin-6(5H)-one (476)

The title compound was synthesized according to the procedure described for the preparation of Example 456 using 6 (266 mg, 1.15 mmol) and benzo[d]-[1,3]dioxol-5-ylmethanamine (697 mg, 4.61 mmol) to provide 476 (67 mg, 17% yield) as a white powder. LC-MS (M+H=346, obsd.=346). $^1$H NMR (400 MHz, DMSO-D6) δ 11.49 (s, 1H), 8.58 (d, J=6.6, 1H), 8.42 (dd, J=1.6, 4.7, 1H), 7.98 (d, J=8.7, 1H), 7.37 (d, J=2.1, 1H), 7.26 (dd, J=4.7, 7.9, 1H), 7.17 (t, J=6.1, 1H), 7.00 (d, J=1.5, 1H), 6.91 (m, 2H), 6.88 (d, J=7.9, 1H), 5.97 (s, 2H), 4.40 (d, J=5.9, 2H).

Example 477

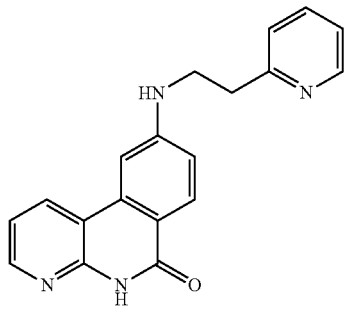 [SMILES: O=c1[nH]c2ncccc2c2cc(NCCc3ccccn3)ccc12]

9-(2-(Pyridin-2-yl)ethylamino)benzo[c][1,8]naph-thyridin-6(5H)-one (477)

The title compound was synthesized according to the procedure described for the preparation of Example 456 using 6 (162 mg, 0.70 mmol) and 2-(pyridin-2-yl)ethanamine (343 mg, 2.81 mmol) to provide 477 (10 mg, 5% yield) as a white powder. LC-MS (M+H=317, obsd.=317). $^1$H NMR (400 MHz, DMSO-D6) δ 11.52 (s, 1H), 8.73 (dd, J=6.6, 27.5, 2H), 8.44 (d, J=4.7, 1H), 8.15 (m, 1H), 8.00 (d, J=8.8, 1H), 7.63 (m, 2H), 7.19 (m, 2H), 6.97 (t, J=43.4, 1H), 3.71 (t, J=6.9, 2H), 3.25 (t, J=6.8, 2H).

Example 478

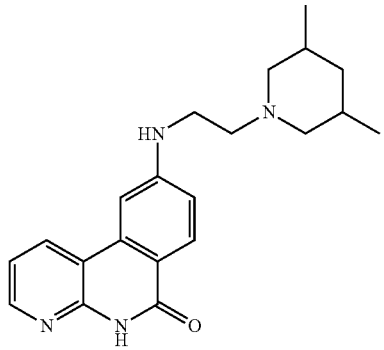 [SMILES: CC1CC(C)CN(CCNc2ccc3c(=O)[nH]c4ncccc4c3c2)C1]

9-(2-(3,5-Dimethylpiperidin-1-yl)ethylamino)benzo[c][1,8]naphthyridin-6(5H)-one (478)

The title compound was synthesized according to the procedure described for the preparation of Example 456 using 6 (171 mg, 0.74 mmol) and 2-(3,5-dimethylpiperidin-1-yl)ethanamine (464 mg, 2.97 mmol) to provide 478 (23 mg, 9% yield) as a white powder. LC-MS (M+H=351, obsd.=351). $^1$H NMR (400 MHz, DMSO-D6) δ 11.58 (s, 1H), 9.48 (s, 1H), 8.73 (d, J=6.7, 1H), 8.46 (dd, J=1.6, 4.7, 1H), 8.06 (d, J=8.7, 1H), 7.42 (d, J=2.1, 1H), 7.29 (dd, J=4.7, 7.9, 1H), 6.96 (dd, J=2.1, 8.8, 1H), 3.70 (s, 2H), 3.52 (d, J=11.1, 2H), 3.30 (d, J=5.3, 2H), 2.56 (dt, J=8.1, 16.4, 2H), 1.89 (s, 2H), 1.77 (d, J=13.0, 1H), 0.91 (t, J=8.4, 6H), 0.80 (dd, J=12.3, 24.8, 1H).

Example 479

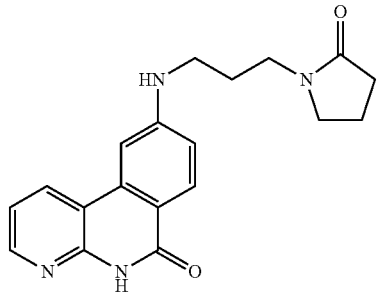 [SMILES: O=C1CCCN1CCCNc1ccc2c(=O)[nH]c3ncccc3c2c1]

9-(3-(2-Oxopyrrolidin-1-yl)propylamino)benzo[c][1,8]naphthyridin-6(5H)-one (479)

The title compound was synthesized according to the procedure described for the preparation of Example 456 using 6 (160 mg, 0.69 mmol) and 1-(3-aminopropyl)pyrrolidin-2-one (395 mg, 2.78 mmol) to provide 479 (15 mg, 7% yield) as a white powder. LC-MS (M+H=337, obsd.=337). $^1$H NMR (400 MHz, DMSO-D6) δ 11.47 (s, 1H), 8.67 (d, J=7.7, 1H), 8.43 (d, J=3.2, 1H), 7.99 (d, J=8.8, 1H), 7.19 (m, 2H), 6.90 (dd, J=1.9, 8.7, 1H), 6.64 (s, 1H), 3.27 (m, 4H), 3.24 (s, 2H), 2.23 (t, J=8.0, 2H), 1.87 (m, 2H), 1.73 (m, 2H).

Example 480

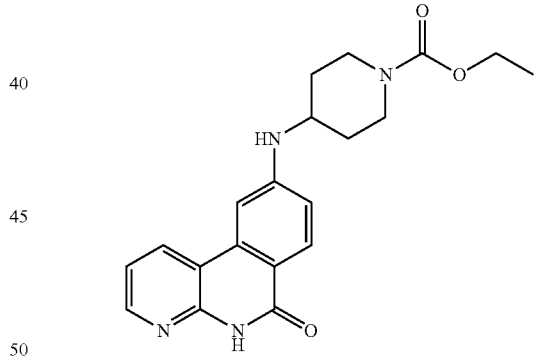

Ethyl 4-(6-oxo-5,6-dihydrobenzo[c][1,8]naphthyridin-9-ylamino)piperidine-1-carboxylate (480)

The title compound was synthesized according to the procedure described for the preparation of Example 456 using 6 (172 mg, 0.75 mmol) and 1-(3-amino-propyl)pyrrolidin-2-one (516 mg, 2.99 mmol) to provide 480 (53 mg, 19% yield) as a white powder. LC-MS (M+H=367, obsd.=367). $^1$H NMR (400 MHz, DMSO-D6) δ 11.48 (s, 1H), 8.69 (d, J=6.7, 1H), 8.43 (dd, J=1.5, 4.7, 1H), 7.99 (d, J=8.8, 1H), 7.39 (d, J=2.0, 1H), 7.27 (dd, J=4.7, 7.9, 1H), 6.91 (dd, J=2.0, 8.8, 1H), 4.05 (q, J=7.1, 2H), 3.97 (d, J=13.0, 2H), 3.81 (s, 1H), 3.05 (s, 2H), 1.97 (d, J=10.2, 2H), 1.32 (dd, J=9.7, 21.0, 2H), 1.20 (t, J=7.1, 3H).

Example 481

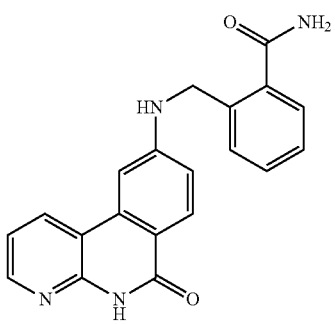 [SMILES: NC(=O)c1ccccc1CNc1ccc2c(=O)[nH]c3ncccc3c2c1]

2-((6-Oxo-5,6-dihydrobenzo[c][1,8]naphthyridin-9-ylamino)methyl)benzamide (481)

462 (51 mg, 0.16 mmol) and NaOH (1M, aqueous, 2 mL) were suspended in dioxane (2 mL), and stirred for 30 minutes at 150° C. The reaction mixture was acidified with HCl (2M in diethyl ether, 1.6 mL), concentrated, and purified via prep-LC-MS to provide 481 (4 mg, 7% yield) as a white powder. LC-MS (M+H=345, obsd.=345). $^1$H NMR (400 MHz, DMSO-D6) δ 8.56 (d, J=7.9, 1H), 8.43 (d, J=3.1, 1H), 8.05 (d, J=8.6, 1H), 7.94 (d, J=6.7, 1H), 7.45 (s, 1H), 7.25 (m, 3H), 6.92 (d, J=8.6, 1H), 6.66 (s, 1H), 5.98 (s, 2H).

Example 482

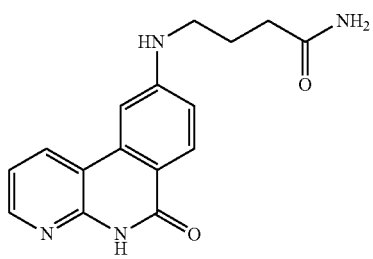 [SMILES: NC(=O)CCCNc1ccc2c(=O)[nH]c3ncccc3c2c1]

4-(6-Oxo-5,6-dihydrobenzo[c][1,8]naphthyridin-9-ylamino)butanamide (482)

460 (100 mg, 0.31 mmol) and NaOH (2.00 M aqueous, 1.54 ml, 3.07 mmol) were suspended MeOH (2 mL), and stirred for 90 minutes at 100° C. The reaction mixture was concentrated to provide the carboxylic acid intermediate. The carboxylic acid intermediate, NH$_4$Cl (117 mg, 3.36 mmol), N-{(dimethylamino)[({2-[(Z)-methyldiazenyl]phenyl}amino)oxy]-methylene}-N-methylmethanaminium hexafluorophosphate (159.54 mg, 0.40 mmol), EDCl*HCl (77 mg, 0.40 mmol), and DIEA (0.08 mL, 0.50 mmol) were suspended in DMF (2 mL), and stirred for 16 h at room temperature. The reaction mixture was diluted with H$_2$O (50 mL) and extracted with EtOAc (3×50 mL). The organic extracts were combined, washed with brine, dried over MgSO$_4$, filtered and concentrated. The crude product was purified directly via prep-LC-MS to provide 482 (5 mg, 5% yield) as a white powder. LC-MS (M+H=297, obsd.=297). $^1$H NMR (400 MHz, DMSO-D6) δ 8.53 (dd, J=6.2, 17.0, 2H), 8.03 (d, J=8.7, 1H), 7.28 (m, 2H), 6.82 (m, 1H), 4.46 (t, J=7.0, 2H), 2.28 (dd, J=14.1, 21.6, 2H), 1.92 (dd, J=7.2, 14.4, 2H).

Example 483

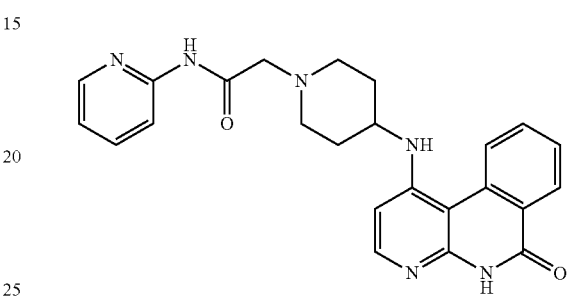

2-(4-(6-Oxo-5,6-dihydrobenzo[c][1,8]naphthyridin-1-ylamino)piperidin-1-yl)-N-(pyridin-2-yl)acetamide (483)

The title compound was synthesized according to the procedure described for the preparation of Example 287 using 358 and 2-chloro-N-pyridin-2-yl-acetamide to provide 483. LC-MS (M+H=429, obsd.=429).

Example 484

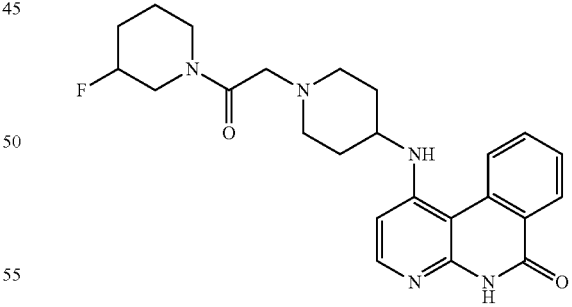

1-(1-(2-(3-Fluoropiperidin-1-yl)-2-oxoethyl)piperidin-4-ylamino)benzo-[c][1,8]naphthyridin-6(5H)-one (484)

The title compound was synthesized according to the procedure described for the preparation of Example 287 using 358 and 2-chloro-1-(3-fluoro-piperidin-1-yl)-ethanone to provide 484. LC-MS (M+H=438, obsd.=438).

Example 485

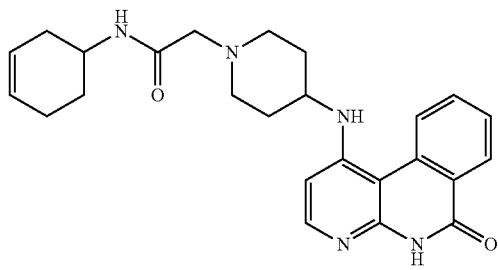 [SMILES: O=C(CN1CCC(Nc2ccnc3[nH]c(=O)c4ccccc4c23)CC1)NC1CC=CCC1]

N-Cyclohexyl-2-(4-(6-oxo-5,6-dihydrobenzo[c][1,8]
naphthyridin-1-ylamino)piperidin-1-yl)acetamide
(485)

The title compound was synthesized according to the procedure described for the preparation of Example 287 using 358 and 2-chloro-N-cyclohexyl-acetamide to provide 485. LC-MS (M+H=434, obsd.=434).

Example 486

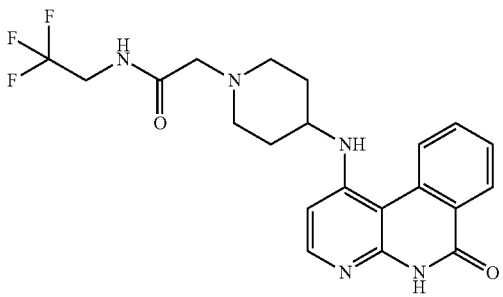 [SMILES: O=C(CN1CCC(Nc2ccnc3[nH]c(=O)c4ccccc4c23)CC1)NCC(F)(F)F]

2-(4-(6-Oxo-5,6-dihydrobenzo[c][1,8]naphthyridin-1-ylamino)piperidin-1-yl)-N-(2,2,2-trifluoroethyl)
acetamide (486)

The title compound was synthesized according to the procedure described for the preparation of Example 287 using 358 and 2-chloro-N-(2,2,2-trifluoro-ethyl)-acetamide to provide 486. LC-MS (M+H=434, obsd.=434).

Example 487

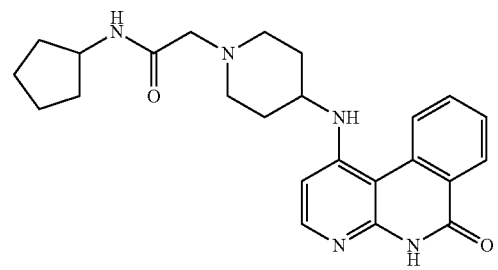 [SMILES: O=C(CN1CCC(Nc2ccnc3[nH]c(=O)c4ccccc4c23)CC1)NC1CCCC1]

N-Cyclopentyl-2-(4-(6-oxo-5,6-dihydrobenzo[c][1,8]naphthyridin-1-ylamino)piperidin-1-yl)acetamide
(487)

The title compound was synthesized according to the procedure described for the preparation of Example 287 using 358 and 2-chloro-N-cyclopentyl-acetamide to provide 487. LC-MS (M+H=420, obsd.=420).

Example 488

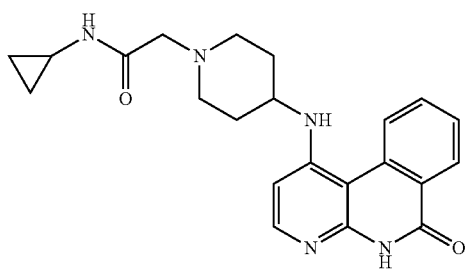 [SMILES: O=C(CN1CCC(Nc2ccnc3[nH]c(=O)c4ccccc4c23)CC1)NC1CC1]

N-Cyclopropyl-2-(4-(6-oxo-5,6-dihydrobenzo[c][1,8]naphthyridin-1-ylamino)piperidin-1-yl)acetamide
(488)

The title compound was synthesized according to the procedure described for the preparation of Example 287 using 358 and 2-chloro-N-cyclopropyl-acetamide to provide 488. LC-MS (M+H=392, obsd.=392).

Example 489

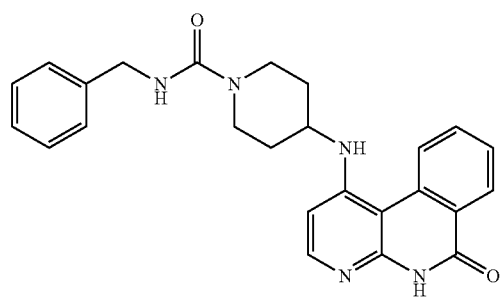 [SMILES: O=C(NCc1ccccc1)N1CCC(Nc2ccnc3[nH]c(=O)c4ccccc4c23)CC1]

N-Benzyl-4-(6-oxo-5,6-dihydrobenzo[c][1,8]naphthyridin-1-ylamino)piperidine-1-carboxamide (489)

The title compound was synthesized according to the procedure described for the preparation of Example 359 using 358 and isocyanatomethyl-benzene to provide 489. LC-MS (M+H=428, obsd.=428).

Example 490

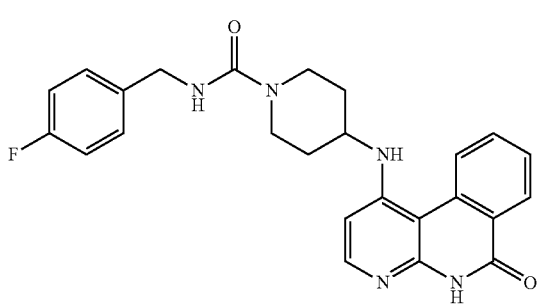 [SMILES: O=C(NCc1ccc(F)cc1)N1CCC(Nc2ccnc3[nH]c(=O)c4ccccc4c23)CC1]

N-(3-Fluorobenzyl)-4-(6-oxo-5,6-dihydrobenzo[c][1,8]naphthyridin-1-ylamino)piperidine-1-carboxamide (490)

The title compound was synthesized according to the procedure described for the preparation of Example 359 using 358 and 1-fluoro-4-isocyanatomethyl-benzene to provide 490. LC-MS (M+H=446, obsd.=446)

Example 491

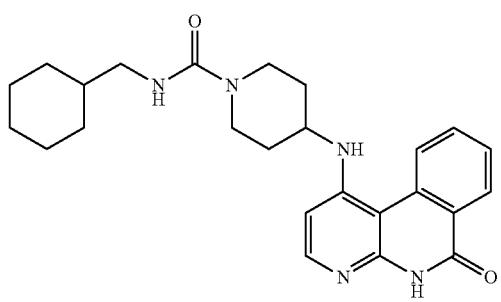 [SMILES: O=C(NCC1CCCCC1)N1CCC(Nc2ccnc3[nH]c(=O)c4ccccc4c23)CC1]

N-(Cyclohexylmethyl)-4-(6-oxo-5,6-dihydrobenzo[c][1,8]naphthyridin-1-ylamino)piperidine-1-carboxamide (491)

The title compound was synthesized according to the procedure described for the preparation of Example 359 using 358 and isocyanatomethyl-cyclohexane to provide 491. LC-MS (M+H=434, obsd.=434)

Example 492

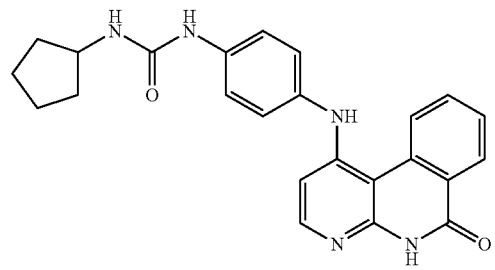 [SMILES: O=C(Nc1ccc(Nc2ccnc3[nH]c(=O)c4ccccc4c23)cc1)NC1CCCC1]

1-Cyclopentyl-3-(4-(6-oxo-5,6-dihydrobenzo[c][1,8]naphthyridin-1-ylamino)phenyl)urea (492)

The title compound was synthesized according to the procedure described for the preparation of Example 342 using 340 and isocyanato-cyclopentane to provide 492. LC-MS (M+H=415, obsd.=415).

Example 493

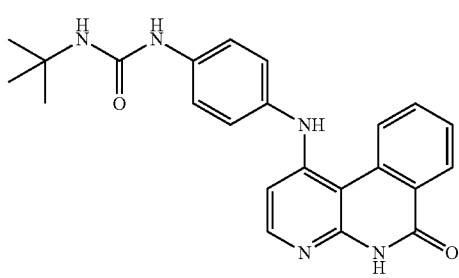 [SMILES: CC(C)(C)NC(=O)Nc1ccc(Nc2ccnc3[nH]c(=O)c4ccccc4c23)cc1]

1-Tert-butyl-3-(4-(6-oxo-5,6-dihydrobenzo[c][1,8]naphthyridin-1-ylamino)phenyl)urea (493)

The title compound was synthesized according to the procedure described for the preparation of Example 342 using 340 and 2-isocyanato-2-methyl-propane to provide 493. LC-MS (M+H=402, obsd.=402).

Example 494

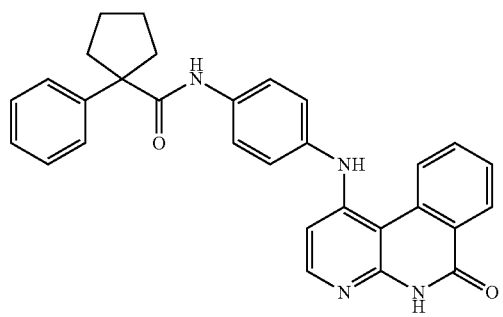 [SMILES: O=C(Nc1ccc(Nc2ccnc3[nH]c(=O)c4ccccc4c23)cc1)C1(c2ccccc2)CCCC1]

N-(4-(6-Oxo-5,6-dihydrobenzo[c][1,8]naphthyridin-1-ylamino)phenyl)-1-phenylcyclopentanecarboxamide (494)

The title compound was synthesized according to the procedure described for the preparation of Example 344 using 340 and 1-phenylcyclopentane-carboxylic acid to provide 494. LC-MS (M+H=475, obsd.=475).

Example 495

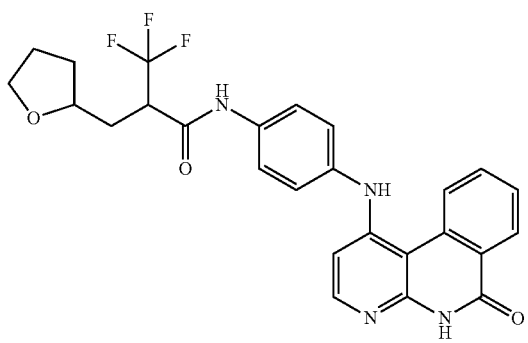 [SMILES: O=C(Nc1ccc(Nc2ccnc3[nH]c(=O)c4ccccc4c23)cc1)C(CC1CCCO1)C(F)(F)F]

3,3,3-Trifluoro-N-(4-(6-oxo-5,6-dihydrobenzo[c][1,8]naphthyridin-1-ylamino)phenyl)-2-((tetrahydrofuran-2-yl)methyl)propanamide (495)

The title compound was synthesized according to the procedure described for the preparation of Example 344 using 340 and 3,3,3-trifluoro-2-(tetrahydro-furan-2-ylmethyl)-propionic acid to provide 495. LC-MS (M+H=497, obsd.=497).

Example 496

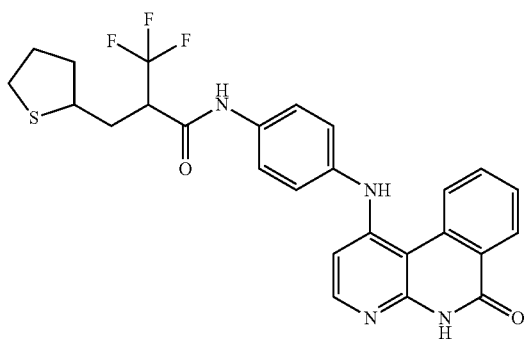 [SMILES: O=C(Nc1ccc(Nc2ccnc3[nH]c(=O)c4ccccc4c23)cc1)C(CC1CCCS1)C(F)(F)F]

3,3,3-Trifluoro-N-(4-(6-oxo-5,6-dihydrobenzo[c][1,8]naphthyridin-1-ylamino) phenyl)-2-((tetrahydrothiophen-2-yl)methyl)propanamide (496)

The title compound was synthesized according to the procedure described for the preparation of Example 344 using 340 and 3,3,3-trifluoro-2-(tetrahydro-thiophen-2-ylmethyl)-propionic acid to provide 496. LC-MS (M+H=513, obsd.=513).

Example 497

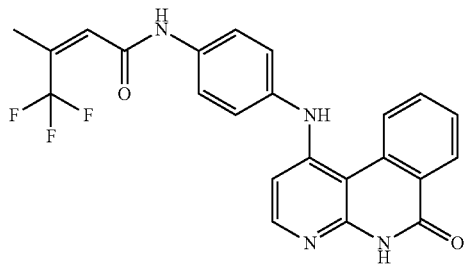 [SMILES: C/C(=C/C(=O)Nc1ccc(Nc2ccnc3[nH]c(=O)c4ccccc4c23)cc1)C(F)(F)F]

(Z)-4,4,4-Trifluoro-3-methyl-N-(4-(6-oxo-5,6-dihydrobenzo[c][1,8]naphthyridin-1-ylamino)phenyl)but-2-enamide (497)

The title compound was synthesized according to the procedure described for the preparation of Example 344 using 340 and (Z)-4,4,4-trifluoro-3-methyl-but-2-enoic acid to provide 497. LC-MS (M+H=439, obsd.=439).

Example 498

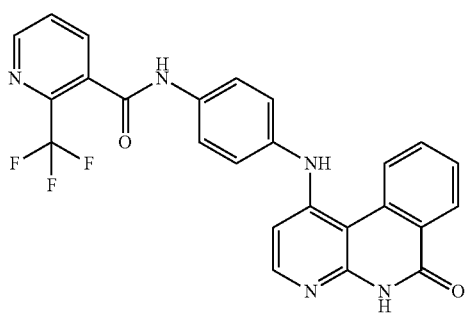 [SMILES: O=C(Nc1ccc(Nc2ccnc3[nH]c(=O)c4ccccc4c23)cc1)c1cccnc1C(F)(F)F]

N-(4-(6-Oxo-5,6-dihydrobenzo[c][1,8]naphthyridin-1-ylamino)phenyl)-2-(trifluoromethyl)nicotinamide (498)

The title compound was synthesized according to the procedure described for the preparation of Example 344 using 340 and 2-trifluoromethyl-nicotinic acid to provide 498. LC-MS (M+H=476, obsd.=476).

Example 499

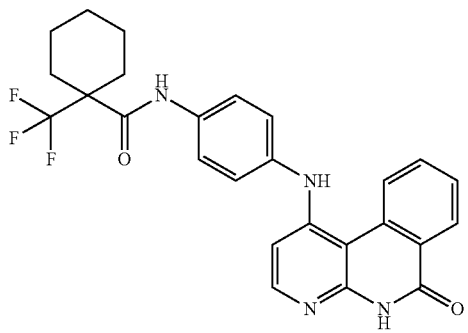 [SMILES: O=C(Nc1ccc(Nc2ccnc3[nH]c(=O)c4ccccc4c23)cc1)C1(C(F)(F)F)CCCCC1]

N-(4-(6-Oxo-5,6-dihydrobenzo[c][1,8]naphthyridin-1-ylamino)phenyl)-1-(trifluoromethyl)cyclohexanecarboxamide (499)

The title compound was synthesized according to the procedure described for the preparation of Example 344 using 340 and 1-trifluoromethyl-cyclohexane-carboxylic acid to provide 499. LC-MS (M+H=481, obsd.=481).

Example 500

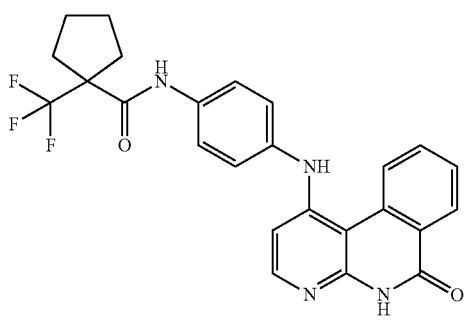 [SMILES: O=C(Nc1ccc(Nc2ccnc3[nH]c(=O)c4ccccc4c23)cc1)C1(C(F)(F)F)CCCC1]

N-(4-(6-Oxo-5,6-dihydrobenzo[c][1,8]naphthyridin-1-ylamino)phenyl)-1-(trifluoromethyl)cyclopentanecarboxamide (500)

The title compound was synthesized according to the procedure described for the preparation of Example 344 using 340 and 1-trifluoromethyl-cyclopentane-carboxylic acid to provide 500. LC-MS (M+H=467, obsd.=467).

Example 501

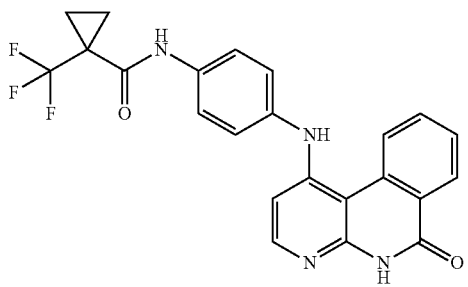 [SMILES: O=C(Nc1ccc(Nc2ccnc3[nH]c(=O)c4ccccc4c23)cc1)C1(C(F)(F)F)CC1]

N-(4-(6-Oxo-5,6-dihydrobenzo[c][1,8]naphthyridin-1-ylamino)phenyl)-1-(trifluoromethyl)cyclopropanecarboxamide (501)

The title compound was synthesized according to the procedure described for the preparation of Example 344 using 340 and 1-trifluoromethyl-cyclopropane-carboxylic acid to provide 501. LC-MS (M+H=439, obsd.=439).

Example 502

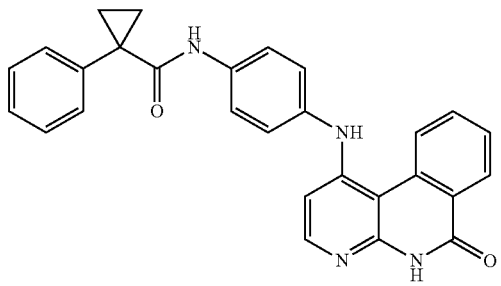 [SMILES: O=C(Nc1ccc(Nc2ccnc3[nH]c(=O)c4ccccc4c23)cc1)C1(c2ccccc2)CC1]

N-(4-(6-Oxo-5,6-dihydrobenzo[c][1,8]naphthyridin-1-ylamino)phenyl)-1-phenylcyclopropanecarboxamide (502)

The title compound was synthesized according to the procedure described for the preparation of Example 344 using 340 and 1-phenylcyclopropane-carboxylic acid to provide 502. LC-MS (M+H=447, obsd.=447).

Example 503

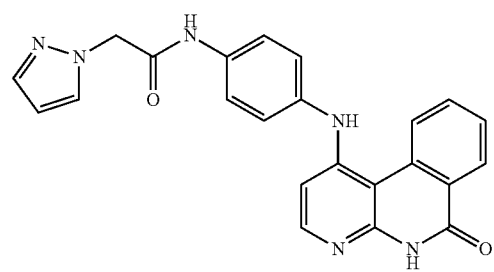 [SMILES: O=C(Cn1cccn1)Nc1ccc(Nc2ccnc3[nH]c(=O)c4ccccc4c23)cc1]

N-(4-(6-Oxo-5,6-dihydrobenzo[c][1,8]naphthyridin-1-ylamino)phenyl)-2-(1H-pyrazol-1-yl)acetamide (503)

The title compound was synthesized according to the procedure described for the preparation of Example 344 using 340 and pyrazol-1-yl-acetic acid to provide 503. LC-MS (M+H=411, obsd.=411).

Example 504

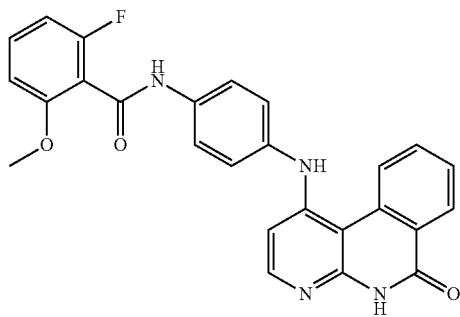 [SMILES: COc1cccc(F)c1C(=O)Nc1ccc(Nc2ccnc3[nH]c(=O)c4ccccc4c23)cc1]

2-Fluoro-6-methoxy-N-(4-(6-oxo-5,6-dihydrobenzo[c][1,8]naphthyridin-1-ylamino)phenyl)benzamide (504)

The title compound was synthesized according to the procedure described for the preparation of Example 344 using 340 and 2-fluoro-6-methoxy-benzoic acid to provide 504. LC-MS (M+H=455, obsd.=455).

Example 505

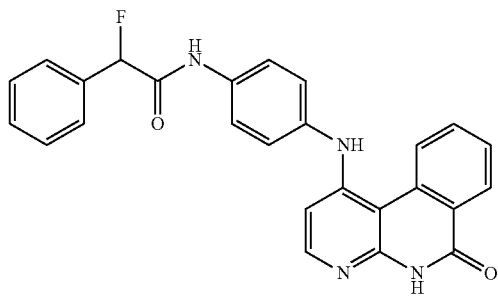 [SMILES: O=C(Nc1ccc(Nc2ccnc3[nH]c(=O)c4ccccc4c23)cc1)C(F)c1ccccc1]

2-Fluoro-N-(4-(6-oxo-5,6-dihydrobenzo[c][1,8]naphthyridin-1-ylamino)phenyl)-2-phenylacetamide (505)

The title compound was synthesized according to the procedure described for the preparation of Example 344 using 340 and fluoro-phenyl-acetic acid to provide 505. LC-MS (M+H=439, obsd.=439).

Example 506

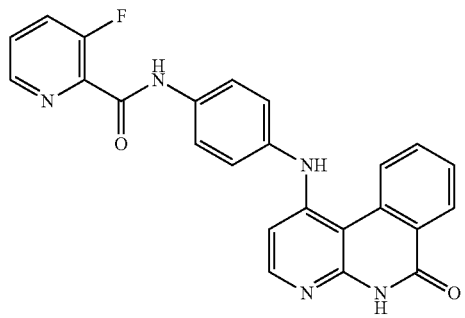 [SMILES: O=C(Nc1ccc(Nc2ccnc3[nH]c(=O)c4ccccc4c23)cc1)c1ncccc1F]

3-Fluoro-N-(4-(6-oxo-5,6-dihydrobenzo[c][1,8]naphthyridin-1-ylamino)phenyl)picolinamide (506)

The title compound was synthesized according to the procedure described for the preparation of Example 344 using 340 and 3-fluoro-pyridine-2-carboxylic acid to provide 506. LC-MS (M+H=426, obsd.=426).
LC-MS Data Were Obtained Using an Agilent 1100 HPLC System
Column: Waters, Xterra MS C18, 2.5 μm, 2.1 mm×20 mm.
Mobile phase: A: 0.1% Formic acid in Water
B: 0.1% Formic acid in Methanol
Gradient: Increase 15% B to 95% B in 3.2 min and hold for 1.4 min.
Decrease 95% B to 15% B for 0.1 min and hold for 2.3 min.
Run time: 7 min
Flow rate: 0.4 ml/min
Injection Volume: User defined
UV: 254 nm,
followed by mass spectrometry on a Finnigan LCQ Duo system (type of ionisation: ESI, positive mode (analysing positively charged analytes)).
Biologica Data
Biochemical Assays for Aurora Activity:
The Aurora assays described here are performed on two Caliper Life Sciences systems: the LC3000 and the Desktop Profiler. These provide data on enzyme activity via measurement of the relative amounts of phosphorylated or unphosphorylated fluorescently labelled substrate peptide at the end of an enzymatic reaction. These different states of peptide are resolved by applying a potential difference across the sample. The presence of the charged phosphate group on the product (as opposed to the substrate) causes a different peptide mobility between the two peptides. This is visualized by excitation of the fluorescent label on the substrate and product peptides and represented as peaks within the analysis software.
LC3000 Method
In order to measure inhibitor activity of Aurora A inhibitors in the Caliper Life Sciences LC3000, a TTP Mosquito liquid handling instrument is used to place 0.25 ul of the appropriate concentration of inhibitor in 100% DMSO (for a dose response curve calculation) into each well of a 384-well plate. To this reaction components are added to a final volume of 25 ul:
  0.067 ng/ul GST-Aurora A (Carna Biosciences 05-101. N-terminal GST fusion with full length Aurora A (1-403 amino acids), accession number NP 940835.1).
  15 uM ATP (Fluke, 02055)
  1 mM DTT (Sigma, D0632)
  1 mM MgCl2 (Sigma, M1028)
  1 uM substrate peptide (sequence FITC-LRRASLG-(CONH2), synthesized by Tufts Peptide Synthesis service.
  100 mM HEPES pH 7.5 (Calbiochem, 391338)
  0.015% Brij-35 (Sigma, B4184)
The reaction is incubated for 90 min at 25 C, and then stopped by the addition of 70 ul of Stop buffer (100 mM HEPES pH 7.5, 0.015% Brij-35, 10 mM EDTA (Sigma, E7889)).
The plate is read on a Caliper LC3000 in an Off-Chip mobility shift assay format, using the following parameters for a 12-sipper chip: screening pressure—1.8 psi, upstream voltage—2700, downstream voltage—1000. These conditions cause unphosphorylated substrate and phosphorylated product peptide to resolve as separate peaks allowing direct measurement of percentage of conversion of substrate to product. The percent conversion can be plotted against concentration of inhibitor to produce a sigmoidal dose response curve, from which an 1050 can be calculated using XLFit for Microsoft Excel.
Desktop Profiler Method
The Desktop Profiler utilizes the same principle as the LC3000 for calculating percentage conversion of a substrate to product. Caliper Life Sciences provides proprietary flash frozen pre-made 384 well plates containing selected kinases. Each column in the 384 well plate contains a particular selected kinase. A second plate, the 'substrate plate' contains a mix of fluorescently labeled peptide substrate and ATP. These are arranged in columns so that transfer for substrate plate to enzyme plate provides the correct enzyme with the correct substrate/ATP concentration. Compounds are added to a thawed enzyme plate in the desired format, in single concentrations. Reactions are initiated by transfer of the substrate/ATP mix from the substrate plate. The enzyme plate is incubated for 90 mins at 25 C. The reaction is stopped by addition of 70 ul of Stop Buffer (100 mM HEPES pH 7.5, 0.015% Brij-35, 10 mM EDTA (Sigma, E7889)).

Reading of the plate in the Profiler is identical to the LC3000, and the ratio between substrate and product peaks provides the activity of the enzyme in that well. This is best represented by a plate heat map which colors each well by percent inhibition as compared to positive and negative controls (no inhibitors and no ATP respectively).

In the following Tables 3a-4-b, which show the results of the desktop profiler measurements, "+" means 50-70% inhibition, "++" means 70-90% inhibition, and "+++" means >90% inhibition. The enzymes tested for profiling were ABL, AKT1, AKT2, AurA, CHK1, CHK2, CK1d, Erk1, Erk2, FYN, GSK3b, INSR, LCK, LYN, MAPKAPK2, MET, MSK1, p38a, PKA, PKCz, PKD2, PRAK, RSK1 and SRC.

TABLE 3a

Compounds of the invention tested against a panel of different enzymes at 10 micromolar concentration of the compound.
Profiler Assay - Percent Inhibition at 10 micromolar

| Compound of Example No. | ABL | AKT1 | AKT2 | AurA | CHK1 | CHK2 | CK1d | Erk1 | Erk2 | FYN | GSK3b | INSR |
|---|---|---|---|---|---|---|---|---|---|---|---|---|
| 5 | | | | | | | | | | | | |
| 6 | | | | + | | | | | | | | |
| 8 | | | | | | | | | | | | |
| 9 | | | | + | | | | | | | | |
| 11 | | | | | | | | | | | | |
| 13 | + | | | | | | | | | | +++ | |
| 16 | | | | | | | | | | | | |
| 17 | | | | | | | | | | | | |
| 19 | | | | | | | | | | | | |
| 26 | | | | ++ | | + | | | | | | |
| 59 | + | | | | | | | | | | | + |
| 51 | | | | | | | | | | | | |
| 27 | | | | ++ | | + | | | | | | |
| 54 | | | | | | | | | | | | |
| 58 | | | | | | | | | | | | |
| 57 | | | | | | | | | | | | |
| 56 | | | | | | | | | | | | |
| 55 | | | | | | | | | | | | |
| 33 | | | | ++ | | | | | | | | |
| 31 | +++ | ++ | +++ | +++ | | + | ++ | ++ | ++ | ++ | ++ | |
| 30 | + | | | +++ | | | | | | | + | |
| 29 | | | | ++ | | | | | | | | |
| 52 | | | | | | | | | | | | |
| 60 | | | | | | | | | | | | |
| 64 | | | | | | | | | | | | |
| 63 | | | | | | | | | | | | |
| 36 | | | | +++ | | ++ | | | | | + | |
| 66 | | | | | | | | | | | | |
| 65 | | | | | | | | | | | | |
| 68 | | | | | | | | | | | | |
| 67 | | | | | | | | | | | | |
| 62 | | | | | | | | | | | | |
| 41 | | | | | | | | | | | | |
| 37 | | | | + | | | | | | | | |
| 38 | | | | + | | | | | | | | |
| 40 | | | | | | | | | | | | |
| 39 | | | | + | | | | | | | | |
| 61 | | | | | | | | | | | | |
| 23 | | | | | | | | | | | | |
| 12 | ++ | | | | | | | | | | + | |
| 10 | | | | | | | | | | | | |
| 81 | +++ | +++ | +++ | +++ | | ++ | ++ | ++ | ++ | +++ | +++ | |
| 82 | ++ | | + | +++ | | + | + | | | +++ | ++ | |
| 83 | | | | | | | + | | | | | |
| 99 | | | | | | | | | | | | |
| 98 | | | | + | | | | | | | + | |
| 97 | | | | | | | | | | | | |
| 103 | ++ | | | | | | | | | | ++ | |
| 96 | ++ | | + | ++ | | + | + | | | | ++ | + |
| 95 | +++ | | | ++ | | + | | | | | +++ | |
| 102 | | | | | | | | | | | | |
| 109 | | | | | | | | | | | | |
| 121 | | | | + | | | | | | | ++ | |
| 120 | | | | +++ | | +++ | + | | | | + | |
| 113 | ++ | | | ++ | | ++ | | | | | | |
| 114 | +++ | | | +++ | | + | | | | | + | |
| 139 | +++ | | | ++ | | + | | | | | +++ | |
| 140 | + | | | | | | | | | | + | |
| 141 | | | | + | | | | | | | | |
| 101 | | | | +++ | | | | | | | | |
| 119 | | | | | | | | | | | | |

TABLE 3b

Compounds of the invention tested against a panel of different enzymes at 10 micromolar concentration of the compound.
Profiler Assay - Percent Inhibition at 10 micromolar

| Compound of Example No. | LCK | LYN | MAPKAPK2 | MET | MSK1 | p38a | PKA | PKCz | PKD2 | PRAK | RSK1 | SRC |
|---|---|---|---|---|---|---|---|---|---|---|---|---|
| 5 | | | | | | | | | | | | |
| 6 | | | | | | | | | | | | |
| 8 | | | | | | | | | | | | |
| 9 | | | | | | | | | | | | |
| 11 | | | | | | | | | | | | |
| 13 | "+" | "++" | | | | | | | | | | "++" |
| 16 | | | | | | | | | | | | |
| 17 | | | | | | | | | | | | |
| 19 | | | | | | | | | | | | |
| 26 | | | | | | | | | | | | |
| 59 | | | | | | | | | | | | |
| 51 | | | | | | | | | | | | |
| 27 | | | | | | | | | | | | |
| 54 | | | | | | | | | | | | |
| 58 | | | | | | | | | | | | |
| 57 | | | | | | | | | | | | |
| 56 | | | | | | | | | | | | |
| 55 | | | | | | | | | | | | |
| 33 | | | | | | | | | | | | |
| 31 | "+++" | "+++" | | | "++" | | "+++" | | "+++" | "++" | "+" | "++" |
| 30 | | "++" | | | | | | | | | | "+" |
| 29 | | | | | | | | | | | | |
| 52 | | | | | | | | | | | | |
| 60 | | | | | | | | | | | | |
| 64 | | | | | | | | | | | | |
| 63 | | | | | | | | | | | | |
| 36 | | | | | | | | | | | | |
| 66 | | | | | | | | | | | | |
| 65 | | | | | | | | | | | | |
| 68 | | | | | | | | | | | | |
| 67 | | | | | | | | | | | | |
| 62 | | | | | | | | | | | | |
| 41 | | | | | | | | | | | | |
| 37 | | | | | | | | | | | | |
| 38 | | | | | | | | | | | | |
| 40 | | | | | | | | | | | | |
| 39 | | | | | | | | | | | | |
| 61 | | | | | | | | | | | | |
| 23 | | | | | | | | | | | | |
| 12 | | | | | | | | | | | | |
| 10 | | | | | | | | | | | | |
| 81 | "+++" | "+++" | "+" | "+++" | "+++" | "+" | "+++" | "+" | "+++" | "++" | "++" | "+++" |
| 82 | | "++" | "+++" | | "+" | | "++" | | "+" | "+++" | "+" | "+" |
| 83 | | | | | | | "+" | | | | | |
| 99 | | | | | | | | | | | | |
| 98 | | "+" | | | | | | | "+" | | | |
| 97 | | | | | | | | | | | | |
| 103 | | "++" | | | | | | | | | "+" | "++" |
| 96 | | "++" | | | | | | | "+" | | | "+" |
| 95 | "++" | "+++" | | | | | | | | | | "+++" |
| 102 | | | | | | | | | | | | |
| 109 | | | | | | | | | | | | |
| 121 | "++" | "++" | | | | | | | | | | "++" |
| 120 | | "++" | | | | | | | | | | "+" |
| 113 | "++" | "+++" | | | | | "+" | | | | | "++" |
| 114 | "+" | "+++" | | | | | | | | | | "+++" |
| 139 | "++" | "+++" | | | | | | | | | | "+++" |
| 140 | | | | | | | | | | | | "+" |
| 141 | | | | | | | | | | | | |
| 101 | | | | | | | | | | | | |
| 119 | | | | | | | | | | | | |

TABLE 4a

Compounds of the invention tested against a panel of different enzymes at 1 micromolar concentration of the compound.

| Compound of Example No. | ABL | AKT1 | AKT2 | AurA | CHK1 | CHK2 | CK1d | Erk1 | Erk2 | FYN | GSK3b | INSR |
|---|---|---|---|---|---|---|---|---|---|---|---|---|
| 25 | | | | "++" | | | | | | | | |
| 31 | | | | | | | | | | | | |
| 30 | | | | "++" | | | | | | | | |
| 29 | | | | "+" | | | | | | | | |
| 27 | | | | | | | | | | | | |
| 26 | | | | | | | | | | | | |
| 33 | | | | "+" | | | | | | | | |
| 36 | | | | "+" | | | | | | | | |
| 34 | | | | "+++" | | | | | | | | |
| 35 | | | | "+++" | | | | | | | | |
| 96 | "++" | | | | | | | | "+" | "++" | | |
| 95 | "+++" | | | "+" | | | | | | "+++" | | |
| 120 | | | | "+++" | "+++" | | | | | | | |
| 113 | "+" | | | "+" | "+" | | | | | "++" | | |
| 114 | "++" | | | "++" | | | | | | "++" | | |
| 88 | | | | | | | | | | | | |
| 125 | "++" | | | | | | | | | "++" | | |

TABLE 4b

Compounds of the invention tested against a panel of different enzymes at 1 micromolar concentration of the compound.

| Compound of Example No. | LCK | LYN | MAPKAPK2 | MET | MSK1 | p38a | PKA | PKCz | PKD2 | PRAK | RSK1 | SRC |
|---|---|---|---|---|---|---|---|---|---|---|---|---|
| 25 | | | | | | | | | | | | |
| 31 | | | | | | | | | | | | |
| 30 | | | | | | | | | | | | |
| 29 | | | | | | | | | | | | |
| 27 | | | | | | | | | | | | |
| 26 | | | | | | | | | | | | |
| 33 | | | | | | | | | | | | |
| 36 | | | | | | | | | | | | |
| 34 | | | | | | | | | | | | |
| 35 | | | | | | | | | | | | |
| 96 | | "++" | | | | "+" | | | | | "+" | |
| 95 | "+" | | | | | | | | | | "+++" | |
| 120 | | "+" | | | | | | | | | | |
| 113 | "+" | "++" | | | | | | | | | "++" | |
| 114 | | "++" | | | | | | | | | "++" | |
| 88 | | | | | | | | | | | | |
| 125 | | | | | | | | | | | | |

Determination of IC$_{50}$ Values According to the LC3000 Method

In the desired wells of a 384-well plate, Aurora A (0.067 ng/ul) was incubated with 15 uM ATP (the KM value), 1 mM DTT, 1 mM MgCl2, and 1 uM peptide substrate (sequence FITC-LRRASLG-(CONH$_2$), FITC=fluorescein isothiocyanate) in 100 mM HEPES pH 7.5 and 0.015% Brij-35 buffer. The reaction was incubated for 90 min at 25 C, and then stopped by the addition of 45 ul of Stop buffer (100 mM HEPES ph 7.5, 0.015% Brij-35, 10 mM EDTA).

The plate was read in a Caliper LC 3000 in an Off-Chip mobility shift assay format, using the following parameters: screening pressure—1.8 psi, upstream voltage—2700, downstream voltage—1000. These conditions cause unphosphorylated substrate peptide to resolve as a peak before that of the phosphorylated peptide product.

In the following table "+" means >100 nM, "++" means 11-100 nM, and "+++" means <11 nM.

A selection of compounds have been tested as provided below in Table 5

| Compound of Example No. | Aurora Kinase A Activity (IC50) |
|---|---|
| 5 | |
| 6 | |
| 8 | |
| 9 | |
| 16 | |
| 17 | |
| 19 | |
| 18 | |
| 15 | |
| 25 | (+) |
| 26 | |
| 24 | |
| 33 | |

-continued

| Compound of Example No. | Aurora Kinase A Activity (IC50) |
|---|---|
| 31 | (+) |
| 32 | (+) |
| 30 | (+) |
| 29 | (+) |
| 36 | (+) |
| 35 | (+) |
| 34 | (+) |
| 44 | (++) |
| 45 | (+) |
| 43 | (+) |
| 42 | (+) |
| 48 | (++) |
| 46 | (+) |
| 47 | (+) |
| 53 | (+) |
| 73 | |
| 72 | (+) |
| 69 | (++) |
| 71 | |
| 83 | |
| 103 | |
| 96 | |
| 97 | |
| 98 | |
| 99 | |
| 100 | |
| 101 | |
| 111 | |
| 89 | |
| 91 | |
| 90 | |
| 92 | |
| 93 | |
| 94 | |
| 95 | |
| 102 | |
| 109 | |
| 110 | |
| 150 | |
| 119 | |
| 120 | (+++) |
| 112 | |
| 113 | |
| 114 | (+) |
| 84 | |
| 122 | |
| 87 | |
| 88 | |
| 125 | |
| 126 | |
| 128 | |
| 129 | |
| 130 | |
| 131 | |
| 132 | |
| 133 | |
| 134 | |
| 135 | |
| 136 | |
| 137 | |
| 138 | |
| 139 | (+) |
| 140 | |
| 141 | |
| 123 | (+) |
| 124 | |
| 142 | |
| 143 | |
| 144 | |
| 145 | |
| 146 | |
| 148 | (+++) |
| 147 | |
| 149 | |
| 151 | |
| 449 | (+) |
| 448 | |

-continued

| Compound of Example No. | Aurora Kinase A Activity (IC50) |
|---|---|
| 450 | |
| 452 | (+) |
| 454 | |
| 453 | |
| 455 | |
| 156 | (+) |
| 456 | |
| 340 | |
| 304 | |
| 305 | |
| 277 | |
| 457 | |
| 379 | (+++) |
| 382 | (+++) |
| 381 | (+++) |
| 380 | (+++) |
| 324 | (++) |
| 295 | |
| 201 | |
| 385 | (+++) |
| 384 | (+++) |
| 383 | (++) |
| 459 | |
| 458 | |
| 296 | (+) |
| 344 | (++) |
| 279 | (+++) |
| 341 | (+) |
| 317 | (+) |
| 285 | (+++) |
| 283 | (++) |
| 386 | (+++) |
| 378 | (+++) |
| 387 | (+++) |
| 388 | (+++) |
| 463 | (+) |
| 461 | (+) |
| 462 | (+) |
| 460 | (+) |
| 464 | (+) |
| 343 | (+++) |
| 275 | (++) |
| 345 | (++) |
| 465 | (+) |
| 468 | (+) |
| 466 | (+) |
| 364 | |
| 469 | (++) |
| 188 | (+) |
| 470 | (++) |
| 346 | (+) |
| 342 | (++) |
| 471 | (+) |
| 326 | (++) |
| 325 | (++) |
| 366 | (+) |
| 472 | |
| 389 | (+++) |
| 390 | (+++) |
| 391 | (+++) |
| 392 | (+) |
| 467 | |
| 482 | |
| 474 | |
| 475 | (+) |
| 351 | (++) |
| 281 | (+++) |
| 393 | (+++) |
| 394 | (+++) |
| 395 | (+++) |
| 396 | (+++) |
| 397 | (+++) |
| 398 | (+++) |
| 399 | (+++) |
| 400 | (++) |
| 473 | |
| 307 | |

-continued

| Compound of Example No. | Aurora Kinase A Activity (IC50) |
|---|---|
| 367 | |
| 294 | (++) |
| 293 | (+++) |
| 401 | (++) |
| 476 | (+) |
| 477 | |
| 478 | |
| 479 | (+) |
| 289 | (++) |
| 354 | (+) |
| 480 | |
| 276 | (++) |
| 286 | (++) |
| 284 | (+++) |
| 290 | (++) |
| 402 | (++) |
| 298 | (+++) |
| 301 | |
| 319 | |
| 481 | |
| 332 | |
| 331 | (+) |
| 282 | (+++) |
| 322 | (+) |
| 291 | (+++) |
| 329 | (++) |
| 330 | (++) |
| 292 | (++) |
| 267 | (+++) |
| 266 | |
| 299 | |
| 300 | (+) |
| 348 | (+) |
| 405 | (++) |
| 308 | (+) |
| 309 | (+) |
| 269 | (++) |
| 268 | (+++) |
| 272 | (+++) |
| 271 | (++) |
| 362 | (+) |
| 365 | |
| 363 | (+) |
| 274 | (++) |
| 160 | (+) |
| 406 | |
| 350 | (++) |
| 407 | |
| 408 | (+) |
| 270 | (++) |
| 423 | (+++) |
| 424 | |
| 425 | |
| 173 | (++) |
| 174 | |
| 446 | (++) |
| 428 | |
| 347 | |
| 280 | (+++) |
| 316 | |
| 333 | (++) |
| 323 | |
| 356 | |
| 355 | (+) |
| 181 | (+) |
| 180 | |
| 429 | |
| 426 | |
| 434 | (++) |
| 358 | |
| 334 | |
| 328 | |
| 327 | (++) |
| 187 | (+) |
| 186 | |
| 184 | |
| 183 | (+) |

-continued

| Compound of Example No. | Aurora Kinase A Activity (IC50) |
|---|---|
| 368 | |
| 357 | (+) |
| 360 | |
| 369 | (+) |
| 430 | (+) |
| 321 | (+++) |
| 320 | (++) |
| 432 | (+++) |
| 433 | (++) |
| 431 | (+) |
| 435 | (+++) |
| 370 | (+) |
| 371 | (+) |
| 372 | (++) |
| 445 | (++) |
| 437 | (+++) |
| 436 | (++) |
| 310 | |
| 311 | |
| 438 | (+++) |
| 447 | (++) |
| 297 | (+++) |
| 318 | |
| 312 | |
| 313 | (+) |
| 314 | (+) |
| 315 | (+) |
| 335 | (+) |
| 336 | |
| 337 | |
| 338 | |
| 339 | |
| 212 | |
| 213 | (++) |
| 214 | |
| 215 | (+) |
| 216 | (++) |
| 218 | |
| 219 | (+) |
| 220 | |
| 221 | |
| 373 | (++) |
| 410 | |
| 411 | |
| 264 | |
| 265 | (+) |
| 416 | (+++) |
| 409 | (+++) |
| 412 | (+++) |
| 413 | (+++) |
| 415 | (+++) |
| 414 | (+++) |
| 439 | (+++) |
| 374 | (++) |
| 375 | |
| 361 | |
| 359 | |
| 227 | |
| 228 | (+) |
| 229 | |
| 440 | (+++) |
| 349 | (+++) |
| 352 | (++) |
| 442 | (+++) |
| 443 | (+++) |
| 444 | (+++) |
| 441 | (+++) |
| 230 | |
| 404 | (+++) |
| 403 | (+++) |
| 303 | (++) |
| 376 | |
| 377 | (+) |
| 417 | (+++) |
| 420 | (+++) |
| 418 | (+++) |
| 506 | (++) |

-continued

| Compound of Example No. | Aurora Kinase A Activity (IC50) |
|---|---|
| 505 | (++) |
| 504 | (+++) |
| 503 | (++) |
| 502 | (++) |
| 419 | (+++) |
| 421 | (++) |
| 422 | (++) |
| 501 | (++) |
| 500 | (++) |
| 499 | (++) |
| 498 | (+++) |
| 495 | (++) |
| 494 | (++) |
| 484 | |
| 486 | |
| 487 | |
| 492 | |
| 493 | |
| 485 | (+) |
| 288 | (+) |
| 483 | (+) |
| 287 | (+) |
| 488 | (+) |
| 489 | |
| 490 | |
| 491 | |

Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., In Vitro 18:538-549).

It is understood that in light of the teachings of this invention to one of ordinary skill in the art that certain changes and modifications may be made thereto without departing from the spirit and scope of the invention.

What is claimed is:
1. A compound according to formula V:

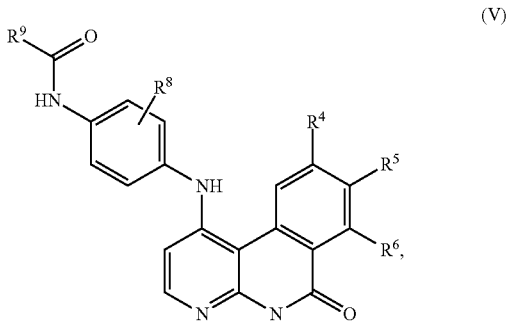

(V)

which conforms to subformulae; A, B, C, D, E, F, G, H, J, K, L and M of formula (V), wherein:
in Subformula A
$R^9$ is phenyl, unsubstituted, or monosubstituted or independently disubstituted, by methoxy, $CF_3$, F, $CH_3$ or Cl,
$R^8$ is H or F,
one of $R^4$, $R^5$, $R^6$ is hydroxymethyl, N-(2-(dimethylamino)ethyl)carbamoyl, COONH2, (4- Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$, while the remaining two of $R^4$, $R^5$, $R^6$ are H,
in Subformula B
$R^9$ is phenyl, unsubstituted, or monosubstituted, or independently disubstituted, by methoxy, $CF_3$, F, $CH_3$ or Cl,
$R^8$ is H,
one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl) carbamoyl or $CF_3$, while the remaining two of $R^4$, $R^5$, $R^6$ are H,
in Subformula C
$R^9$ is phenyl, unsubstituted, or monosubstituted, or independently disubstituted, by methoxy, $CF_3$, F, $CH_3$ or Cl,
$R^8$ is H,
$R^4$, $R^5$, $R^6$ are H,
in Subformula D
$R^9$ is phenyl,
$R^8$ is H,
one of $R^4$, $R^5$, $R^6$ is hydroxymethyl, N-(2-(dimethylamino)ethyl)carbamoyl, COONH2, (4- Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, carboxylic acid 2-morpholin-4-yl-ethyl amidyl, N-(3-(dimethylamino)propyl)carbamoyl or $CF_3$, while the remaining two of $R^4$, $R^5$, $R^6$ are H,
in Subformula E
$R^9$ is phenyl, unsubstituted, or monosubstituted, or independently disubstituted, by methoxy, $CF_3$, F, $CH_3$ or Cl,
$R^8$ is H,
$R^4$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N -(2,3-dihydroxypropyl)carbamoyl, $COOCH_2CH_3$, aminomethyl, 3-morpholin-4-yl -propyl amidyl, 2-hydroxy ethyl amidyl, methoxy, F, Cl, 2-morpholin-4-yl-ethyl amidyl, N-(3- (dimethylamino)propyl)carbamoyl or $CF_3$, $R^5$, $R^6$ are H,
in Subformula F
$R^9$ is phenyl, unsubstituted, or monosubstituted, or independently disubstituted, by methoxy, $CF_3$, F, $CH_3$ or Cl,
$R^8$ is H,
$R^5$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N -(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3- (dimethylamino)propyl)carbamoyl or $CF_3$,
$R^4$, $R^6$ are H,
in Subformula G
$R^9$ is phenyl, unsubstituted, or monosubstituted, or independently disubstituted, by methoxy, $CF_3$, F, $CH_3$ or Cl,
$R^8$ is H,
$R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N -(2, 3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3- (dimethylamino)propyl)carbamoyl or $CF_3$, $R^4$, $R^5$ are H, in Subformula H $R^9$ is phenyl, substituted by $CF_3$ and F, $R^8$ is H, one of $R^4$, $R^5$, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$, while the remaining two of $R^4$, $R^5$, $R^6$ are H, in Subformula J $R^9$ is phenyl, substituted by $CF_3$ and F, $R^8$ is H, $R^6$ is hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3- (dimethylamino)propyl)carbamoyl or $CF_3$, $R^4$, $R^5$ are H, in Subformula K $R^9$ is phenyl, $R^8$ is H, $R^5$, $R^6$ are independently hydroxymethyl, N-(2-(dimethylamino)ethyl)carbamoyl, COONH2, (4-Methylpiperazine-1-carbonyl), $COOCH_3$, COOH, N-(2-aminoethyl)carbamoyl, N-(2,3-dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$, $R^4$ is H, in Subformula L $R^9$ is cyclohexyl, phenylamino, (trifluoromethyl)pyridyl, $R^8$ is H, one of $R^4$, $R^5$, $R^6$ is hydroxymethyl, N-(2-(dimethylamino)ethyl)carbamoyl, COONH2, (4-Methylpiperazine- 1-carbonyl), $COOCH_3$, COOH, N-(2-aminoethyl)carbamoyl, N-(2,3 -dihydroxypropyl)carbamoyl, $COOCH_2CH_3$, aminomethyl, 3-morpholin-4-yl-propyl amidyl, 2-hydroxy ethyl amidyl, methoxy, F, Cl, 2-morpholin-4-yl-ethyl amidyl, N-(3-(dimethylamino)propyl)carbamoyl or $CF_3$, while the remaining two of $R^4$, $R^5$, $R^6$ are H and in Subformula M $R^9$ is phenyl, unsubstituted, or monosubstituted, or independently disubstituted, by methoxy, $CF_3$, F, $CH_3$ or Cl, $R^8$ is H, $R^4$, $R^5$ are methoxy, $R^6$ is H.

2. A compound selected from the group consisting of:

Methyl 1-(4-benzamidophenylamino)-6-oxo-5,6-dihydrobenzo[c][1,8]naphthyridine-9-carboxylate;

N-(4-(9-(Hydroxymethyl)-6-oxo-5,6-dihydrobenzo[c][1,8]naphthyridin-1-ylamino)phenyl)benzamide;

1-(4-Benzamidophenylamino)-6-oxo-5,6-dihydrobenzo[c][1,8]naphthyridine-9-carboxylic acid;

1-(4-benzamidophenylamino)-6-oxo-5,6-dihydrobenzo[c][1,8]naphthyridine-9-carboxamide;

1-(4-Benzamidophenylamino)-N,N-dimethyl-6-oxo-5,6-dihydrobenzo[c][1,8]naphthyridine-9-carboxamide;

N-(2-Aminoethyl)-1-(4-benzamidophenylamino)-6-oxo-5,6-dihydrobenzo[c][1,8]naphthyridine-9-carboxamide;

1-(4-benzamidophenylamino)-N-(2-(dimethylamino)ethyl)-6-oxo-5,6-dihydrobenzo[c] [1,8]naphthyridine-9-carboxamide;

1-(4-benzamidophenylamino)-N-(2-(4-methylpiperazin-1-yl)ethyl)-6-oxo-5,6-dihydrobenzo[c][1,8]naphthyridine-9-carboxamide;

1-(4-Benzamidophenylamino)-N-(2-hydroxyethyl)-6-oxo-5,6-dihydrobenzo[c][1,8]naphthyridine-9-carboxamide;

N-(4-(9-Chloro-6-oxo-5,6-dihydrobenzo[c][1,8]naphthyridin-l-ylamino)phenyl)benzamide; and 1-(4-(3,4-Difluorobenzamido)phenylamino)-N-(2-(dimethylamino)ethyl)-6-oxo-5,6-dihydrobenzo[c][1,8]naphthyridine-9-carboxamide.

* * * * *